US006642268B2

(12) United States Patent
Keller et al.

(10) Patent No.: US 6,642,268 B2
(45) Date of Patent: Nov. 4, 2003

(54) COMBINATION THERAPY EMPLOYING ILEAL BILE ACID TRANSPORT INHIBITING BENZOTHIPINES AND HMG CO-A REDUCTASE INHIBITORS

(75) Inventors: Bradley T. Keller, Chesterfield, MO (US); Kevin C. Glenn, Maryland Heights, MO (US); Robert E. Manning, St. Louis, MO (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 10/076,091

(22) Filed: Feb. 15, 2002

(65) Prior Publication Data

US 2003/0171426 A1 Sep. 11, 2003

Related U.S. Application Data

(60) Division of application No. 09/676,466, filed on Sep. 29, 2000, now Pat. No. 6,420,417, which is a continuation-in-part of application No. 08/831,284, filed on Mar. 31, 1997, now abandoned, and a continuation-in-part of application No. 08/816,065, filed on Mar. 11, 1997, now abandoned, which is a continuation of application No. 08/517,051, filed on Aug. 21, 1995, now abandoned, which is a continuation-in-part of application No. 08/305,526, filed on Sep. 12, 1994, now abandoned.
(60) Provisional application No. 60/040,660, filed on Mar. 11, 1997, and provisional application No. 60/013,119, filed on Mar. 11, 1996.

(51) Int. Cl.[7] .................... A61K 31/38; A61K 31/35
(52) U.S. Cl. ........................ 514/431; 514/460
(58) Field of Search .................... 514/431, 460

(56) References Cited

U.S. PATENT DOCUMENTS

| 3,262,850 A | 7/1966 | Glynne |
| 3,287,370 A | 11/1966 | Mohrbacher |
| 3,389,144 A | 6/1968 | Mohrbacher |
| 3,520,891 A | 7/1970 | Mohrbacher |
| 3,674,836 A | 7/1972 | Creger |
| 3,692,895 A | 9/1972 | Nelson |
| 3,694,446 A | 9/1972 | Houlihan et al. |
| 3,714,190 A | 1/1973 | Boissier |
| 3,781,328 A | 12/1973 | Witte |
| 3,948,973 A | 4/1976 | Phillips |
| 3,962,261 A | 6/1976 | Zinnes |
| 3,972,878 A | 8/1976 | Schirmann |
| 3,983,140 A | 9/1976 | Endo |
| 4,002,750 A | 1/1977 | Ambrogi |
| 4,058,552 A | 11/1977 | Mieville |
| 4,185,109 A | 1/1980 | Rosen |
| 4,231,938 A | 11/1980 | Monaghan |
| 4,251,526 A | 2/1981 | McCall |
| 4,346,227 A | 8/1982 | Terahara |
| 4,410,629 A | 10/1983 | Terahara et al. |
| 4,444,784 A * | 4/1984 | Hoffman et al. ............ 424/279 |
| 4,448,979 A | 5/1984 | Terahara et al. |
| 4,559,332 A | 12/1985 | Grob |
| 5,075,293 A | 12/1991 | Reifschneider |
| 5,153,184 A | 10/1992 | Reifschneider |
| 5,158,943 A | 10/1992 | Sohda |
| 5,244,887 A | 9/1993 | Straub |
| 5,260,316 A | 11/1993 | Van Duzer |
| 5,334,600 A | 8/1994 | Van Duzer |
| 5,350,761 A | 9/1994 | Van Duzer |
| 5,354,772 A | 10/1994 | Kathawala |
| 5,430,116 A | 7/1995 | Kramer |
| 5,502,045 A | 3/1996 | Miettinen |
| 5,512,558 A | 4/1996 | Enhsen |
| 5,519,001 A | 5/1996 | Rampratap |
| 5,602,152 A | 2/1997 | Berthelon |
| 5,610,151 A | 3/1997 | Glombik |
| 5,663,165 A | 9/1997 | Brieaddy |
| 5,703,188 A | 12/1997 | Mandeville |
| 5,705,524 A | 1/1998 | McGee |
| 5,723,458 A | 3/1998 | Brieaddy |
| 5,767,115 A | 6/1998 | Rosenblum |
| 5,929,062 A | 7/1999 | Haines |
| 5,994,391 A | 11/1999 | Lee |
| 6,020,330 A | 2/2000 | Enhsen |
| 6,034,118 A | 3/2000 | Bischofberger |
| 6,337,327 B1 * | 1/2002 | Tuffin et al. ............. 514/226.5 |
| 6,355,672 B1 * | 3/2002 | Yasuma et al. ............. 514/431 |
| 6,376,537 B1 * | 4/2002 | Weinberg ................... 514/460 |
| 6,384,034 B2 * | 5/2002 | Simitchieva et al. ........ 514/252 |
| 6,441,022 B1 * | 8/2002 | Frick et al. ................. 514/431 |
| 6,441,029 B1 * | 8/2002 | Elson ......................... 514/456 |
| 6,455,574 B1 * | 9/2002 | Buch .......................... 514/427 |
| 6,462,091 B1 * | 10/2002 | Keller et al. ................ 514/655 |

FOREIGN PATENT DOCUMENTS

| AU | 30209/92 | 12/1992 |
| AU | 61946/94 | 6/1994 |
| AU | 61948/94 | 6/1994 |
| AU | 61949/94 | 6/1994 |
| CA | 2025294 | 3/1991 |

(List continued on next page.)

OTHER PUBLICATIONS

A. Barrett et al., "Total Synthesis and Stereochemical Assignment of the Quinquecyclopropane–Containing Cholesteryl Ester Transfer Protein Inhibitor U–106305", J. Amer. Chem. Soc., 1996, 118, pp. 7863–7864.
P. Barter et al., "High Density Lipoproteins and Coronary Heart Disease", Atherosclerosis, 121 1996, pp. 1–12.
A. Beckwith et al., "Iododediazoniation of Arenediazonium Salts Accompanied by Aryl Radical Ring Closure" J. Org. Chem. 1987, vol. 52, pp. 1922–1930.

(List continued on next page.)

*Primary Examiner*—Deborah C. Lambkin
(74) *Attorney, Agent, or Firm*—Banner & Witcoff, Ltd.

(57) ABSTRACT

Provided are novel benzothiepines, derivatives, and analogs thereof; pharmaceutical compositions containing them; and methods of using these compounds and compositions in medicine, particularly in the prophylaxis and treatment of hyperlipidemic conditions such as those associated with atherosclerosis or hypercholesterolemia, in mammals. Also provided are compositions and methods for combination therapy employing ileal bile acid transport inhibitors and HMG Co—A reductase inhibitors for the treatment of hyperlipidemic conditions.

18 Claims, No Drawings

FOREIGN PATENT DOCUMENTS

| | | |
|---|---|---|
| CA | 2078588 | 3/1993 |
| CA | 2085782 | 6/1993 |
| CA | 2085830 | 6/1993 |
| DE | 1211258 | 2/1968 |
| DE | 3 122 499 A1 | 12/1981 |
| DE | 196 27 430 A1 | 8/1996 |
| EP | 0 022 487 A1 | 9/1980 |
| EP | 0 067 086 | 10/1982 |
| EP | 0 129 748 | 2/1985 |
| EP | 0 033 538 B1 | 11/1985 |
| EP | 0 250 265 | 6/1987 |
| EP | 0 244 364 A2 | 11/1987 |
| EP | 0 338 331 | 6/1989 |
| EP | 0 379 161 | 1/1990 |
| EP | 0 409 281 A1 | 1/1991 |
| EP | 0 531 901 A2 | 2/1992 |
| EP | 0 508 425 A1 | 9/1992 |
| EP | 0 549 967 A1 | 12/1992 |
| EP | 0 526 402 A1 | 2/1993 |
| EP | 0 559 064 A2 | 2/1993 |
| EP | 0 563 731 A1 | 3/1993 |
| EP | 0 568 898 A1 | 4/1993 |
| EP | 0 818 197 A1 | 6/1997 |
| EP | 0 818 448 A1 | 6/1997 |
| EP | 0 796 846 A1 | 7/1997 |
| EP | 0 801 060 A1 | 10/1997 |
| FR | 2 661 676 A1 | 2/1990 |
| GB | 2 077 264 A | 12/1981 |
| GB | 1 211 258 | 2/1986 |
| GB | 2 305 665 | 4/1997 |
| GB | 2 329 334 | 3/1999 |
| JP | 10-287662 | 10/1998 |
| WO | 89/01477 | 2/1989 |
| WO | 91/08205 | 6/1991 |
| WO | 92/17467 | 10/1992 |
| WO | 92/18115 | 10/1992 |
| WO | 92/18462 | 10/1992 |
| WO | 93/16055 | 8/1993 |
| WO | 93/21146 | 10/1993 |
| WO | 94/18183 | 8/1994 |
| WO | 94/18184 | 8/1994 |
| WO | 94/24087 | 10/1994 |
| WO | 95/21843 | 8/1995 |
| WO | 96/05188 | 2/1996 |
| WO | 96/08484 | 3/1996 |
| WO | 96/16051 | 5/1996 |
| WO | 96/40255 | 12/1996 |
| WO | 97/03953 | 2/1997 |
| WO | 97/33882 | 9/1997 |
| WO | 97/49387 | 12/1997 |
| WO | 97/49736 | 12/1997 |
| WO | 98/02432 | 1/1998 |
| WO | 98/06405 | 2/1998 |
| WO | 98/23593 | 6/1998 |
| WO | 98/35937 | 8/1998 |
| WO | WO 98/38182 | 9/1998 |
| WO | 98/38182 | 9/1998 |
| WO | 98/39299 | 9/1998 |
| WO | WO 98/40375 | 9/1998 |
| WO | 98/40375 | 9/1998 |
| WO | 98/56757 | 12/1998 |
| WO | 99/11259 | 3/1999 |
| WO | 99/11260 | 3/1999 |
| WO | 99/11263 | 3/1999 |
| WO | 99/14174 | 3/1999 |
| WO | 99/14204 | 3/1999 |
| WO | 99/14215 | 3/1999 |
| WO | 99/32478 | 7/1999 |
| WO | 99/35135 | 7/1999 |
| WO | 99/64409 | 12/1999 |
| WO | 00/35889 | 6/2000 |

OTHER PUBLICATIONS

D. Bilheimer et al., "Mevinolin and Colestipol Stimulate Receptor–Mediated Clearance of Low Density Lipoprotein From Plasma In Familial Hypercholesterolemia Heterzygotes", Proc. Natl. Acad. Sci. USA, vol. 80, Jul. 1983, pp. 4124–4128.

C. Bisgaier et al., Cholesteryl Ester Transfer Protein Inhibition By PD 140195, Lipids, vol. 29, No. 12, 1994, pp. 811–818.

D. Blankenhorn et al., "Beneficial Effects of Combined Colestipol–Niacin Therapy On Coronary Atherosclerosis and Coronary Venous Bypass Grafts", JAMA, Jun. 19, 1987, vol. 257, No. 23, pp. 3233–3240.

D. Blankenhorn et al., "Beneficial Effects of Colestipol–Niacin Therapy on the Common Carotid Artery", Circulation vol. 88, Jul. 1, 1993, pp. 20–28.

P. Bonin et al., "A Peptide Inhibitor Of Cholesteryl Ester Transfer Protein Identified By Screening a Bacteriophage Display Library", Journal of Peptide Research, 51, 1998, pp. 216–225.

G. Brown, et al., "Regression of Coronary Artery Disease As A Result of Intensive Lipid–Lowering Therapy in Men With High Levels of Apolipoprotein B", The New England Journal of Medicine, vol. 323, Nov. 8, 1990, No. 19, pp. 1289–1339.

M. Brown et al., Induction of 3–hydroxy–3Methylglutaryl Coenzyme A Reductase Activity in Human Fibroblasts Incubated with Compactin (ML–236B), A Competitive Inhibitor of the Reductase, The Journal of Biological Chemistry, vol. 253, No. 4, Feb. 22, 1978, pp. 1121–1128.

S. Busch et al., "Cholesteryl Ester Analogs Inhibit Cholesteryl Ester But Not Triglyceride Transfer Catalyzed By The Plasma Cholesteryl Ester–Triglyceride Transfer Protein", Lipids, vol. 25, No. 4 (1990), pp. 216–220.

C. Camoutis et al., "N–Substituted 4, 5–Dihydro–1, 2–Benzothiazepin–3–One 1, 1–Dioxide", J. Heterocyclic Chem. 17, pp. 1135–1136 (1980).

L. Cashin–Hemphill et al., "Beneficial Effects of Colestipol–Niacin on Coronary Atherosclerosis A 4–Year Follow–up", JAMA, Dec. 19, 1990, vol. 264, No. 23, pp. 3013–3017.

P. Catsoulacos et al., "Synthesis of Some N–Substituted 4,5–Dihydro–7,8–dimethoxybenzothiazepin–3–one 1,1–Dioxides", J. Heterocyclic Chem., vol. 13 (1976), pp. 1309–1314.

P. Catsoulacos et al., "Thiazo Compounds. Derivatives of 4, 5–Dihydro–7,8–Dimethoxybenzothiazepin–3 one 1,1–Dioxides", Journal of Chemical and Engineering Data, vol. 22, No. 3, 1977, pp. 353–354.

K. Cho et al., "A Peptide From Hog Plasma the Inhibits Human Cholesteryl Ester Transfer Protein", Biochemica et Biophysica Acta, 1391, 1998, pp. 133–144.

D. Connolly et al., "Inactivation of Cholesteryl Ester Transfer Protein by Cysteine Modification", Biochemical and Biophysical Research Communications 223, pp. 42–47, 1996.

S. Coval et al., "Weidendoil–A and–B, Cholesteryl Ester Transfer Protein Inhibitors From The Marine Sponge Xestosponga Weidenmayeri", Bioorganic & Medicinal Chemistry Letter, vol. 5, No. 6, pp. 605–610, 1995.

J. Davignon et al., "Apolipoprotienin E and Atherosclerosis: Quest for an APO E Receptor Defect Leads to the Discovery of Pseudo Type IIi Dyslipoproteinemia in a Family", Atherosclerosis IX, pp. 199–203.

J. Davignon et al., "Comparative Efficacy and Safety of Pravastatin, Nicotinic Acid and The Two Combined in Patients with Hypercholesterolemia", The American Journal of Cardiology, Feb. 15, 1994, pp. 339–345.

C. East et al., "Combination Drug Therapy for Familial Combined Hyperlipidemia", Annals of Internal Medicine, Jul. 1, 1988, pp. 25–32.

J. Emmerich et al., "Efficacy and Safety of Simvastatin (Alone or in Association with Cholestyramine) A 1 yr. Study in 66 Patients with Type II Hyperlipoproteinaemia", European Heart Journal (1990), 11, pp. 149–155.

D. Erkelens, "Combination Drug Therapy with HMG Co A Reductase Inhibitors and Bile Acid Sequestrants for Hypercholesterolmia", Cardiology, 1990, 77, (suppl 4). pp. 33–38.

H. Ginsberg, "Update on the Treatment of Hypercholesterolemia, with a Focus on HGM–CoA Reductase Inhibitors and Combination Regimens", Clinical Cardiology 18, pp. 307–315, (1995).

C. Glueck et al., "Gemfibrozil–Lovasatin Therapy for Primary Hyperlipoproteinemias" The American Journal of Cardiology, Jul. 1, 1992, vol. 70, No. 1, pp. 1–9.

S. Grundy et al., "Influence of Combined Therapy with Mevinolin and Interruption of Bile–Acid Reabsorption on Low Density Lipoproteins in Heterozygous Familial Hypercholesterolemia", Annals of Internal Medicine, 1985, 103: pp. 339–343.

H. Gylling et al., "Effects of Inhibiting Cholestrol Absorption and Synthesis on Cholesterol and Lipoprotein Metabolism in Hypercholesterolemic Non–Insulin–Dependent Diabetic Men", Journal of Lipid Research, vol. 37, 1996, pp. 1776–1785.

E. Haber, "Molecular Cardiovascular Medicine" Scientific American, pp. 35–40.

V. Hegde et al., "A Depsipeptide Fungal Metabolite Inhibitor of Cholesteryl Ester Transfer Protein", Bioorganic & Medicinal Chemistry Letters 8, 1998, pp. 1277–1280.

L. Hellberg et al., "5a–Hydroxy–3a–Cholestanecarboxylic" The New Journal of Organic Synthesis, vol. 15, No. 1–2, Feb.–Apr. 1983, pp. 154–156.

J. Heubi et al., "Primary Bile Acid Malabsorption: Defective in Vitro Ileal Active Bile Acid Transport", Gastroenterology 1982, 83: pp. 804–811.

N. Hoogerbrugge et al., "The Additional Effects of Acipimox to Simvastatin in the Treatment of Combined Hyperlipidaemia", Journal of Internal Medicine, 1997, 241: pp. 151–155.

N. Hoogerbrugge et al., "The Effacy and Safety of Pravastatin, Compared to and in Combination with Bile Acid Binding Resins, In Familial Hypercholesterolaemia", Journal of Internal Medicine 1990, 228; pp. 261–266.

A. Hutchesson et al., "Dual Bezafibrate–Simvastatin Therapy for Combined Hyperlipidaemia", Journal of Clinical Pharmacy and Therapeutics 1994, 19, pp. 387–389.

T. Ichihashi, "Mechanism of Hypocholesterolemic Action of S–8921 in Rats: S–8921 Inhibits Ileal Bile Acid Absorption", The Journal of Pharmacology and Experimental Therapeutics, vol. 284, No. 1, pp. 43–50.

D. Illingworth, et al., "Influence of Lovstatin plus Gemfibrozil on Plasma Lipids and Lipoproteins in Patients With Heterozygous Familial Hypercholesterolemia", Circulation vol. 79, No. 3, Mar. 1989, 590–596.

D. Illingworth, "Mevinolin Plus Colestipol in Therapy for Severe Heterozygous Familial Hypercholesterolemia", Annalos of Internal Medicine, 1984; 101, pp. 598–604.

International Search Report mailed May 23, 2000 based on PCT/US 99/27942.

International Search Report mailed May 23, 2000 based on PCT/US 99/27943.

International Search Report mailed May 23, 2000 based on PCT/US 99/27944.

International Search Report mailed May 23, 2000 based on PCT/US 99/27945.

International Search Report mailed May 18, 2000 based on PCT/US 99/27947.

International Search Report mailed May 15, 2000 based on PCT/US 99/27948.

International Search Report mailed May 17, 2000 based on PCT/US 99/27949.

J. Kane, et al., "Regression of Coronary Atherosclerosis During Treatment of Familial Hypercholesterolemia With Combined Drug Regimens", JAMA, Dec. 19, 1990, Chapter 26, vol. 264, No. 23, pp. 3007–3012.

A. Katritzky et al., "Preparation of 6–7–and 8–Membered Sultams By Friedel–Crafts Cyclization Of w–Phenylalkanesulfamoyl Chlorides", Organic Preparations and Procedures Int., 24 (4), pp. 463–467 (1992).

T. Kazumi et al., "Effects of Niceritrol On Elevated Serum Lipoprotein LP (A) Levels in Diabetic Patients With or Without Overt Proteinuria", Current Therapeutic Research, vol. 55, No. 5, May 1994, pp. 546–551.

W. Kramer, et al., "Intestinal Bile Acid Absorption", The Journal of Biological Chemistry. vol. 268, No. 24 Issue of Aug. 25, pp. 18035–18046, 1993.

Kuo, M.S. et al., "Discovery, Isolation, Structure Elucidation, and Biosynthesis of U–106305, a Choresteryl Ester Transfer Protein Inhibitor from UC 11136", J. Am. Chem. Soc. 117, pp. 10629–10634 (1995).

Kvis, K. et al., "Benzocycloheptenes and Heterocyclic Analogues as Potential Drugs. VII, 4–Phenyl–,3,4, 5–Tetrahydro–1–Benzothiepins and Some Related Compounds", Chem. Commun./Vo.37/(1973) pp. 3808–3816.

Lee, J.C. et al., "A Cholesteryl Ester Transfer Protein Inhibitor from an Insect–associated Fungus", The Journal of Antibiotics 49(7), pp. 693–696.

A.M. Lees et al., "Therapy of Hypercholesterolemia With Mevinolin And Other Lipid–Lowering Drugs", Arteriosclerosis 6, 1986, p. 544a.

T. Leren et al., "Effects of Lovastatin Alone and in Combination with Cholestyramine on Serum Lipids and Apolipoproteins in Heterozygotes for Familial Hypercholesterolemia", International Journal of Research and Investigation on Atherosclerosis and Related Diseases, 73, (1988), pp. 135–141.

M. Lewis, et al., Effects of 2164U90 on Ileal Bile Acid Absorption and Serum Cholesterol in Rats and Mice, Journal of Lipid Research, vol. 36, 1995, pp. 1098–1105.

R. Lewis, Hawley's Condensed Chemical Dictionary, p. 1238.

W. Ling et al., "Minireview Dietary Phytosterols A Review of Metabolism, Benefits and Side Effects", Life Sciences, vol. 57, No. 3, 1995, pp. 195–206.

H. Mabuchi et al., "Reduction of Serum Cholestrol in Heterozygous Patients with Familial Hypercholesterolemia", The New England Journal of Medicine, vol. 308, Mar. 17, 1983, pp. 609–613.

M. Malloy et al., "Complementarity of Colestipol, Niacin, and Lovastatin in Treatment of Severe Familial Hypercholesterolemia", Annals of Internal Medicine 1987; 107: pp. 616–623.

W. Mandeville et al., Bile Acid Sequestrants: Their Use In Combination With Other Lipid–Lowering Agents, Idrugs 1999 vol. 2., No. 3, pp. 237–242.

G. Marais et al., "Rhabdomyolysis and Acute Renal Failure Induced by Combination Lovastatin and Gemfibrozil Therapy", Annals of Internal Medicine, Feb. 1, 1990, vol. 112, No. 3, pp. 228–230.

P. McCarthy, "New Approaches to Atherosclerosis: An Overview", Medicinal Research Reviews, vol. 13, No. 2, 1993, pp. 139–159.

R. Morin, Regulation of Lipid Transfer Between Lipoproteins By An Endogenous Plasma Protein: Selective Inhibition Among Lipoprotein Classes, Journal of Lipid Research, vol. 35, 1994, pp. 836–847.

F. Nerdel et al., "Quartermay Salts of B–Amino Aldehydes and B–Iodoaldehydes", Chemische Berichte (Ed. H. Zahn), vol. 98 (1965), pp. 728–734.

M. Newman et al., "The Conversion of Phenols to Thiophenols via Dialkylthiocarbamates", The Journal of Organic Chemistry, vol. 31, Sep.–Dec. 1966, pp. 3980–3984.

A. Orahovats et al., "A Ring Enlargement from Seven–to Ten–Membered–Ring Sulfonamide Derivatives", Helvetica Chimica Acta, vol. 79, (1996), pp. 1121–1128.

H. Pan et al., "Pharmacokinetics and Pharmacodynamics of Pravastatin Alone and With Cholestyramine in Hypercholesterolemia", Clin. Pharmacol Ther. (1980) 9, 313, pp. 201–207.

N. Panagiotopoulos et al., "N(P–Bromophenyl)–4,5–Dihydro–7,8–Dimethoxy Benzothiazepine—ONE 1,1–Dioxide C17 H16 brNO5S", Cryst. Struct. Comm. (1980) 9, pp. 313–319.

R. Pasternak et al., "Effect of Combination Therapy with Lipid–Reducing Drugs in Patients with Coronary Heart Disease and "Normal" Cholesterol Levels", Annals of Internal Medicine, Oct. 1, 1996, vol. 125, No. 7, pp. 529–538.

R. Patra et al., "Conformational and Steric Requirements of the Slide Chain for Sulphur Participation in Benzthiepin Derivatives", Tetrahedron Letters, vol. 30, No. 32, pp. 4279–4282, 1989.

R. Pierce et al., Myopathy and Rhabdomyolysis Associated with Lovastatin–Gemfibrozil Combination Therapy, JAMA, Jul. 4, 1990, vol. 264, No. 1, pp. 71–75.

W. Pirkle et al., "Trichlorosilane–Induced Cleavage. A Mild Method for Retrieving Carbinols From Carbamates", Journal Organic Chemistry, vol. 42, No. 15, 1977, pp. 2781–2782.

W. Pirkle et al., "Dynamic NMR Studies of Disatereomeric Carbamates: Implications toward the Determination of Relative Configuration by NMR", Journal of Organic Chemistry, vol. 44, No. 26, 1979, pp. 4891–4896.

W. Pirkle et al., "An Example of Automated Liquid Chromatography Synthesis of a Broad–Spectrum Resolving Agent and Resolution of 1–(Naphthyl) 2,2,2–Trifluroethanol", The Journal of Organic Chemistry vol. 39, No. 26, 1974, pp. 3904–3906.

T. Pietzonka et al., "Phosphonate–Containing Analogs of Cholesteryl Ester as Novel Inhibitors of Cholesteryl Ester Transfer Protein", Bioorganic & Medicinal Chemistry Letters, vol. 6, No. 16, pp. 1951–1954.

Pravastatin Multicenter Study Group II, "Comparative Efficacy and Safety of Pravastatin and Cholestyramine Alone and Combined in Patients with Hypercholesterolemia", Archives of Internal Medicine, vol. 153, Jun. 14, 1993, pp. 1321–1328.

E. Reihner et al., Regulation of Hepatic Cholesterol Metabolism in Humans: Stimulatory Effects of Cholestyramine on HMG–CoA Reductase Activity and Low Density Lipoprotein Receptor Expression in Gallstone Patients, Journal of Lipid Research, vol. 31, 1990, pp. 2219–2226.

R. Remick et al., "Comparison of Fluoxetine and Desipramine in Depressed Outpatients", Therapeutic Research, vol. 53, No. 5, May 1993, pp. 457–483.

S. Rosenblum et al., Discovery of 1–(4–Fluorophenyl)–(3R)– [3–(4–fluorophenyl)–(3S)–hydroxypropyl]–(4S)–(4– hydroxyphenyl)–2–azetidinone (SCH 58235): A Designed, Potent, Orally Active Inhibitor of Cholesterol Absorption, Journal of Medicinal Chemistry, 1998, vol. 41, No. 6, pp. 973–980.

G. Salem et al., "Benzothiazine and Benzothizepine Derivatives: Structures of N–p–Bromophenyl–6, 7–Dimethoxy–1, 2–Benzothiazin–3(4H)–One 1, 1–Dioxide (BBTZ) and 4, 5–Dihydro–8,9–Dimethoxy–N–(5–Methyl–2–Pyridly)–1, 2–Benzothiazepin–3–One 1, 1–Dioxide (MPTE)", Acta Cryst. (1986) C42, pp. 1581–1584.

J. Sasaki et al., "Effects of Fluvastatin, A New Inhibitor of HGM–CoA Reductase, and Niceritol on Serum Lipids, Lipoproteins and Cholesterol Ester Transfer Activity In Primary Hypercholesterolemic Patients", International Journal of Clinical Pharmacology and Therapeutics, vol. 33, No. 7, 1995, pp. 420–426.

K. Sindelar et al., Neurotropic and Psychotropic Compounds. XXIX. Derivatives of 2,3,4, 5–Tetrahydro–1–Benzothiepin, Chemical Commun., vol. 33, 1968, pp. 4315–4327.

K. Sindelar et al., Benzocycloheptenes and Hetelrocyclic Analogues as Potential Drugs. III. Further Synthetic Experiments in the Series of 1–Benzothiepin Derivatives, vol. 37, 1972, 1195–1206.

C. Sirtori, "New Targets for Lipid Lowering and Atherosclerosis Prevention", Pharmac. Ther. vol. 67, No. 3., pp. 433–447, 1995.

Y. Son, "Purification and Characterization of Human Plasma Proteins that Inhibit Lipid Transfer Activities", Biochemica et Biophysica Acta, 795, 1984, pp. 473–480.

D. Sprecher et al., "Low–Dose Combined Therapy with Fluvastin and Cholestramine in Hyerlipidemic Patients", Ann Intern Med. 1994; 120: pp. 537–543.

C.I. Stassinopoulou, et al., "C NMR Spectra of Benzothiazepinone, Benzothiazinone and Benzosulphonamide N–Substituted Derivatives" Department of Biology, Nuclear Research Center.

E. Stedronsky et al., "Interaction of Bile Acids and Cholesterol with Non–Systemic Agents Having Hypocholesterolemic Properties", Biochimica et Biophysica Acta., 1210, 1994, pp. 255–287.

I. Stein, et al., "Effects of Simvastatin and Cholestyramine in Familial and Nonfamilial Hypercholesterolemia", Arch Intern Med. vol. 150, Feb. 1990, pp. 341–345.

E. Stein, et al., "Lovastatin Alone and in Combination for Treatment of Primary Hypercholesterolema", Alan R. Liss, Inc. 1988, pp. 281–293.

K. Suckling, et al., Cholesterol Lowering and Bile Acid Excretion in the Hamster with Cholestyramine Treatment, Atherosclerosis, 89, (1991) pp. 183–190.

T. Swenson, "Mechanism of Cholesteryl Ester Transfer Protein Inhibition by a Neutralizing Monoclonal Antibody and Mapping of the Monoclonal Antibody Epitope", The Journal of Biological Chemistry, vol. 264, No. 24, Aug. 25, pp. 14318–14326, 1989.

A. Tall, "Plasma Cholesteryl Ester Transfer Protein", Journal of Lipid Research, vol. 34, 1993, pp. 1255–1274.

Y. Tamura et al., Novel Conversions of Benzo [b] thiophen–3 (2–H)–ones into 1, 2–Benzisothiazole and Tetrahydro–1, 2–Benzothiazepin–5–One Systems via Sulphimide Intermediates, J.C.S. Perkin I, pp. 2830–2834.

K. Thurmond et al., "Water–Soluble Knedel–like Structures: The Preparation of Shell–Cross–Linked Small Particles", Journal American Chemistry Soc. vol. 118, No. 30, 1996, pp. 7239–7240.

P. Tyle, "Iontophoretic Devices for Drug Delivery", Pharmaceutical Research, vol. 3 No. 6 1986, pp. 318–325.

M. Une et al., Metabolism of 3a, 7a–Dihydroxy–7b–Methyl–5b–Cholanoic Acid and 3a, 7B–Dihydroxy–7a–Methyl–5B–Cholanoic Acid Hamsters, Biochemica et Biophysica Acta, 833 (1985), pp. 196–202.

J. Vacek et al., Comparison of Lavastatin (20 mg) and Nicotinic Acid (1.2 g) with Either Drug Alone for Type II Hyperlipoproteinemia, The American Journal of Cardiology, vol. 76, Jul. 15, 1995, pp. 182–184.

M. Van Heek et al., "In Vivo Metabolism–Based Discovery of a Potent Cholesterol Absorption Inhibitor, SCH58235, in the Rat and Rhesus Monkey Through the Identification of the Active Metabolites of SCH48461", The Journal of Pharmacology and Experimental Therapeutics, vol. 283, No. 1, pp. 157–754.

G. Vega et al., "Treatment of Primary Moderate Hypercholesterolemia with Lovastatin (Mevinolin) and Colestipol", JAMA, Jan. 2, 1987, vol. 257, No. 1, pp. 33–37.

G. Wess et al., "Synthesis and Biological Activity of Bile Acid–Derived HMG–CoA Reductase Inhibitors. The Role of 21–Methyl in Recognition of HMG–CoA Reductase and the Ileal Bile Acid Transport System", Journal of Medicinal Chemistry 1994, 37, pp. 3240–3246.

J. Wetterau et al., "An MTP Inhibitor that Normalizes Atherogenic Lipoprotein Levels in WHHL Rabbits", Science vol. 282, Oct. 23, 1998, pp. 751–754.

O. Wiklund et al., "Pravastatin and Gemfibrozil Alone and in Combination for the Treatment of Hypercholesterolemia", The American Journal of Medicine vol. 94, Jan. 1993, pp. 13–19.

S. Wirebaugh et al., "A Retrospective Review of the Use of Lipid–Lowering Agents in Combination, Specifically, Gemfibrozol and Lovastatin", Pharmacotherapy vol. 12, No. 6, 1992, pp. 445–450.

J. Witztum, "Drugs Used in the Treatment of Hyperlipoproteinemias", The Pharmacological Basis of Therapeutics, $9^{th}$ Edition, pp. 875–894.

Yan Xia et al. "Substituted 1,3,5–Triazines as Cholesteral Ester Transfer Protein Inhibitors", Bioorganic & Medicinal Chemistry Letters, vol. 6, No. 7, 1996, pp. 919–922.

A. Yamamoto et al., "Effects of Probucol on Xanthomata Regression in Familial Hypercholesterolemia", Am Journal Cardiolgy, 1986, 57: pp. 29H–35H.

K. Ytre–Arne et al., "Simvastatin and Cholestyramine in the Long–Term Treatment of Hypercholesterolaemia", Journal of Internal Medicine (1989): 226, pp. 285–290.

Angelin, B., "Regulation of Hepatic Cholesterol Metabolism in Man," Ann. Med. 23, pp. 10–27 (1991).

Blum, C. B., "Comparision of Properties of Four Inhibitors of 3–Hydroxy–3–Methylglutaryl–Coenzyme A Reductase," Am. J. Cardiol., 73(14), 3D–11D, (1994).

Cayen, M. N., "Dispositi9n, Metabolism and Pharmacokinetics of Anthyperlipidemic Agents in Laboratory Animals and Man," Pharmac. & Ther., 29, pp. 157–204 (1985).

Da Col, et al., "Tolerability and Efficacy of Combination Therapy with Simvastatin Plus Gemfibroail in Type II Refractory Familial Combined Hyperlipidemia," Curr. Therap. Research, vol. 53, No. 5, pp. 473–483 (1993).

Davignon, et al., "HMG CoA Reductase Inhibitors: A look back and a look ahead," Can. J. Cardiol., 8(8), pp. 843–864 (1992).

Endo, A. "Chemistry, biochemistry and pharmacology of HMG–Co–A reductase inhibitors," Klin. Wochemschr. 66, pp. 421–427 (1988).

Kramer et al., "Bile acid derived HMG–CoA reductase inhibitors,", Biochemica dt Biophysica Acta, 1227 pp. 137–154 (1994).

Marcus, A., "Role of the HMG–CoA Reductase Inhibitors in the Treatment of Dyslipidemia: An Evolutionary Review," CVR&R, pp. 13–27 (Jan. 1996).

* cited by examiner

COMBINATION THERAPY EMPLOYING ILEAL BILE ACID TRANSPORT INHIBITING BENZOTHIPINES AND HMG CO-A REDUCTASE INHIBITORS

CROSS-REFERENCE TO RELATED APPLICATIONS

This application is a divisional of U.S. application Ser. No. 09/676,466, filed Sep. 29, 2000, now U.S. Pat. No. 6,420,417 which is a divisional application of U.S. Ser. No. 09/037,308, filed Mar. 9, 1998, now U.S. Pat. No. 268,392, which claims the benefit of priority of U.S. provisional application Ser. No. 60/040,660, filed Mar. 11, 1997. U.S. Ser. No. 09/037,308 is also a continuation-in-part application of U.S. Ser. No. 08/831,284, filed Mar. 31, 1997, now abandoned, which is a continuation application of U.S. Ser. No. 08/517,051, filed Aug. 21, 1995, now abandoned, which is a continuation-in-part application of U.S. Ser. No. 08/305,526, filed Sep. 13, 1994, now abandoned. U.S. Ser. No. 09/037,308 is a continuation-in-part application of U.S. Ser. No. 08/816,065, filed Mar. 11, 1997, now abandoned, which claims priority from U.S. provisional application Ser. No. 60/013,119, filed Mar. 11, 1996.

BACKGROUND OF THE INVENTION

1. Field of the Invention

The present invention relates to novel benzothiepines, derivatives and analogs thereof, in combination with HMG Co—A reductase inhibitors, pharmaceutical compositions containing them, and use of these compositions in medicine, particularly in the prophylaxis and treatment of hyperlipidemic conditions such as is associated with atherosclerosis or hypercholesterolemia is mammals.

2. Description of the Related Art

It is well-settled that hyperlipidemic conditions associated with elevated concentrations of total cholesterol and low-density lipoprotein cholesterol are major risk factors for coronary heart disease and particularly atherosclerosis. Interfering with the circulation of bile acids within the lumen of the intestinal tract is found to reduce the levels of serum cholesterol is a causal relationship. Epidemiological data has accumulated which indicates such reduction leads to an improvement in the disease state of atherosclerosis. Stedronsky, in "Interaction of bile acids and cholesterol with nonsystemic agents having hypocholesterolemic properties," *Biochimica et Biophysica Acta.* 1210 (1994) 255–287 discusses the biochemistry, physiology and known active agents surrounding bile acids and cholesterol.

Pathophysiologic alterations are shown to be consistent with interruption of the enterohepatic circulation of bile acids in humans by Heubi, J. E., et al. See "Primary Bile Acid Malabsorption: Defective in Vitro Ileal Active Bile Acid Transport", *Gastroenterology*, 1982:83:804–11.

In fact, cholestyramine binds the bile acids in the intestinal tract, thereby interfering with their normal enterohepatic circulation (Reihnér E. et al, in "Regulation of hepatic cholesterol metabolism in humans: stimulatory effects of cholestyramine on HMG—CoA reductase activity and low density lipoprotein receptor expression in gallstone patients", *Journal of Lipid Research*, Volume 31, 1998, 2219–2225 and Suckling et al, "Cholesterol Lowering and bile acid excretion in the hamster with cholestyramine treatment", *Atherosclerosis*, 89(1991) 183–190). This results in an increase in liver bile acid synthesis by the liver using cholesterol as well as an upregulation or the liver LDL receptors which enhances clearance of cholesterol and decreases serum LDL cholesterol levels.

In another approach to the reduction or recirculation of bile acids, the ileal bile acid transport system is a putative pharmaceutical target for the treatment of hypercholesterolemia based on an interruption or the enterohepatic circulation with specific transport inhibitors (Kramer, et al, "Intestinal Bile Acid Absorption" *The Journal of Biological Chemistry*, Vol. 268, No. 24, Issue of Aug. 25, pp. 18035–18046, 1993).

In a series of patent applications, eg Canadian latent Application Nos. 2,025,294; 2,078,588; 2,085,782; and 2,085,830; and EP Application Nos. 0 379 161; 0 549 967; 0 559 064; and 0 563 731, Hoechst Aktiengesellschaft discloses polymers of various naturally occurring constituents of the enterohepatic circulation system and their derivatives, including bile acid, which inhibit the physiological bile acid transport with the goal of reducing the LDL cholesterol level sufficiently to be effective as pharmaceuticals and; in particular for use as hypocholesterolemic agents.

In vitro bile acid transportinhibition is disclosed to show hypolipidemic activity in The Wellcome Foundation Limited disclosure or the world patent application number WO 93/16055 for "Hypolipidemic Benzothiazepine Compounds"

Selected benzothiepines are disclosed in world patent application number WO 93/321146 for numerous uses including fatty acid metabolism and coronary vascular diseases.

Other selected benzothiepines are known for use as hypolipaemic and hypocholesterolemic agents, especially for the treatment of prevention of atherosclerosis as disclosed by application Nos. EP 508425, FR 2661676, and WO 92/18462, each of which is limited by an amide bonded to the carbon adjacent the phenyl ring of the fused bicyclo benzothiepine ring.

The above references show continuing efforts to find safe, effective agents for the prophylaxis and treatment of hyperlipidemic diseases and their usefulness as hypocholesterolemic agents.

Additionally selected benzothiepines are disclosed for use in various disease states not within the present invention utility. These are EP 568 898A as abstracted by Derwent Abstract No. 93-351589; WO 89/1477/A as abstracted in Derwent Abstract No. 89-370688; U.S. Pat. No. 3,520,891 abstracted in Derwent 50701R-B; U.S. Pat. No. 3,287,370, U.S. Pat. No. 3,389,144; U.S. Pat. No. 3,694,046 abstracted in Derwent Abstr. No. 65860T-B and WO 92/18462.

HMG Co—A reductase inhibitors have been used as cholesterol-lowering agents. This class of compounds inhibits 3-hydroxy-3-methylglutaryl-coenzyme A (HMG Co—A) reductase. This enzyme catalyzes the conversion of HMG Co—A to mevalonate, which is an early and rate-limiting step in the biosynthesis of cholesterol.

Benzothiazepine anti-hyperlipidemic agents are disclosed in WO 94/18183, WO 94/18184, WO 96/05188, WO 96/16051, AU-A-30209/92, AU-A-61946/94, AU-A-61948/94, and AU-A-61949/94.

The present invention furthers such efforts by providing novel pharmaceutical compositions and methods for the treatment of hyperlipidemic conditions.

SUMMARY OF THE INVENTION

Accordingly, among its various aspects, the present invention provides compounds of formula (I):

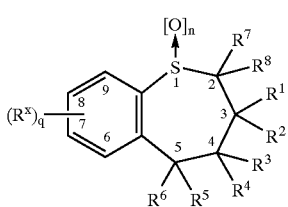

(I)

wherein:
q is an integer from 1 to 4;
n is an integer from 0 to 2;
$R^1$ and $R^2$ are independently selected from the group consisting of H, alkyl, alkenyl, alkenyl, haloalkyl, alkylaryl, arylalkyl, alkoxy, alkoxyalkyl, dialkylamino, alkylthio, (polyalkyl)aryl, and cycloalkyl,
wherein alkyl, alkenyl, alkynyl, haloalkyl, alkylaryl, arylalkyl, alkoxy, alkoxyalkyl, dialkylamino, alkylthio, (polyalkyl) aryl, and cycloalkyl optionally are e substituted with one or more substituents selected from the group consisting of $OR^9$, $NR^9R^{10}$, $N^-NR^9NR^{10}R^WA^-$, $SR^9$, $S^+R^9R^{10}A^-$, $P^-R^9R^{10}R^{11}A^-$, $S(O)R^9$, $SO_2R^9$, $SO_3R^9$, $CO_2R^9$, CN, halogen, oxo, and $CONR^9R^{10}$,
wherein alkyl, alkenyl, alkynyl, alkylaryl, alkoxy, alkoxyalkyl, (polyalkyl)aryl, and cycloalkyl optionally have one oz more carbons replaced by O, $NR^9$, $N^+NR^9R^{10}A—$, S, SO, $SO_2$, $S^+R^9A—$, $P^{30}NR^9R^{10}A—$, or phenylene,
wherein $R^9$, $R^{10}$, and $R^W$ are independently selected from the group consisting of H, alkyl, alkenyl, alkynyl, cycloalkyl, aryl, acyl, heterocycle, heteroaryl, ammoniumalkyl, alkylammoniumalkyl, and arylalkyl; or
$R^1$ and $R^2$ taken together with the carbon to which they are attached form $C_3$–$C_{10}$ cycloalkylidene;
$R^3$ and $R^4$ are independently selected from the group consisting of H, alkyl, alkenyl, alkynyl, acyloxy, aryl, heterocycle, heteroaryl, $OR^9$, $NR^9R^{10}$, $SR^9$, $S(O)R^9$, $SO^2R^9$, and $SO_3R^9$, wherein R' and $R^{10}$ are as defined above; or
$R^3$ and $R^4$ together form =O, $=NOR^{11}$, =S, $=NMR^{11}R^{12}$, $=NR^9$, or $=CR^{11}R^{12}$,
wherein $R^{11}$ and $R^{12}$ are independently selected from the group consisting of H, alkyl, alkenyl. alkenyl, aryl, arylalkyl, alkenylalkyl, alkynylalkyl, heterocycle, heteroaryl carboxyalkyl, carboalkoxyalkyl, cycloalkyl, cycloalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$,
wherein $R^9$ and $R^{10}$ are as defined above provided that both $R^3$ and $R^4$ cannot be OH, $NH_2$ and SH, or
$R^{11}$ and $R^{12}$ together with the nitrogen or carbon atom to which they are attached form a cyclic ring;
$R^5$ and $R^6$ are independently selected from the group consisting of H, alkyl, alkenyl, alkenyl, aryl, cycloalkyl, heterocycle, heteroaryl; quaternary heterocycle, quaternary heteroaryl $SR^9$, $A(O)R^9$, $SO_2R^9$,l and $SO_3R^9$,
wherein alkyl, alkenyl, alkynyl, aryl, cycloalkyl, heterocycle, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, heteroaryl, arylalkyl, quaternary heterocycle, quaternary heteroaryl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}NR^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A—$, $P(OR^{13})OR^{14}$, $S^-R^{13}R^{14}A^-$, and $N^+NR^9R^{11}R^{12}A^-$,
wherein:
$A^-$ is a pharmaceutically acceptable anion and M is a pharmaceutically acceptable cation,
said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A—$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A^-$, and $P(O)(OR^7)OR^8$, and
wherein said alkyl, alkenyl, alkynyl, polyalkyl, polyether, aryl, haloalkyl, cycloalkyl, heterocycle and heteroaryl can optionally have one or more carbons replaced by O, $NR^7$, $N^+R^7R^8A—$, S, SO, $SO_2$, $S^+R^7A—$, $PR^7$, $P(O)R^7$, $P^+R^7R^8A—$, or phenylene, and $R^{13}$, $R^{14}$, and $R^{15}$ are independently selected from the group consisting of hydrogen, alkyl, alkenyl, alkenyl, polyalkyl, aryl, arylalkyl, cycloalkyl, heterocycle, heteroaryl quaternary heterocycle, quaternary heteroaryl, and quaternary heteroarylalkyl,
wherein, alkyl, alkenyl, alkynyl, arylalkyl, heterocycle, heteroaryl, and polyalkyl optionally have one or more carbons replaced by O, NR', $N^+R^9R^{10}A—$, S, SO, $SO_2$, $S^+R^9A^-$, $PR^9$, $P^{30}R^9R^{10}A—$, $P(O)R^9$, phenylene, carbohydrate, amino acid, peptide, or polypeptide, and $R^{13}$, $R^{14}$, and $R^{15}$ are optionally substituted with one or none groups selected from the group consisting of sulfoalkyl, heterocycle, heteroaryl, quaternary heterocycle, quaternary heteroaryl, $OR^9$, $NR^9R^{10}$, $N^+NR^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^{30}R^9NR^{10}R^{11}A—$, $S^+R^9R^{10}A—$, and C(O))M,
wherein $R^{16}$ and $R^{17}$, are independently selected from the substituents constituting $R^9$ and M; or
$R^{14}$ and $R^{15}$, together with the nitrogen atom to which they are attached, form a cyclic ring;
$R^7$ and $R^8$ are independently selected from the group consisting of hydrogen and alkyl; and
one or more $R^x$ are independently selected from the group consisting of H, alkyl, alkenyl, alkynyl, polyalkyl, acyloxy, aryl, arylalkyl, halogen, haloalkyl, cycloalkyl, heterocycle, heteroaryl polyether, quaternary heterocycle, quaternary heteroaryl, $OR^{13}$, $NR^{13}R^{14}$, $SR^{13}$, $S(O)R^{13}$, $S(O)R^{13}$, $SO_3R^{13}$, $S^+R^{13}R^{14}A—$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_nNR^{18}$, $NR^{13}R^{18}$, $NR^{18}OR^{14}$, $N^+NR^9R^{11}R^{12}A^-$, $P^+R^9R^{11}R^{12}A^-$, amino acid, peptide, polypeptide, and carbohydrate,
wherein alkyl, alkenyl, are alkynyl, cycloalkyl, aryl, polyalkyl, heterocycle, heteroaryl, acyloxy, arylalkyl, haloalkyl, polyether, quaternary heterocycle, and quaternary heteroaryl can be further substituted with $OR^9$, $NR^9R^{10}$, $N^+NR^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^-R^9R^{10}A^-$, or C(O)OM, and wherein $R^{18}$ is selected from the group consisting of acyl, arylalkoxycarbonyl, arylalkyl, heterocycle, heteroaryl, alkyl, quaternary heterocycle, and quaternary heteroaryl wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A—$, S, SO, $SO_2$, $S^+R^{13}A—$, $PR^{13}$, $P(O)R^{13}P^+R^{13}R^{14}A—$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $N^+R^9R^{10}A—$, S, SO, $SO_2$, $S^+R^9A—$, $PR^9$, $P^+R^9R^{10}A—$, wherein quaternary heterocycle and quaternary heteroaryl are optionally substituted with one or more groups selected from the group consisting of alkyl, alkenyl, alkenyl, polyalkyl, polyether, aryl, haloalkyl, cycloalkyl, heterocycle, heteroaryl, arylalkyl, halogen oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A—$, $P(OR^{13})OR^{14}$, $S^-SR^{13}R^{14}A^-$, and $N^+NR^9R^{11}R^{12}, A^{31}$, provided that both $R^5$ and $R^6$ cannot be hydrogen, OH, or SH, and when $R^5$ is OH, $R^1$, $R^2$, $R^3$, $R^4$, $R^7$, and $R^8$ cannot be all hydrogen;

provided that when $R^5$ or $R^4$ is phenyl, only one of $R^1$ or $R^2$ is H;

provided that when q=1 and $R^6$ is styryl, anilido, or anilinocarbonyl, only one of $R^5$ or $R^6$ is alkyl; or a pharmaceutically acceptable salt, solvate, or prodrug thereof.

Preferably, $R^5$ and $R^6$ can independently be selected from the group consisting of H, aryl, heterocycle, heteroaryl, quaternary heterocycle, and quanternary heteroaryl, wherein said aryl, heterocycle, heteroaryl, quaternary heterocycle, and quaternary heteroaryl can be substituted with one or more substituted groups independently selected from the group consisting of alkyl, alkenyl, alkenyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2NR^{13}R^{14}$, $C(O)NR^{13}R^{14}$, C(O)OM $COR^{13}$, $P(O)R^{13}R^{14}$, $P^+R^{13}R^{14}R^{15}A—$, $P(OR^{13})OR^{14}$, $S^+R^{13}R^{14}A—$, and $N^+NR^9R^{11}R^{12}A^-$, wherein said alkyl, alkenyl, alkynyl, polyalkyl, polyether, aryl, haloalkyl, cycloalkyl, heterocycle and heteroaryl can optionally have one of more carbons replaced by O, $NR^7$, $N^+R^7R^8A—$, SO, $SO_2$, $S^+R^7A—$, $PR^7$, $P(O)R^7$ $P^+R^7R^8A—$, or phenylene wherein said alkyl, alkenyl, alkynyl, polyalkyl, polyether, aryl, haloalkyl, cycloalkyl, heterocycle and heteroaryl can be further substituted with one or more substituent groups selected from the group consisting of $OR^7$, $NR^7R^8$, $SR^7$, $S(O)R^7$, $SO_3R^7$, $CO_2R^7$, CN, oxo, $CONR^7R^8$, $N^-R^7R^8R^9A—$, alkyl, alkenyl, alkynyl, aryl, cycloalkyl, heterocycle, heteroaryl, arylalkyl, quaternary heterocycle, quaternary heteroaryl, $P(O)R^7R^8$, $P^+R^7R^8R^9A—$, and $P(O)(OR^7)OR^8$.

More preferably $R^5$ or $R^6$ has the formula:

wherein:

t is an integer from 0 to 5;

Ar is selected from the group consisting of phenyl, thiophenyl, pyridyl, piperazinyl piperonyl, pyrrolyl, naphthyl, furanyl, anthracenyl, quinolinyl, isoquinolinyl quinoxalinyl, imidazolyl, pyrazolyl, oxazolyl, isoxazolyl, pyrimidinyl, thiazolyl, triazolyl, isothiazolyl, indolyl, benzoimidazolyl, benzoxazoly, benzothiazolyl, and benzoisothiazolyl; and one or more $R^y$ are independently selected from the group consisting of H, alkyl, alkenyl, alkenyl, aryl, cycloalkyl, heterocycle, heteroaryl: quaternary heterocycle, quaternary heteroaryl $OR^9$, $SR^9$, $S(O)R^9$, $SO_2R^9$,l and $SO_3R^9$, wherein alkyl, alkenyl, alkenyl, aryl, cycloalkyl, heterocycle, and heteroaryl can be substituted with one or more substituent groups independently selected from the group consisting of alkyl, alkenyl, alkenyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A—$, $P(OR^{13)OR14}$, $S^-R^{13}R^{14}A^-$, and $N^+R^9R^{11}R^{12}A^-$, wherein said alkyl, alkenyl, alkynyl, polyalkyl, polyether, aryl, haloalkyl, cycloalkyl, heterocycle, and heteroaryl can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A—$, alkyl, alkenyl, alkynyl, aryl, cycloalkyl, heterocycle, heteroaryl, arylalkyl, quaternary heterocycle, quaternary heteroaryl $P(O)R^7R^8$, $P^+R^7R^8R^9A—$, and $P(O)(OR^7)OR^8$, and wherein said alkyl, alkenyl, alkenyl, polyalkyl, polyether, aryl, haloalkyl, cycloalkyl, heterocycle and heteroaryl can optionally have one of more carbons replaced by O, $NR^7$, $N^+R^7R^8A—$, S, SO, $SO_2$, $S^+R^7A—$, $PR^7$, $P(O)R^7$, $P^+R^7R^8A—$, or phenylene.

Most preferably, $R^5$ or $R^6$ has the formula (II):

(II)

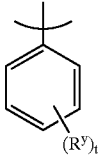

The invention is further directed to a compound selected from among:

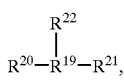
(Formula DII)

and

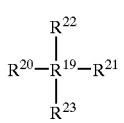
(Formula DIII)

wherein $R^{19}$ is selected from the group consisting of alkane diyl, alkane diyl, alkane diyl, polyalkane diyl, alkoxy diyl, polyether diyl, polyalkoxy diyl, carbohydrate, amino acid, peptide, and polypeptide, wherein alkane diyl, alkene diyl, alkyne diyl, polyalkane diyl, alkoxy diyl, polyether diyl, polyalkoxy diyl, carbohydrate, amino acid, peptide, and polypeptide can optionally have one or more carbon atoms replaced by O, $NR^7$, $N^+R^7R^8$, S, SO, $SO_2$, $S^+R^7R^8$, $PR^7$, $P^+P^7R^8$, phenylene, heterocycle, heteroaryl, quaternary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkenyl, polyalkyl, polyether, aryl, haloalkyl, cycloalkyl, heterocycle, heteroaryl, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $R^{13}R^{14}R^{15}A^-$, $P(OR^{13})OR^{14}$, $S^-R^{13}R^{14}A^-$, and $N^+R^9R^{11}R^{12}A^-$;

wherein $R^{19}$ further comprises functional linkages by which $R^{19}$ is bonded to $R^{20}$, $R^{21}$, or $R^{22}$ in the compounds of Formulae DII and DIII, and $R^{23}$ in the compounds of Formula DIII. Each of $R^{20}$, $R^{21}$, or $R^{22}$ and $R^{23}$ comprises a benzothiepine moiety as described above that is therapeutically effective in inhibiting ileal bile acid transport.

The invention is also directed to a compound selected from among Formula DI, Formula DII and Formula DIII in which each of $R^{20}$, $R^{21}$, $R^{22}$ and $R^{23}$ comprises a benzothiepine moiety corresponding to the Formula:

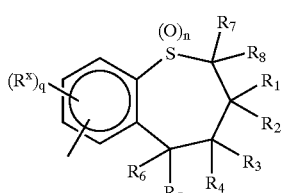
(Formula DIV)

or:

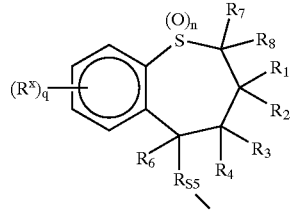
(Formula DIVA)

wherein $R^1$, $R^2$, $R^3$, $R^4$, $R^5$, $R^6$, $R^7$, $R^8$, $R^x$, q and n are as defined in Formula I as described above, and $R^{55}$ is either a covalent bond or arylene.

In compounds of Formula DIV, it is particularly preferred that each of $R^{20}$, $R^{21}$, and $R^{22}$ in Formula DII and DIII, and $R^{23}$ in Formula DIII, be bonded at its 7-or 8-position to $R^{19}$. In compounds of Formula DIVA it is particularly preferred that $R^{55}$ comprise a phenylene moiety bonded at a m- of p-carbon thereof to $R^{19}$.

Examples of Formula DI include:

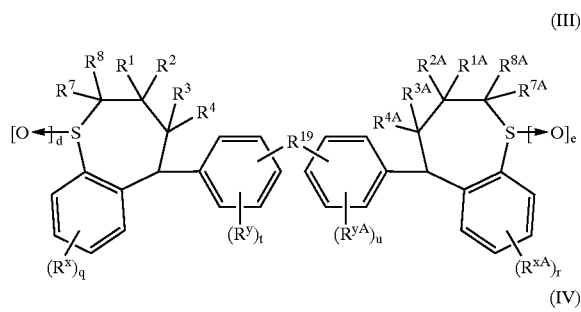
(III)

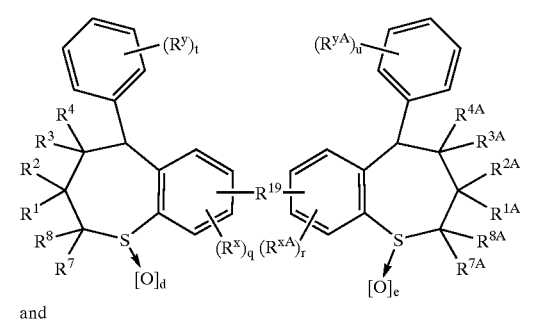
(IV)

and

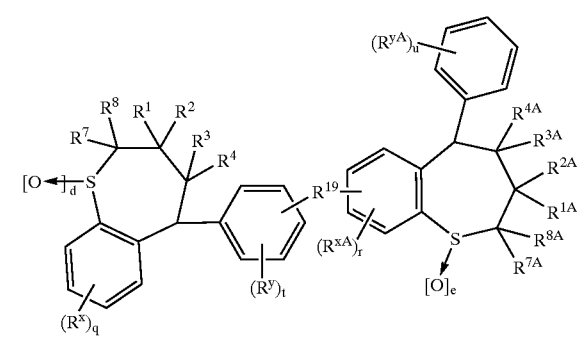
(V)

In any of the dimeric or multimeric structures discussed immediately above, benzothiepine compounds of the present invention can be used alone or in various combinations.

In any of the compounds of the present invention, $R^1$ and $R^2$ can be ethyl/butyl or butyl/butyl, Other compounds useful in the present invention as ileal bile acid transport inhibitors are shown in Appendix A.

In another aspect, the present invention provides a pharmaceutical composition for the prophylaxis or treatment of a disease or condition for which a bile acid transport inhibitor is indicated, such as a hyperlipidemic condition, for example, atherosclerosis. Such compositions comprise any of the compounds disclosed above, alone or in combination in an amount effective to reduce bile acid levels is in the blood, or to reduce transport thereof across digestive system membranes, and a pharmaceutically acceptable carrier, excipient, or diluent.

In a further aspect, the present invention also provides a method of treating a disease or condition in mammals including humans for which a bile acid transport inhibitor is indicated, comprising administering to a patient in need thereof a compound of the present invention in an effective amount in unit dosage form or in divided doses.

In yet a further aspect, the present invention also provides processes for the preparation of compounds of the present invention.

In yet another aspect, the present invention provides a combination therapy comprising the use of a first amount of an ileal bile acid transport inhibitor and a second amount of a HMG Co—A reductase inhibitor useful to treat hyperlipidemic disorders, wherein said first and second amounts together comprise an anti-hyperlipidemic condition effective amount of said compounds.

HMG Co—A reductase inhibitor-compounds useful in the present invention are shown in Appendix B.

Further scope of the applicability of the present invention will became apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

The following detailed description is provided to aid those skilled is the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

Definitions

In order to aid the reader in understanding the following detailed description, the following definitions are provided:

"Alkyl", "alkenyl," and alkynyl, unless otherwise noted are each straight chain or branched chain hydrocarbons of from one to twenty carbons for alkyl or two to twenty carbons for alkenyl and alkenyl in the present invention and therefore mean, for example, methyl, ethyl, propyl, butyl, pentyl or hexyl and ethenyl, propenyl, butenyl, pentenyl, or hexenyl and ethynyl, propynyl, butynyl, pentynyl, or hexynyl respectively and isomers thereof.

"Aryl" means a fully unsaturated mono- or multi-ring carbocyle, including, but not limited to, substituted or unsubstituted phenyl, naphthyl, of anthracenyl.

"Heterocycle" means a saturated or unsaturated mono- or multi-ring carbocycle wherein one or more carbon atoms can be replaced by N, S, P, or O. This includes, for example, the following structures:

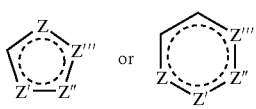

wherein Z, Z', Z" or Z'" is C, S, P, O, or N, with the proviso that one of Z, Z', Z" or Z'" is other than carbon, but is not O or S when attached to another Z atom by a double bond or when attached to another O or S atom. Furthermore, the optional substituents are understood to be attached to Z, Z', Z" of Z'" only when each is C.

The term "heteroaryl" menus a fully unsaturated heterocycle.

In either "heterocycle" or "heteroaryl," the point of attachment to the molecule of interest can be at the heteroatom or elsewhere within the ring.

The term "quaternary heterocycle" means a heterocycle in which one or more of the heteroatoms, for example, O, N, S, or P, has such a number or bends that it is positively charged. The point of attachment of the quaternary heterocycle to the molecule of interest can be at a heteroatom or elsewhere.

The term "quaternary heteroaryl" means a heteroaryl in which one or more of the heteroatoms, for example, O, N, S, or P, has such a number of bonds that it is positively charged. The point of attachment of the quaternary heteroaryl to the molecule of interest can be at a heteroatom or elsewhere.

The term "halogen" means a fluoro chloro, bromo of iodo group.

The term "haloalkyl" means alkyl substituted with one or more halogens.

The term "cycloalkyl" means a mono- or multi-ringed carbocycle wherein each ring contains three to ten carbon atoms, and wherein any ring can contain one or more double or triple bonds.

The term "diyl" means a diradical moiety wherein said moiety has two points of attachment to molecules of interest.

The term "oxo" means a doubly bonded oxygen.

The term "polyalkyl" means a branched or straight hydrocarbon chain having a molecular weigh up to about 20,000, more preferably up to about 10,000, host preferably up to about 5,000.

The term "polyether" means a polyalkyl wherein one or more carbons are replaced by oxygen, wherein the polyether has a molecular weight up to about 20,000, none preferably up to about 10,000, most preferably up to about 5,000.

The term "polyalkoxy" means a polymer or alkylene oxides, wherein the polyalkoxy has a molecular weight up to about 20,000, more preferably up to about 10,000, most preferably up to about 5,000.

The term "cycloaklylidene" means a mono- or multi-ringed carbocycle wherein a carbon within the ring structure is doubly bonded to an atom which is not within the ring structures.

The term "carbohydrate" means a mono-, di-, tri- or polysaccharide wherein the polysaccharide can have a molecular weight of up to about 20,000, for example, hydroxypropyl-methylcellulose or chitosan.

The term "peptide" means polyamino acid containing up to about 100 amino acid units.

The term "polypeptide" means polyamino acid containing from about 100 amino acid units to about 1000 amino acid units, more preferably from about 100 amino acid units to about 750 amino acid units, most preferably from about 100 amino acid units to about 500 amino acid units.

The term "alkylammoniumalkyl" means a $NH_2$ group or a mono-, di- or tri-substituted amino group, any of which is bonded to an alkyl wherein said alkyl is bonded to the molecule of interest.

The term "triazolyl" includes all positional isomers. In all other heterocycles and heteroaryls which contain more than one ring heteroatom and for which isomers are possible, such isomers are included in the definition of said heterocycles and heteroaryls.

The term "sulfoalkyl" means an alkyl group to which a sulfonate group is bonded, wherein said alkyl is bonded to the molecule of interest.

The term "active compound" means a compound of the present invention which inhibits transport of bile acids.

When used in combination for example "alkylaryl" of "arylalkyl," the individual terms listed above have the meaning indicated above.

The term "a bile acid transport inhibitor" means a compound capable of inhibiting absorption of bile acids from the intestine into the circulatory system of a mammal, such as a human. This includes increasing the fecal excretion of bile acids, as well as reducing the blood plasma of serum concentrations of cholesterol and cholesterol ester, and more specifically, reducing LDL and VLDL cholesterol. Conditions or diseases which benefit from the prophylaxis or treatment by bile acid transport inhibition include, for example, a hyperlipidemic condition such as atherosclerosis.

The phrase "combination therapy" refers to the administration of an ileal bile acid transport inhibitor and a HMG Co—A reductase inhibitor to treat a hyperlipidemic condition, for example atherosclerosis and hypercholesterolemia. Such administration encompasses co-administration of these inhibiters in a substantially simultaneous manner, such as in a single capsule having a fixed ratio of active ingredients or in multiple, separate capsules for each inhibitor agent. In addition, such administration also encompasses use of each type of inhibitor in a sequential manner. In either case, the treatment regimen will provide beneficial effects of the drug combination in treating the hyperlipidemic condition The phrase "therapeutically effective" is intended to qualiity the combined amount of inhibitors in the combination therapy. This combined amount will achieve the goal of reducing or eliminating the hyperlipidemic condition.

Compounds

The compounds of the present invention can have at least two as asymmetrical carbon atoms, and therefore include racemates and stereoisomers, such as diastereomers and enantiomers, in both pure form and in admixture. Such stereoisomers can be prepared using conventional techniques, either by reacting enantiomeric starting materials, of by separating isomers of compounds of the present invention.

Isomers may include geometric isomers, for example cis isomers or trans isomers across a double bond. All such isomers are contemplated among the compounds of the present invention.

The compounds of the present invention also include tautomers.

The compounds of the present invention as discussed below include their salts, solvates and prodrugs.
Compound Syntheses The starting materials for use is the preparation of the compounds of the invention are known or cam be prepared by conventional methods known to a skilled person or in an analogous manner to processes described is the art.

Generally, the compounds of the present invention can be prepared by the procedures described below.

For example, as shown in Scheme I, reaction of aldehyde II with formaldehyde and sodium hydroxide yields the hydroxyaldehyde III which is converted to mesylate IV with methanesulfonyl chloride and triethylamine similar to the procedure described in Chem. Ber. 98, 728–734 (1965). Reaction of mesylate IV with thiophenol V, prepared by the procedure described is WO 93/16055, in the presence of triethylamine yields keto-aldehyde VI which can be cyclized with the reagent, prepared from zinc and titanium trichloride in refluxing ethylene glycol dimethyl ether (DME), to give a mixture of 2,3-dihydrobenzothiepine VII and two racemic stereoisomers of benzothiepin- (5H)-4-one VIII when $R^1$ and $R^2$ are nonequivalent. Oxidation of VII with 3 equivalents of m-chloro-perbenzoic acid (MCPBA) gives isomeric sulfone-epoxides IX which upon hydrogenation with palladium on carbon as the catalyst yield a mixture of four racemic stereoisomers of 4-hydroxy-2,3,4,5-tetrahydrobenzothiepine-1,1-dioxides X and two racemic stereoisomers of 2,3,4,5-tetrahydrobenzothiepine-1,1-dioxides XI when $R^1$ and $R^2$ are nonequivalent.

Optically active compounds of the present invention can be prepared by using optically active starting material III or by resolution of compounds X with optical resolution agents well known in the art as described in J. Org. Chem., 39, 3904 (1974), ibid., 42, 2781 (1977), and ibid., 44, 4891 (1979).

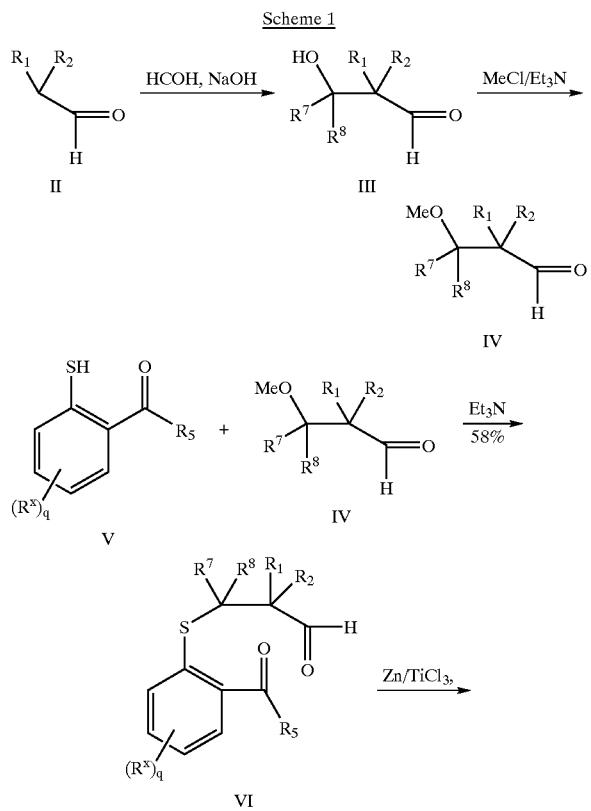

Scheme 1

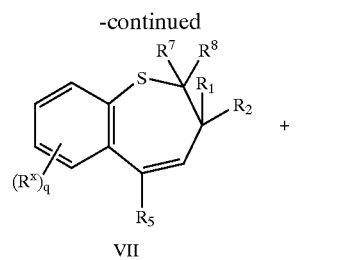

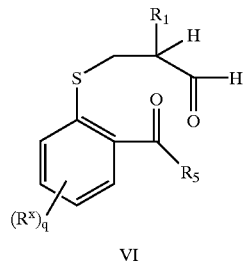

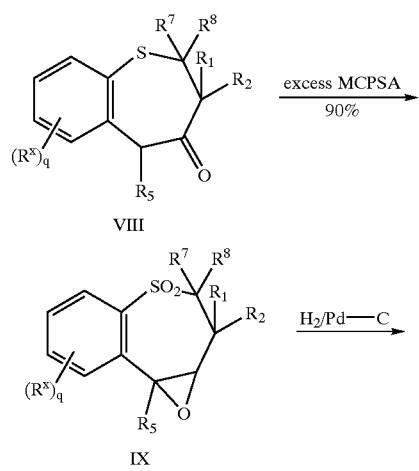

Benzothiepin-(5H)-4-one VIII can be oxidized with MCPBA to give the benzothiepin-(5H)-4-one-1,1-dioxide XII which can be reduced with sodium borohydride to give four racemic stereoisomers of X. The two stereoisomers of X, Xa and Xb, having the OH group and $R^3$ on the opposite sides or the benzothiepine ring can be converted to the other two isomers of X, Xc and Xd, having the OH group and $R^3$ on the same side of the benzothiepine ring by reaction in methylene chloride with 40–50% sodium hydroxide is the presence of a phase transfer catalyst (PTC). The transformation can also be carried out with potassium t-butoxide in THF.

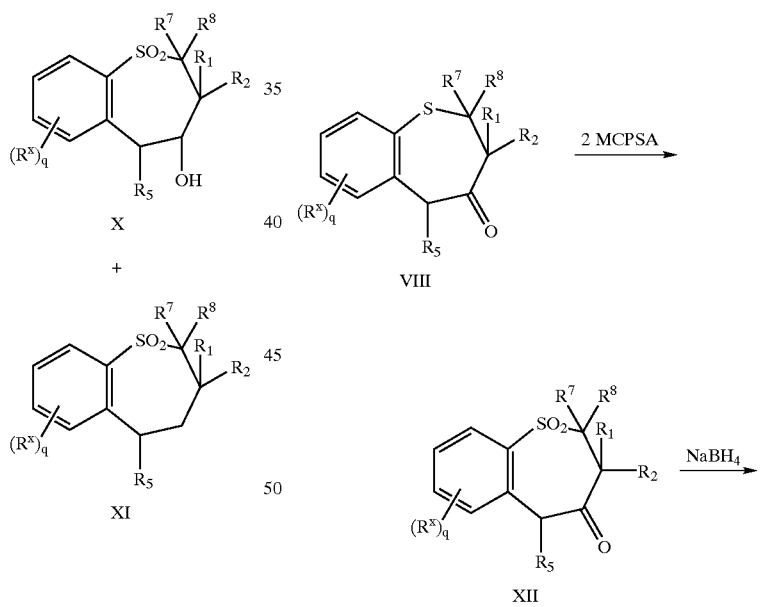

Alternatively, keto-aldehyde VI where $R^2$ is H can be prepared by reaction of thiophenol V with a 2-substituted acrolein.

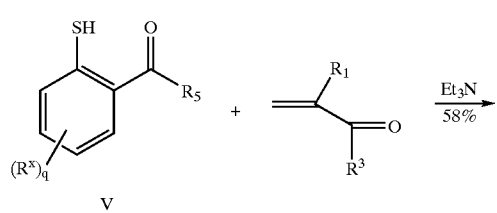

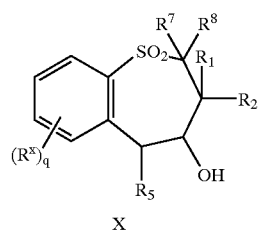

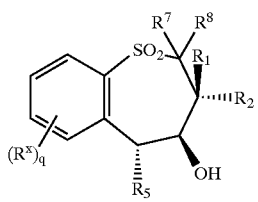

Xa or

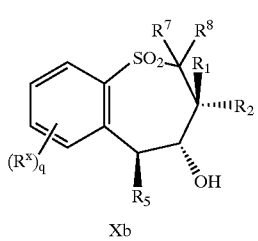

Xb

NaOH, PTC/CH$_2$Cl$_2$ →

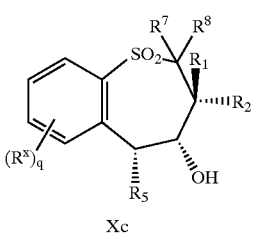

Xc

+

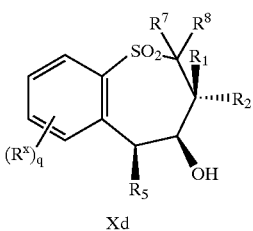

Xd when R$_1$ = Bu, R$_2$ = Et, R$_5$ = Ph, X = H, q = 4
6a = Xa
6b = Xb
6c = Xc
6d = Xd The compounds of the present invention where R$^3$ is OR, NRR' or S(O)$_a$R and R$^4$ is hydroxy can be prepared by reaction of epoxide IX where R$^5$ is H with thiol, alcohol, or amine in the presence of a base.

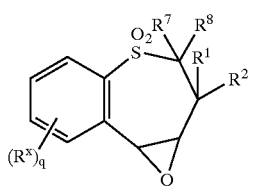

↘ HOR, or HNRR$^1$ or HS(O)$_n$R base

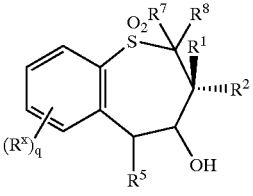

R$^5$ = OR, NRR$^1$, S(O)$_a$R

Another route to Xc and Xd of the present invention is shown in Scheme 2. Compound VI is oxidized to compound XIII with two equivalent of m-chloroperbenzoic acid. Hydrogenolysis of compound XIII with palladium on carbon yields compound XIV which can be cyclized with either potassium t-butoxide or sodium hydroxide under phase transfer conditions to a mixture of Xc and Xd. Separation of Xc and Xd can be accomplished by either HPLC or fractional crystallization.

The thiophenols XVIII and V used in the present invention can also be prepared according to the Scheme 3. Alkylation of phenol XV with an arylmethyl chloride in a nonpolar solvent according to the procedure in *J. Chem. Soc.*, 2431–2432 (1958) gives the ortho substituted phenol XVI. The phenol XVI can be converted to the thiophenol XVIII via the thiocarbamate XVII by the procedure described in *J. Org. Chem.*, 31, 3980 (1966). The phenol XVI is first reacted with dimethyl thiocarbamoyl chloride and triethylamine to give thiocarbamate XVII which is thermally rearranged at 200–300° C., and the rearranged product is hydrolyzed with sodium hydroxide to yield the thiophenol XVIII. Similarly, Thiophenol V can also be prepared from 2-acylphenol XIX via the intermediate thiocarbamate XX.

Scheme 2

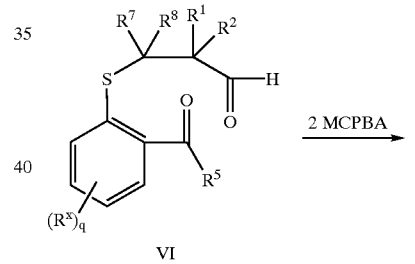

VI

↓ 2 MCPBA

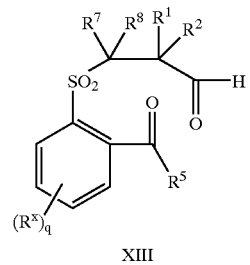

XIII

↓ Pd/C—H$_2$

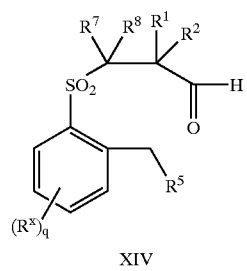

XIV

↓ KOtBu

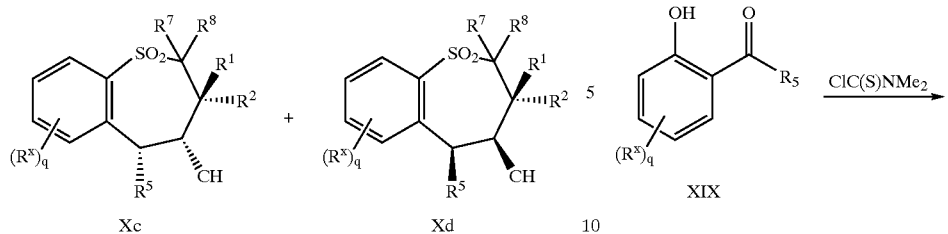

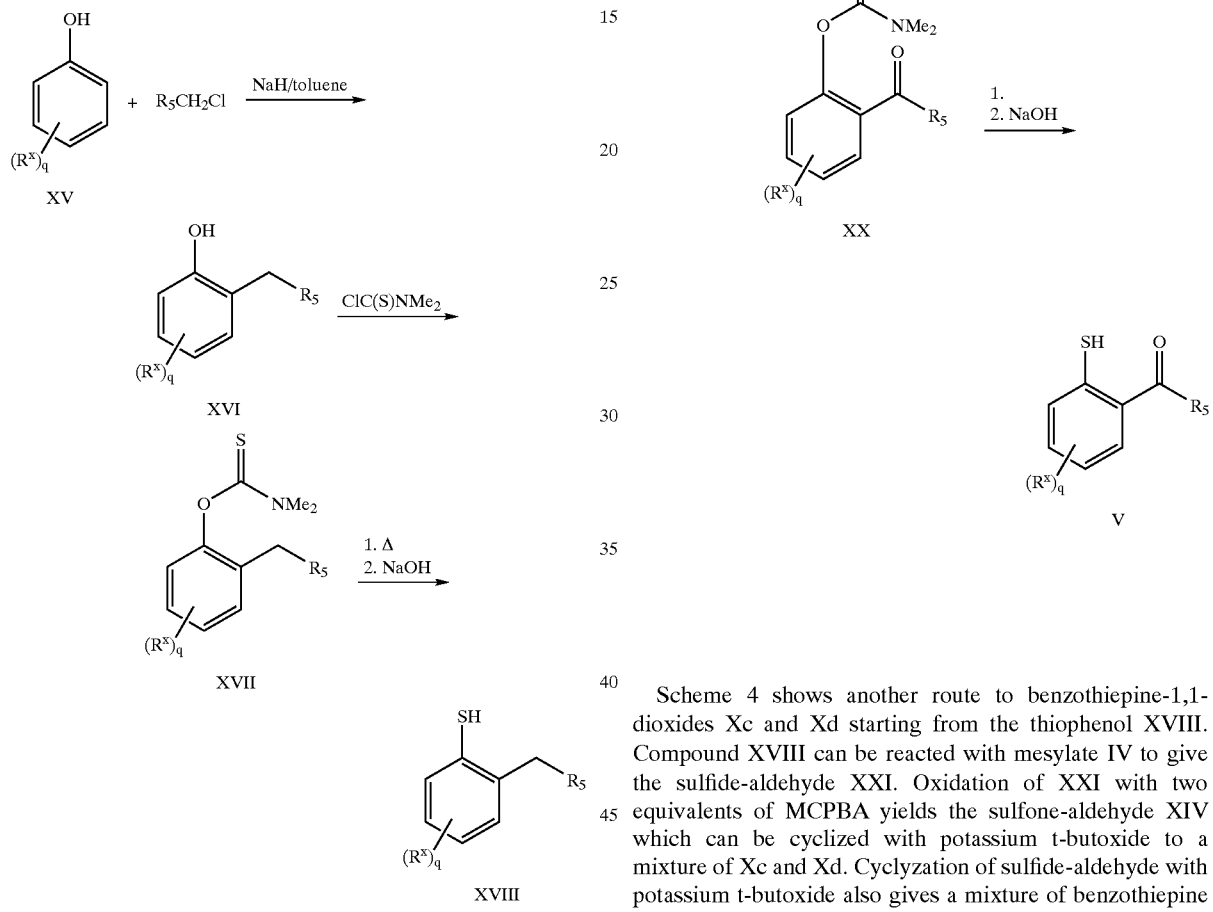

Scheme 4 shows another route to benzothiepine-1,1-dioxides Xc and Xd starting from the thiophenol XVIII. Compound XVIII can be reacted with mesylate IV to give the sulfide-aldehyde XXI. Oxidation of XXI with two equivalents of MCPBA yields the sulfone-aldehyde XIV which can be cyclized with potassium t-butoxide to a mixture of Xc and Xd. Cyclyzation of sulfide-aldehyde with potassium t-butoxide also gives a mixture of benzothiepine XXIIc and XXIId.

Scheme 4

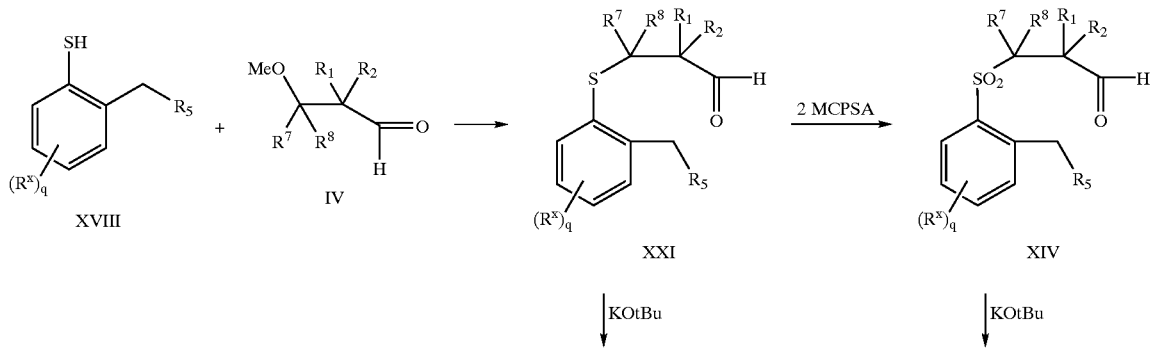

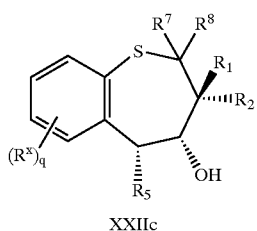

XXIIc

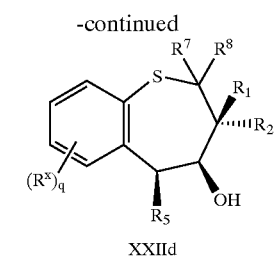

XXIId

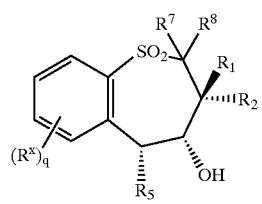

Xc

+

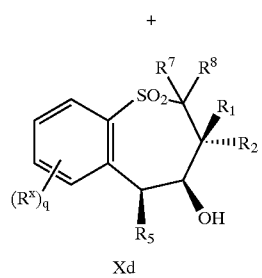

Xd

Examples of amine- and hydroxylamine-containing compounds of the present invention can be prepared as shown in Scheme 5 and Scheme 6. 2-Chloro-5-nitrobenzophenone is reduced with triethylsilane and trifluoromethane sulfonic acid to 2-chloro-5-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIV which can be reduced by hydrogenation to the hydroxylamine XXV. Protecting the hydroxylamine XXV with di-t-butyldicarbonate gives the N,O-di-(t-butoxycarbonyl)hydroxylamino derivatice XXVI. Cyclization of XXVI with potassium t-butoxide and removal of the t-butoxycarbonyl protecting group gives a mixture of hydroxylamino derivatives XXVIIc and XXVIId. The primary amine XXXIIIc and XXXIIId derivatives can also be prepared by further hydrogenation of XXIV or XXVIIc and XXVIId.

Scheme 5

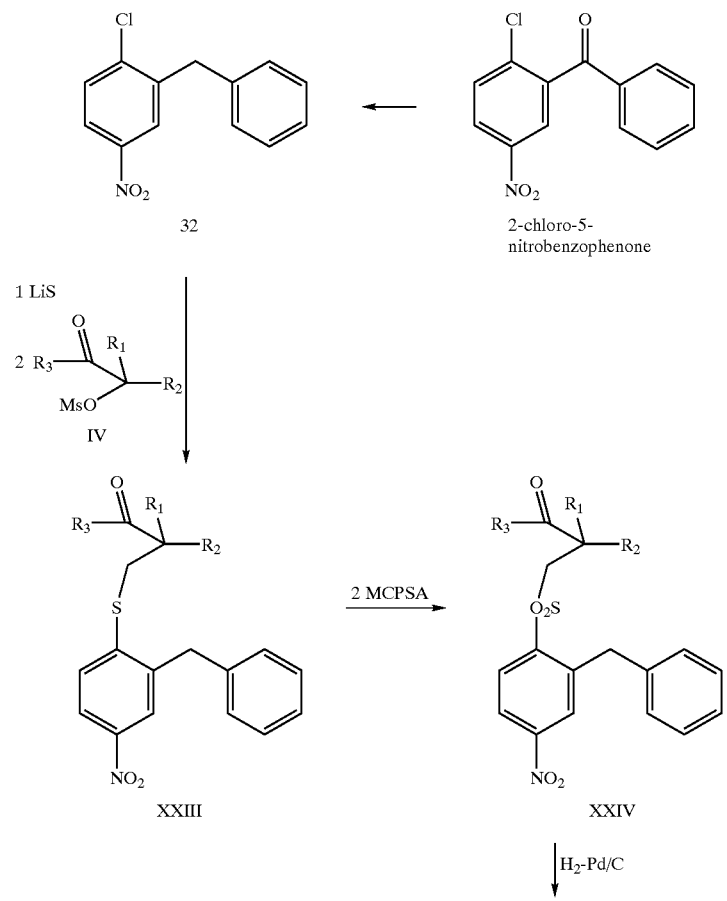

-continued
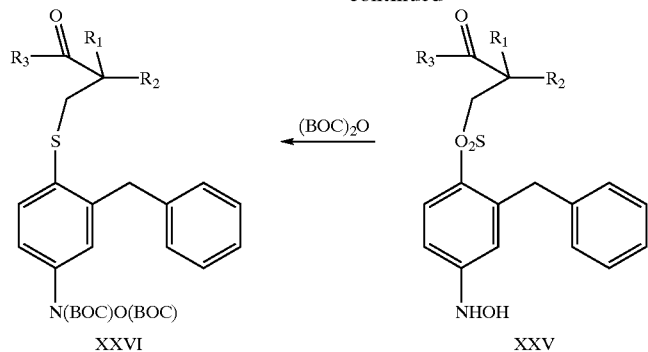
1 potassium t-bonxides
2 acid welop
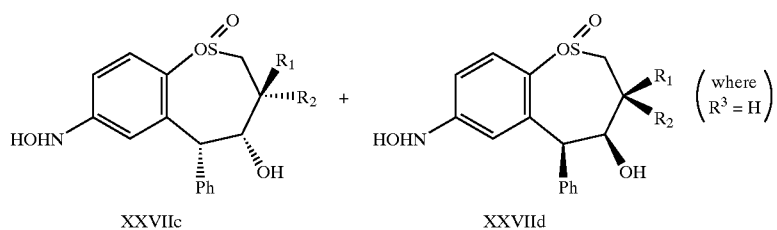
In Scheme 6, reduction of the sulfone-aldehyde XXV with hydrogen followed by reductive alkylation of the resulting amino derivative with hydrogen and an aldehyde catalyzed by palladium on carbon in the same reaction vessel yields the substituted amine derivative
Scheme 6
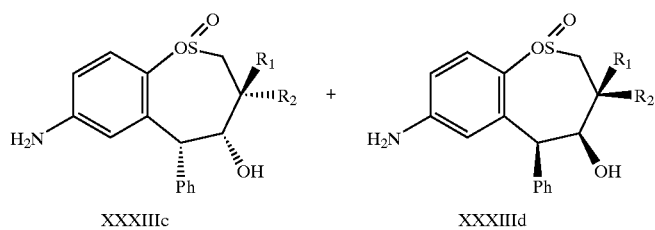
-continued
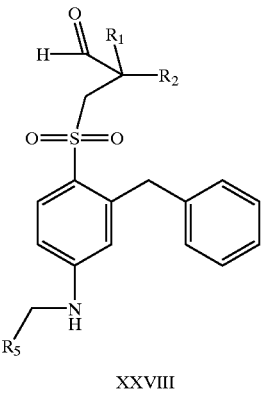
HOtBu
THF

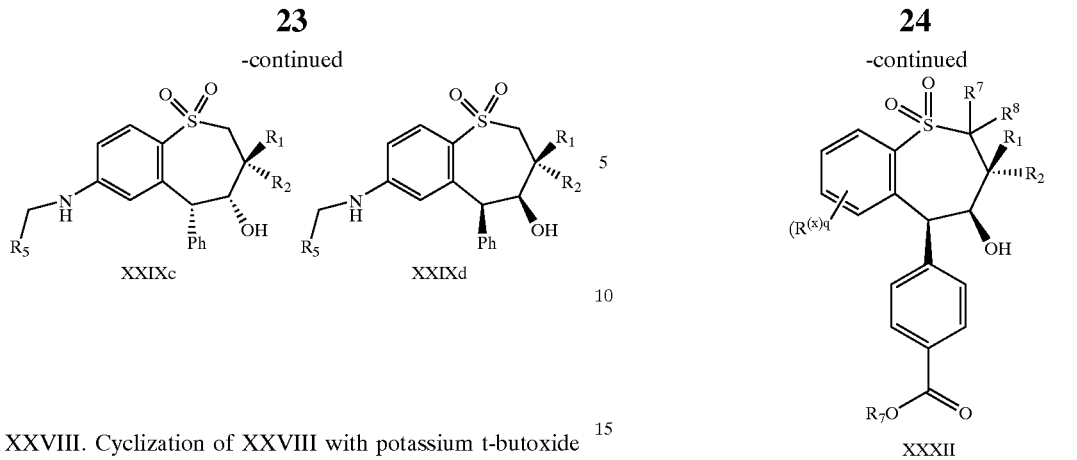

XXVIII. Cyclization of XXVIII with potassium t-butoxide yields of mixture of substituted amino derivatives of this invention XXIXc and XXIXd.

Scheme 7 describes one of the methods of introducing a substituent to the aryl ring at the 5-position of benzothiepine. Iodination of 5-phenyl derivative XXX with iodine catalyzed by mercuric triflate gives the iodo derivative XXXI, which upon palladium-catalyzed carbonylation in an alcohol yields the carboxylate XXXII. Hydrolysis of the carboxylate and derivatization of the resulting acid to acid derivatives are well known in the art.

Abbreviations used in the foregoing description have the following meanings:

THF - - - tetrahydrofuran

PTC - - - phase transfer catalyst

Aliquart 336 - - - methyltricaprylylammonium chloride

MCPBA - - - m-chloroperbenzoic acid

Celite - - - a brand of diatomaceous earth filtering aid

DMF - - - dimethylformamide

DME - - - ethylene glycol dimethyl ether

BOC - - - t-butoxycarbonyl group

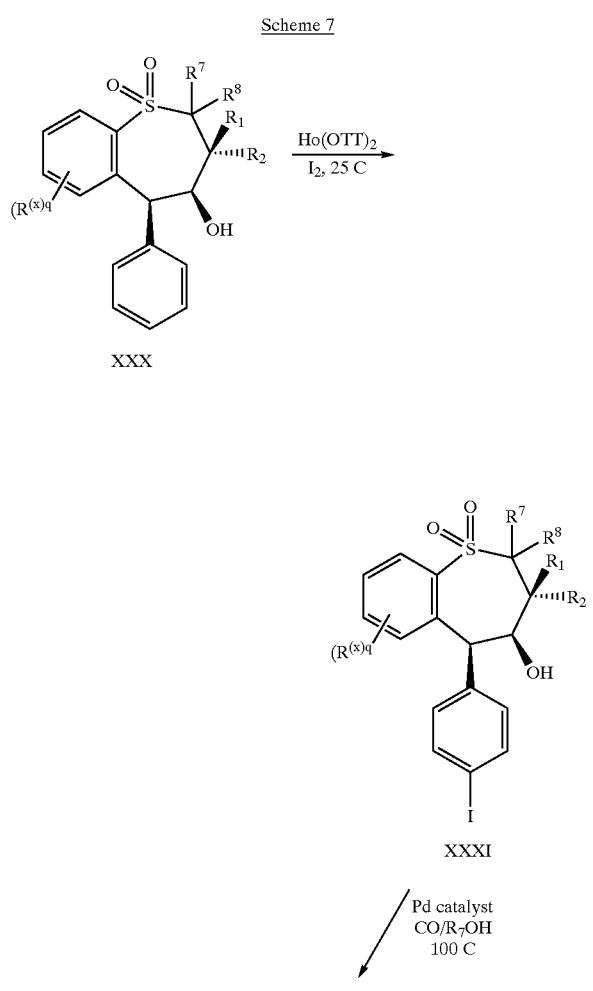

$R^1$ and $R^2$ can be selected from among substituted and unsubstituted $C_1$ to $C_{10}$ alkyl wherein the substituent(s) can be selected from among alkylcarbonyl, alkoxy, hydroxy, and nitrogen-containing heterocycles joined to the $C_1$ to $C_{10}$ alkyl through an ether linkage. Substituents at the 3-carbon can include ethyl, n-propyl, n-butyl, n-pentyl, isobutyl, isopropyl, —$CH_2C(=O)C_2H_5$, —$CH_2OC_2H_5$, and —$CH_2O$—(4-picoline). Ethyl, n-propyl, n-butyl, and isobutyl are preferred. In certain particularly preferred compounds of the present invention, substituents $R^1$ and $R^2$ are identical, for example n-butyl/n-butyl, so that the compound is achiral at the 3-carbon. Eliminating optical isomerism at the 3-carbon simplifies the selection, synthesis, separation, and quality control of the compound used as an ileal bile acid transport inhibitor. In both compounds having a chiral 3-carbon and those having an achiral 3-carbon, substituents ($R^x$) on the benzo- ring can include hydrogen, aryl, alkyl, hydroxy, halo, alkoxy, alkylthio, alkylsulfinyl, alkylsulfonyl, haloalkyl, haloalkoxy, (N)-hydroxy-carbonylalkyl amine, haloalkylthio, haloalkylsulfinyl, haloalkylsufonyl, amino, N-alkylamino, N,N-dialkylamino, (N)-alkoxycarbamoyl, (N)-aryloxycarbamoyl, (N)-aralkyloxycarbamoyl, trialkyl-ammonium (especially with a halide counterion), (N)-amido, (N)-alkylamido, -N-alkylamido, -N,N-dialkylamido, (N)-haloalkylamido, (N)-sulfonamido, (N)-alkylsulfonamido, (N)-haloalkylsulfonamido, carboxyalkylamino, trialkyl-ammonium salt, (N)-carbamic acid, alkyl or benzyl ester, N-acylamine, hydroxylamine, haloacylamine, carbohydrate, thiophene a trialkyl ammonium salt having a carboxylic acid or hydroxy substituent on one or more of the alkyl substituents, and alkylene bridge having a quaternary ammonium salt substituted thereon. —[Or(CH$_2$)$_w$]$_x$—X where x is 2 to 12, w is 2 or 3 and X is a halo or a quaternary ammonium salt, and (N)-nitrogen containing heterocycle wherein the nitrogen of said heterocycle is optionally quaternized. Among the preferred species which may constitute R$^x$ are methyl, ethyl, isopropyl, t-butyl; hydroxy, methoxy, ethoxy, isopropoxy, methylthio, iodo, bromo, fluoro, methylsulfinyl, methylsulfonyl, ethylthio, amino, hydroxylamine, N-methylamino, N,N-dimethylamino, N,N-diethylamino, (N)-benzyloxycarbamoyl, trimethylammonium, A$^-$, —NHC(=O)CH$_3$, —NHC(=O)C$_5$H$_{11}$, —NHC(=O)C$_6$H$_{13}$, carboxethylamino, (N)-morpholinyl, (N)-azetidinyl, (N)-N-methylazetidinium A$^-$, (N)-pyrrolidinyl, pyrrolyl, (N)-N-methylpyridinium A$^-$, (N)-N-methylmorpholinium A$^-$, and N-N"-methylpiperazinyl, (N)-bromomethylamido, (N)-N-hexylamino, thiophene, —N$^-$(CH$_3$)$_2$CO$_2$H I$^-$, —NCH$_3$CH$_2$CO$_2$H,-(N)-N"dimethylpiperazinium I$^-$, (N)-t-butyloxycarbamoyl, (N)-methylsulfonamido, (N)N"-methylpyrrolidinium, and —(OCH$_2$CH$_2$)$_3$I, where A$^-$ is a pharmaceutically acceptable anion. The benzo ring can be mono-substituted at the 6, 7 or 8 position, or disubstituted at the 7- and -8 positions. Also included are the 6,7,8-trialkoxy compounds, for example the 6,7,8-trimethoxy compounds. A variety of other substituents can be advantageously present on the 6,7, 8, and/or 9- positions of the benzo ring, including, for example, guanidinyl, cycloalkyl, carbohydrate (e.g., a 5 or 6 carbon monosaccharide), peptide, and quaternary ammonium salts linked to the ring via poly (oxyalkylene) linkages, e.g., —(OCH$_2$CH$_2$)$_x$—N$^*$R$^{13}$R$^{14}$R$^{15}$A$^-$, where x is 2 to 10. Exemplary compounds are those set forth below in Table 1.

TABLE 1

Alternative compounds #3 (Family F101.xxx.yyy)*

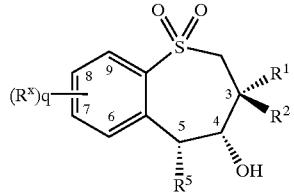

| Prefix (FFF.xxx.yyy) | Cpd # | R$^1$=R$^2$ | R$^5$ | (R$^x$)q |
|---|---|---|---|---|
| F101.001 | 01 | n-propyl | Ph— | 7-methyl |
|  | 02 | n-propyl | Ph— | 7-ethyl |
|  | 03 | n-propyl | Ph— | 7-iso-propyl |
|  | 04 | n-propyl | Ph— | 7-tert-butyl |
|  | 05 | n-propyl | Ph— | 7-OH |
|  | 06 | n-propyl | Ph— | 7-CCH$_3$ |
|  | 07 | n-propyl | Ph— | 7-O(iso-propyl) |
|  | 08 | n-propyl | Ph— | 7-SCH$_3$ |
|  | 09 | n-propyl | Ph— | 7-SCCH$_3$ |
|  | 10 | n-propyl | Ph— | 7-SO$_2$CH$_3$ |

General Notes

In the description of the substituents *(N)* indicates that a nitrogen bearing substituent is bonded to the ring structure via the nitrogen atom.

Similarly, 2-thiophene indicates a bond in the 2 position of the thiophene ring. A similar convention is used for other heterocyclic substituents.

| Abbreviations and Definitions | | | |
|---|---|---|---|
| 11 | n-propyl | Ph- | 7-SCH$_2$2CH$_3$ |
| 12 | n-propyl | Ph- | 7-NH$_2$ |
| 13 | n-propyl | Ph- | 7-NHOH |
| 14 | n-propyl | Ph- | 7-NHCH$_3$ |
| 15 | n-propyl | Ph- | 7-N(CH$_3$)2 |
| 16 | n-propyl | Ph- | 7-N$^+$(CH$_3$)$_3$, I$^-$ |
| 17 | n-propyl | Ph- | 7-NHC(=O)CH$_3$ |
| 18 | n-propyl | Ph- | 7-N(CH$_2$CH$_3$)$_2$ |
| 19 | n-propyl | Ph- | 7-NMeCH$_2$CO$_2$H |
| 20 | n-propyl | Ph- | 7-N$^+$(Me)$_2$CH$_2$CO$_2$H, I$^-$ |
| 21 | n-propyl | Ph- | 7-(N)-morpholine |
| 22 | n-propyl | Ph- | 7-(N)-azetidine |
| 23 | n-propyl | Ph- | 7-(N)—N-methylazetidinium, I$^-$ |
| 24 | n-propyl | Ph- | 7-(N)-pyrrolidine |
| 25 | n-propyl | Ph- | 7-(N)—N-methyl-pyrrolidinium, I$^-$ |
| 26 | n-propyl | Ph- | 7-(N)—N-methyl-morpholinium, I$^-$ |
| 27 | n-propyl | Ph- | 7-(N)—N'-methylpiperazine |
| 28 | n-propyl | Ph- | 7-(N)—N'-dimethylpiperazinium, I$^-$ |
| 29 | n-propyl | Ph- | 7-NH-CBZ |
| 30 | n-propyl | Ph- | 7-NHC(O)C$_5$H$_{11}$ |
| 31 | n-propyl | Ph- | 7-NHC(O)CH$_2$Br |
| 32 | n-propyl | Ph- | 7-NH—C(NH)NH$_2$ |
| 33 | n-propyl | Ph- | 7-(2)-thiophene |
| 34 | n-propyl | Ph- | 8-methyl |
| 35 | n-propyl | Ph- | 8-ethyl |
| 36 | n-propyl | Ph- | 8-iso-propyl |
| 37 | n-propyl | Ph- | 8-tert-butyl |
| 38 | n-propyl | Ph- | 8-OH |
| 39 | n-propyl | Ph- | 8-OCH$_3$ |
| 40 | n-propyl | Ph- | 8-O(iso-propyl) |
| 41 | n-propyl | Ph- | 8-SCH$_3$ |
| 42 | n-propyl | Ph- | 8-SOCH$_3$ |
| 43 | n-propyl | Ph- | 8-SO$_2$CH$_3$ |
| 44 | n-propyl | Ph- | 8-SCH$_2$CH$_3$ |
| 45 | n-propyl | Ph- | 8-NH$_2$ |
| 46 | n-propyl | Ph- | 8-NHOH |
| 47 | n-propyl | Ph- | 8-NHCH$_3$ |
| 48 | n-propyl | Ph- | 8-N(CH$_3$)$_2$ |
| 49 | n-propyl | Ph- | 8-N$^+$(CH$_3$)$_3$, I$^-$ |
| 50 | n-propyl | Ph- | 9-NHC(=O)CH$_3$ |
| 51 | n-propyl | Ph- | 8-N(CH$_2$CH$_3$)$_2$ |
| 52 | n-propyl | Ph- | 8-NMeCH$_2$CO$_2$H |
| 53 | n-propyl | Ph- | 8-N$^+$(Me)$_2$CH$_2$CO$_2$H |
| 54 | n-propyl | Ph- | 8-(N)-morpholine |
| 55 | n-propyl | Ph- | 8-(N)azetidine |
| 56 | n-propyl | Ph- | 8-(N)—N-methylazetidinium, I$^-$ |
| 57 | n-propyl | Ph- | 8-(N)-pyrrolidine |
| 58 | n-propyl | Ph- | 8-(N)—N-methyl-pyrrolidinium, I$^-$ |
| 59 | n-propyl | Ph- | 8-(N)—N-methyl-morpholinium, I$^-$ |
| 60 | n-propyl | Ph- | 8-(N)—N'-methylpiperazine |
| 61 | n-propyl | Ph- | 8-(N)—N'-dimethylpiperazinium, I$^-$ |
| 62 | n-propyl | Ph- | 8-NH-CBZ |
| 63 | n-propyl | Ph- | 8-NHC(O)C$_5$H$_{11}$ |
| 64 | n-propyl | Ph- | 8-NHC(O)CH$_2$Br |
| 65 | n-propyl | Ph- | 8-NH—C(NH)NH$_2$ |
| 66 | n-propyl | Ph- | 8-(2)-thiophene |
| 67 | n-propyl | Ph- | 9-methyl |
| 68 | n-propyl | Ph- | 9-ethyl |
| 69 | n-propyl | Ph- | 9-iso-propyl |
| 70 | n-propyl | Ph- | 9-tert-butyl |
| 71 | n-propyl | Ph- | 9-OH |
| 72 | n-propyl | Ph- | 9-OCH$_3$ |
| 73 | n-propyl | Ph- | 9-O(iso-propyl) |
| 74 | n-propyl | Ph- | 9-SCH$_3$ |
| 75 | n-propyl | Ph- | 9-SOCH$_3$ |
| 76 | n-propyl | Ph- | 9-SO$_2$CH$_3$ |
| 77 | n-propyl | Ph- | 9-SCH$_2$CH$_3$ |
| 78 | n-propyl | Ph- | 9-NH$_2$ |
| 79 | n-propyl | Ph- | 9-NHOH |
| 80 | n-propyl | Ph- | 9-NHCH$_3$ |
| 81 | n-propyl | Ph- | 9-N(CH$_3$)$_2$ |
| 82 | n-propyl | Ph- | 9-N+(CH$_3$)$_3$, I$^-$ |
| 83 | n-propyl | Ph- | 9-NHC(=O)CH$_3$ |
| 84 | n-propyl | Ph- | 9-N(CH$_2$CH$_3$)$_2$ |
| 85 | n-propyl | Ph- | 9-NMeCH$_2$CO$_2$H |
| 86 | n-propyl | Ph- | 9-N$^+$(Me)$_2$CH$_2$CO$_2$H, I$^-$ |
| 87 | n-propyl | Ph- | 9-(N)-morpholine |

-continued

Abbreviations and Definitions

| | | | |
|---|---|---|---|
| 88 | n-propyl | Ph- | 9-(N)-azetidine |
| 89 | n-propyl | Ph- | 9-(N)—N-methylazetidinium, I$^-$ |
| 90 | n-propyl | Ph- | 9-(N)-pyrrolidine |
| 91 | n-propyl | Ph- | 9-(N)—N-methyl-pyrrolidinium, I$^-$ |
| 92 | n-propyl | Ph- | 9-(N)—N-methyl-morpholinium, I$^-$ |
| 93 | n-propyl | Ph- | 9-(N)—N'-methylpiperazine |
| 93 | n-propyl | Ph- | 9-(N)—N'-dimethylpiperazinium, I$^-$ |
| 95 | n-propyl | Ph- | 9-NH-CBZ |
| 96 | n-propyl | Ph- | 9-NHC(O)C$_5$H$_{11}$ |
| 97 | n-propyl | Ph- | 9-NHC(O)CH$_2$Br |
| 98 | n-propyl | Ph- | 9-NH—C(NH)NH$_2$ |
| 99 | n-propyl | Ph- | 9-(2)-thiophene |
| 100 | n-propyl | Ph- | 7-OCH$_3$, 8-OCH$_3$ |
| 101 | n-propyl | Ph- | 7-SCH$_3$, 8-OCH$_3$ |
| 102 | n-propyl | Ph | 7-SCH$_3$, 8-SCH$_3$ |
| 103 | n-propyl | Ph- | 6-OCH$_3$, 7-OCH$_3$, 8-OCH$_3$ |

NH—CBZ is defined as —HNC(=O)OCH$_2$Ph

| Prefix (FFF.xxx. | Cpd# yyy) | R$^1$ – R$^2$ | R$^5$ | (R$^x$)q |
|---|---|---|---|---|
| F101.002 | 01 | n-butyl | Ph- | 7-methyl |
| | 02 | n-butyl | Ph- | 7-ethyl |
| | 03 | n-butyl | Ph- | 7-iso-propyl |
| | 04 | n-butyl | Ph- | 7-tert-butyl |
| | 05 | n-butyl | Ph- | 7-OH |
| | 06 | n-butyl | Ph- | 7-OCH$_3$ |
| | 07 | n-butyl | Ph- | 7-O(iso-propyl) |
| | 08 | n-butyl | Ph- | 7-SCH$_3$ |
| | 09 | n-butyl | Ph- | 7-SOCH$_3$ |
| | 10 | n-butyl | Ph- | 7-SO$_2$CH$_3$ |
| | 11 | n-butyl | Ph- | 7-SCH$_2$CH$_3$ |
| | 12 | n-butyl | Ph- | 7-NH$_2$ |
| | 13 | n-butyl | Ph- | 7-NHOH |
| | 14 | n-butyl | Ph- | 7-NHCH$_3$ |
| | 15 | n-butyl | Ph- | 7-N(CH$_3$)$_2$ |
| | 16 | n-butyl | Ph- | 7-N$^+$(CH$_3$)$_3$, I$^-$ |
| | 17 | n-butyl | Ph- | 7-NHC(=O)CH$_3$ |
| | 18 | n-butyl | Ph- | 7-N(CH$_2$CH$_3$)$_2$ |
| | 19 | n-butyl | Ph- | 7-NMeCH$_2$CO$_2$H |
| | 20 | n-butyl | Ph- | 7-N$^+$(Me)$_2$CH$_2$CO$_2$H, I$^-$ |
| | 21 | n-butyl | Ph- | 7-(N)-morpholine |
| | 22 | n-butyl | Ph- | 7-(N)-azetidine |
| | 23 | n-butyl | Ph- | 7-(N)—N-methylazetidinium, I$^-$ |
| | 24 | n-butyl | Ph- | 7-(N)-pyrrolidine |
| | 25 | n-butyl | Ph- | 7-(N)—N-methyl-pyrrolidinium, I$^-$ |
| | 26 | n-butyl | Ph- | 7-(N)—N-methyl-morpholinium, I$^-$ |
| | 27 | n-butyl | Ph- | 7-(N)—N'-methylpiperazine |
| | 28 | n-butyl | Ph- | 7-(N)—N'-dimethylpiperazinium, I$^-$ |
| | 29 | n-butyl | Ph- | 7-NH-CBZ |
| | 30 | n-butyl | Ph- | 7-NHC(O)C$_5$H$_{11}$ |
| | 31 | n-butyl | Ph- | 7-NHC(O)CH$_2$Br |
| | 32 | n-butyl | Ph- | 7-NH—C(NH)NH$_2$ |
| | 33 | n-butyl | Ph- | 7-(2)-thiophene |
| | 34 | n-butyl | Ph- | 8-methyl |
| | 35 | n-butyl | Ph- | 8-ethyl |
| | 36 | n-butyl | Ph- | 8-iso-propyl |
| | 37 | n-butyl | Ph- | 8-tert-butyl |
| | 38 | n-butyl | Ph- | 8-OH |
| | 39 | n-butyl | Ph- | 8-OCH$_3$ |
| | 40 | n-butyl | Ph- | 8-O(iso-propyl) |
| | 41 | n-butyl | Ph- | 8-SCH$_3$ |
| | 42 | n-butyl | Ph- | 8-SOCH$_3$ |
| | 43 | n-butyl | Ph- | 8-SO$_2$CH$_3$ |
| | 44 | n-butyl | Ph- | 8-SCH$_2$CH$_3$ |
| | 45 | n-butyl | Ph- | 8-NH$_2$ |
| | 46 | n-butyl | Ph- | 8-NHOH |
| | 47 | n-butyl | Ph- | 8-NHCH$_3$ |
| | 48 | n-butyl | Ph- | 8-N(CH$_3$)$_2$ |
| | 49 | n-butyl | Ph- | 8-N$^+$(CH$_3$)$_3$, I$^-$ |
| | 50 | n-butyl | Ph- | 8-NHC(=O)CH$_3$ |
| | 51 | n-butyl | Ph- | 8-N(CH$_2$CH$_3$)$_2$ |

-continued

| Prefix (FFF.xxx. | Cpd# yyy) | R$^1$ – R$^2$ | R$^5$ | (R$^x$)q |
|---|---|---|---|---|
| | 52 | n-butyl | Ph- | 8-NMeCH$_2$CO$_2$H |
| | 53 | n-butyl | Ph- | 8-N$^+$(Me)$_2$CH$_2$CO$_2$H, I$^-$ |
| | 54 | n-butyl | Ph- | 8-(N)-morpholine |
| | 55 | n-butyl | Ph- | 8-(N)-azetidine |
| | 56 | n-butyl | Ph- | 8-(N)—N-methylazetidinium, I$^-$ |
| | 57 | n-butyl | Ph- | 8-(N)-pyrrolidine |
| | 58 | n-butyl | Ph- | 8-(N)—N-methyl-pyrrolidinium, I$^-$ |
| | 59 | n-butyl | Ph- | 8-(N)—N-methyl-morpholinium, I$^-$ |
| | 60 | n-butyl | Ph- | 8-(N)—N'-methylpiperazine |
| | 61 | n-butyl | Ph- | 8-(N)—N'-dimethylpiperazinium, I$^-$ |
| | 62 | n-butyl | Ph- | 8-NH-CBZ |
| | 63 | n-butyl | Ph- | 8-NHC(O)C$_5$H$_{11}$ |
| | 64 | n-butyl | Ph- | 8-NHC(O)CH$_2$Br |
| | 65 | n-butyl | Ph- | 8-NH—C(NH)NH$_2$ |
| | 66 | n-butyl | Ph- | 8-(2)-thiophene |
| | 67 | n-butyl | Ph- | 9-methyl |
| | 68 | n-butyl | Ph- | 9-ethyl |
| | 69 | n-butyl | Ph- | 9-iso-propyl |
| | 70 | n-butyl | Ph- | 9-tert-butyl |
| | 71 | n-butyl | Ph- | 9-OH |
| | 72 | n-butyl | Ph- | 9-OCH$_3$ |
| | 73 | n-butyl | Ph- | 9-O(iso-propyl) |
| | 74 | n-butyl | Ph- | 9-SCH$_3$ |
| | 75 | n-butyl | Ph- | 9-SOCH$_3$ |
| | 76 | n-butyl | Ph- | 9-SO$_2$CH$_3$ |
| | 77 | n-butyl | Ph- | 9-SCH$_2$CH$_3$ |
| | 78 | n-butyl | Ph- | 9-NH$_2$ |
| | 79 | n-butyl | Ph- | 9-NHOH |
| | 80 | n-butyl | Ph- | 9-NHCH$_3$ |
| | 81 | n-butyl | Ph- | 9-N(CH$_3$)$_2$ |
| | 82 | n-butyl | Ph- | 9-N$^+$(CH$_3$)$_3$, I$^-$ |
| | 83 | n-butyl | Ph- | 9-NHC(=O)CH$_3$ |
| | 84 | n-butyl | Ph- | 9-N(CH$_2$CH$_3$)$_2$ |
| | 85 | n-butyl | Ph- | 9-NMeCH$_2$CO$_2$H |
| | 86 | n-butyl | Ph- | 9-N$^+$(Me)$_2$CH$_2$CO$_2$H, I$^-$ |
| | 87 | n-butyl | Ph- | 9-(N)-morpholine |
| | 88 | n-butyl | Ph- | 9-(N)-azetidine |
| | 89 | n-butyl | Ph- | 9-(N)—N-methylazetidinium, I$^-$ |
| | 90 | n-butyl | Ph- | 9-(N)-pyrrolidine |
| | 91 | n-butyl | Ph- | 9-(N)—N-methyl-pyrrolidinium, I$^-$ |
| | 92 | n-butyl | Ph- | 9-(N)—N-methyl-morpholinium, I$^-$ |
| | 93 | n-butyl | Ph- | 9-(N)—N'-methylpiperazine |
| | 93 | n-butyl | Ph- | 9-(N)—N'-dimethylpiperazinium, I$^-$ |
| | 95 | n-butyl | Ph- | 9-NH-CBZ |
| | 96 | n-butyl | Ph- | 9-NHC(O)C$_5$H$_{11}$ |
| | 97 | n-butyl | Ph- | 9-NHC(O)CH$_2$Br |
| | 98 | n-butyl | Ph- | 9-NH—C(NH)NH$_2$ |
| | 99 | n-butyl | Ph- | 9-(2)-thiophene |
| | 100 | n-butyl | Ph- | 7-OCH$_3$, 8-OCH$_3$ |
| | 101 | n-butyl | Ph- | 7-SCH$_3$, 8-OCH$_3$ |
| | 102 | n-butyl | Ph- | 7-SCH$_3$, 8-SCH$_3$ |
| | 103 | n-butyl | Ph- | 6-OCH$_3$, 7-OCH$_3$, 8-OCH$_3$ |

| Prefix (FFF.xxx. | Cpd# yyy) | R$^1$ – R$^2$ | R$^5$ | (R$^x$)q |
|---|---|---|---|---|
| F101.003 | 01 | n-pentyl | Ph- | 7-methyl |
| | 02 | n-pentyl | Ph- | 7-ethyl |
| | 03 | n-pentyl | Ph- | 7-iso-propyl |
| | 04 | n-pentyl | Ph- | 7-tert-butyl |
| | 05 | n-pentyl | Ph- | 7-OH |
| | 06 | n-pentyl | Ph- | 7-OCH$_3$ |
| | 07 | n-pentyl | Ph- | 7-O(iso-propyl) |
| | 08 | n-pentyl | Ph- | 7-SCH$_3$ |
| | 09 | n-pentyl | Ph- | 7-SOCH$_3$ |
| | 10 | n-pentyl | Ph- | 7-SO$_2$CH$_3$ |
| | 11 | n-pentyl | Ph- | 7-SCH$_2$CH$_3$ |
| | 12 | n-pentyl | Ph- | 7-NH$_2$ |
| | 13 | n-pentyl | Ph- | 7-NHOH |
| | 14 | n-pentyl | Ph- | 7-NHCH$_3$ |
| | 15 | n-pentyl | Ph- | 7-N(CH$_3$)$_2$ |

-continued

| Prefix (FFF.xxx. | Cpd# yyy) | R¹ – R² | R⁵ | (Rˣ)q |
|---|---|---|---|---|
| | 16 | n-pentyl | Ph- | 7-N⁺(CH₃)₃, I⁻ |
| | 17 | n-pentyl | Ph- | 7-NHC(=O)CH₃ |
| | 18 | n-pentyl | Ph- | 7-N(CH₂CH₃)₂ |
| | 19 | n-pentyl | Ph- | 7-NMeCH₂CO₂H |
| | 20 | n-pentyl | Ph- | 7-N⁺(Me)₂CH₂CO₂H, I⁻ |
| | 21 | n-pentyl | Ph- | 7-(N)-morpholine |
| | 22 | n-pentyl | Ph- | 7-(N)-azetidine |
| | 23 | n-pentyl | Ph- | 7-(N)—N-methylazetidinium, I⁻ |
| | 24 | n-pentyl | Ph- | 7-(N)-pyrrolidine |
| | 25 | n-pentyl | Ph- | 7-(N)—N-methyl-pyrrolidinium, I⁻ |
| | 26 | n-pentyl | Ph- | 7-(N)—N-methyl-morpholinium, I⁻ |
| | 27 | n-pentyl | Ph- | 7-(N)—N'-methylpiperazine |
| | 28 | n-pentyl | Ph- | 7-(N)—N'-dimethylpiperazinium, I⁻ |
| | 29 | n-pentyl | Ph- | 7-NH-CBZ |
| | 30 | n-pentyl | Ph- | 7-NHC(O)C₅H₁₁ |
| | 31 | n-pentyl | Ph- | 7-NHC(O)CH₂Br |
| | 32 | n-pentyl | Ph- | 7-NH—C(NH)NH₂ |
| | 33 | n-pentyl | Ph- | 7-(2)-thiophene |
| | 34 | n-pentyl | Ph- | 8-methyl |
| | 35 | n-pentyl | Ph- | 8-ethyl |
| | 36 | n-pentyl | Ph- | 8-iso-propyl |
| | 37 | n-pentyl | Ph- | 8-tert-butyl |
| | 38 | n-pentyl | Ph- | 8-OH |
| | 39 | n-pentyl | Ph- | 8-OCH₃ |
| | 40 | n-pentyl | Ph- | 8-O(iso-propyl) |
| | 41 | n-pentyl | Ph- | 8-SCH₃ |
| | 42 | n-pentyl | Ph- | 8-SOCH₃ |
| | 43 | n-pentyl | Ph- | 8-SO₂CH₃ |
| | 44 | n-pentyl | Ph- | 8-SCH₂CH₃ |
| | 45 | n-pentyl | Ph- | 8-NH₂ |
| | 46 | n-pentyl | Ph- | 8-NHOH |
| | 47 | n-pentyl | Ph- | 8-NHCH₃ |
| | 48 | n-pentyl | Ph- | 8-N(CH₃)₂ |
| | 49 | n-pentyl | Ph- | 8-N⁺(CH₃)₃, I⁻ |
| | 50 | n-pentyl | Ph- | 8-NHC(=O)CH₃ |
| | 51 | n-pentyl | Ph- | 8-N(CH₂CH₃)₂ |
| | 52 | n-pentyl | Ph- | 8-NMeCH₂CO₂H |
| | 53 | n-pentyl | Ph- | 8-N⁺(Me)₂CH₂CO₂H, I⁻ |
| | 54 | n-pentyl | Ph- | 8-(N)-morpholine |
| | 55 | n-pentyl | Ph- | 8-(N)-azetidine |
| | 56 | n-pentyl | Ph- | 8-(N)—N-methylazetidinium, I⁻ |
| | 57 | n-pentyl | Ph- | 8-(N)-pyrrolidine |
| | 58 | n-pentyl | Ph- | 8-(N)—N-methyl-pyrrolidinium, I⁻ |
| | 59 | n-pentyl | Ph- | 8-(N)—N-methyl-morpholinium, I⁻ |
| | 60 | n-pentyl | Ph- | 8-(N)—N'-methylpiperazine |
| | 61 | n-pentyl | Ph- | 8-(N)—N'-dimethylpiperazinium, I⁻ |
| | 62 | n-pentyl | Ph- | 8-NH-CBZ |
| | 63 | n-pentyl | Ph- | 8-NHC(O)C₅H₁₁ |
| | 64 | n-pentyl | Ph- | 8-NHC(O)CH₂Br |
| | 65 | n-pentyl | Ph- | 8-NH—C(NH)NH₂ |
| | 66 | n-pentyl | Ph- | 8-(2)-thiophene |
| | 67 | n-pentyl | Ph- | 9-methyl |
| | 68 | n-pentyl | Ph- | 9-ethyl |
| | 69 | n-pentyl | Ph- | 9-iso-propyl |
| | 70 | n-pentyl | Ph- | 9-tert-butyl |
| | 71 | n-pentyl | Ph- | 9-OH |
| | 72 | n-pentyl | Ph- | 9-OCH₃ |
| | 73 | n-pentyl | Ph- | 9-O(iso-propyl) |
| | 74 | n-pentyl | Ph- | 9-SCH₃ |
| | 75 | n-pentyl | Ph- | 9-SOCH₃ |
| | 76 | n-pentyl | Ph- | 9-SO₂CH₃ |
| | 77 | n-pentyl | Ph- | 9-SCH₂CH₃ |
| | 78 | n-pentyl | Ph- | 9-NH₂ |
| | 79 | n-pentyl | Ph- | 9-NHOH |
| | 80 | n-pentyl | Ph- | 9-NHCH₃ |
| | 81 | n-pentyl | Ph- | 9-N(CH₃)₂ |
| | 82 | n-pentyl | Ph- | 9-N⁺(CH₃)₃, I⁻ |
| | 83 | n-pentyl | Ph- | 9-NHC(=O)CH₃ |
| | 84 | n-pentyl | Ph- | 9-N(CH₂CH₃)₂ |
| | 85 | n-pentyl | Ph- | 9-NMeCH₂CO₂H |
| | 86 | n-pentyl | Ph- | 9-N⁺(Me)₂CH₂CO₂H, I⁻ |
| | 87 | n-pentyl | Ph- | 9-(N)-morpholine |
| | 88 | n-pentyl | Ph- | 9-(N)-azetidine |
| | 89 | n-pentyl | Ph- | 9-(N)—N-methylazetidinium, I⁻ |
| | 90 | n-pentyl | Ph- | 9-(N)-pyrrolidine |
| | 91 | n-pentyl | Ph- | 9-(N)—N-methyl-pyrrolidinium, I⁻ |
| | 92 | n-pentyl | Ph- | 9-(N)—N-methyl-morpholinium, I⁻ |
| | 93 | n-pentyl | Ph- | 9-(N)—N'-methylpiperazine |
| | 93 | n-pentyl | Ph- | 9-(N)—N'-dimethylpiperazinium, I⁻ |
| | 95 | n-pentyl | Ph- | 9-NH-CBZ |
| | 96 | n-pentyl | Ph- | 9-NHC(O)C₅H₁₁ |
| | 97 | n-pentyl | Ph- | 9-NHC(O)CH₂Br |
| | 98 | n-pentyl | Ph- | 9-NH—C(NH)NH₂ |
| | 99 | n-pentyl | Ph- | 9-(2)-thiophene |
| | 100 | n-pentyl | Ph- | 7-OCH₃, 8-OCH₃ |
| | 101 | n-pentyl | Ph- | 7-SCH₃, 8-OCH₃ |
| | 102 | n-pentyl | Ph- | 7-SCH₃, 8-SCH₃ |
| | 103 | n-pentyl | Ph- | 6-OCH₃, 7-OCH₃, 8-OCH₃ |

| Prefix (FFF.xxx. | Cpd# yyy) | R¹ – R² | R⁵ | (Rˣ)q |
|---|---|---|---|---|
| F101.004 | 01 | n-hexyl | Ph- | 7-methyl |
| | 02 | n-hexyl | Ph- | 7-ethyl |
| | 03 | n-hexyl | Ph- | 7-iso-propyl |
| | 04 | n-hexyl | Ph- | 7-tert-butyl |
| | 05 | n-hexyl | Ph- | 7-OH |
| | 06 | n-hexyl | Ph- | 7-OCH₃ |
| | 07 | n-hexyl | Ph- | 7-O(iso-propyl) |
| | 08 | n-hexyl | Ph- | 7-SCH₃ |
| | 09 | n-hexyl | Ph- | 7-SOCH₃ |
| | 10 | n-hexyl | Ph- | 7-SO₂CH₃ |
| | 11 | n-hexyl | Ph- | 7-SCH₂CH₃ |
| | 12 | n-hexyl | Ph- | 7-NH₂ |
| | 13 | n-hexyl | Ph- | 7-NHOH |
| | 14 | n-hexyl | Ph- | 7-NHCH₃ |
| | 15 | n-hexyl | Ph- | 7-N(CH₃)₂ |
| | 16 | n-hexyl | Ph- | 7-N⁺(CH₃)₃, I⁻ |
| | 17 | n-hexyl | Ph- | 7-NHC(=O)CH₃ |
| | 18 | n-hexyl | Ph- | 7-N(CH₂CH₃)₂ |
| | 19 | n-hexyl | Ph- | 7-NMeCH₂CO₂H |
| | 20 | n-hexyl | Ph- | 7-N⁺(Me)₂CH₂CO₂H, I⁻ |
| | 21 | n-hexyl | Ph- | 7-(N)-morpholine |
| | 22 | n-hexyl | Ph- | 7-(N)-azetidine |
| | 23 | n-hexyl | Ph- | 7-(N)—N-methylazetidinium, I⁻ |
| | 24 | n-hexyl | Ph- | 7-(N)-pyrrolidine |
| | 25 | n-hexyl | Ph- | 7-(N)—N-methyl-pyrrolidinium, I⁻ |
| | 26 | n-hexyl | Ph- | 7-(N)—N-methyl-morpholinium, I⁻ |
| | 27 | n-hexyl | Ph- | 7-(N)—N'-methylpiperazine |
| | 28 | n-hexyl | Ph- | 7-(N)—N'-dimethylpiperazinium, I⁻ |
| | 29 | n-hexyl | Ph- | 7-NH-CBZ |
| | 30 | n-hexyl | Ph- | 7-NHC(O)C₅H₁₁ |
| | 31 | n-hexyl | Ph- | 7-NHC(O)CH₂Br |
| | 32 | n-hexyl | Ph- | 7-NH—C(NH)NH₂ |
| | 33 | n-hexyl | Ph- | 7-(2)-thiophene |
| | 34 | n-hexyl | Ph- | 8-methyl |
| | 35 | n-hexyl | Ph- | 8-ethyl |
| | 36 | n-hexyl | Ph- | 8-iso-propyl |
| | 37 | n-hexyl | Ph- | 8-tert-butyl |
| | 38 | n-hexyl | Ph- | 8-OH |
| | 39 | n-hexyl | Ph- | 8-OCH₃ |
| | 40 | n-hexyl | Ph- | 8-O(iso-propyl) |
| | 41 | n-hexyl | Ph- | 8-SCH₃ |
| | 42 | n-hexyl | Ph- | 8-SOCH₃ |
| | 43 | n-hexyl | Ph- | 8-SO₂CH₃ |
| | 44 | n-hexyl | Ph- | 8-SCH₂CH₃ |
| | 45 | n-hexyl | Ph- | 8-NH₂ |
| | 46 | n-hexyl | Ph- | 8-NHOH |
| | 47 | n-hexyl | Ph- | 8-NHCH₃ |
| | 48 | n-hexyl | Ph- | 8-N(CH₃)₂ |
| | 49 | n-hexyl | Ph- | 8-N⁺(CH₃)₃, I⁻ |
| | 50 | n-hexyl | Ph- | 8-NHC(=O)CH₃ |
| | 51 | n-hexyl | Ph- | 8-N(CH₂CH₃)₂ |
| | 52 | n-hexyl | Ph- | 8-NMeCH₂CO₂H |
| | 53 | n-hexyl | Ph- | 8-N⁺(Me)₂CH₂CO₂H, I⁻ |
| | 54 | n-hexyl | Ph- | 8-(N)-morpholine |
| | 55 | n-hexyl | Ph- | 8-(N)-azetidine |

-continued

| Prefix (FFF.xxx. | Cpd# yyy) | $R^1 = R^2$ | $R^5$ | $(R^x)q$ |
|---|---|---|---|---|
| | 56 | n-hexyl | Ph- | 8-(N)—N-methylazetidinium, I$^-$ |
| | 57 | n-hexyl | Ph- | 8-(N)-pyrrolidine |
| | 58 | n-hexyl | Ph- | 8-(N)—N-methyl-pyrrolidinium, I$^-$ |
| | 59 | n-hexyl | Ph- | 8-(N)—N-methyl-morpholinium, I$^-$ |
| | 60 | n-hexyl | Ph- | 8-(N)—N'-methylpiperazine |
| | 61 | n-hexyl | Ph- | 8-(N)—N'-dimethylpiperazinium, I$^-$ |
| | 62 | n-hexyl | Ph- | 8-NH-CBZ |
| | 63 | n-hexyl | Ph- | 8-NHC(O)C$_5$H$_{11}$ |
| | 64 | n-hexyl | Ph- | 8-NHC(O)CH$_2$Br |
| | 65 | n-hexyl | Ph- | 8-NH—C(NH)NH$_2$ |
| | 66 | n-hexyl | Ph- | 8-(2)-thiophene |
| | 67 | n-hexyl | Ph- | 9-methyl |
| | 68 | n-hexyl | Ph- | 9-ethyl |
| | 69 | n-hexyl | Ph- | 9-iso-propyl |
| | 70 | n-hexyl | Ph- | 9-tert-butyl |
| | 71 | n-hexyl | Ph- | 9-OH |
| | 72 | n-hexyl | Ph- | 9-OCH$_3$ |
| | 73 | n-hexyl | Ph- | 9-O(iso-propyl) |
| | 74 | n-hexyl | Ph- | 9-SCH$_3$ |
| | 75 | n-hexyl | Ph- | 9-SOCH$_3$ |
| | 76 | n-hexyl | Ph- | 9-SO$_2$CH$_3$ |
| | 77 | n-hexyl | Ph- | 9-SCH$_2$CH$_3$ |
| | 78 | n-hexyl | Ph- | 9-NH$_2$ |
| | 79 | n-hexyl | Ph- | 9-NHOH |
| | 80 | n-hexyl | Ph- | 9-NHCH$_3$ |
| | 81 | n-hexyl | Ph- | 9-N(CH$_3$)$_2$ |
| | 82 | n-hexyl | Ph- | 9-N$^+$(CH$_3$)$_3$, I$^-$ |
| | 83 | n-hexyl | Ph- | 9-NHC(=O)CH$_3$ |
| | 84 | n-hexyl | Ph- | 9-N(CH$_2$CH$_3$)$_2$ |
| | 85 | n-hexyl | Ph- | 9-NMeCH$_2$CO$_2$H |
| | 86 | n-hexyl | Ph- | 9-N$^+$(Me)$_2$CH$_2$CO$_2$H, I$^-$ |
| | 87 | n-hexyl | Ph- | 9-(N)-morpholine |
| | 88 | n-hexyl | Ph- | 9-(N)-azetidine |
| | 89 | n-hexyl | Ph- | 9-(N)—N-methylazetidinium, I$^-$ |
| | 90 | n-hexyl | Ph- | 9-(N)-pyrrolidine |
| | 91 | n-hexyl | Ph- | 9-(N)—N-methyl-pyrrolidinium, I$^-$ |
| | 92 | n-hexyl | Ph- | 9-(N)—N-methyl-morpholinium, I$^-$ |
| | 93 | n-hexyl | Ph- | 9-(N)—N'-methylpiperazine |
| | 93 | n-hexyl | Ph- | 9-(N)—N'-dimethylpiperazinium, I$^-$ |
| | 95 | n-hexyl | Ph- | 9-NH-CBZ |
| | 96 | n-hexyl | Ph- | 9-NHC(O)C$_5$H$_{11}$ |
| | 97 | n-hexyl | Ph- | 9-NHC(O)CH$_2$Br |
| | 98 | n-hexyl | Ph- | 9-NH—C(NH)NH$_2$ |
| | 99 | n-hexyl | Ph- | 9-(2)-thiophene |
| | 100 | n-hexyl | Ph- | 7-OCH$_3$, 8-OCH$_3$ |
| | 101 | n-hexyl | Ph- | 7-SCH$_3$, 8-OCH$_3$ |
| | 102 | n-hexyl | Ph- | 7-SCH$_3$, 8-SCH$_3$ |
| | 103 | n-hexyl | Ph- | 6-OCH$_3$, 7-OCH$_3$, 8-OCH$_3$ |

| Prefix (FFF.xxx. | Cpd# yyy) | $R^1 = R^2$ | $R^5$ | $(R^x)q$ |
|---|---|---|---|---|
| F101.005 | 01 | iso-propyl | Ph- | 7-methyl |
| | 02 | iso-propyl | Ph- | 7-ethyl |
| | 03 | iso-propyl | Ph- | 7-iso-propyl |
| | 04 | iso-propyl | Ph- | 7-tert-butyl |
| | 05 | iso-propyl | Ph- | 7-OH |
| | 06 | iso-propyl | Ph- | 7-OCH$_3$ |
| | 07 | iso-propyl | Ph- | 7-O(iso-propyl) |
| | 08 | iso-propyl | Ph- | 7-SCH$_3$ |
| | 09 | iso-propyl | Ph- | 7-SOCH$_3$ |
| | 10 | iso-propyl | Ph- | 7-SO$_2$CH$_3$ |
| | 11 | iso-propyl | Ph- | 7-SCH$_2$CH$_3$ |
| | 12 | iso-propyl | Ph- | 7-NH$_2$ |
| | 13 | iso-propyl | Ph- | 7-NHOH |
| | 14 | iso-propyl | Ph- | 7-NHCH$_3$ |
| | 15 | iso-propyl | Ph- | 7-N(CH$_3$)$_2$ |
| | 16 | iso-propyl | Ph- | 7-N$^+$(CH$_3$)$_3$, I$^-$ |
| | 17 | iso-propyl | Ph- | 7-NHC(=O)CH$_3$ |
| | 18 | iso-propyl | Ph- | 7-N(CH$_2$CH$_3$)$_2$ |
| | 19 | iso-propyl | Ph- | 7-NMeCH$_2$CO$_2$H |

-continued

| Prefix (FFF.xxx. | Cpd# yyy) | $R^1 = R^2$ | $R^5$ | $(R^x)q$ |
|---|---|---|---|---|
| | 20 | iso-propyl | Ph- | 7-N$^+$(Me)$_2$CH$_2$CO$_2$H, I$^-$ |
| | 21 | iso-propyl | Ph- | 7-(N)-morpholine |
| | 22 | iso-propyl | Ph- | 7-(N)-azetidine |
| | 23 | iso-propyl | Ph- | 7-(N)—N-methylazetidinium, I$^-$ |
| | 24 | iso-propyl | Ph- | 7-(N)-pyrrolidine |
| | 25 | iso-propyl | Ph- | 7-(N)—N-methyl-pyrrolidinium, I$^-$ |
| | 26 | iso-propyl | Ph- | 7-(N)—N-methyl-morpholinium, I$^-$ |
| | 27 | iso-propyl | Ph- | 7-(N)—N'-methylpiperazine |
| | 28 | iso-propyl | Ph- | 7-(N)—N'-dimethylpiperazinium, I$^-$ |
| | 29 | iso-propyl | Ph- | 7-NH-CBZ |
| | 30 | iso-propyl | Ph- | 7-NHC(O)C$_5$H$_{11}$ |
| | 31 | iso-propyl | Ph- | 7-NHC(O)CH$_2$Br |
| | 32 | iso-propyl | Ph- | 7-NH—C(NH)NH$_2$ |
| | 33 | iso-propyl | Ph- | 7-(2)-thiophene |
| | 34 | iso-propyl | Ph- | 8-methyl |
| | 35 | iso-propyl | Ph- | 8-ethyl |
| | 36 | iso-propyl | Ph- | 8-iso-propyl |
| | 37 | iso-propyl | Ph- | 8-tert-butyl |
| | 38 | iso-propyl | Ph- | 8-OH |
| | 39 | iso-propyl | Ph- | 8-OCH$_3$ |
| | 40 | iso-propyl | Ph- | 8-O(iso-propyl) |
| | 41 | iso-propyl | Ph- | 8-SCH$_3$ |
| | 42 | iso-propyl | Ph- | 8-SOCH$_3$ |
| | 43 | iso-propyl | Ph- | 8-SO$_2$CH$_3$ |
| | 44 | iso-propyl | Ph- | 8-SCH$_2$CH$_3$ |
| | 45 | iso-propyl | Ph- | 8-NH$_2$ |
| | 46 | iso-propyl | Ph- | 8-NHOH |
| | 47 | iso-propyl | Ph- | 8-NHCH$_3$ |
| | 48 | iso-propyl | Ph- | 8-N(CH$_3$)$_2$ |
| | 49 | iso-propyl | Ph- | 8-N$^+$(CH$_3$)$_3$, I$^-$ |
| | 50 | iso-propyl | Ph- | 8-NHC(=O)CH$_3$ |
| | 51 | iso-propyl | Ph- | 8-N(CH$_2$CH$_3$)$_2$ |
| | 52 | iso-propyl | Ph- | 8-NMeCH$_2$CO$_2$H |
| | 53 | iso-propyl | Ph- | 8-N$^+$(Me)$_2$CH$_2$CO$_2$H, I$^-$ |
| | 54 | iso-propyl | Ph- | 8-(N)-morpholine |
| | 55 | iso-propyl | Ph- | 8-(N)-azetidine |
| | 56 | iso-propyl | Ph- | 8-(N)—N-methylazetidinium, I$^-$ |
| | 57 | iso-propyl | Ph- | 8-(N)-pyrrolidine |
| | 58 | iso-propyl | Ph- | 8-(N)—N-methyl-pyrrolidinium, I$^-$ |
| | 59 | iso-propyl | Ph- | 8-(N)—N-methyl-morpholinium, I$^-$ |
| | 60 | iso-propyl | Ph- | 8-(N)—N'-methylpiperazine |
| | 61 | iso-propyl | Ph- | 8-(N)—N'-dimethylpiperazinium, I$^-$ |
| | 62 | iso-propyl | Ph- | 8-NH-CBZ |
| | 63 | iso-propyl | Ph- | 8-NHC(O)C$_5$H$_{11}$ |
| | 64 | iso-propyl | Ph- | 8-NHC(O)CH$_2$Br |
| | 65 | iso-propyl | Ph- | 8-NH—C(NH)NH$_2$ |
| | 66 | iso-propyl | Ph- | 8-(2)-thiophene |
| | 67 | iso-propyl | Ph- | 9-methyl |
| | 68 | iso-propyl | Ph- | 9-ethyl |
| | 69 | iso-propyl | Ph- | 9-iso-propyl |
| | 70 | iso-propyl | Ph- | 9-tert-butyl |
| | 71 | iso-propyl | Ph- | 9-OH |
| | 72 | iso-propyl | Ph- | 9-OCH$_3$ |
| | 73 | iso-propyl | Ph- | 9-O(iso-propyl) |
| | 74 | iso-propyl | Ph- | 9-SCH$_3$ |
| | 75 | iso-propyl | Ph- | 9-SOCH$_3$ |
| | 76 | iso-propyl | Ph- | 9-SO$_2$CH$_3$ |
| | 77 | iso-propyl | Ph- | 9-SCH$_2$CH$_3$ |
| | 78 | iso-propyl | Ph- | 9-NH$_2$ |
| | 79 | iso-propyl | Ph- | 9-NHOH |
| | 80 | iso-propyl | Ph- | 9-NHCH$_3$ |
| | 81 | iso-propyl | Ph- | 9-N(CH$_3$)$_2$ |
| | 82 | iso-propyl | Ph- | 9-N$^+$(CH$_3$)$_3$, I$^-$ |
| | 83 | iso-propyl | Ph- | 9-NHC(=O)CH$_3$ |
| | 84 | iso-propyl | Ph- | 9-N(CH$_2$CH$_3$)$_2$ |
| | 85 | iso-propyl | Ph- | 9-NMeCH$_2$CO$_2$H |
| | 86 | iso-propyl | Ph- | 9-N$^+$(Me)$_2$CH$_2$CO$_2$H, I$^-$ |
| | 87 | iso-propyl | Ph- | 9-(N)-morpholine |
| | 88 | iso-propyl | Ph- | 9-(N)-azetidine |
| | 89 | iso-propyl | Ph- | 9-(N)—N-methylazetidinium, I$^-$ |
| | 90 | iso-propyl | Ph- | 9-(N)-pyrrolidine |
| | 91 | iso-propyl | Ph- | 9-(N)—N-methyl-pyrrolidinium, I$^-$ |
| | 92 | iso-propyl | Ph- | 9-(N)—N-methyl-morpholinium, I$^-$ |
| | 93 | iso-propyl | Ph- | 9-(N)—N'-methylpiperazine |
| | 93 | iso-propyl | Ph- | 9-(N)—N'-dimethylpiperazinium, I$^-$ |
| | 95 | iso-propyl | Ph- | 9-NH-CBZ |

| Prefix (FFF.xxx.) | Cpd# yyy | $R^1 = R^2$ | $R^5$ | $(R^x)q$ |
|---|---|---|---|---|
| | 96 | iso-propyl | Ph- | 9-NHC(O)C$_5$H$_{11}$ |
| | 97 | iso-propyl | Ph- | 9-NHC(O)CH$_2$Br |
| | 98 | iso-propyl | Ph- | 9-NH—C(NH)NH$_2$ |
| | 99 | iso-propyl | Ph- | 9-(2)-thiophene |
| | 100 | iso-propyl | Ph- | 7-OCH$_3$, 8-OCH$_3$ |
| | 101 | iso-propyl | Ph- | 7-SCH$_3$, 8-OCH$_3$ |
| | 102 | iso-propyl | Ph- | 7-SCH$_3$, 8-SCH$_3$ |
| | 103 | iso-propyl | Ph- | 6-OCH$_3$, 7-OCH$_3$, 8-OCH$_3$ |

| Prefix (FFF.xxx.) | Cpd# yyy | $R^1 = R^2$ | $R^5$ | $(R^x)q$ |
|---|---|---|---|---|
| F101.006 | 01 | iso-butyl | Ph- | 7-methyl |
| | 02 | iso-butyl | Ph- | 7-ethyl |
| | 03 | iso-butyl | Ph- | 7-iso-propyl |
| | 04 | iso-butyl | Ph- | 7-tert-butyl |
| | 05 | iso-butyl | Ph- | 7-OH |
| | 06 | iso-butyl | Ph- | 7-OCH$_3$ |
| | 07 | iso-butyl | Ph- | 7-O(iso-propyl) |
| | 08 | iso-butyl | Ph- | 7-SCH$_3$ |
| | 09 | iso-butyl | Ph- | 7-SOCH$_3$ |
| | 10 | iso-butyl | Ph- | 7-SO$_2$CH$_3$ |
| | 11 | iso-butyl | Ph- | 7-SCH$_2$CH$_3$ |
| | 12 | iso-butyl | Ph- | 7-NH$_2$ |
| | 13 | iso-butyl | Ph- | 7-NHOH |
| | 14 | iso-butyl | Ph- | 7-NHCH$_3$ |
| | 15 | iso-butyl | Ph- | 7-N(CH$_3$)$_2$ |
| | 16 | iso-butyl | Ph- | 7-N$^+$(CH$_3$)$_3$, I$^-$ |
| | 17 | iso-butyl | Ph- | 7-NHC(=O)CH$_3$ |
| | 18 | iso-butyl | Ph- | 7-N(CH$_2$CH$_3$)$_2$ |
| | 19 | iso-butyl | Ph- | 7-NMeCH$_2$CO$_2$H |
| | 20 | iso-butyl | Ph- | 7-N$^{+(Me)}{_2}$CH$_2$CO$_2$H, I$^-$ |
| | 21 | iso-butyl | Ph- | 7-(N)-morpholine |
| | 22 | iso-butyl | Ph- | 7-(N)-azetidine |
| | 23 | iso-butyl | Ph- | 7-(N)—N-methylazetidinium, I$^-$ |
| | 24 | iso-butyl | Ph- | 7-(N)-pyrrolidine |
| | 25 | iso-butyl | Ph- | 7-(N)—N-methyl-pyrrolidinium, I$^-$ |
| | 26 | iso-butyl | Ph- | 7-(N)—N-methyl-morpholinium, I$^-$ |
| | 27 | iso-butyl | Ph- | 7-(N)—N'-methylpiperazine |
| | 28 | iso-butyl | Ph- | 7-(N)—N'-dimethylpiperazinium, I$^-$ |
| | 29 | iso-butyl | Ph- | 7-NH-CBZ |
| | 30 | iso-butyl | Ph- | 7-NHC(O)C$_5$H$_{11}$ |
| | 31 | iso-butyl | Ph- | 7-NHC(O)CH$_2$Br |
| | 32 | iso-butyl | Ph- | 7-NH—C(NH)NH$_2$ |
| | 33 | iso-butyl | Ph- | 7-(2)-thiophene |
| | 34 | iso-butyl | Ph- | 8-methyl |
| | 35 | iso-butyl | Ph- | 8-ethyl |
| | 36 | iso-butyl | Ph- | 8-iso-propyl |
| | 37 | iso-butyl | Ph- | 8-tert-butyl |
| | 38 | iso-butyl | Ph- | 8-OH |
| | 39 | iso-butyl | Ph- | 8-OCH$_3$ |
| | 40 | iso-butyl | Ph- | 8-O(iso-propyl) |
| | 41 | iso-butyl | Ph- | 8-SCH$_3$ |
| | 42 | iso-butyl | Ph- | 8-SOCH$_3$ |
| | 43 | iso-butyl | Ph- | 8-SO$_2$CH$_3$ |
| | 44 | iso-butyl | Ph- | 8-SCH$_2$CH$_3$ |
| | 45 | iso-butyl | Ph- | 8-NH$_2$ |
| | 46 | iso-butyl | Ph- | 8-NHOH |
| | 47 | iso-butyl | Ph- | 8-NHCH$_3$ |
| | 48 | iso-butyl | Ph- | 8-N(CH$_3$)$_2$ |
| | 49 | iso-butyl | Ph- | 8-N$^+$(CH$_3$)$_3$, I$^-$ |
| | 50 | iso-butyl | Ph- | 8-NHC(=O)CH$_3$ |
| | 51 | iso-butyl | Ph- | 8-N(CH$_2$CH$_3$)$_2$ |
| | 52 | iso-butyl | Ph- | 8-NMeCH$_2$CO$_2$H |
| | 53 | iso-butyl | Ph- | 8-N$^+$(Me)$_2$CH$_2$CO$_2$H, I$^-$ |
| | 54 | iso-butyl | Ph- | 8-(N)-morpholine |
| | 55 | iso-butyl | Ph- | 8-(N)-azetidine |
| | 56 | iso-butyl | Ph- | 8-(N)—N-methylazetidinium, I$^-$ |
| | 57 | iso-butyl | Ph- | 8-(N)-pyrrolidine |
| | 58 | iso-butyl | Ph- | 8-(N)—N-methyl-pyrrolidinium, I$^-$ |
| | 59 | iso-butyl | Ph- | 8-(N)—N-methyl-morpholinium, I$^-$ |
| | 60 | iso-butyl | Ph- | 8-(N)—N'-methylpiperazine |
| | 61 | iso-butyl | Ph- | 8-(N)—N'-dimethylpiperazinium, I$^-$ |
| | 62 | iso-butyl | Ph- | 8-NH-CBZ |
| | 63 | iso-butyl | Ph- | 8-NHC(O)C$_5$H$_{11}$ |
| | 64 | iso-butyl | Ph- | 8-NHC(O)CH$_2$Br |
| | 65 | iso-butyl | Ph- | 8-NH—C(NH)NH$_2$ |
| | 66 | iso-butyl | Ph- | 8-(2)-thiophene |
| | 67 | iso-butyl | Ph- | 9-methyl |
| | 68 | iso-butyl | Ph- | 9-ethyl |
| | 69 | iso-butyl | Ph- | 9-iso-propyl |
| | 70 | iso-butyl | Ph- | 9-tert-butyl |
| | 71 | iso-butyl | Ph- | 9-OH |
| | 72 | iso-butyl | Ph- | 9-OCH$_3$ |
| | 73 | iso-butyl | Ph- | 9-O(iso-propyl) |
| | 74 | iso-butyl | Ph- | 9-SCH$_3$ |
| | 75 | iso-butyl | Ph- | 9-SOCH$_3$ |
| | 76 | iso-butyl | Ph- | 9-SO$_2$CH$_3$ |
| | 77 | iso-butyl | Ph- | 9-SCH$_2$CH$_3$ |
| | 78 | iso-butyl | Ph- | 9-NH$_2$ |
| | 79 | iso-butyl | Ph- | 9-NHOH |
| | 80 | iso-butyl | Ph- | 9-NHCH$_3$ |
| | 81 | iso-butyl | Ph- | 9-N(CH$_3$)$_2$ |
| | 82 | iso-butyl | Ph- | 9-N$^+$(CH$_3$)$_3$, I$^-$ |
| | 83 | iso-butyl | Ph- | 9-NHC(=O)CH$_3$ |
| | 84 | iso-butyl | Ph- | 9-N(CH$_2$CH$_3$)$_2$ |
| | 85 | iso-butyl | Ph- | 9-NMeCH$_2$CO$_2$H |
| | 86 | iso-butyl | Ph- | 9-N$^+$(Me)$_2$CH$_2$CO$_2$H, I$^-$ |
| | 87 | iso-butyl | Ph- | 9-(N)-morpholine |
| | 88 | iso-butyl | Ph- | 9-(N)-azetidine |
| | 89 | iso-butyl | Ph- | 9-(N)—N-methylazetidinium, I$^{-1}$ |
| | 90 | iso-butyl | Ph- | 9-(N)-pyrrolidine |
| | 91 | iso-butyl | Ph- | 9-(N)—N-methyl-pyrrolidinium, I$^-$ |
| | 92 | iso-butyl | Ph- | 9-(N)—N-methyl-morpholinium, I$^-$ |
| | 93 | iso-butyl | Ph- | 9-(N)—N'-methylpiperazine |
| | 93 | iso-butyl | Ph- | 9-(N)—N'-dimethylpiperazinium, I$^-$ |
| | 95 | iso-butyl | Ph- | 9-NH-CBZ |
| | 96 | iso-butyl | Ph- | 9-NHC(O)C$_5$H$_{11}$ |
| | 97 | iso-butyl | Ph- | 9-NHC(O)CH$_2$Br |
| | 98 | iso-butyl | Ph- | 9-NH—C(NH)NH$_2$ |
| | 99 | iso-butyl | Ph- | 9-(2)-thiophene |
| | 100 | iso-butyl | Ph- | 7-OCH$_3$, 8-OCH$_3$ |
| | 101 | iso-butyl | Ph- | 7-SCH$_3$, 8-OCH$_3$ |
| | 102 | iso-butyl | Ph- | 7-SCH$_3$, 8-SCH$_3$ |
| | 103 | iso-butyl | Ph- | 6-OCH$_3$, 7-OCH$_3$, 8-OCH$_3$ |

| Prefix (FFF.xxx.) | Cpd# yyy | $R^1 = R^2$ | $R^5$ | $(R^x)q$ |
|---|---|---|---|---|
| F101.007 | 01 | iso-pentyl | Ph- | 7-methyl |
| | 02 | iso-pentyl | Ph- | 7-ethyl |
| | 03 | iso-pentyl | Ph- | 7-iso-propyl |
| | 04 | iso-pentyl | Ph- | 7-tert-butyl |
| | 05 | iso-pentyl | Ph- | 7-OH |
| | 06 | iso-pentyl | Ph- | 7-OCH$_3$ |
| | 07 | iso-pentyl | Ph- | 7-O(iso-propyl) |
| | 08 | iso-pentyl | Ph- | 7-SCH$_3$ |
| | 09 | iso-pentyl | Ph- | 7-SOCH$_3$ |
| | 10 | iso-pentyl | Ph- | 7-SO$_2$CH$_3$ |
| | 11 | iso-pentyl | Ph- | 7-SCH$_2$CH$_3$ |
| | 12 | iso-pentyl | Ph- | 7-NH$_2$ |
| | 13 | iso-pentyl | Ph- | 7-NHOH |
| | 14 | iso-pentyl | Ph- | 7-NHCH$_3$ |
| | 15 | iso-pentyl | Ph- | 7-N(CH$_3$)$_2$ |
| | 16 | iso-pentyl | Ph- | 7-N$^+$(CH$_3$)$_3$, I$^-$ |
| | 17 | iso-pentyl | Ph- | 7-NHC(=O)CH$_3$ |
| | 18 | iso-pentyl | Ph- | 7-N(CH$_2$CH$_3$)$_2$ |
| | 19 | iso-pentyl | Ph- | 7-NMeCH$_2$CO$_2$H |
| | 20 | iso-pentyl | Ph- | 7-N$^{+(Me)}{_2}$CH$_2$CO$_2$H, I$^-$ |
| | 21 | iso-pentyl | Ph- | 7-(N)-morpholine |
| | 22 | iso-pentyl | Ph- | 7-(N)-azetidine |
| | 23 | iso-pentyl | Ph- | 7-(N)—N-methylazetidinium, I$^-$ |

-continued

| Prefix (FFF.xxx. | Cpd# yyy) | $R^1 = R^2$ | $R^5$ | $(R^x)q$ |
|---|---|---|---|---|
| | 24 | iso-pentyl | Ph- | 7-(N)-pyrrolidine |
| | 25 | iso-pentyl | Ph- | 7-(N)—N-methyl-pyrrolidinium, $I^-$ |
| | 26 | iso-pentyl | Ph- | 7-(N)—N-methyl-morpholinium, $I^-$ |
| | 27 | iso-pentyl | Ph- | 7-(N)—N'-methylpiperazine |
| | 28 | iso-pentyl | Ph- | 7-(N)—N'-dimethylpiperazinium, $I^-$ |
| | 29 | iso-pentyl | Ph- | 7-NH-CBZ |
| | 30 | iso-pentyl | Ph- | 7-NHC(O)$C_5H_{11}$ |
| | 31 | iso-pentyl | Ph- | 7-NHC(O)$CH_2$Br |
| | 32 | iso-pentyl | Ph- | 7-NH—C(NH)$NH_2$ |
| | 33 | iso-pentyl | Ph- | 7-(2)-thiophene |
| | 34 | iso-pentyl | Ph- | 8-methyl |
| | 35 | iso-pentyl | Ph- | 8-ethyl |
| | 36 | iso-pentyl | Ph- | 8-iso-propyl |
| | 37 | iso-pentyl | Ph- | 8-tert-butyl |
| | 38 | iso-pentyl | Ph- | 8-OH |
| | 39 | iso-pentyl | Ph- | 8-OCH$_3$ |
| | 40 | iso-pentyl | Ph- | 8-O(iso-propyl) |
| | 41 | iso-pentyl | Ph- | 8-SCH$_3$ |
| | 42 | iso-pentyl | Ph- | 8-SOCH$_3$ |
| | 43 | iso-pentyl | Ph- | 8-SO$_2$CH$_3$ |
| | 44 | iso-pentyl | Ph- | 8-SCH$_2$CH$_3$ |
| | 45 | iso-pentyl | Ph- | 8-NH$_2$ |
| | 46 | iso-pentyl | Ph- | 8-NHOH |
| | 47 | iso-pentyl | Ph- | 8-NHCH$_3$ |
| | 48 | iso-pentyl | Ph- | 8-N(CH$_3$)$_2$ |
| | 49 | iso-pentyl | Ph- | 8-N$^+$(CH$_3$)$_3$, $I^-$ |
| | 50 | iso-pentyl | Ph- | 8-NHC(=O)CH$_3$ |
| | 51 | iso-pentyl | Ph- | 8-N(CH$_2$CH$_3$)$_2$ |
| | 52 | iso-pentyl | Ph- | 8-NMeCH$_2$CO$_2$H |
| | 53 | iso-pentyl | Ph- | 8-N$^+$(Me)$_2$CH$_2$CO$_2$H, $I^-$ |
| | 54 | iso-pentyl | Ph- | 8-(N)-morpholine |
| | 55 | iso-pentyl | Ph- | 8-(N)-azetidine |
| | 56 | iso-pentyl | Ph- | 8-(N)—N-methylazetidinium, $I^-$ |
| | 57 | iso-pentyl | Ph- | 8-(N)-pyrrolidine |
| | 58 | iso-pentyl | Ph- | 8-(N)—N-methyl-pyrrolidinium, $I^-$ |
| | 59 | iso-pentyl | Ph- | 8-(N)—N-methyl-morpholinium, $I^-$ |
| | 60 | iso-pentyl | Ph- | 8-(N)—N'-methylpiperazine |
| | 61 | iso-pentyl | Ph- | 8-(N)—N'-dimethylpiperazinium, $I^-$ |
| | 62 | iso-pentyl | Ph- | 8-NH-CBZ |
| | 63 | iso-pentyl | Ph- | 8-NHC(O)$C_5H_{11}$ |
| | 64 | iso-pentyl | Ph- | 8-NHC(O)$CH_2$Br |
| | 65 | iso-pentyl | Ph- | 8-NH—C(NH)$NH_2$ |
| | 66 | iso-pentyl | Ph- | 8-(2)-thiophene |
| | 67 | iso-pentyl | Ph- | 9-methyl |
| | 68 | iso-pentyl | Ph- | 9-ethyl |
| | 69 | iso-pentyl | Ph- | 9-iso-propyl |
| | 70 | iso-pentyl | Ph- | 9-tert-butyl |
| | 71 | iso-pentyl | Ph- | 9-OH |
| | 72 | iso-pentyl | Ph- | 9-OCH$_3$ |
| | 73 | iso-pentyl | Ph- | 9-O(iso-propyl) |
| | 74 | iso-pentyl | Ph- | 9-SCH$_3$ |
| | 75 | iso-pentyl | Ph- | 9-SOCH$_3$ |
| | 76 | iso-pentyl | Ph- | 9-SO$_2$CH$_3$ |
| | 77 | iso-pentyl | Ph- | 9-SCH$_2$CH$_3$ |
| | 78 | iso-pentyl | Ph- | 9-NH$_2$ |
| | 79 | iso-pentyl | Ph- | 9-NHOH |
| | 80 | iso-pentyl | Ph- | 9-NHCH$_3$ |
| | 81 | iso-pentyl | Ph- | 9-N(CH$_3$)$_2$ |
| | 82 | iso-pentyl | Ph- | 9-N$^+$(CH$_3$)$_3$, $I^-$ |
| | 83 | iso-pentyl | Ph- | 9-NHC(=O)CH$_3$ |
| | 84 | iso-pentyl | Ph- | 9-N(CH$_2$CH$_3$)$_2$ |
| | 85 | iso-pentyl | Ph- | 9-NMeCH$_2$CO$_2$H |
| | 86 | iso-pentyl | Ph- | 9-N$^+$(Me)$_2$CH$_2$CO$_2$H, $I^-$ |
| | 87 | iso-pentyl | Ph- | 9-(N)-morpholine |
| | 88 | iso-pentyl | Ph- | 9-(N)-azetidine |
| | 89 | iso-pentyl | Ph- | 9-(N)—N-methylazetidinium, $I^{-1}$ |
| | 90 | iso-pentyl | Ph- | 9-(N)-pyrrolidine |
| | 91 | iso-pentyl | Ph- | 9-(N)—N-methyl-pyrrolidinium, $I^-$ |
| | 92 | iso-pentyl | Ph- | 9-(N)—N-methyl-morpholinium, $I^-$ |
| | 93 | iso-pentyl | Ph- | 9-(N)—N'-methylpiperazine |
| | 93 | iso-pentyl | Ph- | 9-(N)—N'-dimethylpiperazinium, $I^-$ |
| | 95 | iso-pentyl | Ph- | 9-NH-CBZ |
| | 96 | iso-pentyl | Ph- | 9-NHC(O)$C_5H_{11}$ |
| | 97 | iso-pentyl | Ph- | 9-NHC(O)$CH_2$Br |
| | 98 | iso-pentyl | Ph- | 9-NH—C(NH)$NH_2$ |
| | 99 | iso-pentyl | Ph- | 9-(2)-thiophene |
| | 100 | iso-pentyl | Ph- | 7-OCH$_3$, 8-OCH$_3$ |
| | 101 | iso-pentyl | Ph- | 7-SCH$_3$, 8-OCH$_3$ |
| | 102 | iso-pentyl | Ph- | 7-SCH$_3$, 8-SCH$_3$ |
| | 103 | iso-pentyl | Ph- | 6-OCH$_3$, 7-OCH$_3$, 8-OCH$_3$ |

| Prefix (FFF.xxx. | Cpd# yyy) | $R^1 = R^2$ | $R^5$ | $(R^x)q$ |
|---|---|---|---|---|
| F101.008 | 01 | CH$_2$C(=O)C$_2$H$_5$ | Ph- | 7-methyl |
| | 02 | CH$_2$C(=O)C$_2$H$_5$ | Ph- | 7-ethyl |
| | 03 | CH$_2$C(=O)C$_2$H$_5$ | Ph- | 7-iso-propyl |
| | 04 | CH$_2$C(=O)C$_2$H$_5$ | Ph- | 7-tert-butyl |
| | 05 | CH$_2$C(=O)C$_2$H$_5$ | Ph- | 7-OH |
| | 06 | CH$_2$C(=O)C$_2$H$_5$ | Ph- | 7-OCH$_3$ |
| | 07 | CH$_2$C(=O)C$_2$H$_5$ | Ph- | 7-O(iso-propyl) |
| | 08 | CH$_2$C(=O)C$_2$H$_5$ | Ph- | 7-SCH$_3$ |
| | 09 | CH$_2$C(=O)C$_2$H$_5$ | Ph- | 7-SOCH$_3$ |
| | 10 | CH$_2$C(=O)C$_2$H$_5$ | Ph- | 7-SO$_2$CH$_3$ |
| | 11 | CH$_2$C(=O)C$_2$H$_5$ | Ph- | 7-SCH$_2$CH$_3$ |
| | 12 | CH$_2$C(=O)C$_2$H$_5$ | Ph- | 7-NH$_2$ |
| | 13 | CH$_2$C(=O)C$_2$H$_5$ | Ph- | 7-NHOH |
| | 14 | CH$_2$C(=O)C$_2$H$_5$ | Ph- | 7-NHCH$_3$ |
| | 15 | CH$_2$C(=O)C$_2$H$_5$ | Ph- | 7-N(CH$_3$)$_2$ |
| | 16 | CH$_2$C(=O)C$_2$H$_5$ | Ph- | 7-N$^+$(CH$_3$)$_3$, $I^-$ |
| | 17 | CH$_2$C(=O)C$_2$H$_5$ | Ph- | 7-NHC(=O)CH$_3$ |
| | 18 | CH$_2$C(=O)C$_2$H$_5$ | Ph- | 7-N(CH$_2$CH$_3$)$_2$ |
| | 19 | CH$_2$C(=O)C$_2$H$_5$ | Ph- | 7-NMeCH$_2$CO$_2$H |
| | 20 | CH$_2$C(=O)C$_2$H$_5$ | Ph- | 7-N$^{+(Me)}$$_2$CH$_2$CO$_2$H, $I^-$ |
| | 21 | CH$_2$C(=O)C$_2$H$_5$ | Ph- | 7-(N)-morpholine |
| | 22 | CH$_2$C(=O)C$_2$H$_5$ | Ph- | 7-(N)-azetidine |
| | 23 | CH$_2$C(=O)C$_2$H$_5$ | Ph- | 7-(N)—N-methyl-azetidinium, $I^-$ |
| | 24 | CH$_2$C(=O)C$_2$H$_5$ | Ph- | 7-(N)-pyrrolidine |
| | 25 | CH$_2$C(=O)C$_2$H$_5$ | Ph- | 7-(N)—N-methyl-pyrrolidinium, $I^-$ |
| | 26 | CH$_2$C(=O)C$_2$H$_5$ | Ph- | 7-(N)—N-methyl-morpholinium, $I^-$ |
| | 27 | CH$_2$C(=O)C$_2$H$_5$ | Ph- | 7-(N)—N'-methylpiperazine |
| | 28 | CH$_2$C(=O)C$_2$H$_5$ | Ph- | 7-(N)—N'-dimethylpiperazinium, $I^-$ |
| | 29 | CH$_2$C(=O)C$_2$H$_5$ | Ph- | 7-NH-CBZ |
| | 30 | CH$_2$C(=O)C$_2$H$_5$ | Ph- | 7-NHC(O)C$_5$H$_{11}$ |
| | 31 | CH$_2$C(=O)C$_2$H$_5$ | Ph- | 7-NHC(O)CH$_2$Br |
| | 32 | CH$_2$C(=O)C$_2$H$_5$ | Ph- | 7-NH—C(NH)NH$_2$ |
| | 33 | CH$_2$C(=O)C$_2$H$_5$ | Ph- | 7-(2)-thiophene |
| | 34 | CH$_2$C(=O)C$_2$H$_5$ | Ph- | 8-methyl |
| | 35 | CH$_2$C(=O)C$_2$H$_5$ | Ph- | 8-ethyl |
| | 36 | CH$_2$C(=O)C$_2$H$_5$ | Ph- | 8-iso-propyl |
| | 37 | CH$_2$C(=O)C$_2$H$_5$ | Ph- | 8-tert-butyl |
| | 38 | CH$_2$C(=O)C$_2$H$_5$ | Ph- | 8-OH |
| | 39 | CH$_2$C(=O)C$_2$H$_5$ | Ph- | 8-OCH$_3$ |
| | 40 | CH$_2$C(=O)C$_2$H$_5$ | Ph- | 8-O(iso-propyl) |
| | 41 | CH$_2$C(=O)C$_2$H$_5$ | Ph- | 8-SCH$_3$ |
| | 42 | CH$_2$C(=O)C$_2$H$_5$ | Ph- | 8-SOCH$_3$ |
| | 43 | CH$_2$C(=O)C$_2$H$_5$ | Ph- | 8-SO$_2$CH$_3$ |
| | 44 | CH$_2$C(=O)C$_2$H$_5$ | Ph- | 8-SCH$_2$CH$_3$ |
| | 45 | CH$_2$C(=O)C$_2$H$_5$ | Ph- | 8-NH$_2$ |
| | 46 | CH$_2$C(=O)C$_2$H$_5$ | Ph- | 8-NHOH |
| | 47 | CH$_2$C(=O)C$_2$H$_5$ | Ph- | 8-NHCH$_3$ |
| | 48 | CH$_2$C(=O)C$_2$H$_5$ | Ph- | 8-N(CH$_3$)$_2$ |
| | 49 | CH$_2$C(=O)C$_2$H$_5$ | Ph- | 8-N$^+$(CH$_3$)$_3$, $I^-$ |
| | 50 | CH$_2$C(=O)C$_2$H$_5$ | Ph- | 8-NHC(=O)CH$_3$ |
| | 51 | CH$_2$C(=O)C$_2$H$_5$ | Ph- | 8-N(CH$_2$CH$_3$)$_2$ |
| | 52 | CH$_2$C(=O)C$_2$H$_5$ | Ph- | 8-NMeCH$_2$CO$_2$H |
| | 53 | CH$_2$C(=O)C$_2$H$_5$ | Ph- | 8-N$^+$(Me)$_2$CH$_2$CO$_2$H, $I^-$ |
| | 54 | CH$_2$C(=O)C$_2$H$_5$ | Ph- | 8-(N)-morpholine |
| | 55 | CH$_2$C(=O)C$_2$H$_5$ | Ph- | 8-(N)-azetidine |
| | 56 | CH$_2$C(=O)C$_2$H$_5$ | Ph- | 8-(N)—N-methyl-azetidinium, $I^-$ |

-continued

| Prefix (FFF.xxx. | Cpd# yyy) | $R^1 = R^2$ | $R^5$ | $(R^x)q$ |
|---|---|---|---|---|
| | 57 | $CH_2C(=O)C_2H_5$ | Ph- | 8-(N)-pyrrolidine |
| | 58 | $CH_2C(=O)C_2H_5$ | Ph- | 8-(N)—N-methyl-pyrrolidinium, $I^-$ |
| | 59 | $CH_2C(=O)C_2H_5$ | Ph- | 8-(N)—N-methyl-morpholinium, $I^-$ |
| | 60 | $CH_2C(=O)C_2H_5$ | Ph- | 8-(N)—N'-methylpiperazine |
| | 61 | $CH_2C(=O)C_2H_5$ | Ph- | 8-(N)—N'-dimethyl-piperazinium, $I^-$ |
| | 62 | $CH_2C(=O)C_2H_5$ | Ph- | 8-NH-CBZ |
| | 63 | $CH_2C(=O)C_2H_5$ | Ph- | 8-NHC(O)$C_5H_{11}$ |
| | 64 | $CH_2C(=O)C_2H_5$ | Ph- | 8-NHC(O)$CH_2$Br |
| | 65 | $CH_2C(=O)C_2H_5$ | Ph- | 8-NH—C(NH)$NH_2$ |
| | 66 | $CH_2C(=O)C_2H_5$ | Ph- | 8-(2)-thiophene |
| | 67 | $CH_2C(=O)C_2H_5$ | Ph- | 9-methyl |
| | 68 | $CH_2C(=O)C_2H_5$ | Ph- | 9-ethyl |
| | 69 | $CH_2C(=O)C_2H_5$ | Ph- | 9-iso-propyl |
| | 70 | $CH_2C(=O)C_2H_5$ | Ph- | 9-tert-butyl |
| | 71 | $CH_2C(=O)C_2H_5$ | Ph- | 9-OH |
| | 72 | $CH_2C(=O)C_2H_5$ | Ph- | 9-$OCH_3$ |
| | 73 | $CH_2C(=O)C_2H_5$ | Ph- | 9-O(iso-propyl) |
| | 74 | $CH_2C(=O)C_2H_5$ | Ph- | 9-$SCH_3$ |
| | 75 | $CH_2C(=O)C_2H_5$ | Ph- | 9-$SOCH_3$ |
| | 76 | $CH_2C(=O)C_2H_5$ | Ph- | 9-$SO_2CH_3$ |
| | 77 | $CH_2C(=O)C_2H_5$ | Ph- | 9-$SCH_2CH_3$ |
| | 78 | $CH_2C(=O)C_2H_5$ | Ph- | 9-$NH_2$ |
| | 79 | $CH_2C(=O)C_2H_5$ | Ph- | 9-NHOH |
| | 80 | $CH_2C(=O)C_2H_5$ | Ph- | 9-$NHCH_3$ |
| | 81 | $CH_2C(=O)C_2H_5$ | Ph- | 9-$N(CH_3)_2$ |
| | 82 | $CH_2C(=O)C_2H_5$ | Ph- | 9-$N^+(CH_3)_3$, $I^-$ |
| | 83 | $CH_2C(=O)C_2H_5$ | Ph- | 9-NHC(=O)$CH_3$ |
| | 84 | $CH_2C(=O)C_2H_5$ | Ph- | 9-$N(CH_2CH_3)_2$ |
| | 85 | $CH_2C(=O)C_2H_5$ | Ph- | 9-$NMeCH_2CO_2H$ |
| | 86 | $CH_2C(=O)C_2H_5$ | Ph- | 9-$N^+(Me)_2CH_2CO_2H$, $I^-$ |
| | 87 | $CH_2C(=O)C_2H_5$ | Ph- | 9-(N)-morpholine |
| | 88 | $CH_2C(=O)C_2H_5$ | Ph- | 9-(N)-azetidine |
| | 89 | $CH_2C(=O)C_2H_5$ | Ph- | 9-(N)—N-methyl-azetidinium, $I^{-1}$ |
| | 90 | $CH_2C(=O)C_2H_5$ | Ph- | 9-(N)-pyrrolidine |
| | 91 | $CH_2C(=O)C_2H_5$ | Ph- | 9-(N)—N-methyl-pyrrolidinium, $I^-$ |
| | 92 | $CH_2C(=O)C_2H_5$ | Ph- | 9-(N)—N-methyl-morpholinium, $I^-$ |
| | 93 | $CH_2C(=O)C_2H_5$ | Ph- | 9-(N)—N'-methyl-piperazine |
| | 93 | $CH_2C(=O)C_2H_5$ | Ph- | 9-(N)—N'-dimethyl-piperazinium, $I^-$ |
| | 95 | $CH_2C(=O)C_2H_5$ | Ph- | 9-NH-CBZ |
| | 96 | $CH_2C(=O)C_2H_5$ | Ph- | 9-NHC(O)$C_5H_{11}$ |
| | 97 | $CH_2C(=O)C_2H_5$ | Ph- | 9-NHC(O)$CH_2$Br |
| | 98 | $CH_2C(=O)C_2H_5$ | Ph- | 9-NH—C(NH)$NH_2$ |
| | 99 | $CH_2C(=O)C_2H_5$ | Ph- | 9-(2)-thiophene |
| | 100 | $CH_2C(=O)C_2H_5$ | Ph- | 7-$OCH_3$, 8-$OCH_3$ |
| | 101 | $CH_2C(=O)C_2H_5$ | Ph- | 7-$SCH_3$, 8-$OCH_3$ |
| | 102 | $CH_2C(=O)C_2H_5$ | Ph- | 7-$SCH_3$, 8-$SCH_3$ |
| | 103 | $CH_2C(=O)C_2H_5$ | Ph- | 6-$OCH_3$, 7-$OCH_3$, 8-$OCH_3$ |

| Prefix (FFF.xxx. | Cpd# yyy) | $R^1 = R^2$ | $R^5$ | $(R^x)q$ |
|---|---|---|---|---|
| F101.009 | 01 | $CH_2OC_2H_5$ | Ph- | 7-methyl |
| | 02 | $CH_2OC_2H_5$ | Ph- | 7-ethyl |
| | 03 | $CH_2OC_2H_5$ | Ph- | 7-iso-propyl |
| | 04 | $CH_2OC_2H_5$ | Ph- | 7-tert-butyl |
| | 05 | $CH_2OC_2H_5$ | Ph- | 7-OH |
| | 06 | $CH_2OC_2H_5$ | Ph- | 7-$OCH_3$ |
| | 07 | $CH_2OC_2H_5$ | Ph- | 7-O(iso-propyl) |
| | 08 | $CH_2OC_2H_5$ | Ph- | 7-$SCH_3$ |
| | 09 | $CH_2OC_2H_5$ | Ph- | 7-$SOCH_3$ |
| | 10 | $CH_2OC_2H_5$ | Ph- | 7-$SO_2CH_3$ |
| | 11 | $CH_2OC_2H_5$ | Ph- | 7-$SCH_2CH_3$ |
| | 12 | $CH_2OC_2H_5$ | Ph- | 7-$NH_2$ |

-continued

| Prefix (FFF.xxx. | Cpd# yyy) | $R^1 = R^2$ | $R^5$ | $(R^x)q$ |
|---|---|---|---|---|
| | 13 | $CH_2OC_2H_5$ | Ph- | 7-NHOH |
| | 14 | $CH_2OC_2H_5$ | Ph- | 7-$NHCH_3$ |
| | 15 | $CH_2OC_2H_5$ | Ph- | 7-$N(CH_3)_2$ |
| | 16 | $CH_2OC_2H_5$ | Ph- | 7-$N^+(CH_3)_3$, $I^-$ |
| | 17 | $CH_2OC_2H_5$ | Ph- | 7-NHC(=O)$CH_3$ |
| | 18 | $CH_2OC_2H_5$ | Ph- | 7-$N(CH_2CH_3)_2$ |
| | 19 | $CH_2OC_2H_5$ | Ph- | 7-$NMeCH_2CO_2H$ |
| | 20 | $CH_2OC_2H_5$ | Ph- | 7-$N^{+(Me)}{}_2CH_2CO_2H$, $I^-$ |
| | 21 | $CH_2OC_2H_5$ | Ph- | 7-(N)-morpholine |
| | 22 | $CH_2OC_2H_5$ | Ph- | 7-(N)-azetidine |
| | 23 | $CH_2OC_2H_5$ | Ph- | 7-(N)—N-methylazetidinium, $I^-$ |
| | 24 | $CH_2OC_2H_5$ | Ph- | 7-(N)-pyrrolidine |
| | 25 | $CH_2OC_2H_5$ | Ph- | 7-(N)—N-methyl-pyrrolidinium, $I^-$ |
| | 26 | $CH_2OC_2H_5$ | Ph- | 7-(N)—N-methyl-morpholinium, $I^-$ |
| | 27 | $CH_2OC_2H_5$ | Ph- | 7-(N)—N'-methylpiperazine |
| | 28 | $CH_2OC_2H_5$ | Ph- | 7-(N)—N'-dimethyl-piperazinium, $I^-$ |
| | 29 | $CH_2OC_2H_5$ | Ph- | 7-NH-CBZ |
| | 30 | $CH_2OC_2H_5$ | Ph- | 7-NHC(O)$C_5H_{11}$ |
| | 31 | $CH_2OC_2H_5$ | Ph- | 7-NHC(O)$CH_2$Br |
| | 32 | $CH_2OC_2H_5$ | Ph- | 7-NH—C(NH)$NH_2$ |
| | 33 | $CH_2OC_2H_5$ | Ph- | 7-(2)-thiophene |
| | 34 | $CH_2OC_2H_5$ | Ph- | 8-methyl |
| | 35 | $CH_2OC_2H_5$ | Ph- | 8-ethyl |
| | 36 | $CH_2OC_2H_5$ | Ph- | 8-iso-propyl |
| | 37 | $CH_2OC_2H_5$ | Ph- | 8-tert-butyl |
| | 38 | $CH_2OC_2H_5$ | Ph- | 8-OH |
| | 39 | $CH_2OC_2H_5$ | Ph- | 8-$OCH_3$ |
| | 40 | $CH_2OC_2H_5$ | Ph- | 8-O(iso-propyl) |
| | 41 | $CH_2OC_2H_5$ | Ph- | 8-$SCH_3$ |
| | 42 | $CH_2OC_2H_5$ | Ph- | 8-$SOCH_3$ |
| | 43 | $CH_2OC_2H_5$ | Ph- | 8-$SO_2CH_3$ |
| | 44 | $CH_2OC_2H_5$ | Ph- | 8-$SCH_2CH_3$ |
| | 45 | $CH_2OC_2H_5$ | Ph- | 8-$NH_2$ |
| | 46 | $CH_2OC_2H_5$ | Ph- | 8-NHOH |
| | 47 | $CH_2OC_2H_5$ | Ph- | 8-$NHCH_3$ |
| | 48 | $CH_2OC_2H_5$ | Ph- | 8-$N(CH_3)_2$ |
| | 49 | $CH_2OC_2H_5$ | Ph- | 8-$N^+(CH_3)_3$, $I^-$ |
| | 50 | $CH_2OC_2H_5$ | Ph- | 8-NHC(=O)$CH_3$ |
| | 51 | $CH_2OC_2H_5$ | Ph- | 8-$N(CH_2CH_3)_2$ |
| | 52 | $CH_2OC_2H_5$ | Ph- | 8-$NMeCH_2CO_2H$ |
| | 53 | $CH_2OC_2H_5$ | Ph- | 8-$N^+(Me)_2CH_2CO_2H$, $I^-$ |
| | 54 | $CH_2OC_2H_5$ | Ph- | 8-(N)-morpholine |
| | 55 | $CH_2OC_2H_5$ | Ph- | 8-(N)-azetidine |
| | 56 | $CH_2OC_2H_5$ | Ph- | 8-(N)—N-methylazetidinium, $I^-$ |
| | 57 | $CH_2OC_2H_5$ | Ph- | 8-(N)-pyrrolidine |
| | 58 | $CH_2OC_2H_5$ | Ph- | 8-(N)—N-methyl-pyrrolidinium, $I^-$ |
| | 59 | $CH_2OC_2H_5$ | Ph- | 8-(N)—N-methyl-morpholinium, $I^-$ |
| | 60 | $CH_2OC_2H_5$ | Ph- | 8-(N)—N'-methylpiperazine |
| | 61 | $CH_2OC_2H_5$ | Ph- | 8-(N)—N'-dimethyl-piperazinium, $I^-$ |
| | 62 | $CH_2OC_2H_5$ | Ph- | 8-NH-CBZ |
| | 63 | $CH_2OC_2H_5$ | Ph- | 8-NHC(O)$C_5H_{11}$ |
| | 64 | $CH_2OC_2H_5$ | Ph- | 8-NHC(O)$CH_2$Br |
| | 65 | $CH_2OC_2H_5$ | Ph- | 8-NH—C(NH)$NH_2$ |
| | 66 | $CH_2OC_2H_5$ | Ph- | 8-(2)-thiophene |
| | 67 | $CH_2OC_2H_5$ | Ph- | 9-methyl |
| | 68 | $CH_2OC_2H_5$ | Ph- | 9-ethyl |
| | 69 | $CH_2OC_2H_5$ | Ph- | 9-iso-propyl |
| | 70 | $CH_2OC_2H_5$ | Ph- | 9-tert-butyl |
| | 71 | $CH_2OC_2H_5$ | Ph- | 9-OH |
| | 72 | $CH_2OC_2H_5$ | Ph- | 9-$OCH_3$ |
| | 73 | $CH_2OC_2H_5$ | Ph- | 9-O(iso-propyl) |
| | 74 | $CH_2OC_2H_5$ | Ph- | 9-$SCH_3$ |
| | 75 | $CH_2OC_2H_5$ | Ph- | 9-$SOCH_3$ |
| | 76 | $CH_2OC_2H_5$ | Ph- | 9-$SO_2CH_3$ |
| | 77 | $CH_2OC_2H_5$ | Ph- | 9-$SCH_2CH_3$ |
| | 78 | $CH_2OC_2H_5$ | Ph- | 9-$NH_2$ |
| | 79 | $CH_2OC_2H_5$ | Ph- | 9-NHOH |
| | 80 | $CH_2OC_2H_5$ | Ph- | 9-$NHCH_3$ |
| | 81 | $CH_2OC_2H_5$ | Ph- | 9-$N(CH_3)_2$ |
| | 82 | $CH_2OC_2H_5$ | Ph- | 9-$N^+(CH_3)_3$, $I^-$ |
| | 83 | $CH_2OC_2H_5$ | Ph- | 9-NHC(=O)$CH_3$ |
| | 84 | $CH_2OC_2H_5$ | Ph- | 9-$N(CH_2CH_3)_2$ |
| | 85 | $CH_2OC_2H_5$ | Ph- | 9-$NMeCH_2CO_2H$ |
| | 86 | $CH_2OC_2H_5$ | Ph- | 9-$N^+(Me)_2CH_2CO_2H$, $I^-$ |

-continued

| Prefix (FFF.xxx. | Cpd# yyy) | R¹ = R² | R⁵ | (Rˣ)q |
|---|---|---|---|---|
| | 87 | $CH_2OC_2H_5$ | Ph- | 9-(N)-morpholine |
| | 88 | $CH_2OC_2H_5$ | Ph- | 9-(N)-azetidine |
| | 89 | $CH_2OC_2H_5$ | Ph- | 9-(N)—N-methylazetidinium, $I^{-1}$ |
| | 90 | $CH_2OC_2H_5$ | Ph- | 9-(N)-pyrrolidine |
| | 91 | $CH_2OC_2H_5$ | Ph- | 9-(N)—N-methyl-pyrrolidinium, $I^-$ |
| | 92 | $CH_2OC_2H_5$ | Ph- | 9-(N)—N-methyl-morpholinium, $I^-$ |
| | 93 | $CH_2OC_2H_5$ | Ph- | 9-(N)—N'-methylpiperazine |
| | 93 | $CH_2OC_2H_5$ | Ph- | 9-(N)—N'-dimethyl piperazinium, $I^-$ |
| | 95 | $CH_2OC_2H_5$ | Ph- | 9-NH-CBZ |
| | 96 | $CH_2OC_2H_5$ | Ph- | 9-NHC(O)$C_5H_{11}$ |
| | 97 | $CH_2OC_2H_5$ | Ph- | 9-NHC(O)$CH_2$Br |
| | 98 | $CH_2OC_2H_5$ | Ph- | 9-NH—C(NH)$NH_2$ |
| | 99 | $CH_2OC_2H_5$ | Ph- | 9-(2)-thiophene |
| | 100 | $CH_2OC_2H_5$ | Ph- | 7-$OCH_3$, 8-$OCH_3$ |
| | 101 | $CH_2OC_2H_5$ | Ph- | 7-$SCH_3$, 8-$OCH_3$ |
| | 102 | $CH_2OC_2H_5$ | Ph- | 7-$SCH_3$, 8-$SCH_3$ |
| | 103 | $CH_2OC_2H_5$ | Ph- | 6-$OCH_3$, 7-$OCH_3$, 8-$OCH_3$ |

| Prefix (FFF.xxx. | Cpd# yyy) | R¹ = R² | R⁵ | (Rˣ)q |
|---|---|---|---|---|
| F101.010 | 01 | $CH_2CH(OH)C_2H_5$ | Ph- | 7-methyl |
| | 02 | $CH_2CH(OH)C_2H_5$ | Ph- | 7-ethyl |
| | 03 | $CH_2CH(OH)C_2H_5$ | Ph- | 7-iso-propyl |
| | 04 | $CH_2CH(OH)C_2H_5$ | Ph- | 7-tert-butyl |
| | 05 | $CH_2CH(OH)C_2H_5$ | Ph- | 7-OH |
| | 06 | $CH_2CH(OH)C_2H_5$ | Ph- | 7-$OCH_3$ |
| | 07 | $CH_2CH(OH)C_2H_5$ | Ph- | 7-O(iso-propyl) |
| | 08 | $CH_2CH(OH)C_2H_5$ | Ph- | 7-$SCH_3$ |
| | 09 | $CH_2CH(OH)C_2H_5$ | Ph- | 7-$SOCH_3$ |
| | 10 | $CH_2CH(OH)C_2H_5$ | Ph- | 7-$SO_2CH_3$ |
| | 11 | $CH_2CH(OH)C_2H_5$ | Ph- | 7-$SCH_2CH_3$ |
| | 12 | $CH_2CH(OH)C_2H_5$ | Ph- | 7-$NH_2$ |
| | 13 | $CH_2CH(OH)C_2H_5$ | Ph- | 7-NHOH |
| | 14 | $CH_2CH(OH)C_2H_5$ | Ph- | 7-$NHCH_3$ |
| | 15 | $CH_2CH(OH)C_2H_5$ | Ph- | 7-$N(CH_3)_2$ |
| | 16 | $CH_2CH(OH)C_2H_5$ | Ph- | 7-$N^+(CH_3)_3$, $I^-$ |
| | 17 | $CH_2CH(OH)C_2H_5$ | Ph- | 7-NHC(=O)$CH_3$ |
| | 18 | $CH_2CH(OH)C_2H_5$ | Ph- | 7-$N(CH_2CH_3)_2$ |
| | 19 | $CH_2CH(OH)C_2H_5$ | Ph- | 7-$NMeCH_2CO_2H$ |
| | 20 | $CH_2CH(OH)C_2H_5$ | Ph- | 7-$N^{+(Me)}{}_2CH_2CO_2H$, $I^-$ |
| | 21 | $CH_2CH(OH)C_2H_5$ | Ph- | 7-(N)-morpholine |
| | 22 | $CH_2CH(OH)C_2H_5$ | Ph- | 7-(N)-azetidine |
| | 23 | $CH_2CH(OH)C_2H_5$ | Ph- | 7-(N)—N-methyl-azetidinium, $I^-$ |
| | 24 | $CH_2CH(OH)C_2H_5$ | Ph- | 7-(N)-pyrrolidine |
| | 25 | $CH_2CH(OH)C_2H_5$ | Ph- | 7-(N)—N-methyl-pyrrolidinium, $I^-$ |
| | 26 | $CH_2CH(OH)C_2H_5$ | Ph- | 7-(N)—N-methyl-morpholinium, $I^-$ |
| | 27 | $CH_2CH(OH)C_2H_5$ | Ph- | 7-(N)—N'-methylpiperazine |
| | 28 | $CH_2CH(OH)C_2H_5$ | Ph- | 7-(N)—N'-dimethyl-piperazinium, $I^-$ |
| | 29 | $CH_2CH(OH)C_2H_5$ | Ph- | 7-NH-CBZ |
| | 30 | $CH_2CH(OH)C_2H_5$ | Ph- | 7-NHC(O)$C_5H_{11}$ |
| | 31 | $CH_2CH(OH)C_2H_5$ | Ph- | 7-NHC(O)$CH_2$Br |
| | 32 | $CH_2CH(OH)C_2H_5$ | Ph- | 7-NH—C(NH)$NH_2$ |
| | 33 | $CH_2CH(OH)C_2H_5$ | Ph- | 7-(2)-thiophene |
| | 34 | $CH_2CH(OH)C_2H_5$ | Ph- | 8-methyl |
| | 35 | $CH_2CH(OH)C_2H_5$ | Ph- | 8-ethyl |
| | 36 | $CH_2CH(OH)C_2H_5$ | Ph- | 8-iso-propyl |
| | 37 | $CH_2CH(OH)C_2H_5$ | Ph- | 8-tert-butyl |
| | 38 | $CH_2CH(OH)C_2H_5$ | Ph- | 8-OH |
| | 39 | $CH_2CH(OH)C_2H_5$ | Ph- | 8-$OCH_3$ |
| | 40 | $CH_2CH(OH)C_2H_5$ | Ph- | 8-O(iso-propyl) |
| | 41 | $CH_2CH(OH)C_2H_5$ | Ph- | 8-$SCH_3$ |
| | 42 | $CH_2CH(OH)C_2H_5$ | Ph- | 8-$SOCH_3$ |
| | 43 | $CH_2CH(OH)C_2H_5$ | Ph- | 8-$SO_2CH_3$ |
| | 44 | $CH_2CH(OH)C_2H_5$ | Ph- | 8-$SCH_2CH_3$ |

-continued

| Prefix (FFF.xxx. | Cpd# yyy) | R¹ = R² | R⁵ | (Rˣ)q |
|---|---|---|---|---|
| | 45 | $CH_2CH(OH)C_2H_5$ | Ph- | 8-$NH_2$ |
| | 46 | $CH_2CH(OH)C_2H_5$ | Ph- | 8-NHOH |
| | 47 | $CH_2CH(OH)C_2H_5$ | Ph- | 8-$NHCH_3$ |
| | 48 | $CH_2CH(OH)C_2H_5$ | Ph- | 8-$N(CH_3)_2$ |
| | 49 | $CH_2CH(OH)C_2H_5$ | Ph- | 8-$N^+(CH_3)_3$, $I^-$ |
| | 50 | $CH_2CH(OH)C_2H_5$ | Ph- | 8-NHC(=O)$CH_3$ |
| | 51 | $CH_2CH(OH)C_2H_5$ | Ph- | 8-$N(CH_2CH_3)_2$ |
| | 52 | $CH_2CH(OH)C_2H_5$ | Ph- | 8-$NMeCH_2CO_2H$ |
| | 53 | $CH_2CH(OH)C_2H_5$ | Ph- | 8-$N^+(Me)_2CH_2CO_2H$, $I^-$ |
| | 54 | $CH_2CH(OH)C_2H_5$ | Ph- | 8-(N)-morpholine |
| | 55 | $CH_2CH(OH)C_2H_5$ | Ph- | 8-(N)-azetidine |
| | 56 | $CH_2CH(OH)C_2H_5$ | Ph- | 8-(N)—N-methyl-azetidinium, $I^-$ |
| | 57 | $CH_2CH(OH)C_2H_5$ | Ph- | 8-(N)-pyrrolidine |
| | 58 | $CH_2CH(OH)C_2H_5$ | Ph- | 8-(N)—N-methyl-pyrrolidinium, $I^-$ |
| | 59 | $CH_2CH(OH)C_2H_5$ | Ph- | 8-(N)—N-methyl-morpholinium, $I^-$ |
| | 60 | $CH_2CH(OH)C_2H_5$ | Ph- | 8-(N)—N'-methylpiperazine |
| | 61 | $CH_2CH(OH)C_2H_5$ | Ph- | 8-(N)—N'-dimethyl-piperazinium, $I^-$ |
| | 62 | $CH_2CH(OH)C_2H_5$ | Ph- | 8-NH-CBZ |
| | 63 | $CH_2CH(OH)C_2H_5$ | Ph- | 8-NHC(O)$C_5H_{11}$ |
| | 64 | $CH_2CH(OH)C_2H_5$ | Ph- | 8-NHC(O)$CH_2$Br |
| | 65 | $CH_2CH(OH)C_2H_5$ | Ph- | 8-NH—C(NH)$NH_2$ |
| | 66 | $CH_2CH(OH)C_2H_5$ | Ph- | 8-(2)-thiophene |
| | 67 | $CH_2CH(OH)C_2H_5$ | Ph- | 9-methyl |
| | 68 | $CH_2CH(OH)C_2H_5$ | Ph- | 9-ethyl |
| | 69 | $CH_2CH(OH)C_2H_5$ | Ph- | 9-iso-propyl |
| | 70 | $CH_2CH(OH)C_2H_5$ | Ph- | 9-tert-butyl |
| | 71 | $CH_2CH(OH)C_2H_5$ | Ph- | 9-OH |
| | 72 | $CH_2CH(OH)C_2H_5$ | Ph- | 9-$OCH_3$ |
| | 73 | $CH_2CH(OH)C_2H_5$ | Ph- | 9-O(iso-propyl) |
| | 74 | $CH_2CH(OH)C_2H_5$ | Ph- | 9-$SCH_3$ |
| | 75 | $CH_2CH(OH)C_2H_5$ | Ph- | 9-$SOCH_3$ |
| | 76 | $CH_2CH(OH)C_2H_5$ | Ph- | 9-$SO_2CH_3$ |
| | 77 | $CH_2CH(OH)C_2H_5$ | Ph- | 9-$SCH_2CH_3$ |
| | 78 | $CH_2CH(OH)C_2H_5$ | Ph- | 9-$NH_2$ |
| | 79 | $CH_2CH(OH)C_2H_5$ | Ph- | 9-NHOH |
| | 80 | $CH_2CH(OH)C_2H_5$ | Ph- | 9-$NHCH_3$ |
| | 81 | $CH_2CH(OH)C_2H_5$ | Ph- | 9-$N(CH_3)_2$ |
| | 82 | $CH_2CH(OH)C_2H_5$ | Ph- | 9-$N^+(CH_3)_3$, $I^-$ |
| | 83 | $CH_2CH(OH)C_2H_5$ | Ph- | 9-NHC(=O)$CH_3$ |
| | 84 | $CH_2CH(OH)C_2H_5$ | Ph- | 9-$N(CH_2CH_3)_2$ |
| | 85 | $CH_2CH(OH)C_2H_5$ | Ph- | 9-$NMeCH_2CO_2H$ |
| | 86 | $CH_2CH(OH)C_2H_5$ | Ph- | 9-$N^+(Me)_2CH_2CO_2H$, $I^-$ |
| | 87 | $CH_2CH(OH)C_2H_5$ | Ph- | 9-(N)-morpholine |
| | 88 | $CH_2CH(OH)C_2H_5$ | Ph- | 9-(N)-azetidine |
| | 89 | $CH_2CH(OH)C_2H_5$ | Ph- | 9-(N)—N-methyl-azetidinium, $I^{-1}$ |
| | 90 | $CH_2CH(OH)C_2H_5$ | Ph- | 9-(N)-pyrrolidine |
| | 91 | $CH_2CH(OH)C_2H_5$ | Ph- | 9-(N)—N-methyl-pyrrolidinium, $I^-$ |
| | 92 | $CH_2CH(OH)C_2H_5$ | Ph- | 9-(N)—N-methyl-morpholinium, $I^-$ |
| | 93 | $CH_2CH(OH)C_2H_5$ | Ph- | 9-(N)—N'-methylpiperazine |
| | 93 | $CH_2CH(OH)C_2H_5$ | Ph- | 9-(N)—N'-dimethyl-piperazinium, $I^-$ |
| | 95 | $CH_2CH(OH)C_2H_5$ | Ph- | 9-NH-CBZ |
| | 96 | $CH_2CH(OH)C_2H_5$ | Ph- | 9-NHC(O)$C_5H_{11}$ |
| | 97 | $CH_2CH(OH)C_2H_5$ | Ph- | 9-NHC(O)$CH_2$Br |
| | 98 | $CH_2CH(OH)C_2H_5$ | Ph- | 9-NH—C(NH)$NH_2$ |
| | 99 | $CH_2CH(OH)C_2H_5$ | Ph- | 9-(2)-thiophene |
| | 100 | $CH_2CH(OH)C_2H_5$ | Ph- | 7-$OCH_3$, 8-$OCH_3$ |
| | 101 | $CH_2CH(OH)C_2H_5$ | Ph- | 7-$SCH_3$, 8-$OCH_3$ |
| | 102 | $CH_2CH(OH)C_2H_5$ | Ph- | 7-$SCH_3$, 8-$SCH_3$ |
| | 103 | $CH_2CH(OH)C_2H_5$ | Ph- | 6-$OCH_3$, 7-$OCH_3$, 8-$OCH_3$ |

| Prefix (FFF.xxx. | Cpd # vvv) | R¹=R² | R⁵ | (R¹)q |
|---|---|---|---|---|
| F101.011 | 01 | CH₂O-(4-picoline) | Ph— | 7-methyl |
| | 02 | CH₂O-(4-picoline) | Ph— | 7-ethyl |
| | 03 | CH₂O-(4-picoline) | Ph— | 7-iso-propyl |
| | 04 | CH₂O-(4-picoline) | Ph— | 7-tert-butyl |
| | 05 | CH₂O-(4-picoline) | Ph— | 7-OH |
| | 06 | CH₂O-(4-picoline) | Ph— | 7-CCH₃ |
| | 07 | CH₂O-(4-picoline) | Ph— | 7-o(iso-propyl) |
| | 08 | CH₂O-(4-picoline) | Ph— | 7-SCH₃ |
| | 09 | CH₂O-(4-picoline) | Ph— | 7-SOCH₃ |
| | 10 | CH₂O-(4-picoline) | Ph— | 7-SO₂CH₃ |
| | 11 | CH₂O-(4-picoline) | Ph— | 7-SCH₂CH₃ |
| | 12 | CH₂O-(4-picoline) | Ph— | 7-NH₂ |
| | 13 | CH₂O-(4-picoline) | Ph— | 7-NHOH |
| | 14 | CH₂O-(4-picoline) | Ph— | 7-NHCH₃ |
| | 15 | CH₂O-(4-picoline) | Ph— | 7-N(CH₃)₂ |
| | 16 | CH₂O-(4-picoline) | Ph— | 7-N⁺(CH₃)₃, I⁻ |
| | 17 | CH₂O-(4-picoline) | Ph— | 7-NHC(=O)CH₃ |
| | 18 | CH₂O-(4-picoline) | Ph— | 7-N(CH₂CH₃)₂ |
| | 19 | CH₂O-(4-picoline) | Ph— | 7-NMeCH₂CO₂H |
| | 20 | CH₂O-(4-picoline) | Ph— | 7-N⁻(Me)₂CH₂CO₂H, I⁻ |
| | 21 | CH₂O-(4-picoline) | Ph— | 7-(N)-morpholine |
| | 22 | CH₂O-(4-picoline) | Ph— | 7-(N)-azetidine |
| | 23 | CH₂O-(4-picoline) | Ph— | 7-(N)—N-methylazetidinium, I⁻ |
| | 24 | CH₂O-(4-picoline) | Ph— | 7-(N)-pyrrolidine |
| | 25 | CH₂O-(4-picoline) | Ph— | 7-(N)—N-methyl-pyrrolidinium, I⁻ |
| | 26 | CH₂O-(4-picoline) | Ph— | 7-(N)—N-methyl-morpholinium, I⁻ |
| | 27 | CH₂O-(4-picoline) | Ph— | 7-(N)—N'-methylpiperazine |
| | 28 | CH₂O-(4-picoline) | Ph— | 7-(N)—N'-dimethylpiperazinium, I⁻ |
| | 29 | CH₂O-(4-picoline) | Ph— | 7-NH—CBZ |
| | 30 | CH₂O-(4-picoline) | Ph— | 7-NHC(O)C₅H₁₁ |
| | 31 | CH₂O-(4-picoline) | Ph— | 7-NHC(O)CH₂Br |
| | 32 | CH₂O-(4-picoline) | Ph— | 7-NH—C(NH)NH₂ |
| | 33 | CH₂O-(4-picoline) | Ph— | 7-(2)-thiophene |
| | 34 | CH₂O-(4-picoline) | Ph— | 8-methyl |
| | 35 | CH₂O-(4-picoline) | Ph— | 8-ethyl |
| | 36 | CH₂O-(4-picoline) | Ph— | 8-iso-propyl |
| | 37 | CH₂O-(4-picoline) | Ph— | 8-tert-butyl |
| | 38 | CH₂O-(4-picoline) | Ph— | 8-OH |
| | 39 | CH₂O-(4-picoline) | Ph— | 8-OCH₃ |
| | 40 | CH₂O-(4-picoline) | Ph— | 8-O(iso-propyl) |
| | 41 | CH₂O-(4-picoline) | Ph— | 8-SCH₃ |
| | 42 | CH₂O-(4-picoline) | Ph— | 8-SOCH₃ |
| | 43 | CH₂O-(4-picoline) | Ph— | 8-SO₂CH₃ |
| | 44 | CH₂O-(4-picoline) | Ph— | 8-SCH₂CH₃ |
| | 45 | CH₂O-(4-picoline) | Ph— | 8-NH₂ |
| | 46 | CH₂O-(4-picoline) | Ph— | 8-NHOH |
| | 47 | CH₂O-(4-picoline) | Ph— | 8-NHCH₃ |
| | 48 | CH₂O-(4-picoline) | Ph— | 8-N(CH₃)₂ |
| | 49 | CH₂O-(4-picoline) | Ph— | 8-N⁺(CH₃)₃, I⁻ |
| | 50 | CH₂O-(4-picoline) | Ph— | 8-NHC-(=O)CH₃ |
| | 51 | CH₂O-(4-picoline) | Ph— | 8-N(CH₂CH₃)₂ |
| | 52 | CH₂O-(4-picoline) | Ph— | 8-NMeCH₂CO₂H |
| | 53 | CH₂O-(4-picoline) | Ph— | 8-N⁺(Me)₂CH₂CO₂H, I⁻ |
| | 54 | CH₂O-(4-picoline) | Ph— | 8-(N)-morpholine |
| | 55 | CH₂O-(4-picoline) | Ph— | 8-(N)-azetidine |
| | 56 | CH₂O-(4-picoline) | Ph— | 8-(N)—N-methylazetidinium, I⁻ |
| | 57 | CH₂O-(4-picoline) | Ph— | 8-(N)-pyrrolidine |
| | 58 | CH₂O-(4-picoline) | Ph— | 8-(N)—N-methyl-pyrrolidinium, I⁻ |
| | 59 | CH₂O-(4-picoline) | Ph— | 8-(N)—N-methyl-morpholinium, I⁻ |
| | 60 | CH₂O-(4-picoline) | Ph— | 8-(N)—N'-methylpiperazine |
| | 61 | CH₂O-(4-picoline) | Ph— | 8-(N)—N'-dimethylpiperazinium, I⁻ |
| | 62 | CH₂O-(4-picoline) | Ph— | 8-NH—CBZ |
| | 63 | CH₂O-(4-picoline) | Ph— | 8-NHC(O)C₅H₁₁ |
| | 64 | CH₂O-(4-picoline) | Ph— | 8-NHC(O)CH₂Br |
| | 65 | CH₂O-(4-picoline) | Ph— | 8-NH—C(NH)NH₂ |
| | 66 | CH₂O-(4-picoline) | Ph— | 8-(2)-thiophene |
| | 67 | CH₂O-(4-picoline) | Ph— | 9-methyl |
| | 68 | CH₂O-(4-picoline) | Ph— | 9-ethyl |
| | 69 | CH₂O-(4-picoline) | Ph— | 9-iso-propyl |
| | 70 | CH₂O-(4-picoline) | Ph— | 9-tert-butyl |
| | 71 | CH₂O-(4-picoline) | Ph— | 9-OH |
| | 72 | CH₂O-(4-picoline) | Ph— | 9-OCH₃ |
| | 73 | CH₂O-(4-picoline) | Ph— | 9-O(iso-propyl) |
| | 74 | CH₂O-(4-picoline) | Ph— | 9-SCH₃ |
| | 75 | CH₂O-(4-picoline) | Ph— | 9-SOCH₃ |
| | 76 | CH₂O-(4-picoline) | Ph— | 9-SO₂CH₃ |

-continued

| Prefix (FFF.xxx. | Cpd # vvv) | $R^1=R^2$ | $R^5$ | $(R^1)q$ |
|---|---|---|---|---|
| | 77 | $CH_2O$-(4-picoline) | Ph— | 9-$SCH_2CH_3$ |
| | 78 | $CH_2O$-(4-picoline) | Ph— | 9-$NH_2$ |
| | 79 | $CH_2O$-(4-picoline) | Ph— | 9-NHOH |
| | 80 | $CH_2O$-(4-picoline) | Ph— | 9-$NHCH_3$ |
| | 81 | $CH_2O$-(4-picoline) | Ph— | 9-$N(CH_3)_2$ |
| | 82 | $CH_2O$-(4-picoline) | Ph— | 9-$N^+(CH_3)_3$, $I^-$ |
| | 83 | $CH_2O$-(4-picoline) | Ph— | 9-NHC-(=O)$CH_3$ |
| | 84 | $CH_2O$-(4-picoline) | Ph— | 9-$N(CH_2CH_3)_2$ |
| | 85 | $CH_2O$-(4-picoline) | Ph— | 9-$NMeCH_2CO_2H$ |
| | 86 | $CH_2O$-(4-picoline) | Ph— | 9-$N^+(Me)_2CH_2CO_2H$, $I^-$ |
| | 87 | $CH_2O$-(4-picoline) | Ph— | 9-(N)-morpholine |
| | 88 | $CH_2O$-(4-picoline) | Ph— | 9-(N)-azetidine |
| | 89 | $CH_2O$-(4-picoline) | Ph— | 9-(N)—N-methylazetidinium, $I^-$ |
| | 90 | $CH_2O$-(4-picoline) | Ph— | 9-(N)-pyrrolidine |
| | 91 | $CH_2O$-(4-picoline) | Ph— | 9-(N)—N-methyl-pyrrolidinium, $I^-$ |
| | 92 | $CH_2O$-(4-picoline) | Ph— | 9-(N)—N-methyl-morpholinium, $I^-$ |
| | 93 | $CH_2O$-(4-picoline) | Ph— | 9-(N)—N'-methylpiperazine |
| | 93 | $CH_2O$-(4-picoline) | Ph— | 9-(N)—N'-dimethylpiperazinium, $I^-$ |
| | 95 | $CH_2O$-(4-picoline) | Ph— | 9-NH—CBZ |
| | 96 | $CH_2O$-(4-picoline) | Ph— | 9-NHC(O)$C_5H_{11}$ |
| | 97 | $CH_2O$-(4-picoline) | Ph— | 9-NHC(O)$CH_2Br$ |
| | 98 | $CH_2O$-(4-picoline) | Ph— | 9-NH—C(NH)$NH_2$ |
| | 99 | $CH_2O$-(4-picoline) | Ph— | 9-(2)-thiophene |
| | 100 | $CH_2O$-(4-picoline) | Ph— | 7-$CCH_3$, 8-$OCH_3$ |
| | 101 | $CH_2O$-(4-picoline) | Ph— | 7-$SCH_3$, 8-$CCH_3$ |
| | 102 | $CH_2O$-(4-picoline) | Ph— | 7-$SCH_3$, 8-$SCH_3$ |
| | 103 | $CH_2O$-(4-picoline) | Ph— | 6-$CCH_3$, 7-$CCH_3$, 8-$CCH_3$ |

Additional Structures of the Present Invention

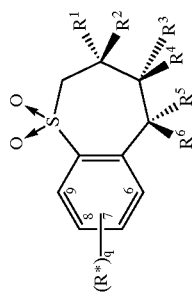
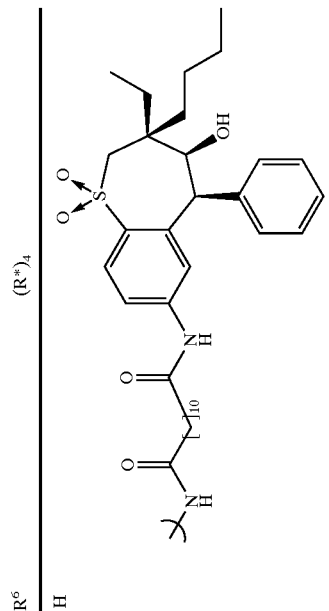
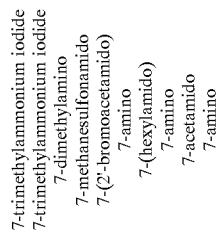

| Compound Number | R¹ | R² | R³ | R⁴ | R⁵ | R⁶ | (R*)₄ |
|---|---|---|---|---|---|---|---|
| 101 | ethyl | n-butyl | OH | H | phenyl | H | at the 7-position |
| 102 | ethyl | n-butyl | OH | H | phenyl | H | 7-trimethylammonium iodide |
| 103 | n-butyl | ethyl | OH | H | phenyl | H | 7-trimethylammonium iodide |
| 104 | ethyl | n-butyl | OH | H | phenyl | H | 7-dimethylamino |
| 105 | ethyl | n-butyl | OH | H | phenyl | H | 7-methanesulfonamido |
| 106 | ethyl | n-butyl | OH | H | phenyl | H | 7-(2'-bromoacetamido) |
| 107 | n-butyl | ethyl | OH | H | 4-(decyloxy)phenyl | H | 7-amino |
| 108 | ethyl | n-butyl | OH | H | phenyl | H | 7-(hexylamido) |
| 109 | ethyl | n-butyl | OH | H | 4-(decyloxy)phenyl | H | 7-amino |
| 110 | ethyl | n-butyl | OH | H | phenyl | H | 7-acetamido |
| 111 | n-butyl | ethyl | OH | H | 4-hydroxyphenyl | H | 7-amino |

-continued

Additional Structures of the Present Invention

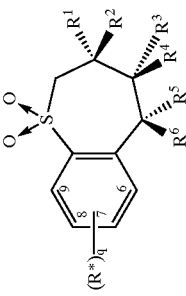

| Compound Number | R¹ | R² | R³ | R⁴ | R⁵ | R⁶ | (R*)$_q$ |
|---|---|---|---|---|---|---|---|
| 112 | ethyl | n-butyl | OH | H | 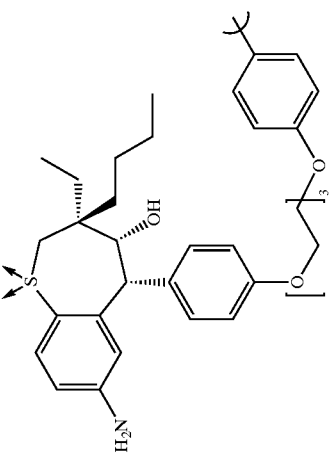 | H | 7-amino |
| 113 | ethyl | n-butyl | OH | H | 4-hydroxyphenyl | H | 7-amino |
| 114 | ethyl | n-butyl | OH | H | 4-methoxyphenyl | H | 7-amino |
| 115 | n-butyl | ethyl | OH | H | 4-methoxyphenyl | H | 7-(O-benzylcarbamato) |
| 116 | n-butyl | ethyl | OH | H | 4-methoxyphenyl | H | 7-(O-benzylcarbamato) |
| 117 | n-butyl | ethyl | OH | H | phenyl | H | 7-(O-benzylcarbamato) |
| 118 | ethyl | n-butyl | OH | H | phenyl | H | 7-(O-benzylcarbamato) |
| 119 | ethyl | n-butyl | OH | H | phenyl | H | 7-(O-benzylcarbamato) |
| 120 | ethyl | n-butyl | OH | H | phenyl | H | 7-(O-tert-butylcarbamato) |
| 121 | ethyl | n-butyl | OH | H | phenyl | H | 7-amino |
| 122 | n-butyl | ethyl | OH | H | phenyl | H | 7-amino |
| 123 | ethyl | n-butyl | OH | H | phenyl | H | 7-hexylamino |
| 124 | n-butyl | ethyl | OH | H | phenyl | H | 7-(hexylamino) |
| 125 | ethyl | n-butyl | OH | H | phenyl | H | 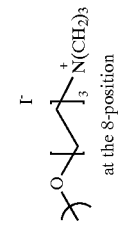 I⁻ at the 8-position |

-continued

Additional Structures of the Present Invention

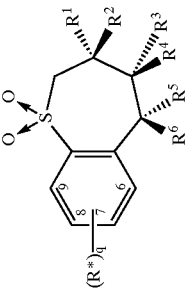

| Compound Number | R¹ | R² | R³ | R⁴ | R⁵ | R⁶ | (R*)₄ |
|---|---|---|---|---|---|---|---|
| 126 | n-butyl | ethyl | OH | H | 4-fluorophenyl | H | 7-(O-benzylcarbamato) |
| 127 | n-butyl | ethyl | OH | H | 4-fluorophenyl | H | 7-amino |
| 128 | ethyl | n-butyl | OH | H | 4-fluorophenyl | H | 7-(O-benzylcarbamato) |
| 129 | ethyl | n-butyl | OH | H | 4-fluorophenyl | H | 7-amino |
| 131 | ethyl | n-butyl | OH | H | 4-fluorophenyl | H | 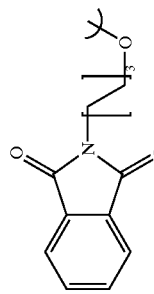 at the 7-position |
| 132 | ethyl | n-butyl | OH | H | phenyl | H | |
| 133 | ethyl | n-butyl | OH | H | phenyl | H |  at the 8-position 8-(hexyloxy) |

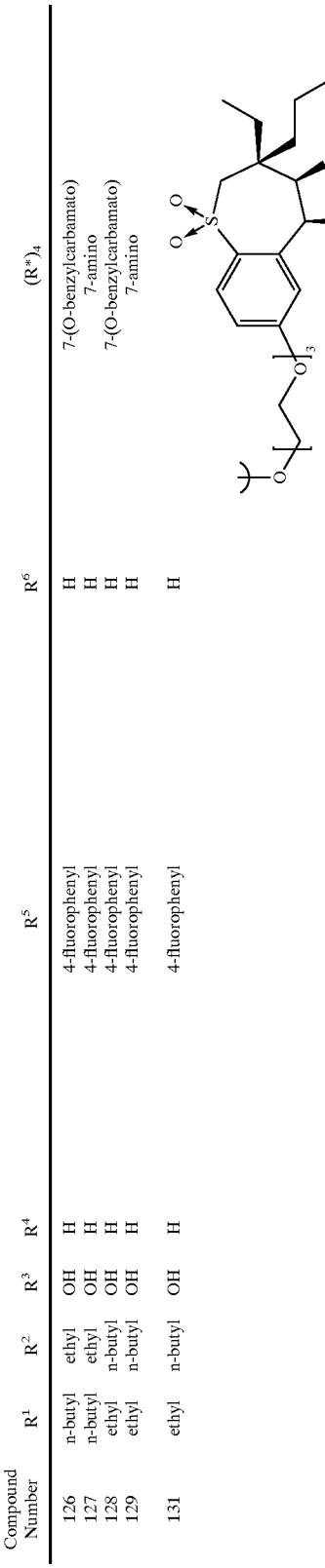

-continued
Additional Structures of the Present Invention
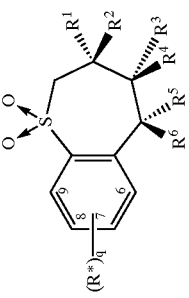
| Compound Number | R¹ | R² | R³ | R⁴ | R⁵ | R⁶ | (R*)₄ |
|---|---|---|---|---|---|---|---|
| 134 | ethyl | n-butyl | OH | H | phenyl | H | 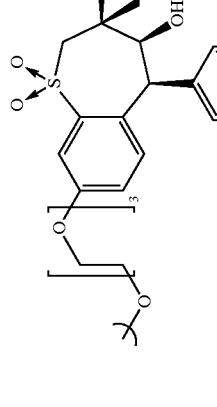 at the 8-position |
| 135 | ethyl | n-butyl | OH | H | phenyl | H | 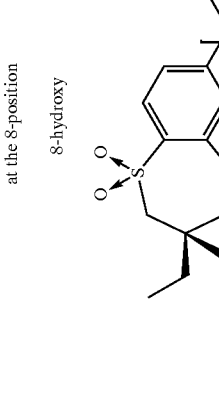 at the 8-position |
| 136 | ethyl | n-butyl | OH | H | phenyl | H | 8-hydroxy |
| 137 | n-butyl | ethyl | OH | H | phenyl | H | 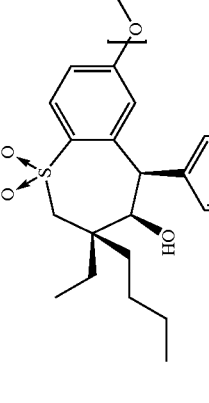 at the 7-position |

-continued

Additional Structures of the Present Invention

| Compound Number | R¹ | R² | R³ | R⁴ | R⁵ | R⁶ | (R*)q |
|---|---|---|---|---|---|---|---|
| 138 | n-butyl | ethyl | OH | H | phenyl | H | 8-acetoxy |
| 139 | n-butyl | ethyl | OH | H | phenyl | H | at the 7-position |
| 142 | ethyl | n-butyl | H | OH | H | 3-methoxyphenyl | 7-methylmercapto |
| 143 | ethyl | n-butyl | OH | H | 3-methoxyphenyl | H | 7-methylmercapto |
| 144 | ethyl | n-butyl | OH | H | 4-fluorophenyl | H | 7-(N-azetidinyl) |
| 262 | ethyl | n-butyl | OH | H | 3-methoxyphenyl | H | 7-methoxy |
| 263 | ethyl | n-butyl | H | OH | H | 3-methoxyphenyl | 7-methoxy |
| 264 | ethyl | n-butyl | OH | H | 3-trifluoromethylphenyl | H | 7-methoxy |
| 265 | ethyl | n-butyl | H | OH | H | 3-trifluoromethylphenyl | 7-methoxy |
| 266 | ethyl | n-butyl | OH | H | 3-hydroxyphenyl | H | 7-hydroxy |
| 267 | ethyl | n-butyl | OH | H | 3-hydroxyphenyl | H | 7-methoxy |
| 268 | ethyl | n-butyl | OH | H | 4-fluorophenyl | H | 7-methoxy |
| 269 | ethyl | n-butyl | H | OH | H | 4-fluorophenyl | 7-methoxy |
| 270 | ethyl | n-butyl | OH | H | 4-fluorophenyl | H | 7-hydroxy |
| 271 | ethyl | n-butyl | OH | H | 3-methoxyphenyl | H | 7-bromo |
| 272 | ethyl | n-butyl | H | OH | H | 3-methoxyphenyl | 7-bromo |

-continued

Additional Structures of the Present Invention

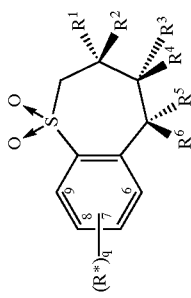

| Compound Number | R¹ | R² | R³ | R⁴ | R⁵ | R⁶ | (R*)₄ |
|---|---|---|---|---|---|---|---|
| 273 | ethyl | n-butyl | H | OH | H | 4-fluorophenyl | 7-fluoro |
| 274 | ethyl | n-butyl | OH | H | 4-fluorophenyl | H | 7-fluoro |
| 275 | ethyl | n-butyl | H | OH | H | 3-methoxyphenyl | 7-fluoro |
| 276 | ethyl | n-butyl | OH | H | 3-methoxyphenyl | H | 7-fluoro |
| 277 | ethyl | n-butyl | OH | H | 3-fluorophenyl | H | 7-methoxy |
| 278 | ethyl | n-butyl | H | OH | 3-fluorophenyl | H | 7-methoxy |
| 279 | ethyl | n-butyl | OH | OH | 3-fluorophenyl | H | 7-methoxy |
| 280 | ethyl | n-butyl | OH | H | 2-fluorophenyl | H | 7-methoxy |
| 281 | ethyl | n-butyl | OH | H | 4-fluorophenyl | H | 7-methylmercapto |
| 282 | ethyl | n-butyl | OH | H | 4-fluorophenyl | H | 7-methyl |
| 283 | ethyl | n-butyl | H | OH | H | 4-fluorophenyl | 7-methyl |
| 284 | ethyl | n-butyl | OH | H | 4-fluorophenyl | H | 7-(4'-morpholino) |
| 285 | | | | | MISSING | | |
| 286 | ethyl | ethyl | OH | H | phenyl | H | 7-(O-benzylcarbamato) |
| 287 | ethyl | ethyl | OH | H | phenyl | H | 7-amino |
| 288 | methyl | methyl | OH | H | phenyl | H | 7-amino |
| 289 | n-butyl | n-butyl | OH | H | phenyl | H | 7-amino |
| 290 | n-butyl | n-butyl | OH | H | phenyl | H | 7-amino |
| 291 | n-butyl | n-butyl | OH | H | phenyl | H | 7-(O-benzylcarbamato) |
| 292 | n-butyl | n-butyl | OH | H | phenyl | H | 7-amino |
| 293 | n-butyl | n-butyl | OH | H | 4-fluorophenyl | H | 7-benzylamino |
| 294 | n-butyl | n-butyl | OH | H | phenyl | H | 7-dimethylamino |
| 295 | ethyl | n-butyl | OH | H | phenyl | H | 7-amino |

-continued
Additional Structures of the Present Invention
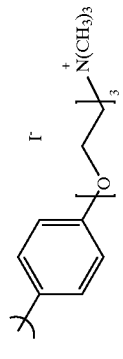
| Compound Number | R¹ | R² | R³ | R⁴ | R⁵ | R⁶ | (R*)q |
|---|---|---|---|---|---|---|---|
| 296 | ethyl | n-butyl | OH | H | 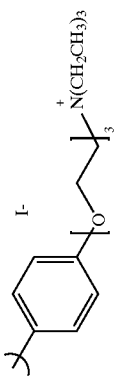 | H | 7-amino |
| 1000 | ethyl | n-butyl | OH | H | 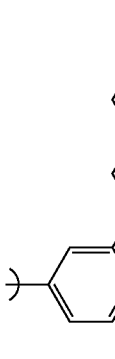 | H | 7-dimethylamino |
| 1001 | ethyl | n-butyl | OH | H | 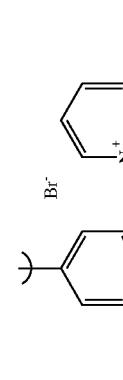 | H | 7-dimethylamino |
| 1002 | ethyl | n-butyl | OH | H |  | H | 7-dimethylamino |
| 1003 | ethyl | n-butyl | OH | H | 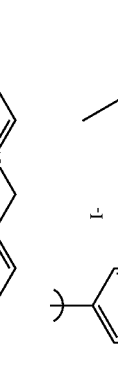 | H | 7-dimethylamino |

-continued
Additional Structures of the Present Invention
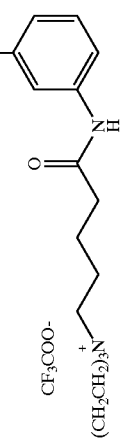
| Compound Number | R¹ | R² | R³ | R⁴ | R⁵ | R⁶ | (R*)$_q$ |
|---|---|---|---|---|---|---|---|
| 1004 | ethyl | n-butyl | OH | H | 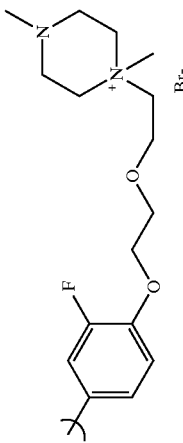 | H | 7-dimethylamino |
| 1005 | n-butyl | n-butyl | OH | H | 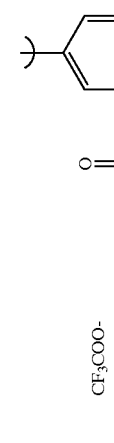 | H | 7-dimethylamino |
| 1006 | n-butyl | n-butyl | OH | H | 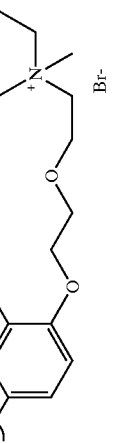 | H | 7-dimethylamino |
| 1007 | n-butyl | n-butyl | OH | H |  | H | 7-dimethylamino |

-continued

Additional Structures of the Present Invention

| Compound Number | R¹ | R² | R³ | R⁴ | R⁵ | R⁶ | (R*)$_q$ |
|---|---|---|---|---|---|---|---|
| 1008 | n-butyl | n-butyl | OH | H | 3-(pyridazinium)propoxy phenyl, I⁻ | H | 7-dimethylamino |
| 1009 | n-butyl | n-butyl | OH | H | 3-[3-(4-dimethylaminopyridinium)propoxy]phenyl, I⁻ | H | 7-dimethylamino |
| 1010 | n-butyl | n-butyl | OH | H | 3-fluoro-4-methoxyphenyl | H | 7-dimethylamino |
| 1011 | n-butyl | n-butyl | OH | H | 3-fluoro-4-(5-triethylammoniumpentyloxy)phenyl, trifluoroacetate salt | H | 7-dimethylamino |
| 1012 | n-butyl | n-butyl | OH | H | 4-hydroxyphenyl | H | 7-dimethylamino; 9-methoxy |
| 1013 | n-butyl | n-butyl | OH | H | 3-fluoro-4-(3-trimethylammoniumpropoxy)phenyl, I⁻ | H | 7-dimethylamino |
| 1014 | n-butyl | n-butyl | OH | H | 4-methoxyphenyl | H | 7-dimethylamino; 9-methoxy |
| 1015 | n-butyl | n-butyl | OH | H | 3-fluoro-4-[2-(1-methylpyrrolidinium)ethoxy]phenyl, Br⁻ | H | 7-dimethylamino |

-continued
Additional Structures of the Present Invention
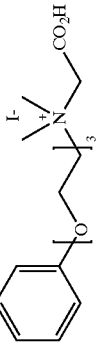
| Compound Number | R¹ | R² | R³ | R⁴ | R⁵ | R⁶ | (R*)₄ |
|---|---|---|---|---|---|---|---|
| 1016 | n-butyl | n-butyl | OH | H | 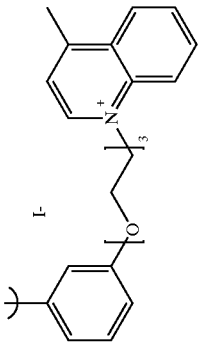 | H | 7-dimethylamino |
| 1017 | n-butyl | n-butyl | OH | H | 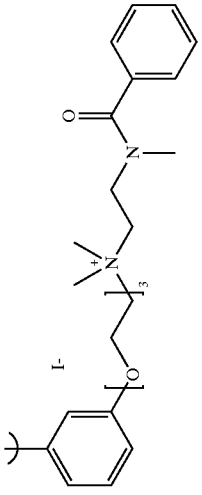 | H | 7-dimethylamino |
| 1018 | n-butyl | n-butyl | OH | H | 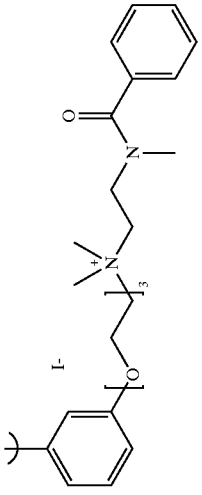 | H | 7-dimethylamino |

-continued
Additional Structures of the Present Invention
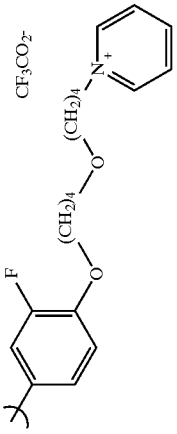
| Compound Number | R¹ | R² | R³ | R⁴ | R⁵ | R⁶ | (R*)$_q$ |
|---|---|---|---|---|---|---|---|
| 1019 | n-butyl | n-butyl | OH | H | 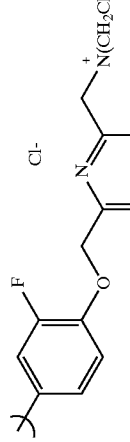 | H | 7-dimethylamino |
| 1020 | n-butyl | n-butyl | OH | H | 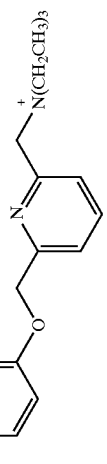 | H | 7-dimethylamino |
| 1021 | n-butyl | n-butyl | OH | H | 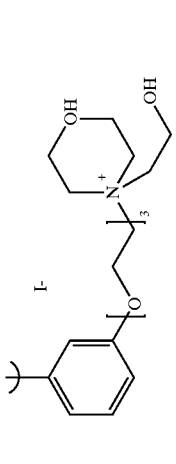 | H | 7-dimethylamino |
| 1022 | n-butyl | n-butyl | OH | H |  | H | 7-dimethylamino |

-continued
Additional Structures of the Present Invention
| Compound Number | $R^1$ | $R^2$ | $R^3$ | $R^4$ | $R^5$ | $R^6$ | $(R^*)_q$ |
|---|---|---|---|---|---|---|---|
| 1023 | n-butyl | n-butyl | OH | H | 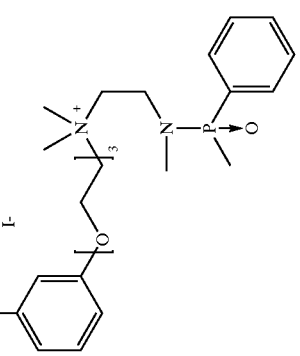 | H | 7-dimethylamino |
| 1024 | n-butyl | n-butyl | OH | H | 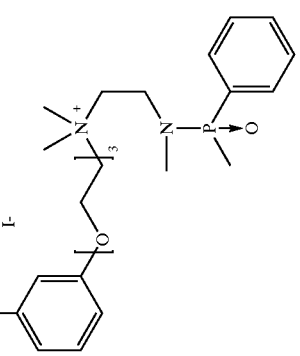 | H | 7-dimethylamino |
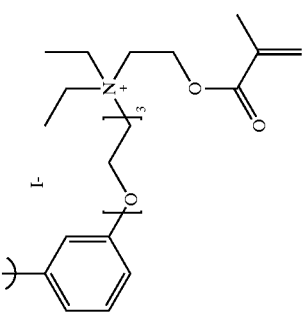

-continued
Additional Structures of the Present Invention
| Compound Number | R¹ | R² | R³ | R⁴ | R⁵ | R⁶ | (R*)$_q$ |
|---|---|---|---|---|---|---|---|
| 1025 | n-butyl | n-butyl | OH | H | 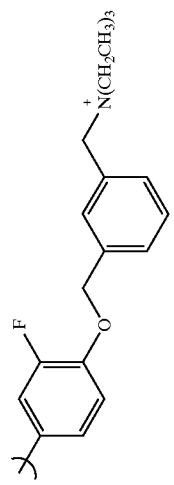 | H | 7-dimethylamino |
| 1026 | n-butyl | n-butyl | OH | H | 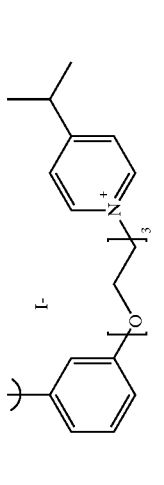 | H | 7-dimethylamino |
| 1027 | n-butyl | n-butyl | OH | H | 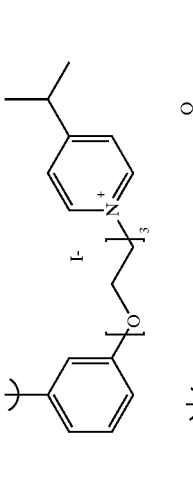 | H | 7-dimethylamino |
| 1028 | n-butyl | n-butyl | OH | H | 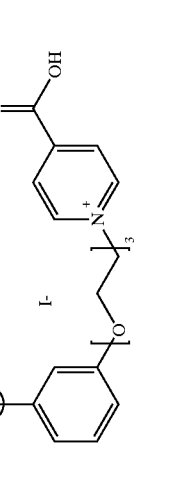 | H | 7-dimethylamino |

-continued
Additional Structures of the Present Invention
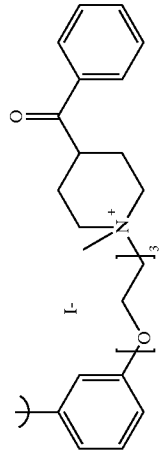
| Compound Number | R[1] | R[2] | R[3] | R[4] | R[5] | R[6] | (R*)[4] |
|---|---|---|---|---|---|---|---|
| 1029 | n-butyl | n-butyl | OH | H | 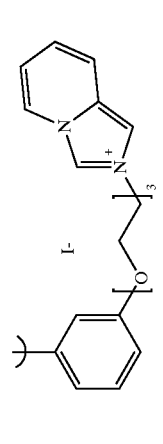 | H | 7-dimethylamino |
| 1030 | n-butyl | n-butyl | OH | H | 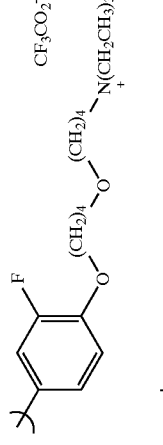 | H | 7-dimethylamino |
| 1031 | n-butyl | n-butyl | OH | H | 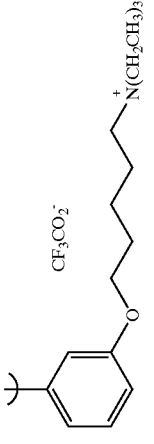 | H | 7-dimethylamino |
| 1032 | n-butyl | n-butyl | OH | H |  | H | 7-dimethylamino |

-continued
Additional Structures of the Present Invention
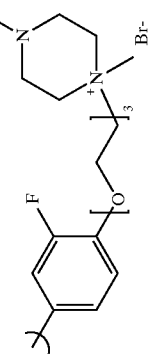
| Compound Number | R¹ | R² | R³ | R⁴ | R⁵ | R⁶ | (R*)₄ |
|---|---|---|---|---|---|---|---|
| 1033 | n-butyl | n-butyl | OH | H | 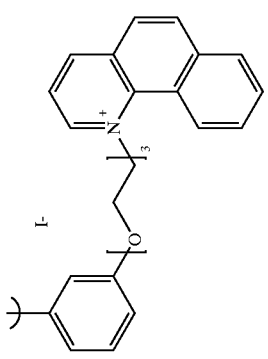 | H | 7-dimethylamino |
| 1034 | n-butyl | n-butyl | OH | H | (see structure) | H | 7-dimethylamino |

Additional Structures of the Present Invention

| Compound Number | $R^1$ | $R^2$ | $R^3$ | $R^4$ | $R^5$ | $R^6$ | $(R^*)_q$ |
|---|---|---|---|---|---|---|---|
| 1035 | n-butyl | n-butyl | OH | H | 3-(O-(CH$_2$)$_3$-N$^+$(CH$_3$)$_2$-CH$_2$CH$_2$-N(Et)-P(=O)(Ph)(CH$_3$)) phenyl, I$^-$ | H | 7-dimethylamino |
| 1036 | n-butyl | n-butyl | OH | H | 3-(O-(CH$_2$)$_3$-(4-(CO$_2$CH$_2$CH$_3$)pyridinium)) phenyl, I$^-$ | H | 7-dimethylamino |
| 1037 | n-butyl | n-butyl | OH | H | 4-hydroxyphenyl | H | 7-dimethylamino |
| 1038 | n-butyl | n-butyl | OH | H | 3-(O-CH$_2$CH$_2$-N$^+$(CH$_3$)$_3$) phenyl, I$^-$ | H | 7-dimethylamino |
| 1039 | n-butyl | n-butyl | OH | H | phenyl | H | 7-dimethylamino |

-continued
Additional Structures of the Present Invention
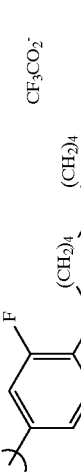
| Compound Number | R¹ | R² | R³ | R⁴ | R⁵ | R⁶ | (R*)q |
|---|---|---|---|---|---|---|---|
| 1040 | n-butyl | n-butyl | OH | H |  | H | 7-dimethylamino |
| 1041 | n-butyl | n-butyl | OH | H | ???How does this differ from 732817 | H | 7-dimethylamino |
| 1042 | n-butyl | n-butyl | OH | H | 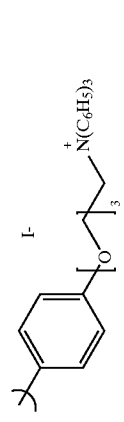 | H | 7-dimethylamino |
| 1043 | n-butyl | n-butyl | OH | H | 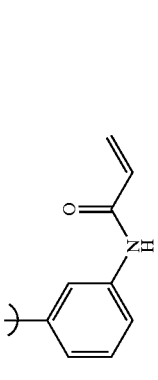 | H | 7-dimethylamino |

-continued

Additional Structures of the Present Invention

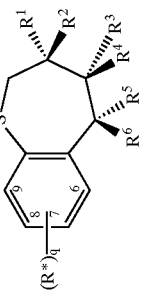

| Compound Number | R$^1$ | R$^2$ | R$^3$ | R$^4$ | R$^5$ | R$^6$ | (R*)$_4$ |
|---|---|---|---|---|---|---|---|
| 1044 | n-butyl | n-butyl | OH | H | ![](CF$_2$CO$_2^-$ / 2-F-phenoxy-(CH$_2$CH$_2$O)-CH$_2$CH$_2$-N$^+$(CH$_2$CH$_3$)$_3$) | H | 7-dimethylamino |
| 1045 | n-butyl | n-butyl | OH | H | CF$_2$CO$_2^-$ / 2-F-phenoxy-(CH$_2$)$_3$-N$^+$(CH$_2$CH$_3$)$_3$ | H | 7-dimethylamino |
| 1046 | n-butyl | n-butyl | OH | H | 3-aminophenyl | H | 7-dimethylamino |
| 1047 | n-butyl | n-butyl | OH | H | I$^-$ / 3-phenyl-(CH$_2$CH$_2$O)$_3$-CH$_2$CH$_2$-N$^+$(CH$_2$CH$_3$)$_2$-CH$_2$CH$_2$-N(CH$_2$CH$_3$)$_2$ | H | 7-dimethylamino |
| 1048 | n-butyl | n-butyl | OH | H | I$^-$ / 4-phenoxy-(CH$_2$CH$_2$O)$_3$-CH$_2$CH$_2$-N$^+$(CH$_2$CH$_3$)$_3$ | H | 7-dimethylamino |
| 1049 | n-butyl | n-butyl | OH | H | Br$^-$ / 2-F-phenoxy-(CH$_2$CH$_2$O)-CH$_2$CH$_2$-N$^+$(pyridinium) | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1050 | n-butyl | n-butyl | OH | H | | H | 7-dimethylamino |
| 1051 | n-butyl | n-butyl | OH | H | | H | 7-dimethylamino |
| 1052 | n-butyl | n-butyl | OH | H | | H | 7-dimethylamino |

-continued
Additional Structures of the Present Invention
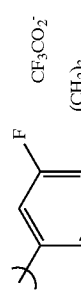
| Compound Number | $R^1$ | $R^2$ | $R^3$ | $R^4$ | $R^5$ | $R^6$ | $(R^*)_4$ |
|---|---|---|---|---|---|---|---|
| 1053 | n-butyl | n-butyl | OH | H | 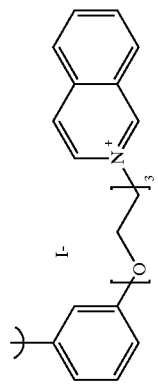 | H | 7-dimethylamino |
| 1054 | n-butyl | n-butyl | OH | H | 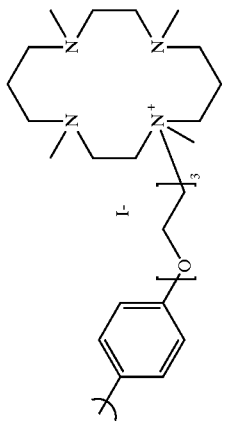 | H | 7-dimethylamino |
| 1055 | n-butyl | n-butyl | OH | H |  | H | 7-dimethylamino |

-continued
Additional Structures of the Present Invention
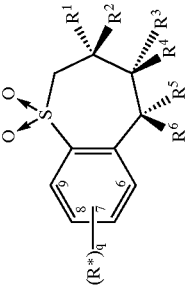
| Compound Number | R¹ | R² | R³ | R⁴ | R⁵ | R⁶ | (R*)₄ |
|---|---|---|---|---|---|---|---|
| 1056 | n-butyl | n-butyl | OH | H | 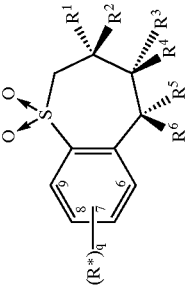 | H | 7-dimethylamino |
| 1057 | n-butyl | n-butyl | OH | H | 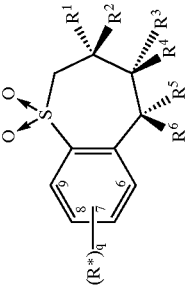 | H | 7-dimethylamino |
| 1058 | n-butyl | n-butyl | OH | H | 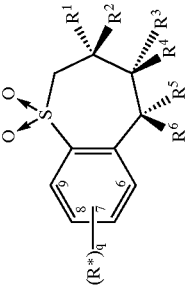 | H | 7-dimethylamino |
| 1059 | n-butyl | n-butyl | OH | H | 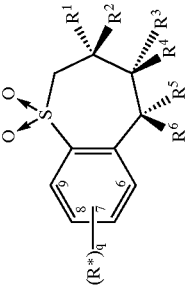 | H | 7-dimethylamino |
| 1060 | ethyl | n-butyl | OH | H | 3-fluoro-4-methoxyphenyl | H | 7-methylamino |

-continued
Additional Structures of the Present Invention
| Compound Number | R$^1$ | R$^2$ | R$^3$ | R$^4$ | R$^5$ | R$^6$ | (R*)$_4$ |
|---|---|---|---|---|---|---|---|
| 1061 | n-butyl | n-butyl | OH | H | 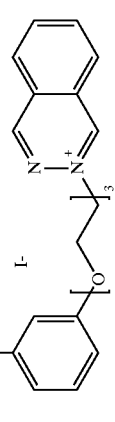 | H | 7-methylamino |
| 1062 | n-butyl | n-butyl | OH | H | 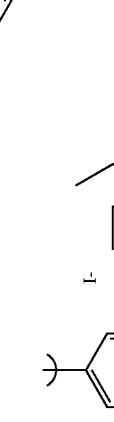 | H | 7-methylamino |
| 1063 | n-butyl | n-butyl | OH | H | 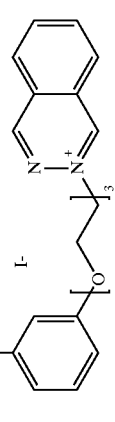 | H | 7-methylamino |

-continued
Additional Structures of the Present Invention

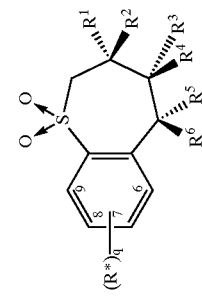

| Compound Number | R$^1$ | R$^2$ | R$^3$ | R$^4$ | R$^5$ | R$^6$ | (R*)$_4$ |
|---|---|---|---|---|---|---|---|
| 1064 | n-butyl | n-butyl | OH | H | piperidinyl-ethyl-pyridinium-propyl-O-phenyl (I⁻) | H | 7-methylamino |
| 1065 | n-butyl | n-butyl | OH | H | N((CH$_2$CH$_2$O)$_2$CH$_3$)$_3$⁺ propyl-O-phenyl (I⁻) | H | 7-dimethylamino |
| 1066 | n-butyl | n-butyl | OH | H | phenanthridinium-propyl-O-phenyl (I⁻) | H | 7-dimethylamino |
| 1067 | n-butyl | n-butyl | OH | H | thiophen-3-yl | H | 9-dimethylamino |

-continued
Additional Structures of the Present Invention
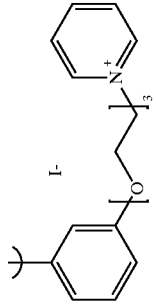
| Compound Number | R¹ | R² | R³ | R⁴ | R⁵ | R⁶ | (R*)₄ |
|---|---|---|---|---|---|---|---|
| 1068 | n-butyl | n-butyl | OH | H | 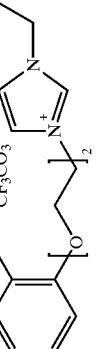 | H | 7-dimethylamino |
| 1069 | n-butyl | n-butyl | OH | H | phenyl | H | 7-dimethylamino; 9-dimethylamino |
| 1070 | n-butyl | n-butyl | OH | H | 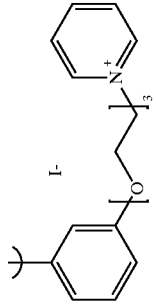 | H | 7-dimethylamino |
| 1071 | n-butyl | n-butyl | OH | H | 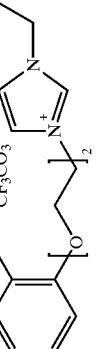 | | 7-dimethylamino |

-continued

Additional Structures of the Present Invention

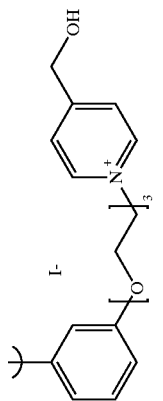

| Compound Number | $R^1$ | $R^2$ | $R^3$ | $R^4$ | $R^5$ | $R^6$ | $(R^*)_4$ |
|---|---|---|---|---|---|---|---|
| 1072 | n-butyl | n-butyl | OH | H | 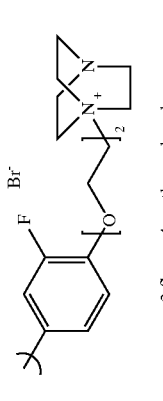 | H | 7-dimethylamino |
| 1073 | n-butyl | n-butyl | OH | H | 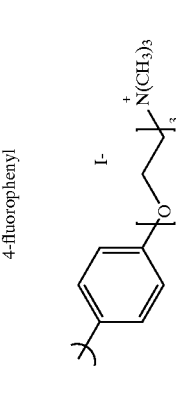 | H | 7-dimethylamino |
| 1074 | ethyl | n-butyl | OH | H | 3-fluoro-4-methoxyphenyl | H | 7-dimethylamino; |
| 1075 | n-butyl | n-butyl | OH | H | 4-fluorophenyl | H | 7-dimethylamino; 9-dimethylamino |
| 1076 | n-butyl | n-butyl | OH | H | 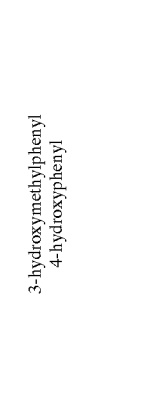 | H | 7-dimethylamino |
| 1077 | n-butyl | n-butyl | OH | H | 3-hydroxymethylphenyl | H | 7-dimethylamino |
| 1078 | ethyl | n-butyl | OH | H | 4-hydroxyphenyl | H | 7-dimethylamino |

-continued
Additional Structures of the Present Invention
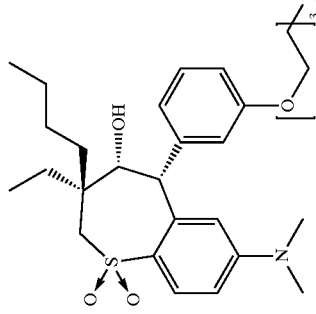
| Compound Number | R¹ | R² | R³ | R⁴ | R⁵ | R⁶ | (R*)q |
|---|---|---|---|---|---|---|---|
| 1079 | ethyl | n-butyl | OH | H |  | H | 7-dimethylamino |
| 1080 | n-butyl | n-butyl | OH | H | 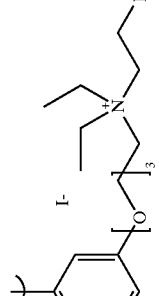 | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1081 | n-butyl | n-butyl | OH | H | ![structure with diethyl-(2-oxopropyl)ammonium iodide ether on phenyl] | H | 7-dimethylamino |
| 1082 | n-butyl | n-butyl | OH | H | 2-pyridyl | H | 7-dimethylamino |
| 1083 | n-butyl | n-butyl | OH | H | ![structure with 2-methylpyridinium iodide propyl ether on phenyl] | H | 7-dimethylamino |
| 1084 | n-butyl | n-butyl | OH | H | ![structure with 4-ethylpyridinium iodide propyl ether on phenyl] | H | 7-dimethylamino |
| 1085 | n-butyl | n-butyl | OH | H | thiophen-3-yl | H | 7-dimethylamino |

-continued
Additional Structures of the Present Invention
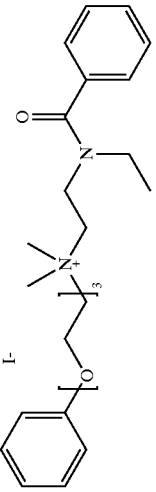
| Compound Number | R¹ | R² | R³ | R⁴ | R⁵ | R⁶ | (R*)$_q$ |
|---|---|---|---|---|---|---|---|
| 1086 | n-butyl | n-butyl | OH | H | 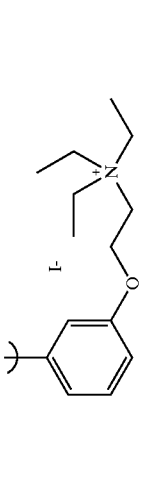 | H | 7-dimethylamino |
| 1087 | n-butyl | n-butyl | OH | H | 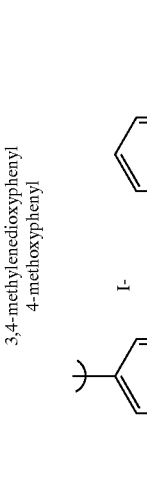 3,4-methylenedioxyphenyl 4-methoxyphenyl | H | 7-dimethylamino |
| 1088 | ethyl | n-butyl | OH | H | | H | 7-dimethylamino |
| 1089 | ethyl | n-butyl | OH | H | | H | 7-dimethylamino |
| 1090 | n-butyl | n-butyl | OH | H | 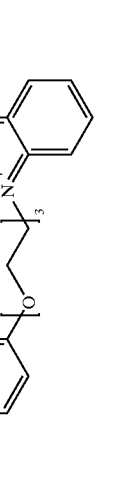 | H | 7-dimethylamino |

-continued
Additional Structures of the Present Invention
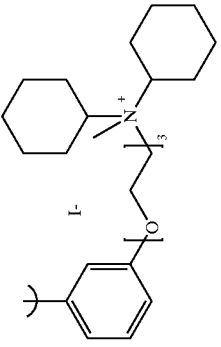
| Compound Number | $R^1$ | $R^2$ | $R^3$ | $R^4$ | $R^5$ | $R^6$ | $(R^*)_4$ |
|---|---|---|---|---|---|---|---|
| 1091 | n-butyl | n-butyl | OH | H | 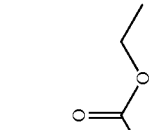 | H | 7-dimethylamino |
| 1092 | n-butyl | n-butyl | OH | H | 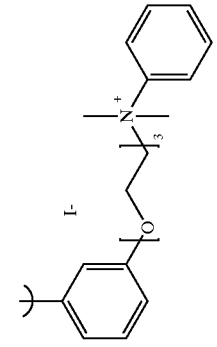 | H | 7-dimethylamino |
| 1093 | n-butyl | n-butyl | OH | H | 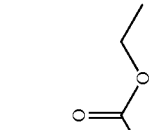 | H | 7-dimethylamino |

-continued
Additional Structures of the Present Invention
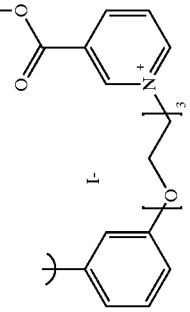
| Compound Number | R¹ | R² | R³ | R⁴ | R⁵ | R⁶ | (R*)$_q$ |
|---|---|---|---|---|---|---|---|
| 1094 | n-butyl | n-butyl | OH | H | 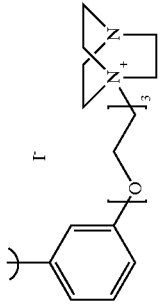 | H | 7-dimethylamino |
| 1095 | n-butyl | n-butyl | OH | H | | H | 7-dimethylamino |
| 1096 | n-butyl | n-butyl | OH | H | | H | 7-dimethylamino |
| 1097 | n-butyl | n-butyl | OH | H | 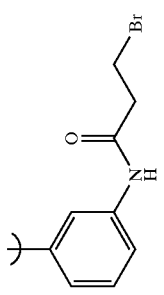 | H | 7-dimethylamino |

-continued

Additional Structures of the Present Invention

| Compound Number | $R^1$ | $R^2$ | $R^3$ | $R^4$ | $R^5$ | $R^6$ | $(R^*)_4$ |
|---|---|---|---|---|---|---|---|
| 1098 | n-butyl | n-butyl | OH | H | (structure with F-phenyl-O-linker-S-N(CH$_2$CH$_3$)$_3$ I⁻) | H | 7-dimethylamino |
| 1099 | ethyl | n-butyl | OH | H | 4-methoxyphenyl | H | 7-dimethylamino |
| 1100 | n-butyl | n-butyl | OH | H | 4-methoxyphenyl | H | 7-dimethylamino |
| 1101 | n-butyl | n-butyl | OH | H | (4-dimethylamino-pyridinium structure, CF$_3$CO$_3$⁻) | H | 7-dimethylamino |
| 1102 | n-butyl | n-butyl | OH | H | 3-carboxymethylphenyl | H | 7-dimethylamino |
| 1103 | n-butyl | n-butyl | OH | H | (phenyl-O-linker-N⁺(CH$_3$)$_3$ I⁻) | H | 7-dimethylamino |
| 1104 | n-butyl | n-butyl | OH | H | (bicyclic amidine structure with I⁻) | H | 7-dimethylamino |
| 1105 | n-butyl | n-butyl | OH | H | 5-piperonyl (with phenyl-O-linker) | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1106 | n-butyl | n-butyl | OH | H | 3-hydroxyphenyl | H | 7-dimethylamino |
| 1107 | n-butyl | n-butyl | OH | H | pyridinium-N-benzyl, Br⁻ | H | 7-dimethylamino |
| 1108 | n-butyl | n-butyl | OH | H | 3-pyridyl | H | 7-dimethylamino |
| 1109 | n-butyl | n-butyl | OH | H | 4-(2-pyridylmethoxy)-3-fluorophenyl | H | 7-dimethylamino |
| 1110 | n-butyl | n-butyl | OH | H | 4-(pyrrolidin-1-yl)pyridinium-N-(CH₂)₃O-phenyl, I⁻ | H | 7-dimethylamino |
| 1111 | n-butyl | n-butyl | OH | H | 4-(2-carboxyethyl)pyridinium-N-(CH₂)₃O-(3-fluorophenyl), CF₃CO₃⁻ | H | 7-dimethylamino |

-continued

Additional Structures of the Present Invention

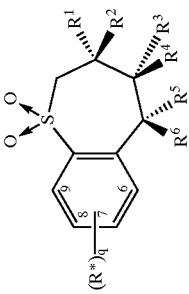

| Compound Number | R¹ | R² | R³ | R⁴ | R⁵ | R⁶ | (R*)₄ |
|---|---|---|---|---|---|---|---|
| 1112 | n-butyl | n-butyl | OH | H | 4-pyridyl | H | 7-dimethylamino |
| 1113 | n-butyl | n-butyl | OH | H | 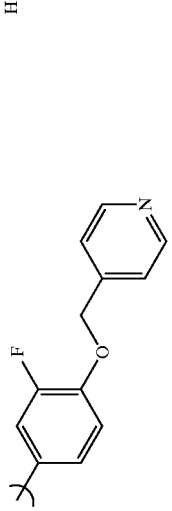 | H | 7-dimethylamino |
| 1114 | n-butyl | n-butyl | OH | H | 3-methoxyphenyl | H | 7-methylamino |
| 1115 | n-butyl | n-butyl | OH | H | 4-fluorophenyl | H | 7-dimethylamino |
| 1116 | ethyl | n-butyl | OH | H | 3-tolyl | H | 7-dimethylamino |
| 1117 | ethyl | n-butyl | OH | H | 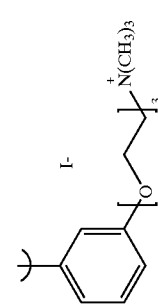 | H | 7-dimethylamino |
| 1118 | ethyl | n-butyl | OH | H | 3-fluoro-4-hydroxyphenyl | H | 7-dimethylamino |
| 1119 | n-butyl | n-butyl | OH | H | 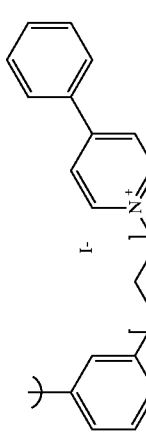 | H | 7-dimethylamino |

-continued

Additional Structures of the Present Invention

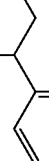

| Compound Number | R¹ | R² | R³ | R⁴ | R⁵ | R⁶ | (R*)$_q$ |
|---|---|---|---|---|---|---|---|
| 1120 | n-butyl | n-butyl | OH | H |  | H | 7-dimethylamino |
| 1121 | n-butyl | n-butyl | OH | H |  | H | 7-dimethylamino |
| 1122 | n-butyl | n-butyl | OH | H |  | H | 7-dimethylamino |
| 1123 | n-butyl | n-butyl | OH | H | phenyl | H | 7-dimethylamino |
| 1124 | n-butyl | n-butyl | OH | H | 3-methoxyphenyl | H | 7-dimethylamino |
| 1125 | n-butyl | n-butyl | OH | H | 3-chloro-4-methoxyphenyl | H | 7-dimethylamino |
| 1126 | ethyl | n-butyl | OH | H |  | H | 7-dimethylamino |

-continued

Additional Structures of the Present Invention

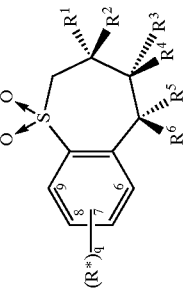

| Compound Number | R¹ | R² | R³ | R⁴ | R⁵ | R⁶ | (R*)₄ |
|---|---|---|---|---|---|---|---|
| 1127 | n-butyl | n-butyl | OH | H | | H | 7-dimethylamino |
| 1128 | n-butyl | n-butyl | OH | H | 3-fluoro-4-hydroxyphenyl | H | 7-dimethylamino |
| 1129 | n-butyl | n-butyl | OH | H | 4-fluorophenyl | H | 9-dimethylamino |
| 1130 | n-butyl | n-butyl | OH | H | 3-chloro-4-fluorophenyl | H | 7-dimethylamino |
| 1131 | ethyl | n-butyl | OH | H | 4-methoxyphenyl | H | 7-dimethylamino |
| 1132 | n-butyl | n-butyl | OH | H | ![](tetrahydroisoquinolinium-propyl-phenoxy) | H | 7-dimethylamino |
| 1133 | n-butyl | n-butyl | OH | H | 4-cyanomethylphenyl | H | 7-dimethylamino |
| 1134 | ethyl | n-butyl | OH | H | | H | 7-dimethylamino |
| 1135 | n-butyl | n-butyl | OH | H | 3,4-dimethoxyphenyl | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1136 | n-butyl | n-butyl | OH | H | 3-(phenoxy with I(CH₂)₃O-) | H | 7-dimethylamino |
| 1137 | n-butyl | n-butyl | OH | H | 4-fluorophenyl | H | 9-(2',2'-dimethylhydrazino) |
| 1138 | n-butyl | n-butyl | OH | H | 4-tert-butyl-N-[(CH₂)₃O-aryl-(CH₂)₂N⁺(CH₂CH₃)₂] I⁻ | H | 7-dimethylamino |
| 1139 | n-butyl | n-butyl | OH | H | 3,4-difluorophenyl | H | 7-dimethylamino |
| 1140 | n-butyl | n-butyl | OH | H | 3-methoxyphenyl | H | 7-(2',2'-dimethylhydrazino) |
| 1141 | n-butyl | n-butyl | OH | H | 4-fluorophenyl | H | 7-ethylmethylamino |
| 1142 | n-butyl | n-butyl | OH | H | 2-F,4-[-O(CH₂)₂S(CH₂)₂N(CH₂CH₃)₂]phenyl | H | 7-dimethylamino |
| 1143 | n-butyl | n-butyl | H | OH | H | 3-fluoro-4-methoxy-phenyl | |
| 1144 | n-butyl | n-butyl | OH | H | 5-piperonyl | H | 7-dimethylamino |
| 1145 | n-butyl | n-butyl | OH | H | 4-methoxyphenyl | H | 9-dimethylamino |

-continued

Additional Structures of the Present Invention

| Compound Number | R¹ | R² | R³ | R⁴ | R⁵ | R⁶ | (R*)$_q$ |
|---|---|---|---|---|---|---|---|
| 1146 | n-butyl | n-butyl | OH | H | ![structure with (CH₂)₁₀-O-phenyl-N(CH₃)₃⁺ I⁻] | H | 7-dimethylamino |
| 1147 | n-butyl | n-butyl | OH | H | 3-methoxyphenyl | H | 7-diethylamino |
| 1148 | n-butyl | n-butyl | OH | H | 4-fluorophenyl | H | 7-dimethylsulfonium, fluoride salt |
| 1149 | n-butyl | n-butyl | OH | H | 4-fluorophenyl | H | 7-ethylamino |
| 1150 | n-butyl | n-butyl | OH | H | 3-methoxyphenyl | H | 7-ethylmethylamino |
| 1151 | n-butyl | ethyl | OH | H | 3-fluoro-4-methoxyphenyl | H | 7-dimethylamino |
| 1152 | n-butyl | n-butyl | OH | H | phenyl | H | 7-(ethoxymethyl)methylamino |
| 1153 | n-butyl | n-butyl | OH | H | 4-fluorophenyl | H | 7-methylamino |
| 1154 | n-butyl | n-butyl | OH | H | 3-methoxyphenyl | H | 9-methoxy |
| 1155 | n-butyl | n-butyl | OH | H | 4-fluorophenyl | H | 7-methyl |
| 1156 | n-butyl | n-butyl | OH | H | 4-fluorophenyl | H | 7-methylmercapto |
| 1157 | n-butyl | n-butyl | OH | H | 4-fluorophenyl | H | 7-fluoro; 9-dimethylamino |
| 1158 | n-butyl | n-butyl | OH | H | 4-pyridinyl, hydrochloride salt | H | 7-methoxy |
| 1159 | n-butyl | n-butyl | OH | H | phenyl | H | 7-dimethylamino |
| 1160 | n-butyl | n-butyl | OH | H | 4-fluorophenyl | H | 7-diethylamino |
| 1161 | n-butyl | n-butyl | OH | H | 3,5-dichloro-4-methoxyphenyl | H | 7-dimethylamino |
| 1162 | n-butyl | n-butyl | OH | H | phenyl | H | 7-dimethylamino |
| 1163 | n-butyl | n-butyl | OH | H | 3-(dimethylamino)phenyl | H | 7-methoxy |
| 1164 | n-butyl | n-butyl | OH | H | 4-pyridinyl | H | 7-methoxy |
| 1165 | n-butyl | n-butyl | OH | H | 3-fluoro-4-methoxyphenyl | H | 7-trimethylammonium iodide |
| 1166 | n-butyl | n-butyl | OH | H | 3-hydroxyphenyl | H | 7-trimethylammonium iodide |

-continued

Additional Structures of the Present Invention

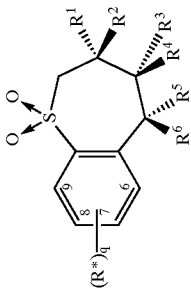

| Compound Number | R¹ | R² | R³ | R⁴ | R⁵ | R⁶ | (R*)₄ |
|---|---|---|---|---|---|---|---|
| 1167 | n-butyl | n-butyl | OH | H | ![Cl-substituted allyloxyphenyl group] | H | 7-dimethylamino |
| 1168 | n-butyl | n-butyl | OH | H | 4-hydroxyphenyl | H | 7-trimethylammonium iodide |
| 1169 | n-butyl | n-butyl | OH | H | phenyl | H | 8-dimethylamino |
| 1170 | n-butyl | n-butyl | OH | H | 3-methoxyphenyl | H | 7-ethylpropylamino |
| 1171 | n-butyl | n-butyl | OH | H | 4-(trifluoromethylsulfonyloxy)phenyl | H | 7-dimethylamino |
| 1172 | n-butyl | n-butyl | OH | H | 4-pyridinyl | H | 7-methoxy |
| 1173 | n-butyl | n-butyl | OH | H | 4-fluorophenyl | H | 7-ethylpropylamino |
| 1174 | ethyl | n-butyl | OH | H | 3-methoxyphenyl | H | 7-phenyl |
| 1175 | ethyl | n-butyl | OH | H | 3-methoxyphenyl | H | 7-methylsulfonyl |
| 1176 | n-butyl | n-butyl | OH | H | 4-fluorophenyl | H | 9-fluoro |
| 1177 | n-butyl | n-butyl | OH | H | 3-methoxyphenyl | H | 7-butylmethylamino |
| 1178 | n-butyl | n-butyl | OH | H | 3-(trifluoromethylsulfonyloxy)phenyl | H | 7-dimethylamino |
| 1179 | n-butyl | n-butyl | OH | H | phenyl | H | 8-methoxy |
| 1180 | n-butyl | n-butyl | OH | H | 4-fluorophenyl | H | 7-trimethylammonium iodide |
| 1181 | n-butyl | n-butyl | OH | H | phenyl | H | 7-butylmethylamino |
| 1182 | n-butyl | n-butyl | OH | H | 4-(dimethylamino)phenyl | H | 7-methoxy |
| 1183 | n-butyl | n-butyl | OH | H | 3-methoxyphenyl | H | 7-fluoro; |
| 1184 | n-butyl | n-butyl | OH | H | 4-fluorophenyl | H | 9-fluoro |
| 1185 | n-butyl | n-butyl | OH | H | 4-fluorophenyl | H | 7-fluoro; |
| 1186 | n-butyl | n-butyl | OH | H | phenyl | H | 9-fluoro |
| 1187 | n-butyl | n-butyl | OH | H | 4-fluorophenyl | H | 7-methyl |
| 1188 | n-butyl | n-butyl | OH | H | 4-methoxyphenyl | H | 7-trimethylammonium iodide |
| 1189 | n-butyl | n-butyl | OH | H | 3,4-difluorophenyl | H | 7-trimethylammonium iodide |
| 1190 | n-butyl | n-butyl | OH | H | 2-bromophenyl | H | 7-bromo |
| 1191 | n-butyl | n-butyl | OH | H | 4-(dimethylamino)phenyl | H | 7-hydroxy |
| 1192 | n-butyl | n-butyl | OH | H | 3-(dimethylamino)phenyl | H | 7-hydroxy |
| 1193 | n-butyl | n-butyl | OH | H | 4-(2-(2-methylpropyl))phenyl | H | 7-dimethylamino |

-continued
Additional Structures of the Present Invention
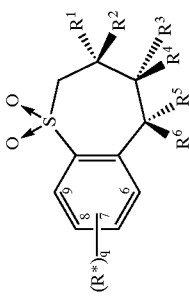
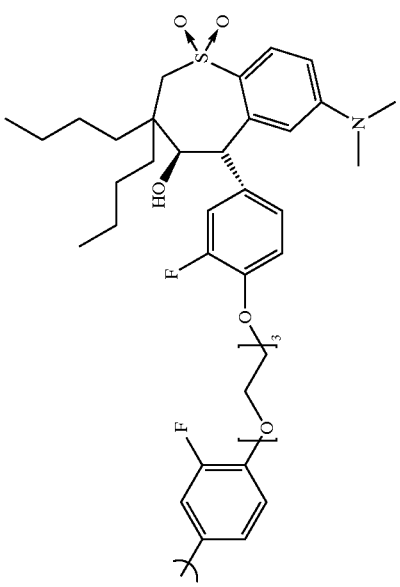
| Compound Number | R¹ | R² | R³ | R⁴ | R⁵ | R⁶ | (R*)_q |
|---|---|---|---|---|---|---|---|
| 1194 | n-butyl | n-butyl | OH | H | | H | 7-dimethylamino |
| 1195 | n-butyl | n-butyl | OH | H | 4-methoxyphenyl | H | 7-(4'-methylpiperzin-1-yl) |
| 1196 | n-butyl | n-butyl | OH | H | 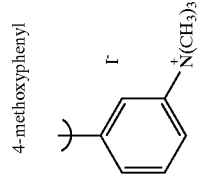 | H | 7-methoxy |
| 1197 | n-butyl | n-butyl | R3 + R4 = oxo | R3 + R4 = oxo | phenyl | H | 7-(N-methylformamido) |
| 1198 | n-butyl | n-butyl | OH | H | 4-(pyridinyl-N-oxide) | H | 7-methoxy |

-continued
Additional Structures of the Present Invention
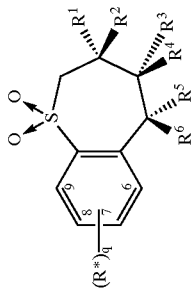
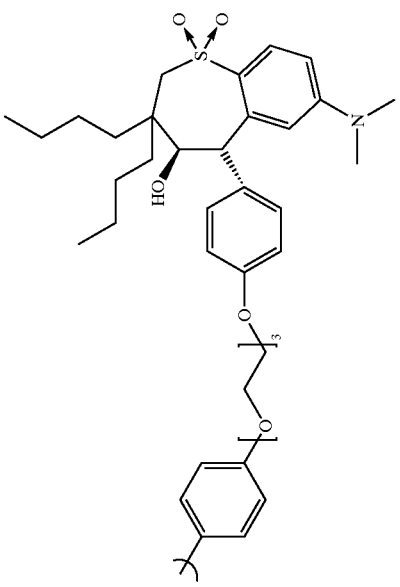
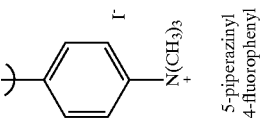
| Compound Number | R¹ | R² | R³ | R⁴ | R⁵ | R⁶ | (R*)q |
|---|---|---|---|---|---|---|---|
| 1199 | n-butyl | n-butyl | OH | H | | H | 7-dimethylamino |
| 1200 | n-butyl | n-butyl | H | OH | H | phenyl | 7-dimethylamino |
| 1201 | n-butyl | n-butyl | OH | H | H | H | 7-methyl |
| 1202 | n-butyl | n-butyl | OH | H | | H | 7-methoxy |
| 1203 | n-butyl | n-butyl | OH | H | 5-piperazinyl | H | 7-(4'-tert-butylphenyl) |
| 1204 | n-butyl | n-butyl | OH | H | 4-fluorophenyl | H | 7-methoxy |

-continued

Additional Structures of the Present Invention

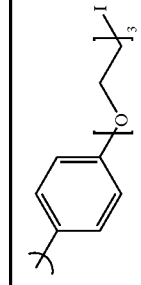

| Compound Number | $R^1$ | $R^2$ | $R^3$ | $R^4$ | $R^5$ | $R^6$ | $(R^*)_4$ |
|---|---|---|---|---|---|---|---|
| 1205 | n-butyl | n-butyl | OH | H | 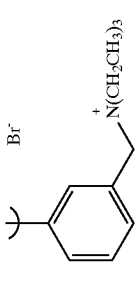 | H | 7-dimethylamino |
| 1206 | n-butyl | n-butyl | OH | H | 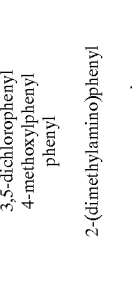 | H | 7-dimethylamino |
| 1207 | n-butyl | n-butyl | OH | H | 3,5-dichlorophenyl | H | 7-dimethylamino |
| 1208 | n-butyl | n-butyl | OH | H | 4-methoxyphenyl | H | 7-dimethylamino |
| 1209 | n-butyl | n-butyl | acetoxy | H | phenyl | H | 7-dimethylphenyl |
| 1210 | n-butyl | n-butyl | OH | H | 2-(dimethylamino)phenyl | H | 7-dimethylamino |
| 1211 | ethyl | n-butyl | OH | H | | | 7-dimethylamino |

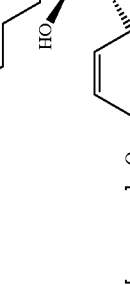

-continued

Additional Structures of the Present Invention

| Compound Number | R¹ | R² | R³ | R⁴ | R⁵ | R⁶ | (R*)₄ |
|---|---|---|---|---|---|---|---|
| 1212 | n-butyl | n-butyl | OH | H | 4-methoxyphenyl | H | 9-(4'-morpholino) |
| 1213 | n-butyl | ethyl | H | OH | H | 3-fluoro-4-methoxyphenyl | 7-dimethylamino |
| 1214 | n-butyl | ethyl | OH | H | phenyl | H | 7-(N-methylformamido) |
| 1215 | n-butyl | n-butyl | OH | H | 4-methoxyphenyl | H | 9-methylmercapto |
| 1216 | ethyl | n-butyl | OH | H | 5-piperonyl | H | 7-bromo |
| 1217 | n-butyl | n-butyl | OH | H | 4-carboxyphenyl | H | 7-dimethylamino |
| 1218 | n-butyl | n-butyl | OH | H | 4-methoxyphenyl | H | 9-methylsulfonyl |
| 1219 | n-butyl | n-butyl | OH | H | 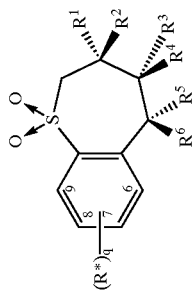 | H | 7-dimethylamino |
| 1220 | n-butyl | n-butyl | OH | H | 3-methoxyphenyl | H | 7-isopropylamino |
| 1221 | n-butyl | n-butyl | OH | H | ![CO2CH3 phenyl] | H | 7-dimethylamino |
| 1222 | n-butyl | n-butyl | OH | H | 3-methoxyphenyl | H | 7-ethylamino 8-bromo; |
| 1223 | n-butyl | n-butyl | OH | H | phenyl | H | 7-methylamino |
| 1224 | n-butyl | n-butyl | OH | H | 3-nitrophenyl | H | 7-fluoro |
| 1225 | n-butyl | ethyl | OH | H | 3-methylphenyl | H | 7-dimethylamino |
| 1226 | ethyl | n-butyl | OH | H | 5-piperonyl | H | 7-bromo |
| 1227 | n-butyl | n-butyl | OH | H | 4-fluorophenyl | H | 7-(tert-butylamino) 8-bromo; |
| 1228 | n-butyl | n-butyl | OH | H | 2-pyrrolyl | H | 7-dimethylamino |

-continued

Additional Structures of the Present Invention

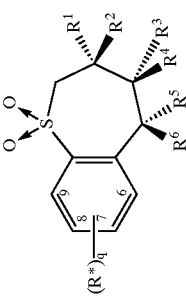

| Compound Number | R$^1$ | R$^2$ | R$^3$ | R$^4$ | R$^5$ | R$^6$ | (R*)$_q$ |
|---|---|---|---|---|---|---|---|
| 1229 | n-butyl | n-butyl | OH | H | 3-chloro-4-hydroxyphenyl | H | 7-dimethylamino |
| 1230 | n-butyl | n-butyl | OH | H | phenyl | H | 9-dimethylamino; 7-fluoro |
| 1231 | n-butyl | n-butyl | OH | H | ![naphthyl-OMe] | H | 7-dimethylamino |
| 1232 | n-butyl | n-butyl | H | OH | 3-thiophenyl | H | 9-dimethylamino |
| 1233 | n-butyl | n-butyl | OH | H | ![phenyl-CH2-N+(CH3)2-CH2CH2-N(CH3)2 Br-] | H | 7-dimethylamino |
| 1234 | n-butyl | n-butyl | OH | H | ![phenyl-N+(CH3)3 Br-] | H | 7-dimethylamino |
| 1235 | n-butyl | n-butyl | OH | H | ![phenyl-O-CH2CH2-N(CH2CH3)2] | H | 7-dimethylamino |

-continued

Additional Structures of the Present Invention

| Compound Number | R¹ | R² | R³ | R⁴ | R⁵ | R⁶ | (R*)q |
|---|---|---|---|---|---|---|---|
| 1236 | n-butyl | n-butyl | OH | H | 4-(bromomethyl)phenyl | H | 7-dimethylamino |
| 1237 | n-butyl | n-butyl | OH | H | 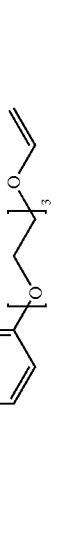 | H | 7-dimethylamino |
| 1238 | n-butyl | n-butyl | OH | H | 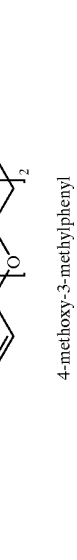 | H | 7-dimethylamino |
| 1239 | n-butyl | n-butyl | OH | H | 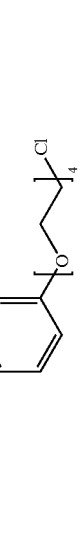 | H | 7-dimethylamino |
| 1240 | n-butyl | n-butyl | OH | H | 4-methoxy-3-methylphenyl | H | 7-dimethylamino |
| 1241 | n-butyl | n-butyl | OH | H | 3-(dimethylaminomethyl)phenyl | H | 7-dimethylamino |
| 1242 | n-butyl | n-butyl | OH | H | 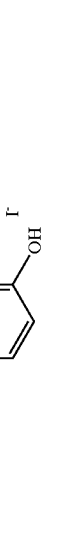 | H | 7-dimethylamino |
| 1243 | n-butyl | n-butyl | OH | H |  | H | 7-dimethylamino |

Additional Structures of the Present Invention

| Compound Number | R¹ | R² | R³ | R⁴ | R⁵ | R⁶ | (R*)₄ |
|---|---|---|---|---|---|---|---|
| 1244 | n-butyl | n-butyl | OH | H | 3-methoxyphenyl | H | 7-(1'-methylhydrazido) |
| 1245 | n-butyl | n-butyl | OH | H | ⌐ | H | 7-dimethylamino |
| 1246 | n-butyl | n-butyl | OH | H | 3-(bromomethyl)phenyl | H | 7-dimethylamino |
| 1247 | n-butyl | n-butyl | OH | H | (naphthol structure) | H | 7-dimethylamino |
| 1248 | n-butyl | n-butyl | OH | H | (CH₂N(CH₃)₂-hydroxyphenyl) | H | 7-dimethylamino |
| 1249 | n-butyl | n-butyl | OH | H | (CF₃CO₂⁻ trimethylammonium ethanol benzyl) | H | 7-dimethylamino |
| 1250 | n-butyl | n-butyl | OH | H | 3-(dimethylamino)phenyl | H | 7-dimethylamino |
| 1251 | n-butyl | n-butyl | OH | H | 1-naphthyl | H | 7-dimethylamino |

-continued

Additional Structures of the Present Invention

[Structure: tricyclic benzothiepine sulfone with (R*)q on benzene ring, positions 6,7,8,9 labeled, R¹ R² on one carbon, R³ R⁴ on next, R⁵ R⁶ on benzylic carbon]

| Compound Number | R¹ | R² | R³ | R⁴ | R⁵ | R⁶ | (R*)₄ |
|---|---|---|---|---|---|---|---|
| 1252 | n-butyl | n-butyl | OH | H | [4-(3-(N⁺(CH₂CH₃)₃)propoxy)phenyl], I⁻ | H | 7-dimethylamino |
| 1253 | n-butyl | n-butyl | OH | H | [2-methoxy-5-(CH₂N⁺(CH₃)₃)phenyl], I⁻ | H | 7-dimethylamino |
| 1254 | n-butyl | n-butyl | OH | H | [4-(pyridinium-CH₂)phenyl], Br⁻ | H | 7-dimethylamino |
| 1255 | n-butyl | n-butyl | OH | H | [3-(CH₂N⁺(CH₃)₂CH₂CH₂N⁺(CH₃)₃)phenyl], I⁻ | H | 7-dimethylamino |
| 1256 | n-butyl | n-butyl | OH | H | 3-nitrophenyl | H | 7-dimethylamino 8-bromo; |
| 1257 | n-butyl | n-butyl | OH | H | phenyl | H | 7-dimethylamino 9-(tert-butylamino) |
| 1258 | n-butyl | n-butyl | OH | H | 4-fluorophenyl | H | 7-dimethylamino |
| 1259 | ethyl | n-butyl | H | OH | H | phenyl | 7-dimethylamino |
| 1260 | ethyl | n-butyl | OH | H | 3-hydroxyphenyl | H | 7-dimethylamino |

-continued

Additional Structures of the Present Invention

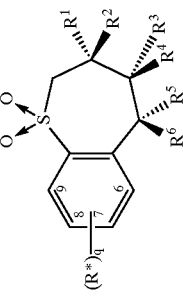

| Compound Number | R¹ | R² | R³ | R⁴ | R⁵ | R⁶ | (R*)₄ |
|---|---|---|---|---|---|---|---|
| 1261 | n-butyl | n-butyl | OH | H | 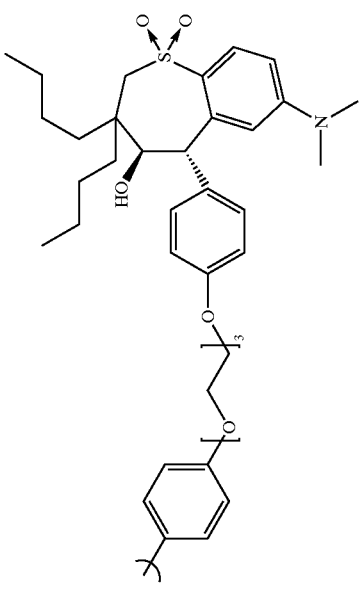 | H | 7-dimethylamino |
| 1262 | n-butyl | n-butyl | OH | H | 2-thiophenyl | H | 7-dimethylamino |
| 1263 | n-butyl | n-butyl | OH | H | 5-piperonyl | H | 7-bromo |
| 1264 | n-butyl | n-butyl | OH | H | 4-fluorophenyl | H | 7-isopropylamino |
| 1265 | n-butyl | n-butyl | OH | H | 4-fluorophenyl | H | 9-isopropylamino |
| 1266 | n-butyl | n-butyl | OH | H | 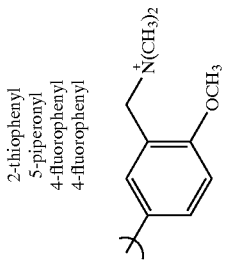 | H | 7-dimethylamino |
| 1267 | n-butyl | ethyl | OH | H | 5-piperonyl | H | 7-carboxy, methyl ester |
| 1268 | n-butyl | n-butyl | OH | H | 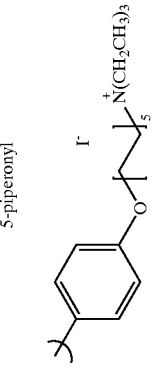 | H | 7-dimethylamino |

-continued
Additional Structures of the Present Invention
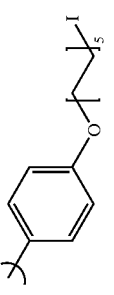
| Compound Number | R[1] | R[2] | R[3] | R[4] | R[5] | R[6] | (R*)[4] |
|---|---|---|---|---|---|---|---|
| 1269 | n-butyl | n-butyl | OH | H | 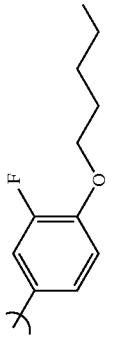 | H | 7-dimethylamino |
| 1270 | n-butyl | n-butyl | OH | H | 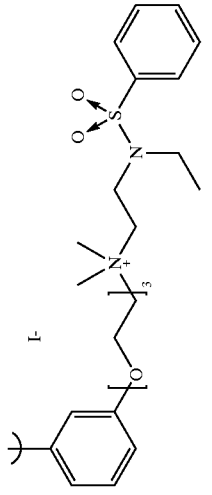 | H | 7-dimethylamino |
| 1271 | n-butyl | n-butyl | OH | H | 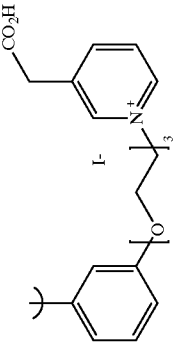 | H | 7-dimethylamino |
| 1272 | n-butyl | n-butyl | OH | H |  | H | 7-dimethylamino |

-continued
Additional Structures of the Present Invention
| Compound Number | R¹ | R² | R³ | R⁴ | R⁵ | R⁶ | (R*)q |
|---|---|---|---|---|---|---|---|
| 1273 | n-butyl | n-butyl | OH | H | 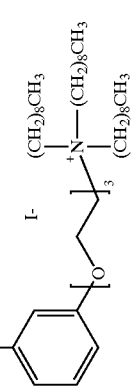 | H | 7-dimethylamino |
| 1274 | n-butyl | n-butyl | OH | H | 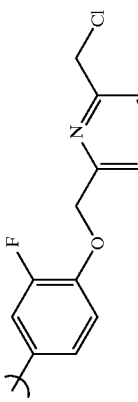 | H | 7-dimethylamino |
| 1275 | n-butyl | n-butyl | OH | H | 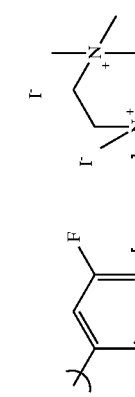 | H | 7-dimethylamino |
| 1276 | n-butyl | n-butyl | OH | H | 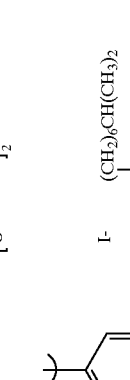 | H | 7-dimethylamino |

-continued

Additional Structures of the Present Invention

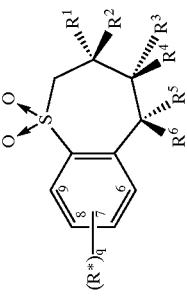

| Compound Number | $R^1$ | $R^2$ | $R^3$ | $R^4$ | $R^5$ | $R^6$ | $(R^*)_4$ |
|---|---|---|---|---|---|---|---|
| 1277 | n-butyl | n-butyl | OH | H | 2-F-4-(O-(CH$_2$)$_2$-N(CH$_3$)-(CH$_2$)$_2$-CO$_2$H)-phenyl | H | 7-dimethylamino |
| 1278 | n-butyl | n-butyl | OH | H | 3-(O-(CH$_2$)$_3$-N$^+$((CH$_2$)$_4$CH$_3$)$_3$) I$^-$-phenyl | H | 7-dimethylamino |
| 1279 | n-butyl | n-butyl | OH | H | 3-(O-(CH$_2$)$_3$-N$^+$((CH$_2$)$_5$CH$_3$)$_3$) I$^-$-phenyl | H | 7-dimethylamino |
| 1280 | n-butyl | n-butyl | OH | H | 2-F-4-(CH$_2$-C(O)-N(CH$_3$)-CH$_2$-CH$_2$-N(CH$_3$)$_2$)-phenyl | H | 7-dimethylamino |

-continued

Additional Structures of the Present Invention

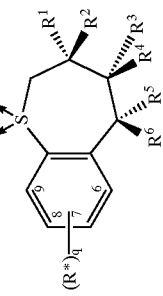

| Compound Number | R¹ | R² | R³ | R⁴ | R⁵ | R⁶ | (R*)q |
|---|---|---|---|---|---|---|---|
| 1281 | n-butyl | n-butyl | OH | H | phenyl) | H | 7-dimethylamino |
| 1282 | ethyl | n-butyl | OH | H | 3-fluoro-4-methoxyphenyl | H | 7-trimethylammonium iodide |
| 1283 | n-butyl | n-butyl | OH | H | 4-hydroxymethylphenyl | H | 7-dimethylamino |
| 1284 | n-butyl | n-butyl | OH | H | 4-fluorophenyl | H | 9-ethylamino |
| 1285 | n-butyl | ethyl | OH | H | phenyl | H | 7-dimethylamino |
| 1286 | n-butyl | n-butyl | OH | H | CF₃CO₂⁻ ... N⁺((CH₂)₃CH₃)₃ (2-fluoro-4-substituted phenoxy propyl) | H | 7-dimethylamino |
| 1287 | n-butyl | ethyl | OH | H | 4-hydroxyphenyl | H | 7-dimethylamino |
| 1288 | n-butyl | n-butyl | OH | H | (4-bromophenoxyethyl-pyrrolidinium iodide substituted phenyl) | H | 7-dimethylamino |
| 1289 | n-butyl | n-butyl | OH | H | (tri-alkyl ammonium iodide substituted phenoxy phenyl) | H | 7-dimethylamino |

-continued
Additional Structures of the Present Invention
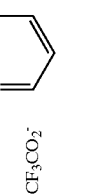
| Compound Number | $R^1$ | $R^2$ | $R^3$ | $R^4$ | $R^5$ | $R^6$ | $(R^*)_4$ |
|---|---|---|---|---|---|---|---|
| 1290 | n-butyl | n-butyl | OH | H | 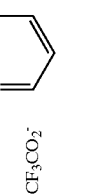 | H | 7-dimethylamino |
| 1291 | n-butyl | n-butyl | OH | H | 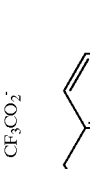 | H | 7-dimethylamino |
| 1292 | n-butyl | n-butyl | OH | H | 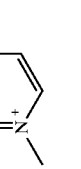 | H | 7-dimethylamino |
| 1293 | n-butyl | n-butyl | OH | H | 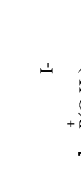 | H | 7-dimethylamino |

-continued
Additional Structures of the Present Invention
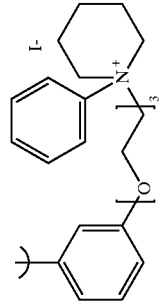
| Compound Number | R¹ | R² | R³ | R⁴ | R⁵ | R⁶ | (R*)₄ |
|---|---|---|---|---|---|---|---|
| 1294 | n-butyl | n-butyl | OH | H |  | H | 7-dimethylamino |
| 1295 | n-butyl | n-butyl | OH | H | 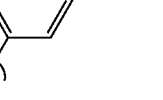 | H | 7-dimethylamino |
| 1296 | n-butyl | n-butyl | OH | H |  | H | 7-dimethylamino |
| 1297 | n-butyl | n-butyl | OH | H |  | H | 7-dimethylamino |

-continued

Additional Structures of the Present Invention

| Compound Number | $R^1$ | $R^2$ | $R^3$ | $R^4$ | $R^5$ | $R^6$ | $(R^*)_4$ |
|---|---|---|---|---|---|---|---|
| 1298 | n-butyl | n-butyl | OH | H | 3-[O-phenyl with N(CH₃)₃⁺(CH₂)₂, I⁻] substituted via N(CH₂)₃ | H | 7-dimethylamino |
| 1299 | n-butyl | n-butyl | OH | H | 2-fluoro-4-[O(CH₂)₂S⁺(CH₂CH₃)₂, SF3⁻] phenyl | H | 7-dimethylamino |
| 1300 | n-butyl | ethyl | H | OH | H | phenyl | 7-dimethylamino |
| 1301 | n-butyl | n-butyl | OH | H | 3-methoxyphenyl | H | 7-trimethylammonium iodide |
| 1302 | n-butyl | n-butyl | OH | H | 3-hydroxyphenyl | H | 9-hydroxyl |
| 1303 | n-butyl | n-butyl | OH | H | 4-[O-CH₂CH₂-N⁺(CH₃)₃, I⁻]phenyl | H | 7-dimethylamino |
| 1304 | n-butyl | n-butyl | OH | H | 3-methoxyphenyl | H | 7-tert-butylamino |
| 1305 | n-butyl | n-butyl | OH | H | 4-fluorophenyl | H | 9-methylamino |
| 1306 | n-butyl | n-butyl | OH | H | 4-[O-C(=O)-C(phenyl)(CF₃)(OCH₃)]phenyl | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1307 | n-butyl | n-butyl | OH | H | H | 4-methoxyphenyl | 9-(4'-morpholino) |
| 1308 | ethyl | n-butyl | OH | H | (camphorsulfonate ester group) | H | 7-dimethylamino |
| 1309 | n-butyl | n-butyl | OH | H | 4-methoxyphenyl | H | 9-fluoro |
| 1310 | ethyl | n-butyl | OH | H | phenyl | H | 7-amino |
| 1311 | n-butyl | ethyl | OH | H | phenyl | H | 7-(hydroxyamino) |
| 1312 | n-butyl | ethyl | OH | H | phenyl | H | 8-hexyloxy |
| 1313 | n-butyl | ethyl | OH | H | phenyl | H | 8-ethoxy |
| 1314 | ethyl | n-butyl | OH | H | phenyl | H | 7-(hydroxylamino) |
| 1315 | ethyl | n-butyl | OH | H | phenyl | H | 7-(hexyloxy) |
| 1316 | n-butyl | n-butyl | OH | H | phenyl | H | 8-hydroxy |
| 1317 | n-butyl | ethyl | OH | H | phenyl | H | trimethylammoniumpropoxy I⁻ at the 8-position |
| 1318 | ethyl | n-butyl | OH | H | phenyl | H | 7-dimethylamino |
| 1319 | ethyl | n-butyl | OH | H | 3-methoxyphenyl | H | 7-fluoro |
| 1320 | ethyl | n-butyl | OH | H | phenyl | H | 7-amino |

-continued
Additional Structures of the Present Invention
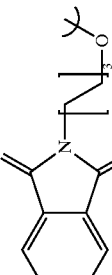
| Compound Number | R¹ | R² | R³ | R⁴ | R⁵ | R⁶ | (R*)₄ |
|---|---|---|---|---|---|---|---|
| 1321 | n-butyl | ethyl | OH | H | phenyl | H | 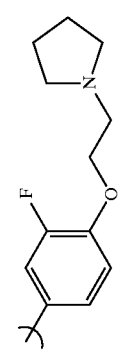 at the 8-position |
| 1322 | n-butyl | n-butyl | OH | H | 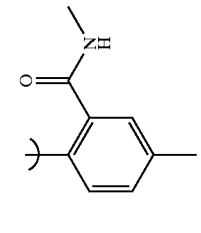 | H | 7-dimethylamino |
| 1323 | n-butyl | n-butyl | OH | H | 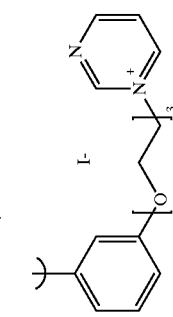 | H | 7-dimethylamino |
| 1324 | n-butyl | n-butyl | OH | H |  | H | 7-dimethylamino |
| 1325 | n-butyl | n-butyl | OH | H | 4-((diethylamino)methyl)phenyl | H | 7-dimethylamino |

-continued
Additional Structures of the Present Invention
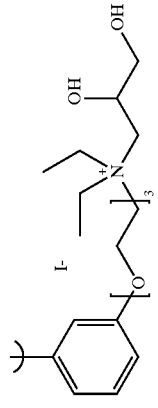
| Compound Number | R¹ | R² | R³ | R⁴ | R⁵ | R⁶ | (R*)₄ |
|---|---|---|---|---|---|---|---|
| 1326 | n-butyl | n-butyl | OH | H | 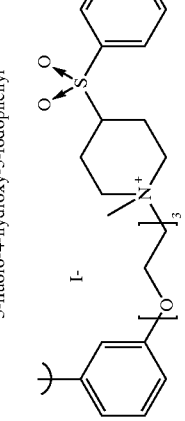 | H | 7-dimethylamino |
| 1327 | n-butyl | n-butyl | OH | H | 3-fluoro-4-hydroxy-5-iodophenyl | H | 7-dimethylamino |
| 1328 | n-butyl | n-butyl | OH | H | 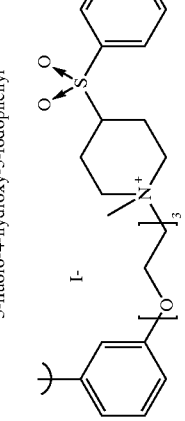 | H | 7-dimethylamino |
| 1329 | n-butyl | n-butyl | OH | H | 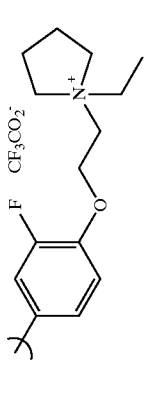 | H | 7-dimethylamino |

-continued
Additional Structures of the Present Invention
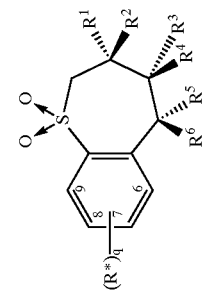
| Compound Number | $R^1$ | $R^2$ | $R^3$ | $R^4$ | $R^5$ | $R^6$ | $(R^*)_4$ |
|---|---|---|---|---|---|---|---|
| 1330 | n-butyl | n-butyl | OH | H | 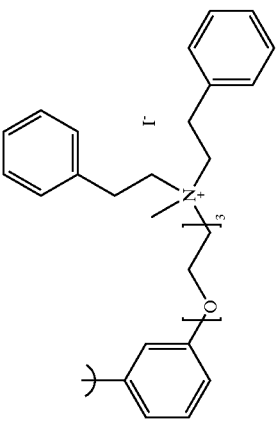 | H | 7-dimethylamino |
| 1331 | n-butyl | n-butyl | OH | H | 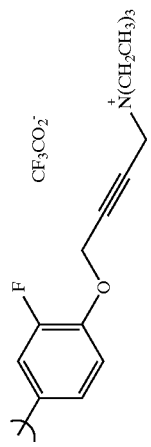 | H | 7-dimethylamino |
| 1332 | n-butyl | n-butyl | OH | H | 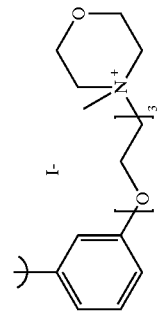 | H | 7-dimethylamino |
| 1333 | n-butyl | n-butyl | OH | H | 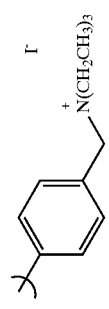 | H | 7-dimethylamino |

-continued
Additional Structures of the Present Invention
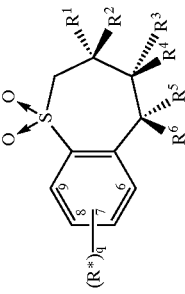
| Compound Number | R¹ | R² | R³ | R⁴ | R⁵ | R⁶ | (R*)₄ |
|---|---|---|---|---|---|---|---|
| 1334 | n-butyl | n-butyl | OH | H | 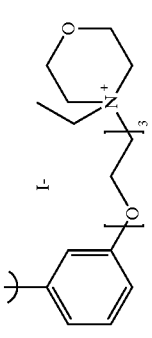 | H | 7-dimethylamino |
| 1335 | n-butyl | n-butyl | OH | H | 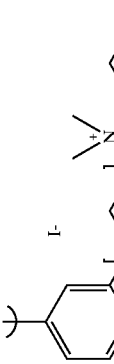 | H | 7-dimethylamino |
| 1336 | n-butyl | n-butyl | OH | H | 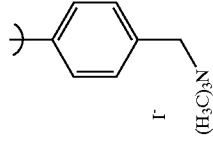 | H | 7-dimethylamino |
| 1337 | n-butyl | n-butyl | OH | H | (H₃O)₃N— phenyl-CH₂— I⁻ | H | 7-dimethylamino |

-continued

Additional Structures of the Present Invention

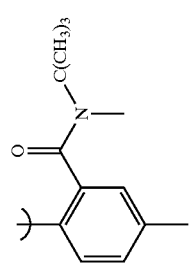

| Compound Number | R¹ | R² | R³ | R⁴ | R⁵ | R⁶ | (R*)₄ |
|---|---|---|---|---|---|---|---|
| 1338 | n-butyl | n-butyl | OH | H | 4-methoxyphenyl | H | 7-(4'-methylpiperazinyl) |
| 1339 | n-butyl | n-butyl | OH | H | 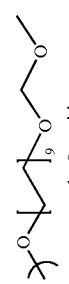 | H | 7-dimethylamino |
| 1340 | n-butyl | ethyl | OH | H | 5-piperonyl | H | 7-methyl |
| 1341 | n-butyl | n-butyl | acetoxy | H | 3-methoxyphenyl | H | 7-dimethylamino |
| 1342 | n-butyl | n-butyl | OH | H | 5-piperonyl | H | 7-(4'-fluorophenyl) |
| 1343 | ethyl | n-butyl | OH | H | phenyl | H | 7-amino |
| 1344 | n-butyl | n-butyl | OH | H | 3-fluoro-4-methoxyphenyl | H | 7-dimethylamino |
| 1345 | ethyl | n-butyl | OH | H | phenyl | H | 7-trimethylammonium iodide |
| 1346 | ethyl | n-butyl | OH | H | phenyl | H | at the 8-position |
| 1347 | n-butyl | n-butyl | OH | H | 3-fluoro-4-methoxyphenyl | H | 7-dimethylamino |
| 1348 | isobutyl | isobutyl | OH | H | phenyl | H | 7-dimethylamino |
| 1349 | ethyl | n-butyl | OH | H | phenyl | H | 7-dimethylamino |
| 1350 | n-butyl | n-butyl | OH | H | 3-fluoro-4-methoxyphenyl | H | 7-trimethylammonium iodide |

-continued
Additional Structures of the Present Invention
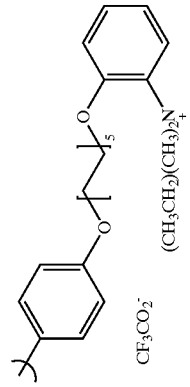
| Compound Number | R¹ | R² | R³ | R⁴ | R⁵ | R⁶ | (R*)₄ |
|---|---|---|---|---|---|---|---|
| 1351 | n-butyl | n-butyl | OH | H | 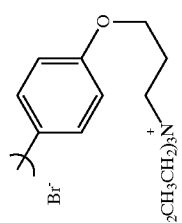 | H | 7-dimethylamino |
| 1352 | n-butyl | n-butyl | OH | H |  | H | 7-dimethylamino |
| 1353 | n-butyl | n-butyl | OH | H | 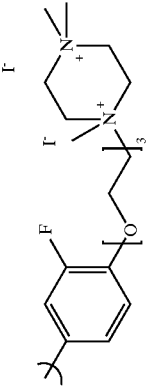 | H | 7-dimethylamino |
| 1354 | n-butyl | n-butyl | OH | H |  | H | 7-dimethylamino |

-continued
Additional Structures of the Present Invention
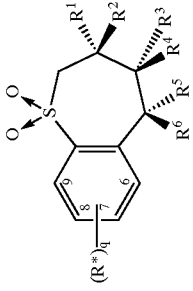
| Compound Number | R¹ | R² | R³ | R⁴ | R⁵ | R⁶ | (R*)₄ |
|---|---|---|---|---|---|---|---|
| 1355 | n-butyl | n-butyl | OH | H | 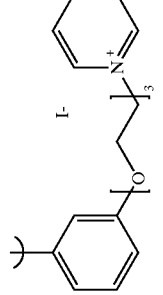 | H | 7-dimethylamino |
| 1356 | n-butyl | n-butyl | OH | H | 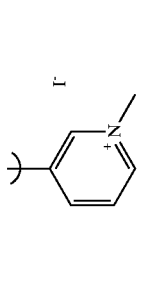 | H | 7-dimethylamino |
| 1357 | n-butyl | n-butyl | OH | H | 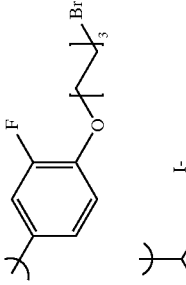 | H | 7-dimethylamino |
| 1358 | n-butyl | n-butyl | OH | H | 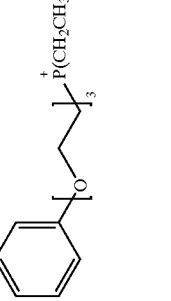 | H | 7-dimethylamino |

-continued
Additional Structures of the Present Invention
| Compound Number | R¹ | R² | R³ | R⁴ | R⁵ | R⁶ | (R*)₄ |
|---|---|---|---|---|---|---|---|
| 1359 | n-butyl | n-butyl | OH | H | 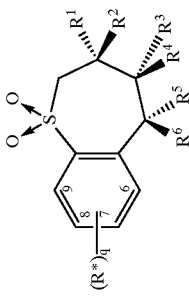 | H | 7-dimethylamino |
| 1360 | n-butyl | n-butyl | OH | H | 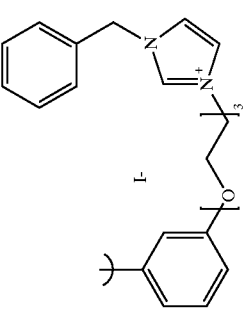 | H | 7-dimethylamino |
| 1361 | n-butyl | n-butyl | OH | H | 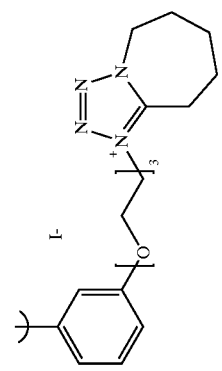 | H | 7-dimethylamino |

Additional Structures of the Present Invention

| Compound Number | R¹ | R² | R³ | R⁴ | R⁵ | R⁶ | (R*)₄ |
|---|---|---|---|---|---|---|---|
| 1362 | n-butyl | n-butyl | OH | H | 3-[O-CH₂CH₂-N⁺(Et)₃ I⁻]-phenyl-CH₂CH₂-C(O)OH linkage | H | 7-dimethylamino |
| 1363 | n-butyl | n-butyl | OH | H | 3-[O-CH₂CH₂-N⁺(Et)₃ I⁻]-phenyl-CH₂CH₂-N(H)-S(O)₂-N(CH₃)₂ | H | 7-dimethylamino |
| 1364 | n-butyl | n-butyl | OH | H | 3-[O-CH₂CH₂-N⁺(Et)₃ I⁻]-phenyl-CH₂CH₂-N(H)-C(O)-NH₂ | H | 7-dimethylamino |
| 1365 | n-butyl | n-butyl | OH | H | 3-[O-CH₂CH₂-N⁺(Et)₃ I⁻]-phenyl-CH₂CH₂-N(H)-S(O)₂-phenyl | H | 7-dimethylamino |

-continued
Additional Structures of the Present Invention
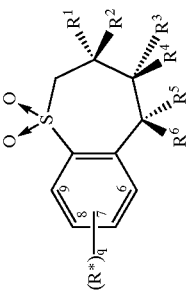
| Compound Number | R¹ | R² | R³ | R⁴ | R⁵ | R⁶ | (R*)₄ |
|---|---|---|---|---|---|---|---|
| 1366 | n-butyl | n-butyl | OH | H | 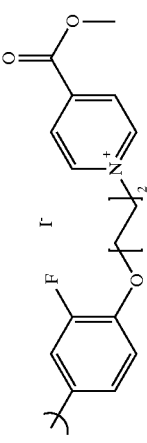 | H | 7-dimethylamino |
| 1367 | n-butyl | n-butyl | OH | H | 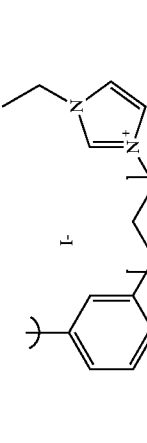 | H | 7-dimethylamino |
| 1368 | n-butyl | n-butyl | OH | H | 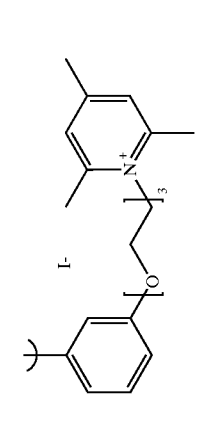 | H | 7-dimethylamino |

Additional Structures of the Present Invention
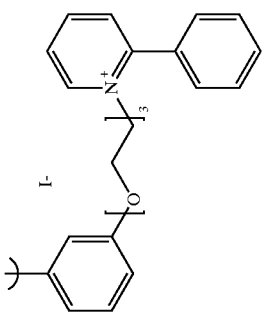
| Compound Number | R¹ | R² | R³ | R⁴ | R⁵ | R⁶ | (R*)₄ |
|---|---|---|---|---|---|---|---|
| 1369 | n-butyl | n-butyl | OH | H | 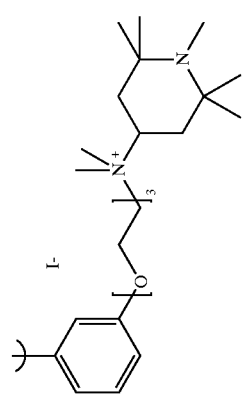 | H | 7-dimethylamino |
| 1370 | n-butyl | n-butyl | OH | H | 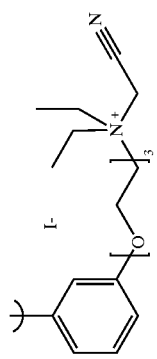 | H | 7-dimethylamino |
| 1371 | n-butyl | n-butyl | OH | H | (see structure) | H | 7-dimethylamino |

-continued
Additional Structures of the Present Invention
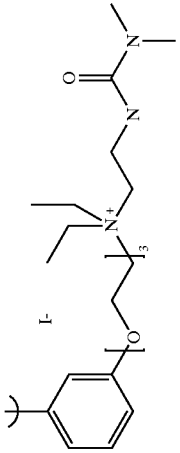
| Compound Number | R¹ | R² | R³ | R⁴ | R⁵ | R⁶ | (R*)$_4$ |
|---|---|---|---|---|---|---|---|
| 1372 | n-butyl | n-butyl | OH | H |  | H | 7-dimethylamino |
| 1373 | n-butyl | n-butyl | OH | H | 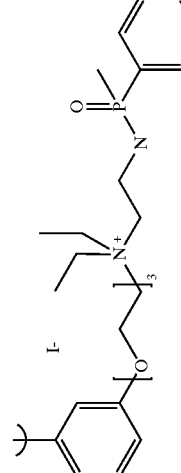 | H | 7-dimethylamino |
| 1374 | n-butyl | n-butyl | OH | H |  | H | 7-dimethylamino |

-continued

Additional Structures of the Present Invention

| Compound Number | R¹ | R² | R³ | R⁴ | R⁵ | R⁶ | (R*)q |
|---|---|---|---|---|---|---|---|
| 1375 | n-butyl | n-butyl | OH | H | | H | 7-dimethylamino |
| 1376 | n-butyl | n-butyl | OH | H | | H | 7-dimethylamino |
| 1377 | n-butyl | n-butyl | OH | H | | H | 7-dimethylamino |
| 1378 | n-butyl | n-butyl | OH | H | | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1379 | n-butyl | n-butyl | OH | H | 4-(CH₂-O-CH₂CH₂-N⁺(CH₃)₃) phenyl, I⁻ | H | 7-dimethylamino |
| 1380 | n-butyl | n-butyl | OH | H | 3-(CH₂CH₂-N⁺(CH₂CH₃)₃) phenyl, I⁻ | H | 7-dimethylamino |
| 1381 | n-butyl | n-butyl | OH | H | 4-(CH₂-O-(2-fluorophenyl))-N-ethylpyridinium, I⁻ | H | 7-dimethylamino |
| 1382 | n-butyl | n-butyl | OH | H | 3-(CH₂-(N-ethylpyridinium))phenyl, I⁻ | H | 7-dimethylamino |

-continued

Additional Structures of the Present Invention

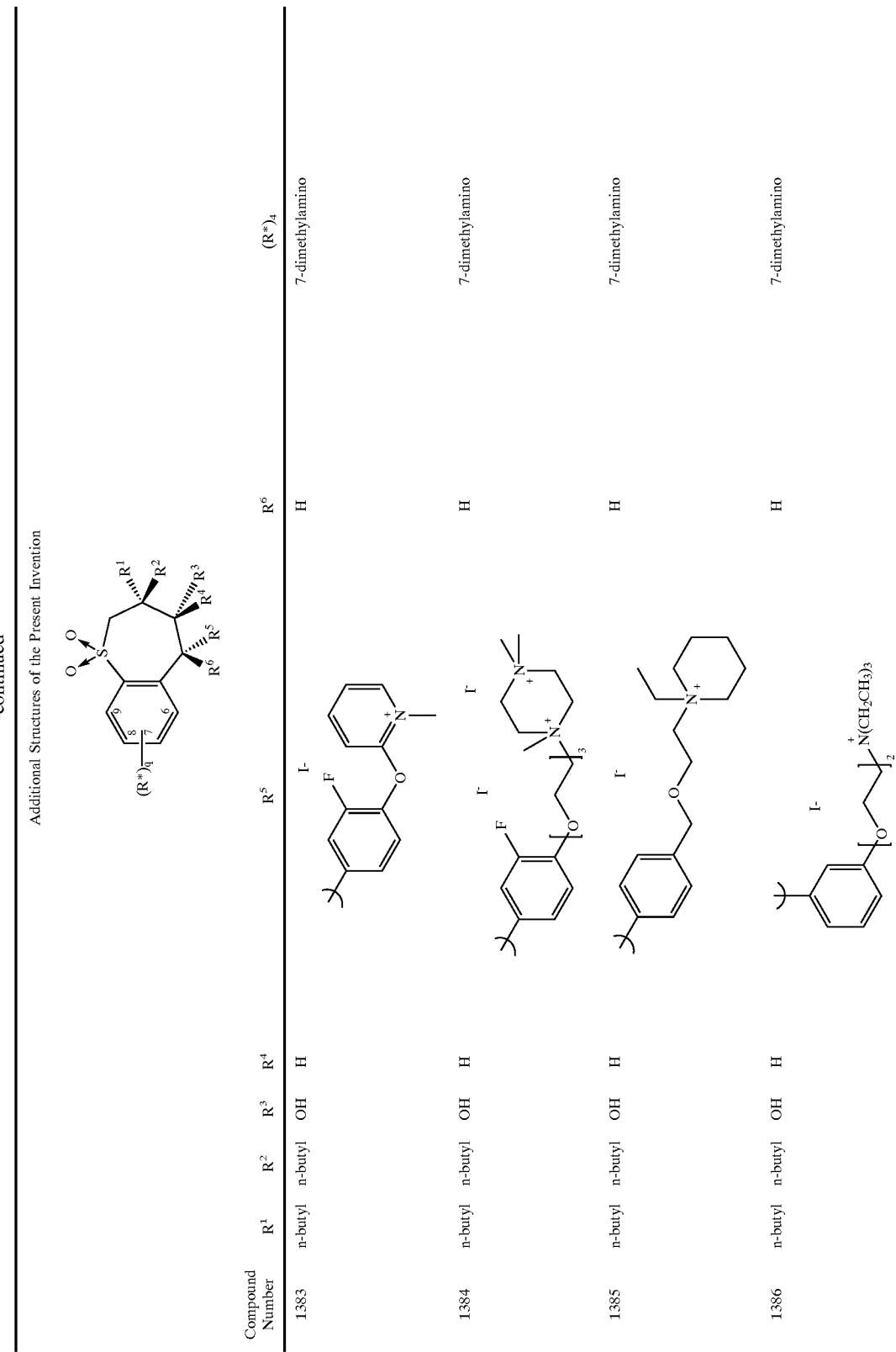

| Compound Number | $R^1$ | $R^2$ | $R^3$ | $R^4$ | $R^5$ | $R^6$ | $(R^*)_q$ |
|---|---|---|---|---|---|---|---|
| 1383 | n-butyl | n-butyl | OH | H | 2-fluoro-4-(N-methylpyridinium-2-yloxy)benzyl, I⁻ | H | 7-dimethylamino |
| 1384 | n-butyl | n-butyl | OH | H | 2-fluoro-4-[(N,N,N',N'-tetramethylpiperazinium)propyloxy]benzyl, 2I⁻ | H | 7-dimethylamino |
| 1385 | n-butyl | n-butyl | OH | H | 4-[(N-ethyl-N-piperidinium)ethyloxymethyl]benzyl, I⁻ | H | 7-dimethylamino |
| 1386 | n-butyl | n-butyl | OH | H | 3-[(triethylammonium)ethyloxy-(CH₂)₂-N(CH₂CH₃)₃]phenyl, I⁻ | H | 7-dimethylamino |

-continued
Additional Structures of the Present Invention
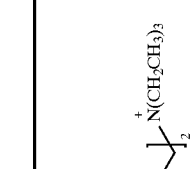
| Compound Number | R¹ | R² | R³ | R⁴ | R⁵ | R⁶ | (R*)q |
|---|---|---|---|---|---|---|---|
| 1387 | n-butyl | n-butyl | OH | H |  | H | 7-dimethylamino |
| 1388 | n-butyl | n-butyl | OH | H | 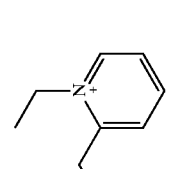 | H | 7-dimethylamino |
| 1389 | n-butyl | n-butyl | OH | H | 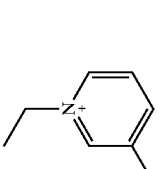 | H | 7-dimethylamino |
| 1390 | n-butyl | n-butyl | OH | H | (structure) | H | 7-dimethylamino |

-continued

Additional Structures of the Present Invention

| Compound Number | R¹ | R² | R³ | R⁴ | R⁵ | R⁶ | (R*)₄ |
|---|---|---|---|---|---|---|---|
| 1391 | n-butyl | n-butyl | OH | H | 2-fluoro-4-(3-(1-ethylpyridinium-2-yl)prop-2-ynyloxy)phenyl, I⁻ | H | 7-dimethylamino |
| 1392 | n-butyl | n-butyl | OH | H | pyridin-2-yl substituted with -O-CH₂CH₂-N⁺(Et)₃, I⁻ | H | 7-dimethylamino |
| 1393 | n-butyl | n-butyl | OH | H | 3-(N-(6-(triethylammonio)hexyl)amino)phenyl, I⁻ | H | 7-dimethylamino |

-continued
Additional Structures of the Present Invention
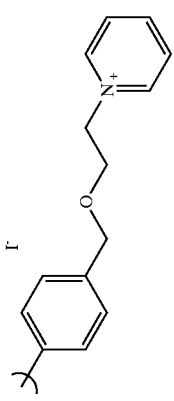
| Compound Number | $R^1$ | $R^2$ | $R^3$ | $R^4$ | $R^5$ | $R^6$ | $(R^*)_4$ |
|---|---|---|---|---|---|---|---|
| 1394 | n-butyl | n-butyl | OH | H | 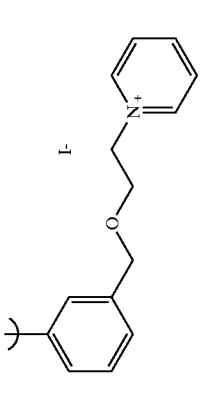 | H | 7-dimethylamino |
| 1395 | n-butyl | n-butyl | OH | H | | H | 7-dimethylamino |
| 1396 | n-butyl | n-butyl | OH | H | | H | 7-dimethylamino |
| 1397 | n-butyl | n-butyl | OH | H | 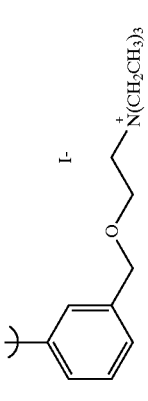 | H | 7-dimethylamino |

-continued
Additional Structures of the Present Invention
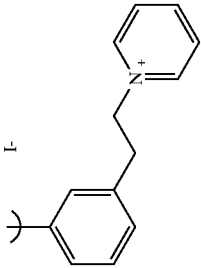
| Compound Number | $R^1$ | $R^2$ | $R^3$ | $R^4$ | $R^5$ | $R^6$ | $(R^*)_q$ |
|---|---|---|---|---|---|---|---|
| 1398 | n-butyl | n-butyl | OH | H | 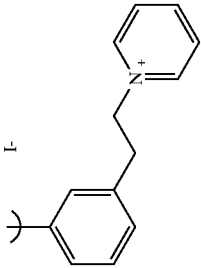 | H | 7-dimethylamino |
| 1399 | n-butyl | n-butyl | OH | H | 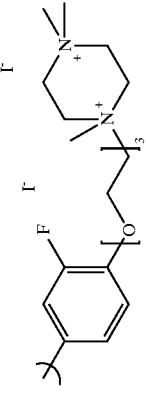 | H | 7-dimethylamino |
| 1400 | n-butyl | n-butyl | OH | H | 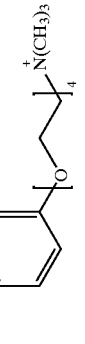 | H | 7-dimethylamino |
| 1401 | n-butyl | n-butyl | OH | H | 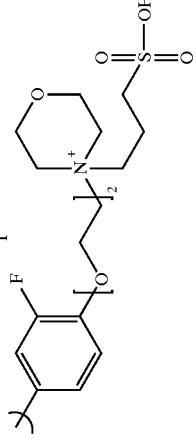 | H | 7-dimethylamino |

-continued
Additional Structures of the Present Invention
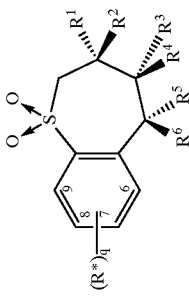
| Compound Number | R¹ | R² | R³ | R⁴ | R⁵ | R⁶ | (R*)₄ |
|---|---|---|---|---|---|---|---|
| 1402 | n-butyl | n-butyl | OH | H | 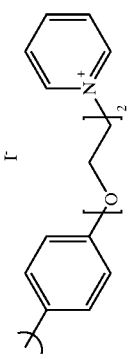 | H | 7-dimethylamino |
| 1403 | n-butyl | n-butyl | OH | H | 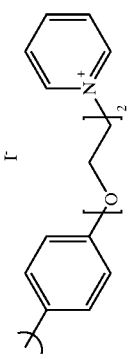 | H | 7-dimethylamino |
| 1404 | n-butyl | n-butyl | OH | H | 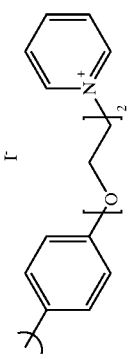 | H | 7-dimethylamino |
| 1405 | n-butyl | n-butyl | OH | H | 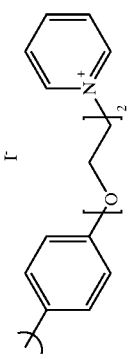 | H | 7-dimethylamino |

-continued
Additional Structures of the Present Invention
| Compound Number | $R^1$ | $R^2$ | $R^3$ | $R^4$ | $R^5$ | $R^6$ | $(R^*)_4$ |
|---|---|---|---|---|---|---|---|
| 1406 | n-butyl | n-butyl | OH | H | 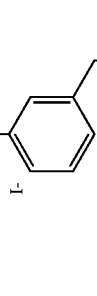 | H | 7-dimethylamino |
| 1407 | n-butyl | n-butyl | OH | H | 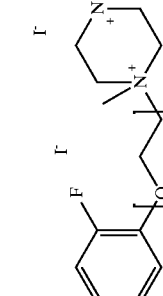 | H | 7-dimethylamino |
| 1408 | n-butyl | n-butyl | OH | H | 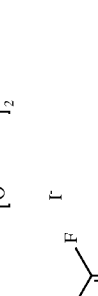 | H | 7-dimethylamino |
| 1409 | n-butyl | n-butyl | OH | H | 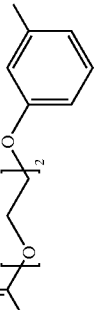 | H | 7-dimethylamino |

-continued
Additional Structures of the Present Invention
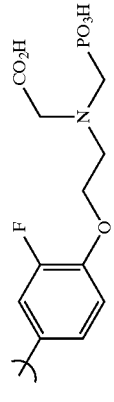
| Compound Number | R¹ | R² | R³ | R⁴ | R⁵ | R⁶ | (R*)₄ |
|---|---|---|---|---|---|---|---|
| 1410 | n-butyl | n-butyl | OH | H | 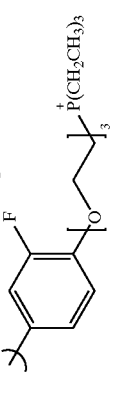 | H | 7-dimethylamino |
| 1411 | n-butyl | n-butyl | OH | H | 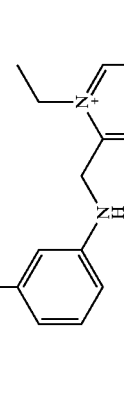 | H | 7-dimethylamino |
| 1412 | n-butyl | n-butyl | OH | H |  | H | 7-dimethylamino |
| 1413 | n-butyl | n-butyl | OH | H | (see structure) | H | 7-dimethylamino |

-continued
Additional Structures of the Present Invention
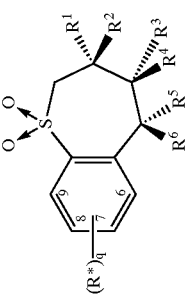
| Compound Number | R¹ | R² | R³ | R⁴ | R⁵ | R⁶ | (R*)₄ |
|---|---|---|---|---|---|---|---|
| 1414 | n-butyl | n-butyl | OH | H | ![](structure with 4-(ethylpyridinium)methyl-NH-phenyl, I⁻) | H | 7-dimethylamino |
| 1415 | n-butyl | n-butyl | OH | H | ![](structure with 1-ethylpyridinium-NH-pyridyl, I⁻) | H | 7-dimethylamino |
| 1416 | n-butyl | n-butyl | OH | H | ![](structure with N⁺(CH₂CH₃)₃-propyl-NH-pyridyl, I⁻) | H | 7-dimethylamino |

-continued
Additional Structures of the Present Invention
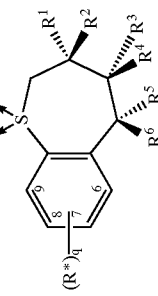
| Compound Number | $R^1$ | $R^2$ | $R^3$ | $R^4$ | $R^5$ | $R^6$ | $(R^*)_q$ |
|---|---|---|---|---|---|---|---|
| 1417 | n-butyl | n-butyl | OH | H | pyridyl-CH$_2$-N$^+$(Et)$_3$ I$^-$ | H | 7-dimethylamino |
| 1418 | n-butyl | n-butyl | OH | H | 2-F-phenoxy-(CH$_2$)$_4$-N$^+$(CH$_2$CH$_2$OH)$_3$ I$^-$ | H | 7-dimethylamino |
| 1419 | n-butyl | n-butyl | OH | H | 2-F-phenoxy-C(CH$_2$N$^+$(CH$_2$CH$_3$)$_3$)$_3$ I$^-$ | H | 7-dimethylamino |

-continued
Additional Structures of the Present Invention
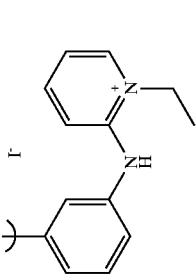
| Compound Number | R¹ | R² | R³ | R⁴ | R⁵ | R⁶ | (R*)₄ |
|---|---|---|---|---|---|---|---|
| 1420 | n-butyl | n-butyl | OH | H | 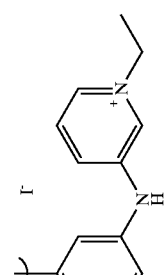 | H | 7-dimethylamino |
| 1421 | n-butyl | n-butyl | OH | H | 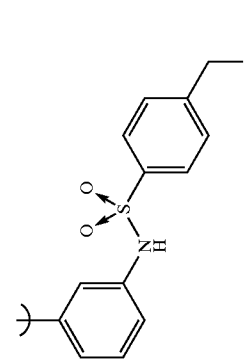 | H | 7-dimethylamino |
| 1422 | n-butyl | n-butyl | OH | H | (see structure) | H | 7-dimethylamino |

-continued
Additional Structures of the Present Invention
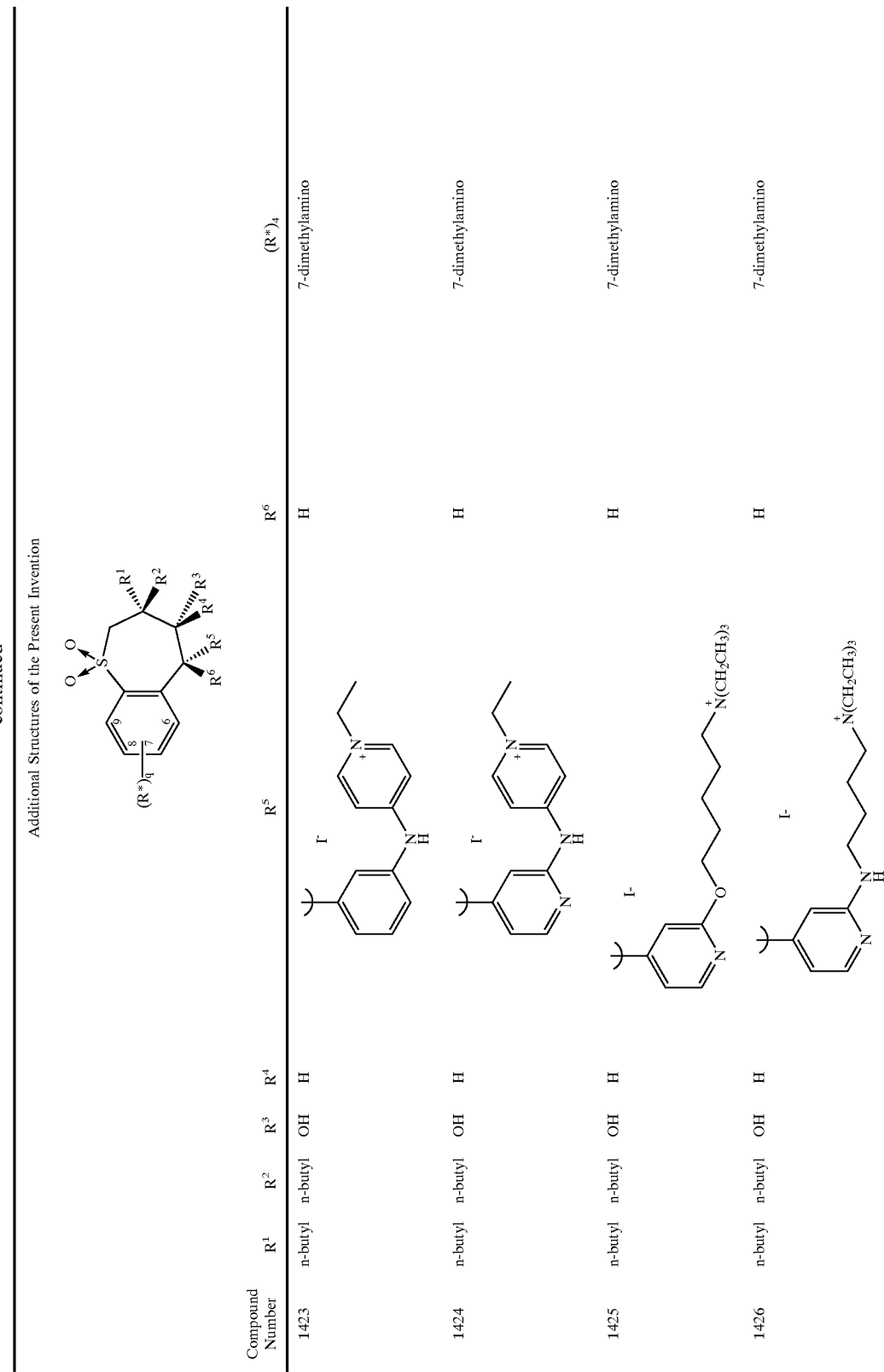
| Compound Number | $R^1$ | $R^2$ | $R^3$ | $R^4$ | $R^5$ | $R^6$ | $(R^*)_4$ |
|---|---|---|---|---|---|---|---|
| 1423 | n-butyl | n-butyl | OH | H | ethyl-pyridinium-NH-phenyl, I⁻ | H | 7-dimethylamino |
| 1424 | n-butyl | n-butyl | OH | H | ethyl-pyridinium-NH-pyridyl, I⁻ | H | 7-dimethylamino |
| 1425 | n-butyl | n-butyl | OH | H | pyridyl-O-(CH2)n-N⁺(CH2CH3)3, I⁻ | H | 7-dimethylamino |
| 1426 | n-butyl | n-butyl | OH | H | pyridyl-NH-(CH2)n-N⁺(CH2CH3)3, I⁻ | H | 7-dimethylamino |

-continued
Additional Structures of the Present Invention
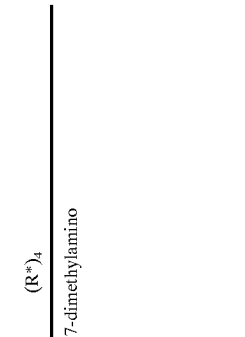
| Compound Number | $R^1$ | $R^2$ | $R^3$ | $R^4$ | $R^5$ | $R^6$ | $(R^*)_4$ |
|---|---|---|---|---|---|---|---|
| 1427 | n-butyl | n-butyl | OH | H |  | H | 7-dimethylamino |
| 1428 | n-butyl | n-butyl | OH | H |  | H | 7-dimethylamino |
| 1429 | n-butyl | n-butyl | OH | H |  | H | 7-dimethylamino |

-continued
Additional Structures of the Present Invention
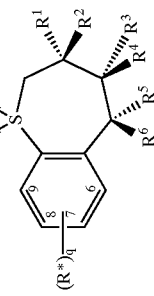
| Compound Number | $R^1$ | $R^2$ | $R^3$ | $R^4$ | $R^5$ | $R^6$ | $(R^*)_q$ |
|---|---|---|---|---|---|---|---|
| 1430 | n-butyl | n-butyl | OH | H | 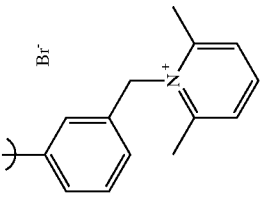 | H | 7-dimethylamino |
| 1431 | n-butyl | n-butyl | OH | H | 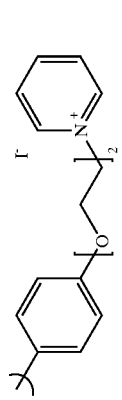 | H | 7-dimethylamino |
| 1432 | n-butyl | n-butyl | OH | H | 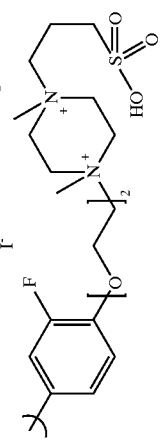 | H | 7-dimethylamino |
| 1433 | n-butyl | n-butyl | OH | H | 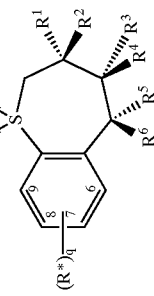 | H | 7-dimethylamino |

-continued
Additional Structures of the Present Invention
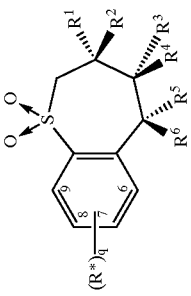
| Compound Number | R¹ | R² | R³ | R⁴ | R⁵ | R⁶ | (R*)₄ |
|---|---|---|---|---|---|---|---|
| 1434 | n-butyl | n-butyl | OH | H | ![structure with phenoxy-pentyl-N⁺(CH₂CH₃)₃ r⁻] | H | 7-dimethylamino |
| 1435 | n-butyl | n-butyl | OH | H | ![structure with fluorophenyl-O-ethyl-N⁺(CH₃)₂-phenyl-OH r⁻] | H | 7-dimethylamino |
| 1436 | n-butyl | n-butyl | OH | H | ![structure with phenoxy-phenyl-pyridinium-ethyl r⁻] | H | 7-dimethylamino |

-continued
Additional Structures of the Present Invention
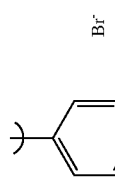
| Compound Number | R¹ | R² | R³ | R⁴ | R⁵ | R⁶ | (R*)$_q$ |
|---|---|---|---|---|---|---|---|
| 1437 | n-butyl | n-butyl | OH | H |  | H | 7-dimethylamino |
| 1438 | n-butyl | n-butyl | OH | H |  | H | 7-dimethylamino |
| 1439 | n-butyl | n-butyl | OH | H |  | H | 7-dimethylamino |
| 1440 | n-butyl | n-butyl | OH | H | 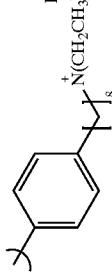 | H | 7-dimethylamino |
| 1441 | n-butyl | n-butyl | OH | H |  | H | 7-dimethylamino |

-continued
Additional Structures of the Present Invention
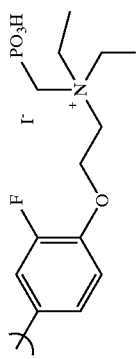
| Compound Number | R¹ | R² | R³ | R⁴ | R⁵ | R⁶ | (R*)₄ |
|---|---|---|---|---|---|---|---|
| 1442 | n-butyl | n-butyl | OH | H | 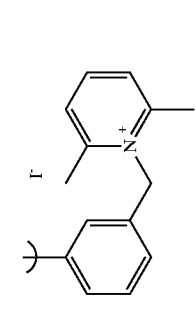 | H | 7-dimethylamino |
| 1443 | n-butyl | n-butyl | OH | H | 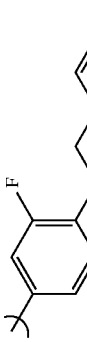 | H | 7-dimethylamino |
| 1444 | n-butyl | n-butyl | OH | H |  | H | 7-dimethylamino |
| 1445 | n-butyl | n-butyl | OH | H |  | H | 7-dimethylamino |

-continued
Additional Structures of the Present Invention
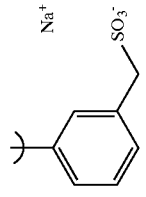
| Compound Number | R¹ | R² | R³ | R⁴ | R⁵ | R⁶ | (R*)₄ |
|---|---|---|---|---|---|---|---|
| 1446 | n-butyl | n-butyl | OH | H | ![](structure with Br⁻, triethylammonium, phenoxy) | H | 7-methoxy; 8-methoxy |
| 1447 | n-butyl | n-butyl | OH | H | ![](structure with Na⁺, SO₃⁻, benzyl) | H | 7-dimethylamino |
| 1448 | n-butyl | n-butyl | OH | H | ![](structure with Na⁺, SO₃⁻, F, phenoxyethyl) | H | 7-dimethylamino |

-continued

Additional Structures of the Present Invention

| Compound Number | $R^1$ | $R^2$ | $R^3$ | $R^4$ | $R^5$ | $R^6$ | $(R^*)_4$ |
|---|---|---|---|---|---|---|---|
| 1449 | n-butyl | n-butyl | OH | H | ![structure with quaternary ammonium bearing two 3-phenylpropyl groups, ethyl, and ethoxyphenyl] | H | 7-dimethylamino |
| 1450 | n-butyl | n-butyl | OH | H | phenyl | H | 7-dimethylamino |
| 1451 | n-butyl | n-butyl | OH | H | 3-(3-sulfopropylamino)phenyl | H | 7-dimethylamino |

221
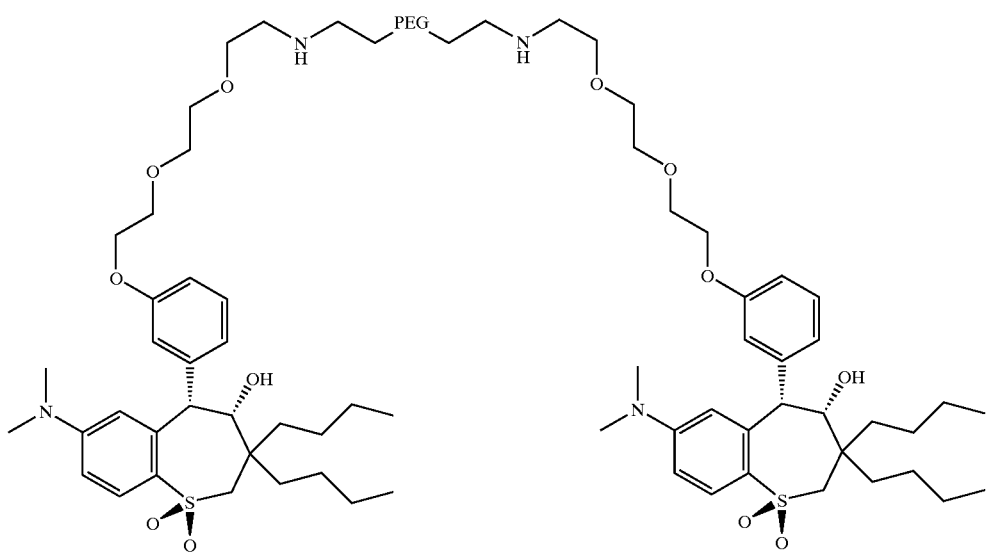
PEG=3400 molecular weight polyethylene glycol polymer chain
222
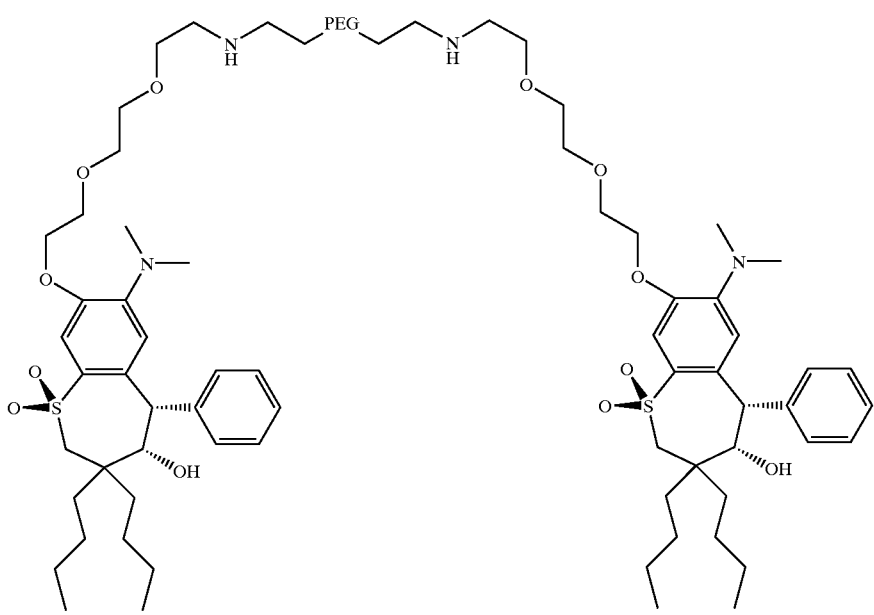

PEG=3400 molecular weight polyethylene glycol polymer chain
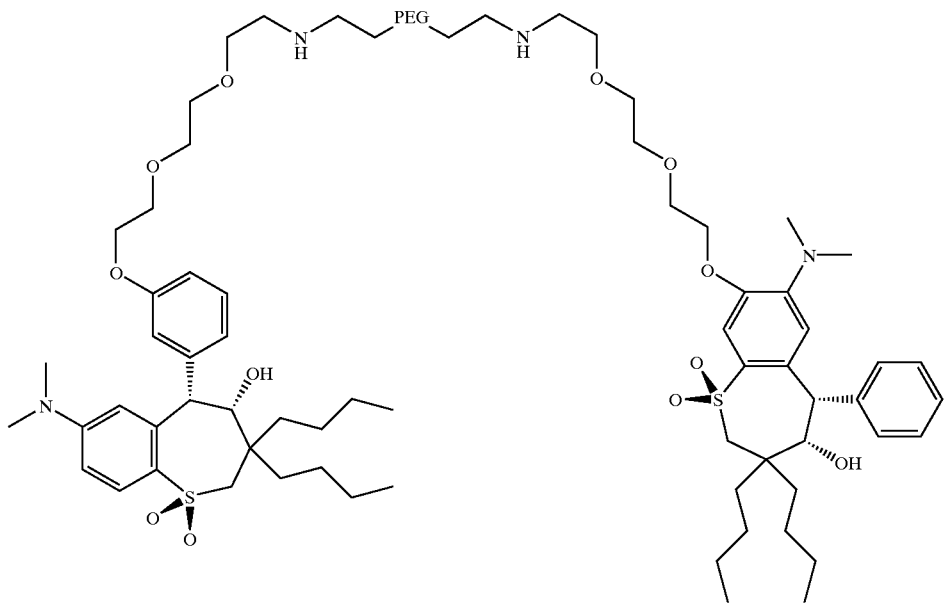
PEG=3400 molecular weight polyethylene glycol polymer chain
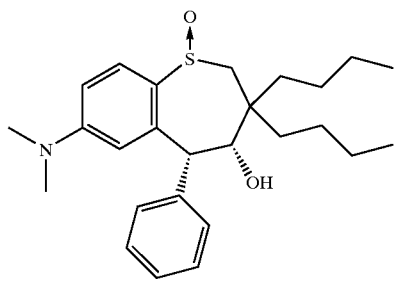
C22 H23 N O3 S
387.542
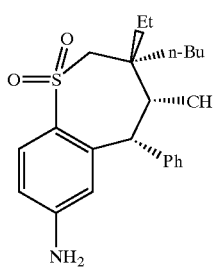
C22 H23 N O3 S
387.543
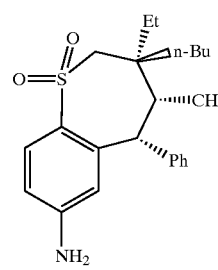
C22 H28 N O3 S
372.529
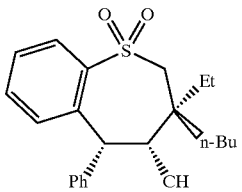
C21 H24 N O3 S
356.486
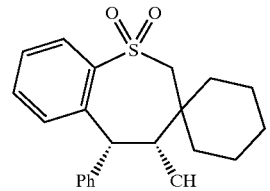
C22 H29 O S
340.53
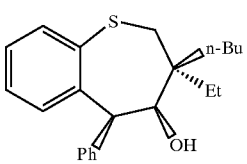
C22 H28 O S
340.53
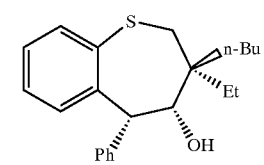
C22 H28 O4 S
388.528
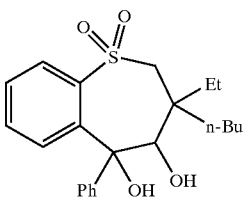

-continued
C22 H32O3 S·C22 H23 O3 S
743.085
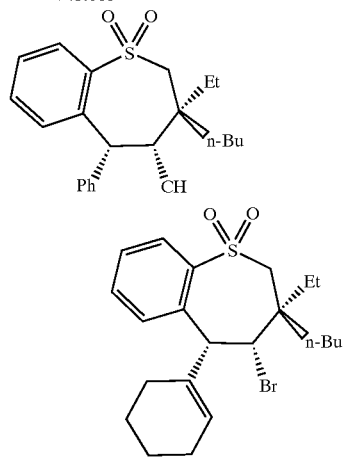
C22 H28 O2 S
356.525
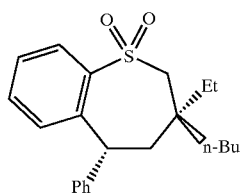
C28 H41 N O3 S
471.784
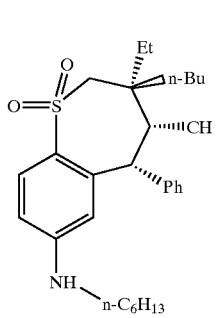
C22 H27 I O3 S
458.425
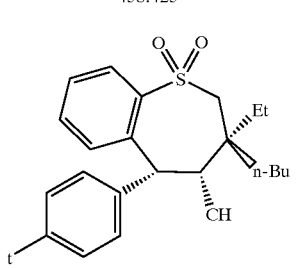
C24 H30 O3 S
430.363
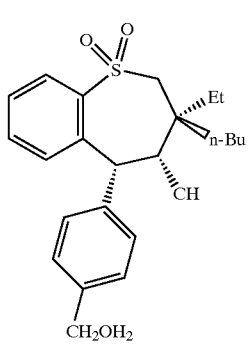
C22 H23 N O4 S
423.542
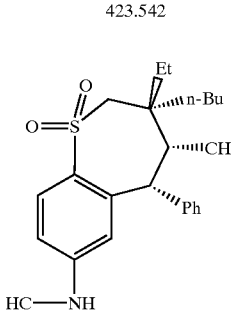
-continued
C22 H23 N O4 S
423.543
C28 H41 N O2 S
471.704
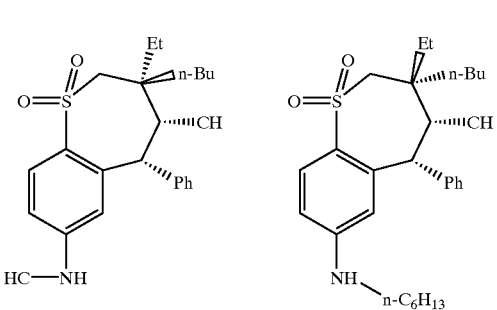
C28 H40 O4 S
472.689
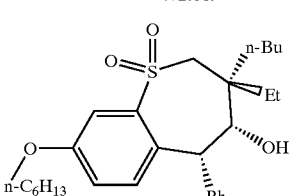
C24 H30 O5 S
438.265
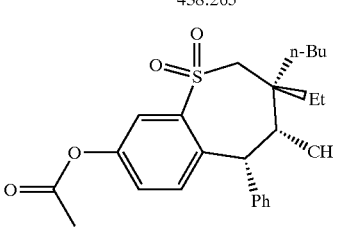
C36 H43 N O6 S
617.807
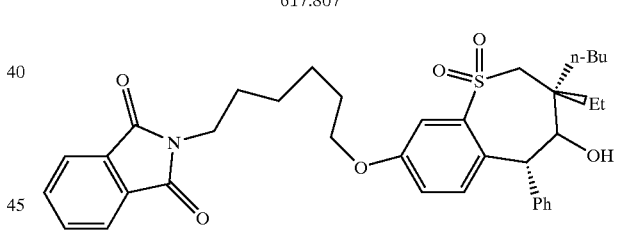
C23 H30 N O4 S
402.525
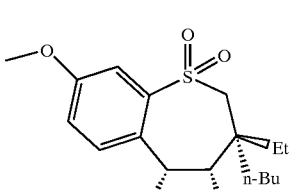
C22 H29 O4 S
388.528
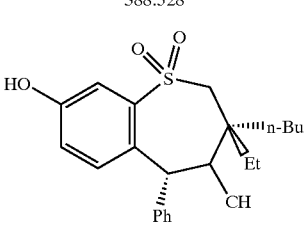

-continued
C24 H32 O4 S
416.582
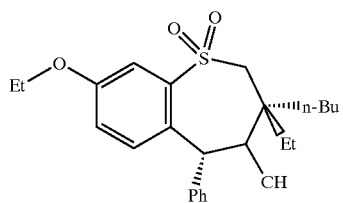
C22 H28 O3 S
372.523
C22 H28 O3 S
372.523
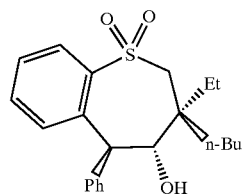
C23 H30 O4 S
402.255
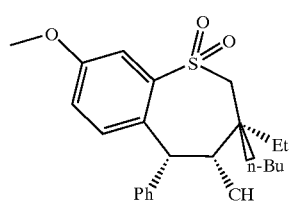
C22 H28 O4 S·C22 H28 O3 S
761.056
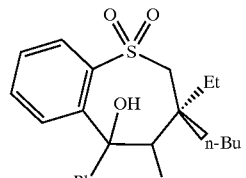
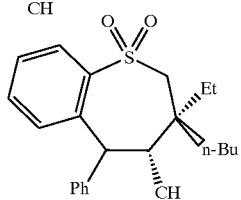
2 C22 H28 O3 S2
404.555
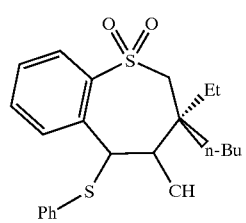 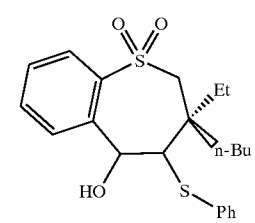
-continued
C22 H26 I2 O3 S
824.322
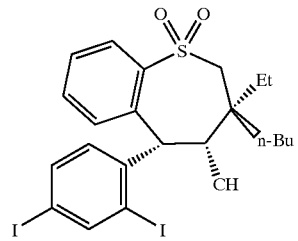
C21 H24 O3 S
236.466
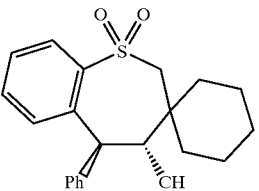
C23 H30 O4 S
402.555
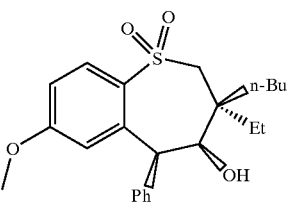
C23 H30 O4 S
402.555
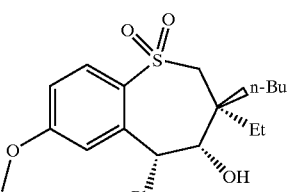
C18 H20 O3 S
316.421
C18 H20 O3 S
316.421
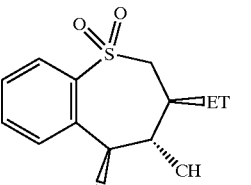 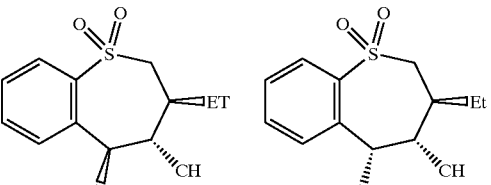
C22 H28 O2 S
356.529
C18 H20 O3 S
380.422
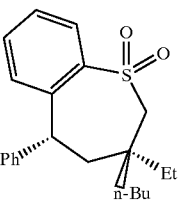 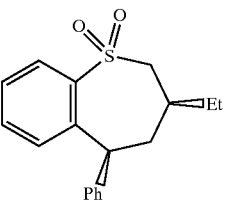

-continued

C22 H28 O3 S
372.529

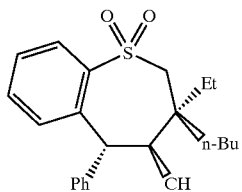

In further compounds of the present invention, $R^5$ and $R^6$ are independently selected from among hydrogen and ring-carbon substituted or unsubstituted aryl, thiophene, pyridine, pyrrole, thiazole, imidazole, pyrazole, pyrimidine, morpholine, N-alkylpyridinium, N-alkyl-piperazinium, N-alkylmorpholinium, or furan in which the substituent(s) are selected from among halo, hydroxyl, trihaloalkyl, alkoxy, amino, N-alkylamino, N,N-dialkylamino, quaternary ammonium salts, a $C_1$ to $C_4$ alkylene bridge having a quaternary ammonium salt substituted thereon, alkoxycarbonyl, aryloxycarbonyl, alkylcarbonyloxy and arylcarbonyloxy, (O,O)-dioxyalkylene, $-[O(CH_2)_v]_xX$ where x is 2 to 12, w is 2 or 3 and X comprises halo or a quaternary ammonium salt, thiophene, pyridine, pyrrole, thiazole, imidazole, pyrazole, or furan. The aryl group of $R^5$ or $R^6$ is preferably phenyl, phenylene, or benzene triyl, i.e., may be unsubstituted, mono-substituted, or di-substituted. Among the species which may constitute the substituents on the aryl ring of $R^5$ or $R^6$ are fluoro, chloro, bromo, methoxy, ethoxy, isopropoxy, trimethylammonium (preferably with an iodide or chloride counterion), methoxycarbonyl, ethoxycarbonyl, formyl, acetyl, propanoyl, (N)-hexyldimethylammonium, hexylenetrimethylammonium, tri(oxyethylene)iodide, and tetra(oxyethylene) trimethylammonium iodide, each substituted at the p-position, the m-position, or both of the aryl ring. Other substituents that can be present on a phenylene, benzene triyl or other aromatic ring include 3,4-dioxymethylene (5-membered ring) and 3,4-dioxyethylene (6-membered ring). Among compounds which have been or can be demonstrated to have desirable ileal bile acid transport inhibiting properties are those in which $R^5$ or $R^6$ is selected from phenyl, p-fluorophenyl, m-fluorophenyl, p-hydroxyphenyl, m-hydroxyphenyl, p-methoxyphenyl, m-methoxyphenyl, p-N,N-dimethylaminophenyl, m-N,N-dimethylaminophenyl, $I^-$ p-$(CH_3)_3$-$N^-$-phenyl, $I^-$ m-$(CH_3)_3$-$N^-$-phenyl, $I^-$ m-$(CH_3)_3$-$N^-$-$CH_2CH_2$-$(OCH_2CH_2)_2$-O-phenyl, $I^-$ p-$(CH_3)_3$-$N^-$-$CH_2CH_2$-$(OCH_2CH_2)_2$-O-phenyl, $I^-$ m-(N,N-dimethyl-piperazinium-(N')-$CH_2$-$OCH_2CH_2)_2$-O-phenyl, 3-methoxy-4-fluorophenyl, thienyl-2-yl, 5-chlorothienyl-2-yl, 3,4-difluorophenyl, $I^-$ p-(N,N-dimethylpiperazinium)-(N')-$CH_2$-$(OCH_2CH_2)_2$-O-phenyl, 3-fluoro-4-methoxyphenyl, -4-pyridinyl, 2-pyridinyl, 3-pyridinyl, N-methyl-4-pyridinium, $I^-$ N-methyl-3-pyridinium, 3,4-dioxymethylenephenyl, 3,4-dioxyethylenephenyl, and p-methoxycarbonylphenyl. Preferred compounds include 3-ethyl-3-butyl and 3-butyl-3-butyl compounds having each of the above preferred $R^5$ substituents in combination with the $R^x$ substituents shown in Table 1. It is particularly preferred that one but not both of $R^5$ and $R^6$ is hydrogen.

It is especially preferred that $R^4$ and $R^6$ be hydrogen, that $R^3$ and $R^5$ not be hydrogen, and that $R^3$ and $R^5$ be oriented in the same direction relative to the plane of the molecule, i.e., both in $\alpha$- or both in $\beta$-configuration. It is further preferred that, where $R^2$ is butyl and $R^1$ is ethyl, then $R^1$ has the same orientation relative to the plane of the molecule as $R^3$ and $R^5$.

Set forth in Table 1A are lists of species of $R^1/R^2$, $R^5/R^6$ and $R^x$.

TABLE 1A

Alternative R groups

| $R^1$, $R^2$ | $R^3$, $R^4$ | $R^5$ | $(R^x)q$ |
|---|---|---|---|
| ethyl | HC— | PH— | 7-methyl |
| n-propyl | H— | p-F—Ph— | 7-ethyl |
| n-butyl | | n-F—Ph— | 7-iso-propyl |
| n-pentyl | | p-$CH_3$O—Ph— | 7-tert-butyl |
| n-hexyl | | | 7-OH |
| iso-propyl | | m-$CH_3$O—Ph— | 7-$CCH_3$ |
| iso-butyl | | p-$(CH_3)_2$N—Ph— | 7-O(iso-propyl) |
| iso-pentyl | | m-$(CH_3)_2$N—Ph— | 7-$SCH_3$ |
| $CH_2C(=O)C_2H_5$ | | $I^-$, p-$(CH_3)_3$—$N^0$—Ph— | 7-$SCCH_3$ |
| $CH_2CC_2H_5$ | | $I^-$, m-$(CH_3)_3$—$N^0$—Ph— | 7-$SO_2CH_3$ |
| $CH_2CH(CH)C_2H_5$ | | $I^-$, p-$(CH_3)_3$—$N^0$—$CH_2CH_2$— | 7-$SCH_2CH_3$ |
| $CH_2O$-(4-picoline) | | $(CCH_2CE_2)_2$—C—Ph— | 7-$NH_2$ |
| | | $I^-$, m-$(CH_3)_3$—$N^0$—$CH_2CH_2$— | 7-NHOH |
| | | $(CCH_2CH_2)_2$—C—Ph | 7-$NHOH_3$ |
| | | $I^-$, p-(N,N— | 7-$N(CH_3)_2$ |
| | | dimethylpiperazine)- | 7-$N^*(CH_3)_3$, $I^-$ |
| | | (N')—$CH_2$—$(CCH_2CH_2)_2$—C— | 7-NHC(=C)$CH_3$ |
| | | Ph— | 7-$N(CH_2CH_3)_2$ |
| | | $I^-$, m-(N,N- | 7-$NMeCE_2CO_2H$ |
| | | dimethylpiperazine)- | 7-$N^*(Me)_2CH_2CO_2H$, $I^-$ |

TABLE 1A-continued

Alternative R groups

[Structure: benzothiepine sulfone with positions 3, 4, 5 bearing R¹, R², R³, R⁴, R⁵, R⁶ and aromatic ring with (Rˣ)q at positions 6, 7, 8, 9]

| R¹, R² | R³, R⁴ | R⁵ | (Rˣ)q |
|---|---|---|---|
| | | (N')—CH₂—(CCH₂CH₂)₂—O—Ph— | 7-(N)-morpholine |
| | | | 7-(N)-azetidine |
| | | m-F, p-CH₃C—Ph— | 7-(N)-N-methylazetidinium, I⁻ |
| | | 3,4,dioxymethylene-Ph | 7-(N)-pyrrolidine |
| | | m-CH₃C—, p-F—Ph— | 7-(N)-N-methyl-pyrrolidinium, I⁻ |
| | | 4-pyridine | 7-(N)-N-methyl-morpholinium, I⁻ |
| | | N-methyl-4-pyridinium, I⁻ | 7-(N)-N'-methylpiperazine |
| | | 3-pyridine | 7-(N)-N'-dimethylpiperazinium, I⁻ |
| | | N-methyl-3-pyridinium, I⁻ | 7-NH—CEZ |
| | | 2-pyridine | 7-NHC(=O)C₅H₁₁ |
| | | p-CH₃C₂C—Ph— | 7-NHC(=O)CH₂Br |
| | | thienyl-2-yl | 7-NH-C(NH)NH₂ |
| | | 5-Cl-thienyl-2-yl | 7-(2)-thiophene |
| | | 3,4-difluoro | 8-methyl |
| | | m-F, P—CH₃O—Ph— | 8-ethyl |
| | | | 8-iso-propyl |
| | | | 8-tert-butyl |
| | | | 8-OH |
| | | | 8-CCH₃ |
| | | | 8-O(iso-propyl) |
| | | | 8-SCH₃ |
| | | | 8-SCCH₃ |
| | | | 8-SO₂CH₃ |
| | | | 8-SCH₂CH₃ |
| | | | 8-NE₂ |
| | | | 8-NECH |
| | | | 8-NHCH₃ |
| | | | 8-N(CH₃)₂ |
| | | | 8-N*(CH₃)₃, I⁻ |
| | | | 8-NHC(=C) CH₃ |
| | | | 8-N(CH₂CH₃)₂ |
| | | | 8-NMeCH₂CO₂H |
| | | | 8-N*(Me)₂CH₂CO₂H, I⁻ |
| | | | 8-(N)-morpholine |
| | | | 8-(N)-azetidine |
| | | | 8-(N)-N-methylazetidinium, I⁻ |
| | | | 8-(N)-pyrrolidine |
| | | | 8-(N)-N-methyl-pyrrolidinium, I⁻ |
| | | | 8-(N)-N-methyl-morpholinium, I⁻ |
| | | | 8-(N)-N'-methylpiperazine |
| | | | 8-(N)-N'-dimethylpiperazinium, I⁻ |
| | | | 8-NH—CEZ |
| | | | 8-NHC(O)C₅H₁₁ |
| | | | 8-NHC(O)CH₂Br |
| | | | 8-NH-C(NH)NH₂ |
| | | | 8-(2)-thiophene |
| | | | 9-methyl |
| | | | 9-ethyl |
| | | | 9-iso-propyl |
| | | | 9-tert-butyl |
| | | | 9-OH |
| | | | 9-CCH₃ |
| | | | 9-O(iso-propyl) |
| | | | 9-SCH₃ |
| | | | 9-SCCH₃ |
| | | | 9-SO₂CH₃ |
| | | | 9-SCH₂CH₃ |
| | | | 9-NH₂ |
| | | | 9-NEOH |
| | | | 9-NHOH₃ |
| | | | 9-N(CH₃)₂ |
| | | | 9-N*(CH₃)₃, I⁻ |
| | | | 9-NHC(=O)CH₃ |
| | | | 9-N(CH₂CH₃)₂ |
| | | | 9-NMeCH₂CO₂H |

TABLE 1A-continued

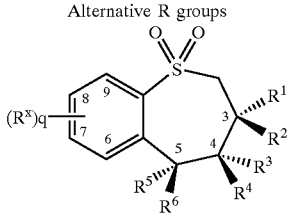

| $R^1$, $R^2$ | $R^3$, $R^4$ | $R^5$ | $(R^x)_q$ |
|---|---|---|---|
| | | | 9-N*(Me)$_2$CH$_2$CO$_2$H, I$^-$ |
| | | | 9-(N)-morpholine |
| | | | 9-(N)-azetidine |
| | | | 9-(N)-N-methylazetidinium, I$^-$ |
| | | | 9-(N)-pyrrolidine |
| | | | 9-(N)-N-methyl-pyrrolidinium, I$^-$ |
| | | | 9-(N)-N-methyl-morpholinium, I$^-$ |
| | | | 9-(N)-N'-methylpiperazine |
| | | | 9-(N)-N'-dimethylpiperazinium, I$^-$ |
| | | | 9-NH—CEZ |
| | | | 9-NHC(O)C$_5$H$_{11}$ |
| | | | 9-NHC(O)CH$_2$Br |
| | | | 9-NH-C(NH)NH$_2$ |
| | | | 9-(2)-thiophene |
| | | | 7-CCH$_3$, 8-CCH$_3$ |
| | | | 7-SCH$_3$, 8-CCH$_3$ |
| | | | 7-SCH$_3$, 8-SCH$_3$ |
| | | | 6-CCH$_3$, 7-CCH$_3$, 8-CCH$_3$ |

Further preferred compounds of the present invention comprise a core structure having two or more pharmaceutically active benzothiepine structures as described above, covalently bonded to the core moiety via functional linkages. Such active benzothiepine structures preferably comprise:

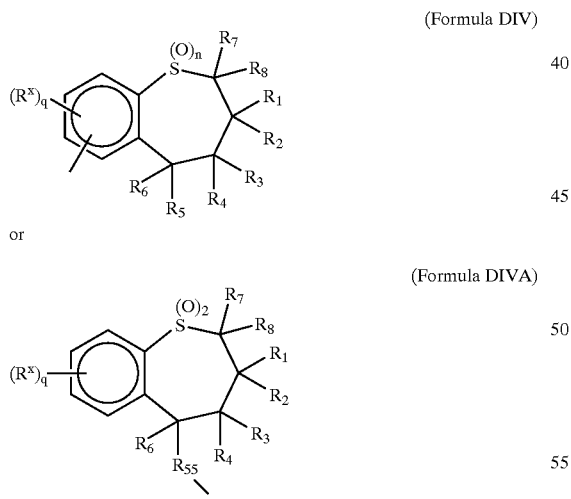

(Formula DIV)

or (Formula DIVA)

where $R^1$, $R^2$, $R^3$, $R^4$, $R^6$, $R^5$, $R^6$, $R^7$, $R^8$, X, q and n are as defined above, and $R^{55}$ is either a covalent bond or arylene.

The core moiety can comprise alkane diyl, alkene diyl, alkyne diyl, polyalkane diyl, alkoxy diyl, polyether diyl, polyalkoxy diyl, carbohydrate, amino acid, and peptide, polypeptide, wherein alkane diyl, alkene diyl, alkyne diyl, polyalkane diyl, alkoxy diyl, polyether diyl, polyalkoxy diyl, carbohydrate, amino acid, and peptide polypeptide, can optionally have one or more carbon replaced by O, NR$^7$, N_R$^7$R$^8$, S, SO, SO$_2$ S$^-$R$^7$R$^8$, PR$^7$, P$^+$R$^7$R$^8$, phenylene, heterocycle, quatarnary heterocycle, quaternary heteroaryl, or aryl, wherein alkane diyl, alkene diyl, alkyne diyl, polyalkane diyl, alkoxy diyl, polyether diyl, polyalkoxy diyl, carbohydrate, amino acid, peptide, and polypeptide can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, OR$^{13}$, NR$^{13}$R$^{14}$, SR$^{13}$, S(O)R$^{13}$, SO$_2$R$^{13}$, SO$_3$R$^{13}$, NR$^{13}$OR$^{14}$, NR$^{13}$NR$^{14}$R$^{15}$, NO$_2$, CO$_2$R$^{13}$, CN, OM, SO$_2$OM, SO$_2$NR$^{13}$R$^{14}$, C(O)NR$^{13}$R$^{14}$, C(O)OM, COR$^{13}$, P(O)R$^{13}$R$^{14}$, P$^+$R$^{13}$R$^{14}$R$^{15}$$_{A-}$, P(OR$^{13}$)OR$^{14}$, S$^-$R$^{13}$R$^{14}$A$^-$, and N$^+$R$^9$R$^{11}$R$^{12}$A$^-$;

wherein said alkyl, alkenyl, alkynyl, polyalkyl, polyether, aryl, haloalkyl, cycloalkyl, and heterocycle can be further substituted with one or more substituent groups selected from the group consisting of OR$^7$, NU$^7$R$^8$, SR$^7$, S(O)R$^7$, SO$_2$R$^7$, SO$_3$R$^7$, CO$_2$R$^7$, CN, oxo, CONR$^7$R$^8$, N$^+$R$^7$R$^8$R$^9$A-, alkyl, alkenyl, alkynyl, aryl, cycloalkyl, heterocycle, arylalkyl, quaternary heterocycle, quaternary heteroaryl, P(O)R$^7$R$^8$, P$^+$R$^7$R$^8$A$^-$, and P(O)(OR$^7$)OR$^8$, and wherein said alkyl, alkenyl, arkynyl, polyalkyl, polyether, aryl, haloalkyl, cycloalkyl, and heterocycle can optionally have one or more carbons replaced by O, NR$^7$, N$^+$R$^7$R$^8$A-, S, SO, SO$_2$, S$^+$R$^7$A-, PR$^7$, P(O)R$^7$, P$^+$R$^7$R$^8$A-, or phenylene.

Exemplary core moieties include:

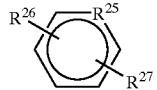

-continued

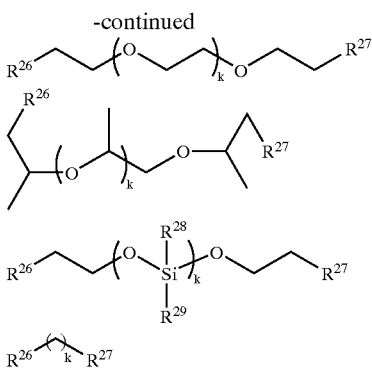

wherein:
R$^{25}$ is selected from the group consisting of C and N, and R$^{26}$ and R$^{27}$ are independently selected from the group consisting of:

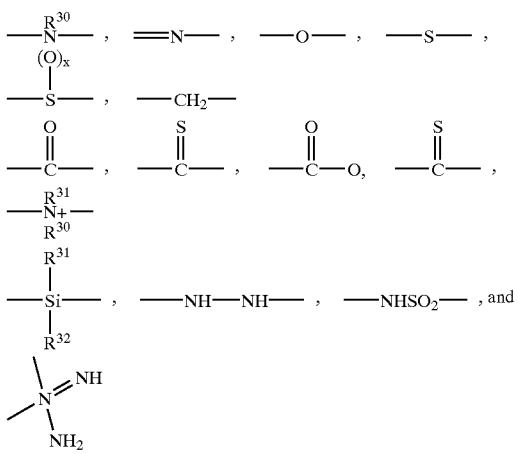

wherein R$^{24}$, R$^{29}$, R$^{30}$ and R$^{31}$ are independently selected from alkyl, alkenyl, alkylaryl, aryl, arylalkyl, cycloalkyl, heterocycle, and heterocycloalkyl, A$^-$ is a pharmaceutically acceptable anion, and k=1 to 10.

In compounds of Formula DIV, R$^{20}$, R$^{21}$, R$^{22}$ in Formulae DII and DIII, and R$^{23}$ in Formula DIII can be bonded at any of their 6-, 7-, 8-, or 9- positions to R$^{19}$. In compounds of Formula DIVA, it is preferred that R$^{55}$ comprises a phenylene moiety bonded at a m- or p-position thereof to R$^{19}$.

In another embodiment, a core moiety backbone, R$^{19}$, as discussed herein in Formulas DII and DIII can be multiply substituted with more than four pendant active benzothiepine units, i.e., R$^{20}$, R$^{21}$, R$^{22}$, and R$^{23}$ as discussed above, through multiple functional groups within the core moiety backbone. The core moiety backbone unit, R$^{19}$, can comprise a single core moiety unit, multimers thereof, and multimeric mixtures of the different core moiety units discussed herein, i.e., alone or in combination. The number of individual core moiety backbone units can range from about one to about 100, preferably about one to about 80, more preferably about one to about 50, and even more preferably about one to about 25. The number of points of attachment of similar or different pendant active benzothiepine units within a single core moiety backbone unit can be in the range from about one to about 100, preferably about one to about 80, more preferably about one to about 50, and even more preferably about one to about 25. Such points of attachment can include bonds to C, S, O, N, or P within any of the groups encompassed by the definition of R$^{19}$.

The more preferred benzothiepine moieties comprising R$^{20}$, R$^{21}$, R$^{22}$ and/or R$^{23}$ conform to the preferred structures as outlined above for Formula I. The 3-carbon on each benzothiepine moiety can be achiral, and the substituents R$^1$, R$^2$, R$^3$, R$^4$, R$^5$ and R$^x$ can be selected from the preferred groups and combinations of substituents as discussed above. The core structures can comprise, for example, poly (oxyalkylene) or oligo(oxyalkylene), especially poly- or oligo(oxyethylene) or poly- or oligo(oxypropylene).

Dosages, Formulations, and Route of Administration

The ileal bile acid transport inhibitor compounds of the present invention can be administered for the prophylaxis and treatment of hyperlipidemic diseases or conditions by any means, preferably oral, that produce contact of these compounds with their site of action in the body, for example in the ileum of a mammal, e.g., a human.

For the prophylaxis or treatment of the conditions referred to above, the compounds of the present invention can be used as the compound per se.

Pharmaceutically acceptable salts are particularly suitable for medical applications because of their greater aqueous solubility relative to the parent compound. Such salts must clearly have a pharmaceutically acceptable anion or cation. Suitable pharmaceutically acceptable acid addition salts of the compounds of the present invention when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, ad trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

The anions of the definition of A$^-$ in the present invention are, of course, also required to be pharmaceutically acceptable and are also selected from the above list.

The compounds of the present invention can be presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

In general, a daily dose can be in the range of from about 0.3 to about 100 mg/kg bodyweight/day, preferably from about 1 mg to about 50 mg/kg bodyweight/day, more preferably from about 3 to about 10 mg/kg bodyweight/day. This total daily dose can be administered to the patient in a single dose, or in proportionate multiple subdoses. Subdoses can be administered 2 to 6 times per day. Doses can be in sustained release form effective to obtain desired results.

Orally administrable unit dose formulations, such as tablets or capsules, can contain, for example, from about 0.1 to about 100 mg of benzothiepine compound, preferably about 1 to about 75 mg of compound, more preferably from about 10 to about 50 mg of compound. In the case of pharmaceutically acceptable salts, the weights indicated above refer to the weight of the benzothiepine ion derived from the salt.

Oral delivery of an ileal bile acid transport inhibitor of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (the ileum) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

When administered intravenously, the dose can, for example, be in the range of from about 0.1 mg/kg body weight to about 1.0 mg/kg body weight, preferably from about 0.25 mg/kg body weight to about 0.75 mg/kg body weight, more preferably from about 0.4 mg/kg body weight to about 0.6 mg/kg body weight. This dose can be conveniently administered as an infusion of from about 10 ng/kg body weight to about 100 ng/kg body weight per minute. Infusion fluids suitable for this purpose can contain, for example, from about 0.1 ng to about 10 mg, preferably from about 1 ng to about 10 mg per milliliter. Unit doses can contain, for example, from about 1 mg to about 10 g of the compound of the present invention. Thus, ampoules for injection can contain, for example, from about 1 mg to about 100 mg.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular compound which is being used. In most cases, the preferred route of administration is oral.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of brining into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active-dispersing agent(s). Molded tablets can be made by molding, in a suitable machine, the powdered compound moistened with an inert liquid diluent.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, preferably about 3% to 15%. As one particular possibility, the compound can be delivered from the patch by electrotransport or iontophoresis, for example, as described in *Pharmaceutical Research*, 3 (6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, and granules noted above comprise one or more compounds of the present invention admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

In combination therapy, administration of the ileal bile acid transport inhibitor and HMG Co-A reductase inhibitor may take place sequentially in separate formulations, or may be accomplished by simultaneous administration in a single formulation or separate formulations. Administration may be accomplished by oral route, or by intravenous, intramuscular, or subcutaneous injections. The formulation may be in the form of a bolus, or in the form of aaqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropylmethyl cellulose, together with one or more of a lubricant, preservative, surface active or dispersing agent.

For oral administration, the pharmaceutical compositions may be in the form of, for example, a tablet, capsule, suspension, or liquid. Capsules, tablets, etc., can be prepared by conventional methods well known in the art. The pharmaceutical composition is preferably made in the form of a dosage unit containing a particular amount of the active ingredient or ingredients. Examples of dosage units are tablets or capsules. These may with advantage contain one or more ileal bile acid transport inhibitors in an amount described above. In the case of HMG Co-A reductase inhibitors, the dose range may be from about 0.01 mg to about 500 mg or any other dose, dependent upon the specific inhibitor, as is known in the art.

The active ingredients may also be administered by injection as a composition wherein, for example, saline, dextrose, or water may be used as a suitable carrier. A suitable daily dose of each active inhibitor is one that achieves the same blood serum level as produced by oral administration as described above.

The active inhibitors may further be administered by any dual combination of oral/oral, oral/parenteral, or parenteral/parenteral route.

Pharmaceutical compositions for use in the treatment methods of the present invention may be administered in oral form or by intravenous administration. Oral administration of the combination therapy is preferred. Dosing for oral administration may be with a regimen calling for single daily dose, or for a single dose every other day, or for multiple, spaced doses throughout the day. The inhibitors which make up the combination therapy may be administered simultaneously, either in a combined dosage form or in separate dosage forms intended for substantially simultaneous oral administration. The inhibitors which make up the combination therapy may also be administered sequentially, with either inhibitor being administered by a regimen calling for two-step ingestion. Thus, a regimen may call for sequential administration of the inhibitors with spaced-apart ingestion of the separate, active agents. The time period between the multiple ingestion steps may range from a few minutes to several hours, depending upon the properties of each inhibitor such as potency, solubility, bioavailability, plasma half-life and kinetic profile of the inhibitor, as well as depending upon the age and condition of the patient. The inhibitors of the combined therapy whether administered simultaneously, substantially simultaneously, or sequentially, may involve a regimen calling for administration of one inhibitor by oral route and the other inhibitor by intravenous route. Whether the inhibitors of the combined therapy are administered by oral or intravenous route, separately or together, each such inhibitor will be contained in a suitable pharmaceutical formulation of pharmaceutically-acceptable excipients, diluents or other formulations components. Examples of suitable pharmaceutically-acceptable formulations containing the inhibitors for oral administration are given above.

Treatment Regimen

The dosage regimen to prevent, give relief from, or ameliorate a disease condition having hyperlipemia as an element of the disease, e.g., atherosclerosis, or to protect against or treat further high cholesterol plasma or blood levels with the compounds and/or compositions of the present invention is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition can begin with the dosages indicated above. Treatment should generally be continued as necessary over a period of several seeks to several months or years until the hyperlipidemic disease condition has been controlled or eliminated. Patients undergoing treatment with the compounds or compositions disclosed herein can be routinely monitored by, for example, measuring serum LDL and total cholesterol levels by any of the methods well known in the art, to determine the effectiveness of the combination therapy. Continuous analysis of such data permits modification of the treatment regimen during therapy so that optimal effective amounts of each type of inhibitor are administered at any point in time, and so that the duration of treatment can be determined as well. In this way, the treatment regimen/dosing schedule can be rationally modified over the course of therapy so that the lowest amount of ileal bile acid transport inhibitor and HMG Co-A reductase inhibitor which together exhibit satisfactory effectiveness is administered, and so that administration is continued only so long as is necessary to successfully treat the hyperlipidemic condition.

A potential advantage of the combination therapy disclosed herein may be reduction of the amount of ileal bile acid transport inhibitor, HMG Co-A reductase inhibitor, or both, effective in treating hyperlipidemic conditions such as atherosclerosis and hypercholesterolemia.

The following non-limiting examples serve to illustrate various aspects of the present invention.

EXAMPLES OF SYNTHETIC PROCEDURES

Preparation 1

2-Ethyl-2-(mesyloxymethyl)hexanal (1)

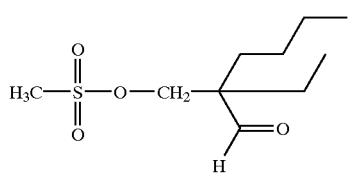

To a cold (10° C.) solution of 12.6 g (0.11 mole) of methanesulfonyl chloride and 10.3 g (0.13 mole) of triethylamine was added dropwise 15.8 g of 2-ethyl-2-(hydroxymethyl)hexanal, prepared according to the procedure described in Chem. Ber. 98, 728–734 (1965), while maintaining the reaction temperature below 30° C. The reaction mixture was stirred at room temperature for 18 h, quenched with dilute HCl and extracted with methylene chloride. The methylene chloride extract was dried over $MgSO_4$ and concentrated in vacuo to give 24.4 g of brown oil.

Preparation 2

2-((2-Benzoylphenylthio)methyl)-2-ethylhexanal (2)

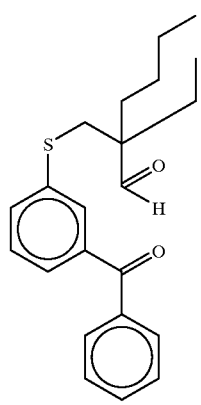

A mixture of 31 g (0.144 mol) of 2-mercaptobenzophenone, prepared according to the procedure described in WO 93/16055, 24.4 g (0.1 mole) of 2-ethyl-2-(mesyloxymethyl)-hexanal (1), 14.8 g (0.146 mole) of triethylamine, and 80 mL of 2-methoxyethyl ether was held at reflux for 24 h. The reaction mixture was poured into 3N HCl and extracted with 300 mL of methylene chloride, The methylene chloride layer was washed with 300 mL of 10% NaOH, dried over $MgSO_4$ and concentrated in vacuo to remove 2-methoxyethyl ether. The residue was purified by HPLC (10% EtOAc-hexane) to give 20.5 g (58%) of 2 as an oil.

Example 1

3-Butyl-3-ethyl-5-phenyl-2,3-dihydrobenzothiepine (3), cis-3-Butyl-3-ethyl-5-phenyl-2,3-dihydrobenzothiepin-(5H) 4-one (4a) and trans-3-Butyl-3-ethyl-5-phenyl-2,3-dihydro-benzothiepin-(5H)4-one (4b)

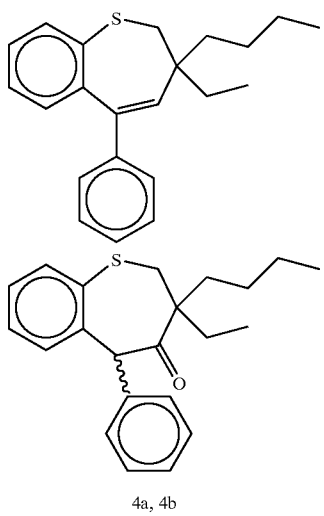

A mixture of 2.6 g (0.04 mole) of zinc dust, 7.2 g (0.047 mole) of $TiCl_3$ and 80 mL of anhydrous ethylene glycol dimethyl ether (DME) was held at reflux for 2 h. The reaction mixture was cooled to 5° C. To the reaction mixture was added dropwise a solution of 3.54 g (0.01 mole) of 2 in 30 mL of DME in 40 min. The reaction mixture was stirred at room temperature for 16 h and then was held at reflux for 2 h and cooled before being poured into brine. The organic was extract into methylene chloride. The methylene chloride extract was dried over $MgSO_4$ and concentrated in vacu. The residue was purified by HPLC (hexane) to give 1.7 g (43%) of 3 as an oil in the first fraction. The second fraction was discarded and the third fraction was further purified by HPLC (hexane) to give 0.07 g (2%) of 4a in the earlier fraction and 0.1 g (3%) of 4b in the later fraction.

Example 2 cis-3-Butyl-3-ethyl-5-phenyl-2,3-dihydrobenzothiepin-(5H)4-one-1,1-dioxide (5a) and trans-3-Butyl-3-ethyl-5-phenyl-2,3-dihydro-benzothiepin-(5H)4-one-1,1-dioxide (5b)

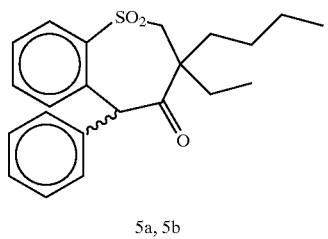

To a solution of 1.2 g (3.5 mmole) of 50–60% MCPBA in 20 mL of methylene chloride was added 0.59 g (1.75 mmole) of a mixture of 4a and 4b in 10 mL of methylene chloride. The reaction mixture was stirred for 20 h. An additional 1.2 g (1.75 mmole) of 50–60% MAPBA was added and the reaction mixture was stirred for an additional 3h then was triturated with 50 mL of 10% NaOH. The insoluble solid was filtered. The methylene chloride layer of the filtrate was washed with brine, dried over MgSO$_4$, and concentrated in vacuo. The residual syrup was purified by HPLC (5% EtOAc-hexane) to give 0.2 g (30%) of 5a as an oil in the first fraction and 0.17 g (26%) of 5b as an oil in the second fraction.

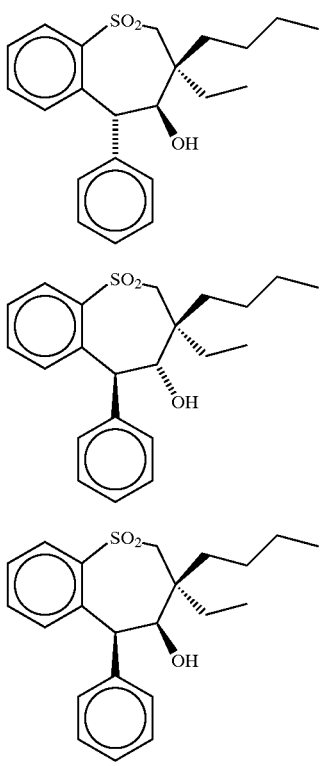

Example 3

(3a,4a,5b) 3-Butyl-3-ethyl-4-hydroxy-5-phenyl-2,3,4,5-tetrahydrobenzothiepine-1,1-dioxide (6a), (3a,4b,5a)⁻3-Butyl-3ethyl-4-hydroxy-5-phenyl-2,3,4,5-tetrahydro-

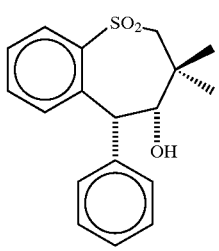

benzothiepine-1,1-dioxide (6b), (3a,4a,5a) 3-Butyl-3-ethyl-4-hydroxy-5-phenyl-2,3,4,5-tetrahydrobenzothiepine-1,1-dioxide (6c), and (3a,4b,5b) 3-Butyl-3-ethyl-4-hydroxy-5-phenyl-2,3,4,5-tetrahydrobenzothiepine-1,1-dioxide (6d)

A. Reduction of 5a and 5b with Sodium Borohydride

To a solution of 0.22 g (0.59 mmole) of 5b in 10 mL of ethanol was added 0.24 g (6.4 mmole) of sodium borohydride. The reaction mixture was stirred at room temperature for 18 h and concentrated in vacuo to remove ethanol. The residue was triturated with water and extracted with methylene chloride. The methylene chloride extract was dried over MgSO$_4$ and concentrated in vacuo to give 0.2 g of syrup. In a separate experiment, 0.45 g of 5a was treated with 0.44 g of sodium borohydride in 10 mL of ethanol and was worked up as described above to give 0.5 g of syrup which was identical to the 0.2 g of syrup obtained above. These two materials were combined and purified by HPLC using 10% EtOAc-hexane as eluant. The first fraction was 0.18 g (27%) of 6a as a syrup. The second fraction was 0.2 g (30%) of 6b also as a syrup. The column was then eluted with 20% EtOAc-hexane to give 0.077 g (11%) of 6c in the third fraction as a solid. Recrystallization from hexane gave a solid, mp 179–181° C. Finally, the column was eluted with 30% EtOAc-hexane to give 0.08 g (12%) of 6d in the fourth fraction as a solid.

Recrystallization from hexane gave a solid, mp 160–161° C.

B. Conversion of 6a to 6c and 6d with NaOH and PTC

To a solution of 0.29 g (0.78 mmole) of 6a in 10 mL CH$_2$Cl$_2$, was added 9 g of 40% NaOH. The reaction mixture was stirred for 0.5 h at room temperature and was added one drop of Aliquat-336 (methyltricaprylylammonium chloride) phase transfer catalyst (PTC). The mixture was stirred for 0.5 h at room temperature before being treated with 25 mL of ice-crystals then was extracted with CH$_2$Cl$_2$ (3×10 ml), dried over MgSO$_4$ and concentrated in vacu to recover 0.17 g of a colorless film. The components of this mixture were separated using an HPLC and eluted with EtOAc-hexane to give 12.8 mg (4%) of 2-(2-benzylphenylsulfonylmethyl)-2-ethylhexanal in the first fraction, 30.9 mg (11%) of 6c in the second fraction and 90.0 mg (31%) of 6d in the third fraction.

Oxidation of 6a to 5b

To a solution of 0.20 g (0.52 mmole) of 6a in 5 mL of CH$_2$Cl$_2$ was added 0.23 g (1.0 mmole) of pyridinium chlorochromate. The reaction mixture was stirred for 2 h then was treated with additional 0.23 g of pyridinium chlorochromate and stirred overnight. The dark reaction mixture was poured into a ceramic filterfrit containing silica gel and was eluted with CH$_2$Cl$_2$. The filtrate was concentrated in vacuo to recover 167 mg (87%) of 5b as a colorless oil.

Example 4

3-Butyl-3-ethyl-5-phenyl-2,3-dihydrobenzothiepine-1,1-dioxide (7)

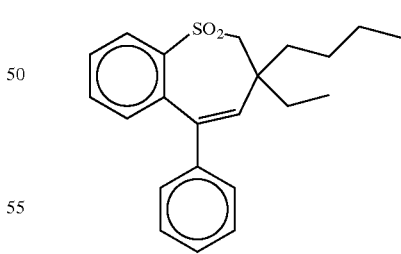

To a solution of 5.13 g (15.9 mmole) of 3 in 50 mL of CH$_2$Cl$_2$ was added 10 g (31.9 mmole) of 50–60% MCPBA (m-chloroperoxybenzoic acid) portionwise causing a mild reflux and formation of a white solid. The reaction mixture was allowed to stir overnight under N$_2$ and was triturated with 25 mL of water followed by 50 mL of 10% NaOH solution. The organic was extracted into CH$_2$Cl$_2$ (4×20 mL). The CH$_2$Cl$_2$ extract was dried over MgSO$_4$ and evaporated to dryness to recover 4.9 g (87%) of an opaque viscous oil.

Example 5

(1aa,2b,8ba) 2-Butyl-2-ethyl-8b-phenyl-1a,2,3,8b-tetrahydro-benzothiepino[4,5-b]oxirene-4,4-dioxide (8a)
(1aa,2a,8ba) 2-Butyl-2-ethyl-8b-phenyl-1a,2,3,8b-tetrahydro-benzothiepino [4,5-b]oxirene-4,4-dioxide (8b)

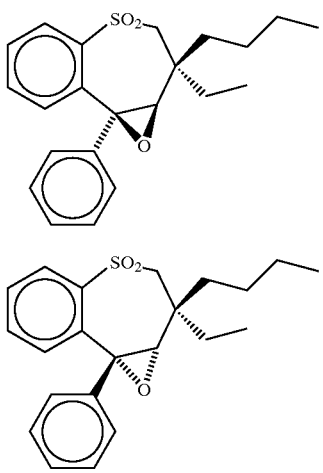

(8b)

(8a)

To 1.3 g (4.03 mole) of 3 in 25 mL of CHCl$_3$ was added portionwise 5 g (14.1 mmole) of 50–60% MCPBA causing a mild exotherm. The reaction mixture was stirred under N$_2$ overnight and was then held at reflux for 3 h. The insoluble white slurry was filtered. The filtrate was extracted with 10% potassium carbonate (3×50 mL), once with brine, dried over MgSO$_4$, and concentrated in vacuo to give 1.37 g of a light yellow oil. Purification by HPLC gave 0.65 g of crystalline product. This product is a mixture of two isomers. Trituration of this crystalline product in hexane recovered 141.7 mg (10%) of a white crystalline product. This isomer was characterized by NMR and mass spectra to be the (1aa,2b,8ba) isomer 8a. The hexane filtrate was concentrated in vacuo to give 206 mg of white film which is a mixture of 30% 8a and 70% 8b by $^1$H NMR.

Example 6 cis-3-Butyl-3-ethyl-5-phenyl-2,3,4,5-tetrahydrobenzothiepine-1,1-dioxide (9a), trans-3-Butyl-3-ethyl-5-phenyl-2,3,4,5-tetrahydrobenzothiepine-1,1-dioxide (9b), and 3-Butyl-3-ethyl-4-hydroxy-5-cyclohexylidine-2,3,4,5-tetrahydrobenzothiepine-1,1-dioxide (10)

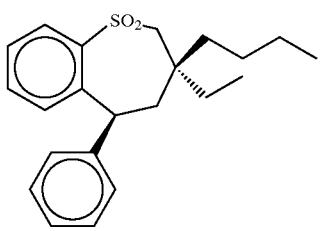

(9a)

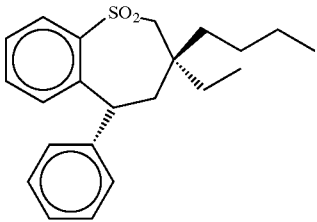

(9b)

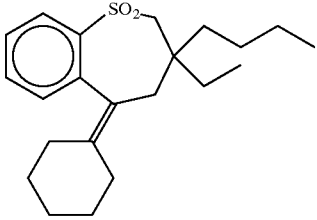

(10)

A mixture of 0.15 g (0.4 mmole) of a 3:7 mixture of 8a and 8b was dissolved in 15 ml MeOH in a 3 oz. Fisher/Porter vessel, then was added 0.1 g of 10% Pd/C catalyst. This mixture was hydrogenated at 70 psi H$_2$ for 5 h and filtered. The filtrate was evaporated to dryness in vacuo to recover 0.117 g of a colorless oil. This material was purified by HPLC eluting with EtOAc-hexane. The first fraction was 4.2 mg (3%) of 9b. The second fraction, 5.0 mg (4%), was a 50/50 mixture of 9a and 9b. The third fraction was 8.8 mg (6%) of 6a. The fourth fraction was 25.5 mg (18%) of 6b. The fifth fraction was 9.6 mg (7%) of a mixture of 6b and a product believed to be 3-butyl-3-ethyl-4,5-dihydroxy-56-phenyl-2,3,4,5-tetrahydrobenzothiepine-1,1-dioxide based on mass spectrum. The sixth fraction was 7.5 mg (5%) of a mixture of 6d and one of the isomers of 10, 10a.

Example 7

In another experiment, a product (3.7 g) from epoxidation of 3 with excess MCPBA in refluxing CHCl$_3$ under air was hydrogenated in 100 mL of methanol using 1g of 10% Pd/C catalyst and 70 psi hydrogen. The product was purified by HPLC to give 0.9 g (25%) of 9b, 0.45 g (13%) of 9a, 0.27 g (7%) of 6a, 0.51 g (14%) of 6b, 0.02 g (1%) of 6c, 0.06 g (2%) of one isomer of 10, 10a and 0.03 g (1%) of another isomer of 10, 10b.

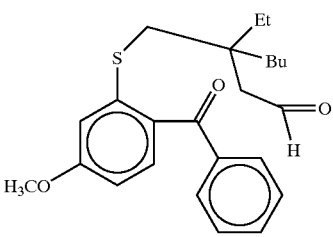

Example 8

2-((2-Benzoylphenylthio)methyl)butyraldehyde (11)

To an ice bath cooled solution of 9.76 g (0.116 mole) of 2-ethylacrolein in 40 mL of dry THF was added 24.6 g (0.116 mole) of 2-mercaptobenzophenone in 40 mL of THF followed by 13 g, (0.128 mole) of triethylamine. The reaction mixture was stirred at room temperature for 3 days, diluted with ether, and was washed successively with dilute HCl, brine, and 1 M potassium carbonate. The ether layer was dried over MgSO$_4$ and concentrated in vacuo. The residue was purified by HPLC (10% EtOAc-hexane) to give 22 g (64%) of 11 in the second fraction. An attempt to further purify this material by kugelrohr distillation at 0.5 torr (160–190° C.) gave a fraction (12.2 g) which contained starting material indicating a reversed reaction during distillation. This material was dissolved in ether (100 mL) and was washed with 50mL of 1 M potassium carbonate three times to give 6.0 g of a syrup which was purified by HPLC (10% EtOAc-hexane) to give 5.6 g of pure 11.

Example 9

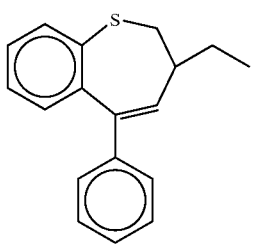

(12)

3-Ethyl-5-phenyl-2,3-dihydrobenzothiepine (12)

To a mixture of 2.61 g (0.04 mole) of zinc dust and 60 mL of DME was added 7.5 g (0.048 mole) of TiCl$_3$. The reaction mixture was held at reflux for 2 h. A solution of 2.98 g (0.01 mole) of 11 was added dropwise in 1 h. The reaction mixture was held at reflux for 18 h, cooled and poured into water. The organic was extracted into ether. The ether layer was washed with brine and filtered through Celite. The filtrate was dried over MgSO$_4$ and concentrated. The residual oil (2.5 g) was purified by HPLC to give 2.06 g (77%) of 12 as an oil in the second fraction.

Example 10

(1aa,2a,8ba) 2-Ethyl-8b-phenyl-1a,2,3,8b-tetrahydrobenzothiepino-[4,5-b]oxirene-4,4-dioxide (13)

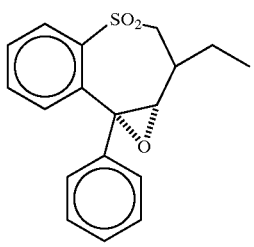

(13)

To a solution of 1.5 g (5.64 mmole) of 12 in 25 ml of CHCl$_3$ was added 6.8 g (19.4 mmole) of 50–60% MCPB portionwise causing an exothem and formation of a white solid. The mixture was stirred at room temperature overnight diluted with 100 ml methylene chloride and washed successively with 10% K$_2$CO$_3$ (4×50 ml), water (twice with 25 ml) and brine. The organic layer was then dried over MgSO$_4$ and evaporated to dryness to recover 1.47 g of an off white solid. $^1$H NMR indicated that only one isomer is present. This solid was slurried in 200 ml of warm Et$_2$O and filtered to give 0.82 g (46%) of 13 as a white solid, mp 185–186.5° C.

Example 11

(3a,4b,5a)-3-Ethyl-4-hydroxy-5-phenyl-2,3,4,5-tetrahydro-benzothiepine-1,1-dioxide (14a), (3a,4b,5b) 3-Ethyl-4-hydroxy-5-phenyl-2,3,4,5-tetrahydrobenzothiepine-1,1-dioxide (14b), and cis-3-Ethyl-5-phenyl-2,3,4,5-tetrahydro-benzothiepine-1,1-dioxide (15)

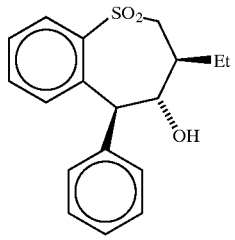

(14a)

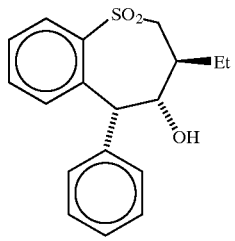

(14b)

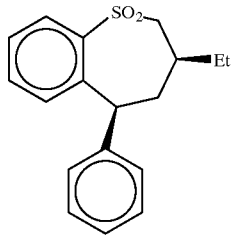

(15)

A mixture of 0.5 g (1.6 mole) of 13, 50 ml of acetic acid and 0.5 g of 10% Pd-C catalyst was hydrogenated with 70 psi hydrogen for 4 h. The crude reaction slurry was filtered and the filtrate was stirred with 150 ml of a saturated NaHCO$_1$ solution followed by 89 g of NaHCO$_3$ powder portionwise to neutralize the rest of acetic acid. The mixture was extracted with methylene chloride (4×25 ml), then the organic layer was dried over MgSO$_4$ and concentrated in vacuo to give 0.44 g (87%) of a voluminous white solid which was purified by HPLC (EtOAc-Hexane) to give 26.8 mg (6%) of 15 in the first fraction, 272 mg (54%), of 14a as a solid, mp 142–143.5° C., in the second fraction, and 35 mg (7%) of impure 14b in the third fraction.

Example 12

2-Ethyl-2-((2-Hydroxymethylphenyl)thiomethyl)hexenal (16)

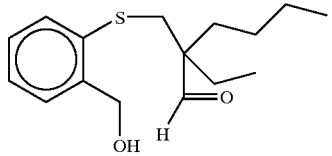

(16)

A mixture of 5.0 g (0.036 mole) of 2-mercaptobenzyl alcohol, 6.4 g (0.032 mole) of 1, 3.6 g (0.036 mole) of triethylamine and 25 mL of 2-methoxyethyl ether was held at reflux for 7 h. Additional 1.1 g of mercaptobenzyl alcohol and 0.72 g of triethylamine was added to the reaction mixture and the mixture was held at reflux for additional 16 h. The reaction mixture was cooled and poured into 6N HCl and extracted with methylene chloride. The methylene chloride extract was washed twice with 10% NaOH, dried over MgSO$_4$ and concentrated in vacuo to give 9.6 g of residue. Purification by HPLC (20% EtOAc-hexane) gave 3.7 g (41%) of 16 as an oil.

Example 13

2-Ethyl-2-((2-formylphenyl)thiomethyl)hexenal (17)

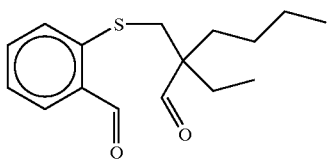

(17)

A mixture of 3.7 g of 16, 5.6 g (0.026 mole) of pyridinium chlorochromate, 2 g of Celite and 30 mL of methylene chloride was stirred for 18 h and filtered through a bed of silica gel. The silica gel was eluted with methylene chloride. The combined methylene chloride eluant was purified by HPLC (20% ETOAc-hexane) to give 2.4 g (66%) of an oil.

Example 14

3-Butyl-3-ethyl-2,3-dihydrobenzothiepine (18)

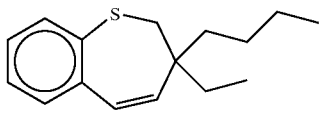

(18)

A mixture of 2.6 g (0.04 mole) of zinc dust, 7.2 g (0.047 mole) of TiCl$_3$, and 50 mL of DME was held at reflux for 2 h and cooled to room temperature. To this mixture was added 2.4 g (8.6 mmole) of 17 in 20 mL of DME in 10 min. The reaction mixture was stirred at room temperature for 2 h and held at reflux for 1 h then was let standing at room temperature over weekend. The reaction mixture was poured into dilute HCl and was stirred with methylene chloride. The methylene chloride-water mixture was filtered through Celite. The methylene chloride layer was washed with brine, dried over MgSO$_4$, and concentrated in vacuo to give 3.0 g of a residue. Purification by HPLC gave 0.41 g (20%) of 18 as an oil in the early fraction.

Example 15

(1aa,2a,8ba) 2-Butyl-2-ethyl-1a,2,3,8b-tetrahydro-benzothiepino[4,5-b]oxirene-4,4-dioxide (19a) and (1aa,2b,8ba) 2-Butyl-2-ethyl-8b-phenyl-1a,2,3,8b-tetrahydro-benzothiepino[4,5-b]oxirene-4,4-dioxide (19b)

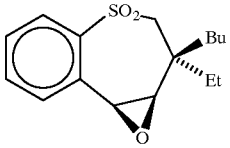

(19a)

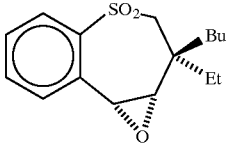

(19b)

To a solution of 0.4 g of 0.4 g (1.6 mmole) of 18 in 30 mL of methylene chloride was added 2.2 g (3.2 mmole) of 50–60% MCPBA. The reaction mixture was stirred for 2 h and concentrated in vacuo. The residue was dissolved in 30 mL of CHCl$_3$ and was held at reflux for 18 h under N$_2$. The reaction mixture was stirred with 100 mL of 10% NaOH and 5 g of sodium sulfite. The methylene chloride layer was washed with brine, dried over MgSO$_4$ and concentrated in vacuo. The residue was purified by HPLC (20% EtOAc-hexane) to give a third fraction which was further purified by HPLC (10% EtOAc-hexane) to give 0.12 g of syrup in the first fraction. Recrystallization from hexane gave 0.08 g (17%) of 19a, mp 89.5–105.5° C. The mother liquor from the first fraction was combined with the second fraction and was further purified by HPLC to give additional 19a in the first fraction and 60 mg of 19b in the second fraction. Crystallization from hexane gave 56 mg of a white solid.

Example 16

3-Butyl-3-ethyl-4,5-dihydroxy-5-phenyl-2,3,4,5-tetrahydro-benzothiepine-1,1-dioxide (20)

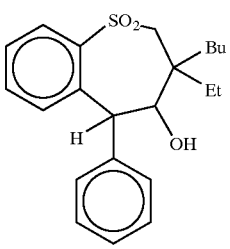

(20)

This product was isolated along with 6b from hydrogenation of a mixture of 8a and 8b.

Example 17

3-Butyl-3-ethyl-4-hydroxy-5-phenylthio-2,3,4,5-tetrahydro-benzothiepine-1,1-dioxide (21)

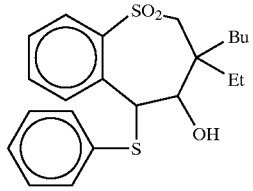
(21)

A mixture of 25 mg (0.085 mmole) of 19b, 0.27 g (2.7 mmole) of thiophenol, 0.37 g (2.7 mmole) of potassium carbonate, and 4 mL of DMF was stirred at room temperature under $N_2$ for 19 h. The reaction mixture was poured into water and extracted with methylene chloride. The methylene chloride layer was washed successively with 10% NaOH and brine, dried over $MgSO_4$, and concentrated in vacuo to give 0.19 g of semisolid which contain substantial amounts of diphenyl disulfide. This material was purified by HPLC (5% EtOAc-hexane) to remove diphenyl disulfide in the first fraction. The column was then eluted with 20% EtOAc-hexane to give 17 mg of a first fraction, 4mg of a second fraction and 11 mg of a third fraction which were three different isomers of 21, i.e. 21a, 21b, and 21c, respectively, by $^1$H NMR and mass spectra.

Example 18

Alternative Synthesis of 6c and 6d

A. Preparation from 2-((2-Benzoylphenylthio)methyl)-2-ethylhexanal (2)

Step 1. 2((2-Benzoylphenylsulfonyl)methyl)-2-ethylhexanal (44)

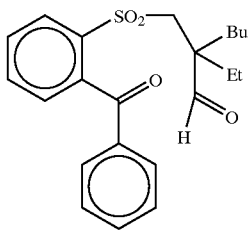
(44)

To a solution of 9.0 g (0.025 mole) of compound 2 in 100 ml of methylene chloride was added 14.6 g (0.025 mol) of 50–60% MCPBA portionwise. The reaction mixture was stirred at room temperature for 64 h then was stirred with 200 ml of 1 M potassium carbonate and filtered through Celite. The methylene chloride layer was washed twice with 300 ml of 1 M potassium carbonate, once with 10% sodium hydroxide and once with brine. The insoluble solid formed during washing was removed by filtration through Celite. The methylene chloride solution was dried and concentrated in vacuo to give 9.2 g (95%) of semisolid. A portion (2.6 g) of this solid was purified by HPLC(10% ethyl acetate-hexane) to give 1.9 g of crystals, mp 135–136° C.

Step 2. 2-((2-Benzylphenylsulfonyl)methyl-2-ethylhexanal (45)

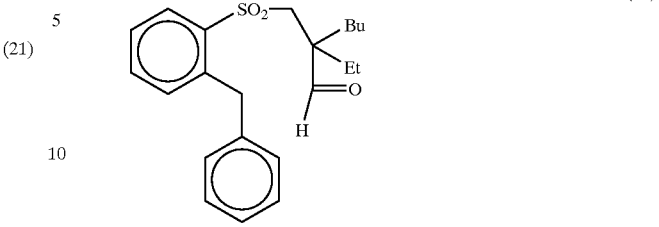
(45)

A solution of 50 g (0.13 mole) of crude 44 in 250 ml of methylene chloride was divided in two portions and charged to two Fisher-Porter bottles. To each bottle was charged 125 ml of methanol and 5 g of 10% Pd/C. The bottles were pressurized with 70 psi of hydrogen and the reaction mixture was stirred at room temperature for 7 h before being charged with an additional 5 g of 10% Pd/C. The reaction mixture was again hydrogenated with 70 psi of hydrogen for 7 h. This procedure was repeated one more time but only 1 g of Pd/C was charged to the reaction mixture. The combined reaction mixture was filtered and concentrated in vacuo to give 46.8 g of 45 as brown oil.

Step 3. (3a,4a,5a) 3-Butyl-3-ethyl-4-hydroxy-5-phenyl-2,3,4,5-tetrahydrobenzothiepine-1,1-dioxide (6c), and (3a,4b,5b) 3-Butyl-3-ethyl-4-hydroxy-5-phenyl-2,3,4,5-tetrahydrobenzothiepine-1,1-dioxide (6d)

To a solution of 27.3 g (73.4 mmole) of 45 in 300 ml of anhydrous THF cooled to 2° C. with an ice bath was added 9.7 g (73.4 mmole) of 95% potassium t-butoxide. The reaction mixture was stirred for 20 min, quenched with 300 ml of 10% HCl and extracted with methylene chloride. The methylene chloride layer was dried over magnesium sulfate and concentrated in vacuo to give 24.7 g of yellow oil. Purification by HPLC (ethyl acetate-hexane) yielded 9.4 g of recovered 45 in the first fraction, 5.5 g (20%) of 6c in the second fraction and 6.5 g (24%) of 6d in the third fraction.

B. Preparation from 2-hydroxydiphenylmethane

Step 1. 2-mercaptodiphenylmethane (46)

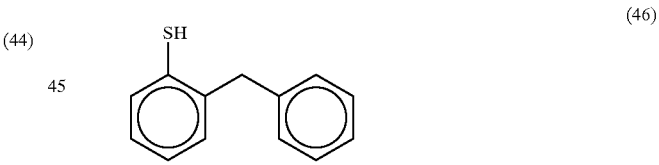
(46)

To a 500 ml flask was charged 16 g (0.33 mol) of 60% sodium hydride oil dispersion. The sodium hydride was washed twice with 50 ml of hexane. To the reaction flask was charged 100 ml of DMF. To this mixture was added a solution of 55.2 g (0.3 mol) of 2-hydroxydiphenylmethane in 200 ml of DMF in 1 h while temperature was maintained below 30° C. by an ice-water bath. After complete addition of the reagent, the mixture was stirred at room temperature for 30 min then cooled with an ice bath. To the reaction mixture was added 49.4 g (0.4 mole) of dimethyl thiocarbamoyl chloride at once. The ice bath was removed and the reaction mixture was stirred at room temperature for 18 h before being poured into 300 ml of water. The organic was extracted into 500 ml of toluene. The toluene layer was washed successively with 10% sodium hydroxide and brine and was concentrated in vacuo to give 78.6 g of a yellow oil which was 95% pure dimethyl 0-2-benzylphenyl thiocarbamate. This oil was heated at 280–300° C. in a kugelrohhr pot under house vacuum for 30 min. The residue was kugelrohr distilled at 1 torr (180–280° C.). The distillate (56.3 g) was crystallized from methanol to give 37.3 g (46%) of the rearranged product dimethyl S-2-benzylphenyl thiocarbmate as a yellow solid. A mixture of 57 g (0.21 mole) of this yellow solid, 30 g of potassium hydroxide and 150 ml of methanol was stirred overnight then was concentrated in vacuo. The residue was diluted with 200 ml of water and extracted with ether. The aqueous layer was made acidic with concentrate HCl, The oily suspension was extracted into ether. The ether extract was dried over magnesium sulfate and concentrated in vacuo. The residue was crystallized from hexane to give 37.1 g (88%) of 2-mercaptodiphenylmethane as a yellow solid.

Step 2. 2-((2-Benzylphenylthio)methyl)-2-ethylhexanal (47)

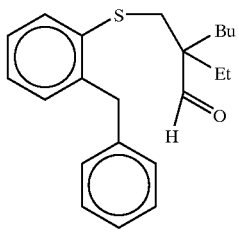

(47)

A mixture of 60 g (03 mole) of yellow solid from step 1, 70 g (0.3 mole) of compound 1 from preparation 1, 32.4 g (0.32 mole) of triethylamine, 120 ml of 2-methoxyethyl ether was held at reflux for 6 hr and concentrated in vacuo. The residue was triturated with 500 ml of water and 30 ml of concentrate HCl. The organic was extracted into 400 ml of ether. The ether layer was washed successively with brine, 10% sodium hydroxide and brine and was dried over magnesium sulfate and concentrated in vacuo. The residue (98.3 g) was purified by HPLC with a 2–5% ethyl acetate-hexane as eluent to give 2-((2-benzylphenylthio)methyl)-2-ethylhexanal 47 as a yellow syrup.

Step 3. 2-((2-Benzylphenylsulfonyl)methyl)-2-ethylhexanal (45)

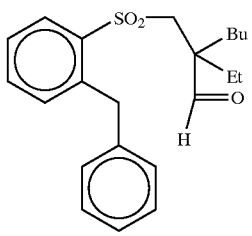

(45)

To a solution of 72.8 g (0.21 mole) of yellow syrup from step 2 in 1 liter of methylene chloride cooled to 10° C. was added 132 g of 50–60% MCPBA in 40 min. The reaction mixture was stirred for 2 h. An additional 13 g of 50–60% MCPBA was added to the reaction mixture. The reaction mixture was stirred for 2 h and filtered through Celite. The methylene chloride solution was washed twice with 1 liter of 1 M potassium carbonate then with 1 liter of brine. The methylene chloride layer was dried over magnesium sulfate and concentrated to 76 g of 2-((2-benzylphenylsulfonyl) methyl)-2-ethylhexanal 45 as a syrup.

Step 4. (3a,4a,5a) 3-Butyl-3-ethyl-4-hydroxy-5-phenyl-2,3,4,5-tetrahydrobenzothiepine-1,1-dioxide (6c), and (3a,4a,5b) 3-Butyl-3-ethyl-4-hydroxy-5-phenyl-2,3,4,5-tetrahydrobenzothiepine-1,1-dioxide (6d)

Reaction of 45 with potassium t-butoxide according to the procedure in step 3 of procedure A gave pure 6c and 6d after HPLC.

Example 19

(3a,4b,5b) 3-Butyl-3-ethyl-4-hydroxy-8-methoxy-5-phenyl-2,3,4,5-tetrahydrobenzothiepine-1,1-dioxide (25) and (3a,4a,5a) 3-Butyl-3-ethyl-4-hydroxy-8-methoxy-5-phenyl-2,3,4,5-tetrahydrobenzothiepine-1,1-dioxide (26)

Step 1. Preparation of 2-((2-benzoyl-4-methoxy phenylthio) methyl)-2-ethylhexanal (22)

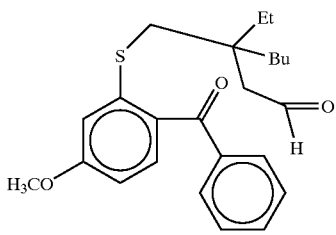

(22)

2-Hydroxy-4-methoxybenzophenone was converted to the dimethyl O-2-benzoyphenyl thiocarbamate by methods previously described in example 18. The product can be isolated by recrystallization from ethanol. Using this improved isolation procedure no chromatography was needed. The thermal rearrangement was performed by reacting the thiocarbamate (5 g) in diphenyl ether at 260° C. as previously described. The improved isolation procedure which avoided a chromatography step was described below.

The crude pyrolysis product was then heated at 65° C. in 100 ml of methanol and 100 ml of THF in the presence of 3.5 g of KOH for 4 h. After removing THF and methanol by rotary evaporation the solution was extracted with 5% NaOH and ether. The base layer was acidified and extracted with ether to obtain a 2.9 g of crude thiophenol product. The product was further purified by titrating the desired mercaptan into base with limited KOH. After acidification and extraction with ether pure 2-mercapto-4-methoxybenzophenone (2.3 g) was isolated.

2-mercapto-4-methoxybenzophenone can readily be converted to the 2-((2-benzoyl-4-methoxyphenylthio)methyl)-2-ethylhexanal (22) by reaction with 2-ethyl-2-(mesyloxymethyl)hexanal (1) as previously described.

Step 2. 2-((2-Benzoyl-5-methoxyphenylsulfonyl) methyl)-2-ethylhexanal (23)

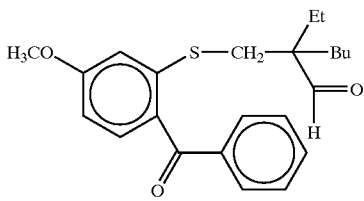

(23)

Substrate 22 was readily oxidized to 2-((2-benzoyl-5-methoxyphenyl-sulfonyl)methyl)-2-ethylhexanal (23) as described in example 18.

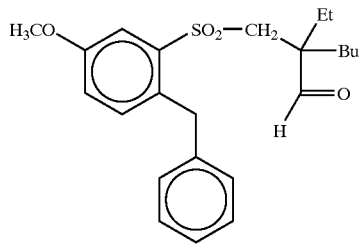

(24)

Step 3. 2-((2-benzyl-5-methoxyphenylsulfonyl)methyl)-2-ethylhexanal (24)

Sulfone 23 was then reduced to 2-((2-benzyl-5-methoxyphenyl-sulfonyl)methyl)-2-ethylhexanal (24) as described in example 18.

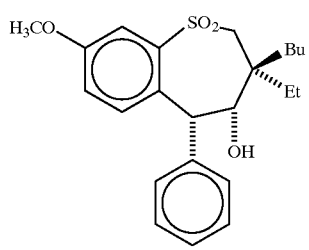

(25)

Step 4. (3a,4b,5b) 3-Butyl-3-ethyl-4-hydroxy-8-methoxy-5-phenyl-2,3,4,5-tetrahydrobenzothiepine-1,1-dioxide (25) and (3a,4a,5a) 3-Butyl-3-ethyl-4-hydroxy-8-methoxy-5-phenyl-2,3,4,5-tetrahydrobenzothiepine-1,1-dioxide (26)

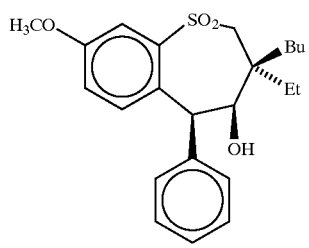

(26)

A 3-neck flask equipped with a powder addition funnel, thermocouple and nitrogen bubbler was charged with 19.8 g (0.05 mole) of sulfone 24 in 100 ml dry THF. The reaction was cooled to −1.6° C. internal temperature by means of ice/salt bath. Slowly add 5.61 g (0.05 mole) of potassium t-butoxide by means of the powder addition funnel. The resulting light yellow solution was maintained at −1.6° C. After 30 min reaction 400 ml of cold ether was added and this solution was extracted with cold 10% HCl. The acid layer was extracted with 300 ml of methylene chloride. The organic layers were combined and dried over magnesium sulfate and after filtration stripped to dryness to obtain 19.9 g of product. $^1$H nmr and glpc indicated a 96% conversion to a 50/50 mixture of 25 and 26. The only other observable compound was 4% starting sulfone 24.

The product was then dissolved in 250 ml of 90/10 hexane/ethyl acetate by warming to 50° C. The solution was allowed to cool to room temperature and in this way pure 26 can be isolated. The crystallization can be enhanced by addition of a seed crystal of 26. After 2 crystallizations the mother liquor which was now 85.4% 25 and has a dry weight of 8.7 g. This material was dissolved in 100 ml of 90/10 hexane/ethyl acetate and 10 ml of pure ethyl acetate at 40 C. Pure 25 can be isolated by seeding this solution with a seed crystal of 25 after storing it overnight at 0 C.

Example 20

(3a,4a,5a) 3-Butyl-3-ethyl-4,8-dihydroxy-5-phenyl-2,3,4,5-tetrahydrobenzothiepine-1,1-dioxide (27)

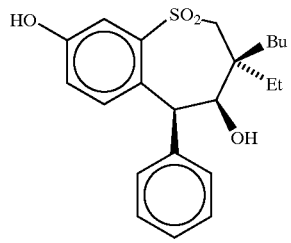

(27)

In a 25 ml round bottomed flask, 1 g of 26 (2.5 mmoles) and 10 ml methylene chloride were cooled to −78° C. with stirring. Next 0.7 ml of boron tribromide (7.5 mmole) was added via syringe. The reaction was allowed to slowly warm to room temperature and stirred for 6 h. The reaction was then diluted with 50 ml methylene chloride and washed with saturated NaCl and then water. The organic layer was dried over magnesium sulfate. The product (0.88 g) 27 was characterized by NMR and mass spectra.

Example 21

General Alkylation of Phenol 27

A 25 ml flask was charged with 0.15 g of 27 (0.38 mmole), 5 ml anhydrous DMF, 54 mg of potassium carbonate (0.38 mmole) and 140 mg ethyl iodide (0.9 mmole). The reaction was stirred at room temperature overnight. The reaction was diluted with 50 ml ethyl ether and washed with water (25 ml) then 5% NaOH (20 ml) and then sat. NaCl. After stripping off the solvent the ethoxylated product 28 was obtained in high yield. The product was characterized by NMR and mass spectra. This same procedure was used to prepare products listed in table 1 from the corresponding iodides or bromides. For higher boiling alkyl iodides and bromides only one equivalent of the alkyl halide was used.

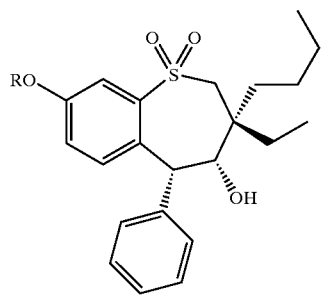

TABLE 1

| Compound No. | R |
|---|---|
| 27 | H |
| 26 | Me |
| 28 | Et |

TABLE 1-continued

| Compound No. | R |
|---|---|
| 29 | hexyl |
| 30 | Ac |
| 31 | (CH2)6-N-pthalimide |

Example 22

(3a,4a,5a) 3-Butyl-3-ethyl-4-hydroxy-7-hydroxyamino-5-phenyl-2,3,4,5-tetrahydrobenzothiepine-1,1-dioxide (37) and (3a,4b,5b) 3-Butyl-3-ethyl-4-hydroxy-7-hydroxyamino-5-phenyl-2,3,4,5-tetrahydrobenzothiepine-1,1-dioxide (38)

Step 1. Preparation of 2-chloro-5-nitrodiphenylmethane

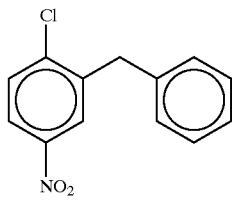
(32)

Procedure adapted from reference: Synthesis—Stuttgart 9 770–772 (1986) Olah G. Et al Under nitrogen, a 3 neck flask was charged with 45 g (0.172 mole) of 2-chloro-5-nitrobenzophenone in 345 ml methylene chloride and the solution was cooled to ice/water temperature. By means of an additional funnel, 150 g (0.172 mole) of trifluoromethane sulfonic acid in 345 ml methylene chloride was added slowly. Next 30 g of triethylsilane (0.172 mole) in 345 ml methylene chloride was added dropwise to the chilled solution. Both addition steps (trifluoromethane sulfonic acid and triethylsilane) were repeated. After the additions were completed the reaction was allowed to slowly warm up to room temperature and stirred for 12 h under nitrogen. The reaction mixture was then poured into a chilled stirred solution of 1600 ml of saturated sodium bicarbonate. Gas evolution occurred. Poured into a 4 liter separatory funnel and separated layers. The methylene chloride layer was isolated and combined with two 500 ml methylene chloride extractions of the aqueous layer. The methylene chloride solution was dried over magnesium sulfate and concentrated in vacuo. The residue was recrystallized from hexane to give 39 g product. Structure 32 was confirmed by mass spectra and proton and carbon NMR.

Step 2. Preparation of 2-((2-benzyl-4-nitrophenylthio)methyl)-2-ethylhexanal (33)

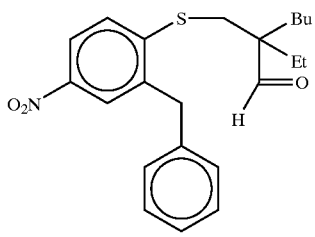
(33)

The 2-chloro-5-nitrodiphenylmethane product 32 (40 g, 0.156 mole) from above was placed in a 2 liter 2 neck flask with water condenser. Next 150 ml DMSO and 7.18 g (0.156 mole) of lithium sulfide was added and the solution was stirred at 75° C. for 12 h. The reaction was cooled to room temperature and then 51.7 g of mesylate IV was added in 90 ml DMSO. The reaction mixture was heated to 80° C. under nitrogen. After 12 h monitored by TLC and added more mysylate if necessary. Continued the reaction until the reaction was completed. Next the reaction mixture was slowly poured into a 1900 ml of 5% acetic aqueous solution with stirring, extracted with 4×700 ml of ether, and dried over MgSO4. After removal of ether, 82.7 g of product was isolated. The material can be further purified by silica gel chromatography using 95% hexane and 5% ethyl acetate. If pure mysylate was used in this step there was no need for further purification. The product 33 was characterized by mass spectra and NMR.

Step 3. Oxidation of the nitro product 33 to the sulfone 2-((2-benzyl-4-nitrophenylsulfonyl)methyl)-2-ethylhexanal (34)

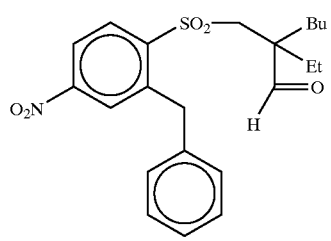
(34)

The procedure used to oxidize the sulfide 33 to the sulfone 34 has been previously described.

Step 4. Reduction of 34 to 2-((2-benzyl-4-hydroxyaminophenylsulfonyl)methyl)-2-ethylhexanal (35)

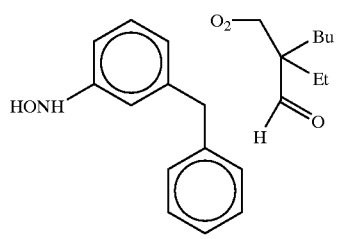
(35)

A 15 g sample of 34 was dissolved in 230 ml of ethanol and placed in a 500 ml rb flask under nitrogen. Next 1.5 g of 10 wt. % Pd/C was added and hydrogen gas was bubbled through the solution at room temperature until the nitro substrate 34 was consumed. The reaction could be readily monitored by silica gel TLC using 80/20 hexane/EtOAc. Product 35 was isolated by filtering off the Pd/C and then stripping off the EtOH solvent. The product was characterized by NMR and mass spectra.

Step 5. Preparation of the 2-((2-benzyl-4-N,O-di-(t-butoxy-carbonyl)hydroxyaminophenylsulfonyl)methyl)-2-ethylhexanal (36).

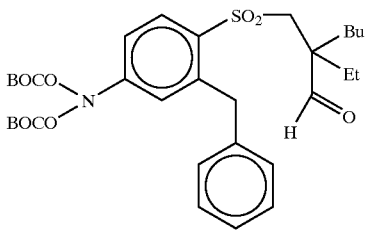
(36)

A 13.35 g sample of 35 (0.0344 mole) in 40 ml of dry THF was stirred in a 250 ml round bottomed flask. Next added 7.52 g (0.0344 mole) of di-t-butyl dicarbonate in 7 ml THF. Heated at 60° C. overnight. Striped off THF and redissolved in methylene chloride. Extracted with 1% HCl; and then 5% sodium bicarbonate.

The product was further purified by column chromatography using 90/10 hexane/ethyl acetate and then 70/30 hexane/ethyl acetate. The product 36 was obtained (4.12 g) which appeared to be mainly the di-(t-butoxycarbonyl) derivatives by proton NMR.

Step 6. (3a,4a,5a) 3-Butyl-3-ethyl-4-hydroxy-7-hydroxyamino-5-phenyl-2,3,4,5-tetrahydrobenzothiepine-1,1-dioxide (37) and (3a,4b,5b) 3-Butyl-3-ethyl-4-hydroxy-7-hydroxyamino-5-phenyl-2,3,4,5-tetrahydrobenzothiepine-1,1-dioxide (38)

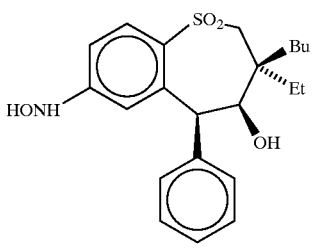
(37)

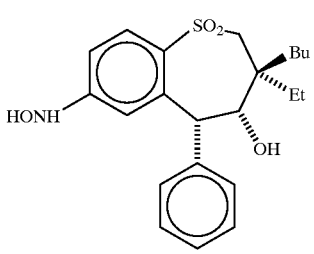
(38)

A 250 ml 3-neck round bottomed flask was charged with 4 g of 36 (6.8 mmoles), and 100 ml of anhydrous THF and cooled to −78° C. under a nitrogen atmosphere. Slowly add 2.29 g potassium tert-butoxide (20.4 mmoles) with stirring and maintaining a −78° C. reaction temperature. After 1 h at −78° C. the addition of base was completed and the temperature was brought to −10° C. by means of a ice/salt bath. After 3 h at −10° C., only trace 36 remained by TLC. Next add 35 ml of deionized water to the reaction mixture at −10° C. and stirred for 5 min. Striped off most of the THF and added to separatory funnel and extracted with ether until all of the organic was removed from the water phase. The combined ether phases were washed with saturated NaCl and then dried over sodium sulfate. The only products by TLC and NMR were the two BOC protected isomers of 37 and 38. The isomers were separated by silica gel chromatography using 85% hexane and 15% ethyl acetate; BOC-37 (0.71 g) and BOC-38 (0.78 g).

Next the BOC protecting group was removed by reacting 0.87 g of BOC-38 (1.78 mmoles) with 8.7 ml of 4 M HCl (34.8 mmoles) in dioxane for 30 min. Next added 4.74 g of sodium acetate (34.8 mmoles) to the reaction mixture and 16.5 ml ether and stirred until clear. After transferring to a separatory funnel extracted with ether and water and then dried the ether layer with sodium sulfate. After removing the ether, 0.665 g of 38 was isolated. Isomer 37 could be obtained in a similar procedure.

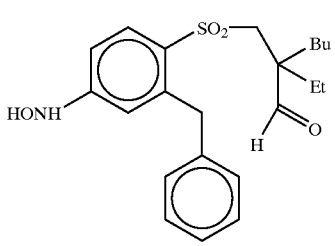
(39)

Example 23

(3a,4a,5a) 3-Butyl-3-ethyl-7-(n-hexylamino)-4-hydroxy-5-phenyl-2,3,4,5-tetrahydrobenzothiepine-1,1-dioxide (40) and (3a,4b,5b) 3-Butyl-3-ethyl-7-(n-hexylamino)-4-hydroxy-5-phenyl-2,3,4,5-tetrahydrobenzothiepine-1,1-dioxide (41)

Step 1. 2-((2-Benzyl-4-(n-hexylamino)phenylsulfonyl) methyl)-2-ethylhexanal (39)

In a Fischer porter bottle weighed out 0.5 g of 34 (1.2 mmoles) and dissolved in 3.8 ml of ethanol under nitrogen. Next added 0.1 g of Pd/C and 3.8 ml of hexanal. Seal and pressure to 50 psi of hydrogen gas. Stirred for 48 h. After filtering off the catalyst and removing the solvent by rotary evaporation 39 was isolated by column chromatography (0.16 g) using 90/10 hexane ethyl acetate and gradually increasing the mobile phase to 70/30 hexane/ethyl acetate. The product was characterized by NMR and mass spectra.

Step 2. (3a,4a,5a) 3-Butyl-3-ethyl-7-(n-hexylamino)-4-hydroxy-5-phenyl-2,3,4,5-tetrahydrobenzothiepine-1,1-dioxide (40) and (3a,4b,5b) 3-Butyl-3-ethyl-7-(n-hexylamino)-4-hydroxy-5-phenyl-2,3,4,5-tetrahydrobenzothiepine-1,1-dioxide (41)

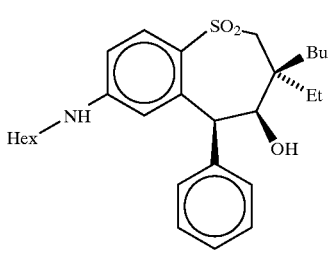
(40)

A 2-neck, 25 ml round bottomed flask with stir bar was charged with 0.158 g 39 (0.335 mmole) and 5 ml anhydrous THF under nitrogen. Cool to −10° C. by means of a salt/water bath. Slowly add 0.113 g of potassium tert butoxide (0.335 mmole). After 15 min at −10° C. all of the starting material was consumed by TLC and only the two isomers 40 and 41 were observed. Next added 5 ml of chilled 10% HCl and stirred at −10° C. for 5 min. Transferred to a separatory funnel and extract with ether. Dried over a sodium sulfate. Proton NMR of the dried product (0.143 g) indicated only the presence of the two isomers 40 and 41. The two isomers were separated by silica gel chromatography using 90/10 hexane ethyl acetate and gradually increasing the mobile phase to 70/30 hexane/ethyl acetate. 40 (53.2 mg); 41 (58.9 mg).

(41)

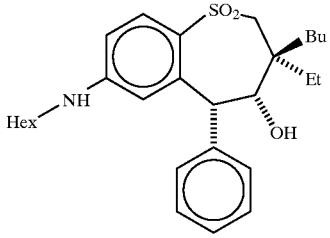

Example 24

Quaternization of Amine Substrates 40 and 41

Amine products such as 40 and 41 can be readily alkylated to quaternary salts by reaction with alkyl halides. For example 40 in DMF with 5 equivalents of methyl iodide in the presence of 2,6 dimethyl lutidine produces the dimethylhexylamino quaternary salt.

Example 25

(3a,4b,5b) 3-Butyl-3-ethyl-4-hydroxy-5-(4-iodophenyl)-2,3,4,5-tetrahydrobenzothiepine-1,1-dioxide (42)

(42)

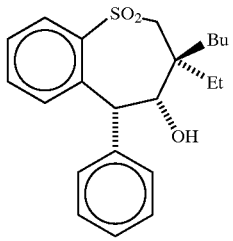

In a 25 ml round bottomed flask 0.5 g (1.3 mmole) of 6d, 0.67 g of mercuric triflate were dissolved in 20 ml of dry methylene chloride with stirring. Next 0.34 g of Iodine was added and the solution was stirred at room temperature for 30 h. The reaction was then diluted with 50 ml methylene chloride and washed with 10 ml of 1 M sodium thiosulfate; 10 ml of saturated KI; and dried over sodium sulfate. See Tetrahedron, Vol.50; No. 17, pp 5139–5146 (1994) Bachki, F. Et al. Mass spectrum indicated a mixture of 6d, mono iodide 42 and a diiodide adduct. The mixture was separated by column chromatography and 42 was characterized bt NMR and mass spectra.

Example 26

(3a,4b,5b) 3-Butyl-5-(4-carbomethoxyphenyl)-3-ethyl-4-hydroxy-2,3,4,5-tetrahydrobenzothiepine-1,1-dioxide (43)

(43)

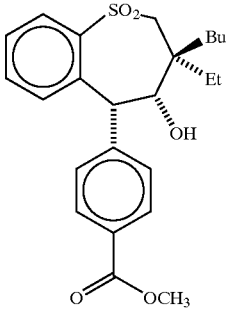

A 0.1 g sample of 42 (0.212 mmole), 2.5 ml dry methanol, 38 μl triethylamine (0.275 mmole), 0.3 ml toluene and 37 mg of palladium chloride (0.21 mmole) was charged to a glass lined mini reactor at 300 psi carbon monoxide. The reaction was heated at 100° C. overnight. The catalyst was filtered and a high yield of product was isolated.

The product was characterized by NMR and mass spectra.

Note the ester functionalized product 43 can be converted to the free acid by hydrolysis.

Example 27

(3a,4a,5a) 3-Butyl-3-ethyl-4-hydroxy-7-methoxy-5-phenyl-2,3,4,5-tetrahydrobenzothiepine-1,1-dioxide (48), and (3a,4b,5b) 3-Butyl-3-ethyl-4-hydroxy-7-methoxy-5-phenyl-2,3,4,5-tetrahydrobenzothiepine-1,1-dioxide (49)

Step 1. 2-Mercapto-5-methoxybenzophenone (50)

(50)

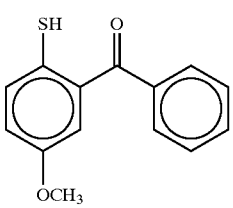

Reaction of 66.2 g of 4-methoxythiophenol with 360 ml of 2.5 N n-butyllithium, 105 g of tetramethylethylenediamine and 66.7 g of benzonitrile in 600 ml cyclohexane according to the procedure in WO 93/16055 gave 73.2 g of brown oil which was kugelrohr distilled to remove 4-methoxythiophenol and gave 43.86 g of crude 50 in the pot residue.

Step 2. 2-((2-Benzoyl-4-methoxyphenylthio)methyl)-2-ethylhexanal (51)

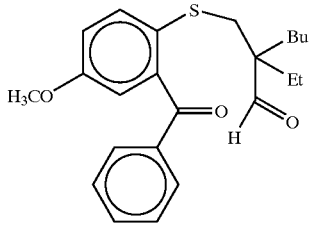
(51)

Reaction of 10 g (0.04 mole) of crude 50 with 4.8 g (0.02 mole) of mesylate 1 and 3.2 ml (0.23 mole) of triethylamine in 50 ml of diglyme according to the procedure for the preparation of 2 gave 10.5 g of crude product which was purified by HPLC (5% ethyl acetate-hexane) to give 1.7 g (22%) of 51.

Step 3. 2-((2-Benzoyl-4-methoxyphenylsulfonyl)methyl)-2-ethyl-hexanal (52)

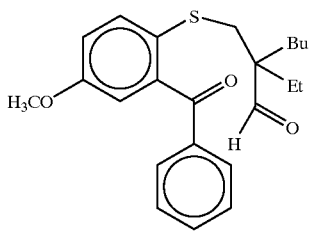
(52)

A solution of 1.2 g (3.1 mmoles) of 51 in 25 ml of methylene chloride was reacted with 2.0 g (6.2 mmoles) of 50–60% MCPBA according to the procedure of step 2 of procedure A in example 18 gave 1.16 g (90%) of 52 as a yellow oil.

Step 4. 2-((2-Benzyl-4-methoxyphenylsulfonyl)methyl)-2-ethylhexanal (53)

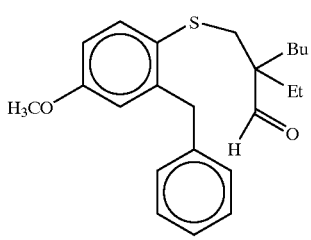
(53)

Hydrogenation of 1.1 g of 52 according to the procedure of step 3 of procedure A of example 18 gave 53 as a yellow oil (1.1 g).

Step 5. (3a,4a,5a) 3-Butyl-3-ethyl-4-hydroxy-7-methoxy-5-phenyl-2,3,4,5-tetrahydrobenzothiepine-1,1-dioxide (48), and (3a,4b,5b) 3-Butyl-3-ethyl-4-hydroxy-7-methoxy-5-phenyl-2,3,4,5-tetrahydrobenzothiepine-1,1-dioxide (49)

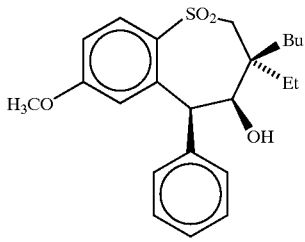
(48)

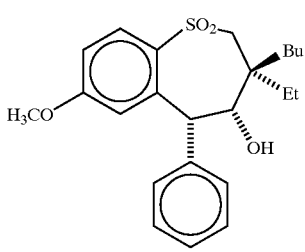
(49)

A solution of 1.1 g of 53, 0.36 g of potassium t-butoxide and 25 ml of anhydrous THF was held at reflux for 2 h and worked up as in step 4 of procedure A of example 18 to give 1.07 g of a crude product which was purified by HPLC to give 40 mg (4%) of 48 as crystals, mp 153–154° C. and 90 mg (8%) of 49 as solid, mp 136–140° C.

Example 28

5-Phenyl-2,3-dihydrospirobenzothiepine-3,1'-cyclohexane (57)

Step 1. 1-(Hydroxymethyl)-cyclohexanecarboxaldehyde (54)

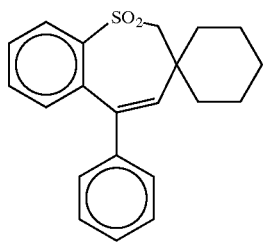
(57)

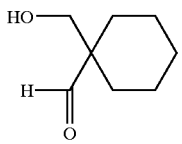
(54)

To a cold (0° C.[1] mixture of 100 g (0.891 mole) of cyclohexanecarboxaldehyde, 76.5 g of 37% of formaldehyde in 225 ml of methanol was added dropwise 90 ml of 1 N Sodium hydroxide in 1 h. The reaction mixture was stirred at room temperature over 48 then was evaporated to remove methanol. The reaction mixture was diluted with water and extracted with methylene chloride. The organic layer was washed with water, brine, and dried over sodium sulfate and concentrated under vacuum to give 75 g (59.7%) of thick oil. Proton NMR and mass spectra were consistent with the product.

Step 2. 1-(mesyloxymethyl)cyclohexanecarboxaldehyde (55)

(55)

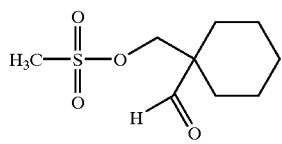

To a cold (0° C.) mixture of alcohol 54 (75 g, 0.54 mole) and 65.29 g (0.57 mole) of methanesulfonyl chloride in 80 ml of methylene chloride was added a solution of pyridine (47.96 g, 0.57 mole) in 40 ml of methylene chloride. The reaction mixture was stirred at room temperature for 18 h then quenched with water, acidified with conc. HCl and extracted with methylene chloride. The organic layer was washed with water, brine, and dried over sodium sulfate and concentrated under vacuum to give 91.63 g (77.8%) of thick oil. Proton NMR and mass spectra were consistent with the product.

Step 3. 1-((2-Benzoylphenylthio)methyl)cyclohexanecarboxaldehyde (56)

(56)

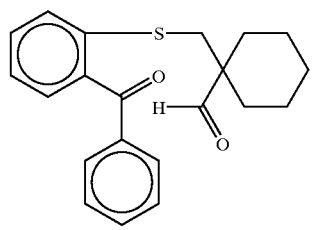

A mixture of 69 g (0.303 mole) of 2-mercaptobenzophenone, 82 g (0.303 mole) of mesylate 55, 32 g of triethylamine, and 150 ml of diglyme was stirred and held at reflux for 24 h. The mixture was cooled, poured into dil. HCl and extracted with methylene chloride. The organic layer was washed with 10% NaOH, water, brine, and dried over sodium sulfate and concentrated under vacuum to remove excess diglyme. This was purified by silica gel flush column (5% EtOAc: Hexane) and gave 18.6 g (75.9%) of yellow oil. Proton NMR and mass spectra were consistent with the product.

Step 4. 5-Phenyl-2,3-dihydrospirobenzothiepine-3,1'-cyclohexane (57)

(57)

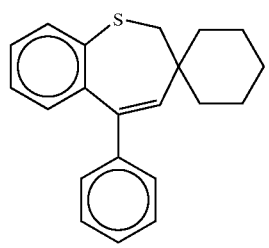

To a mixture of 6.19 g of zinc dust and 100 ml of dry DME was added TiCl₃ (16.8 g, 0.108 mole). The reaction mixture was heated to reflux for 2 h. A solution of compound 56 (8.3 g, 0.023 mole) in 50 ml of DME was added dropwise to the reaction mixture in 1 h and the mixture was held at reflux for 18 h. The mixture was cooled, poured into water and extracted with ether. The organic layer was washed with water, brine, and dried over sodium sulfate, filtered through celite and concentrated under vacuum. The residue was purified by HPLC (10% EtOAc: Hexane) to give 4.6 g (64%) of white solid, mp 90–91° C. Proton and carbon NMR and mass spectra were consistent with the product.

Example 29

8b-Phenyl-1a,2,3,8b-tetrahydrospiro(benzothiepino[4,5-b]oxirene-2,1'-cyclohexane)-4,4-dioxide (58)

(58)

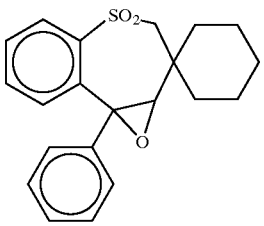

To a solution of 57 (4.6 g, 15 mmole) in 50 ml chloroform under nitrogen was added 55% MCPBA (16.5 g, 52.6 mmole) portionwise with spatula. The reaction was held at reflux for 18 h and washed with 10% NaOH (3×), water, brine, and dried over sodium sulfate and concentrated under vacuum to give 5 g of crude product. This was recrystallized from Hexane/EtOAc to give 4.31 g (81%) of yellow solid, mp 154–155° C. Proton and carbon NMR and mass spectra were consistent with the product.

Example 30 trans-4-Hydroxy-5-phenyl-2,3,4,5-tetrahydro spiro(benzothiepine-3,1'-cyclohexane)-1,1-dioxide (59)

(59)

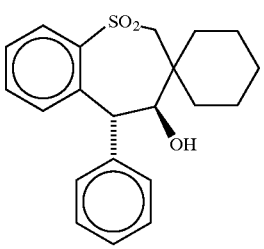

A mixture of 0.5 g (1.4 mmoles) of 58, 20 ml of ethanol, 10 ml of methylene chloride and 0.4 g of 10% Pd/C catalyst was hydrogenated with 70 psi hydrogen for 3 h at room temperature. The crude reaction slurry was filtered through Celite and evaporated to dryness. The residue was purified by HPLC (10% EtOAc-Hexane, 25% EtOAc-Hexane). The first fraction was 300 mg (60%) as a white solid, mp 99–100° C. Proton NMR showed this was a trans isomer. The second fraction gave 200 mg of solid which was impure cis isomer.

Example 31 cis-4-Hydroxy-5-phenyl-2,3,4,5-tetrahydro spiro(benzothiepine-3,1'-cyclohexane)-1,1-dioxide (60)

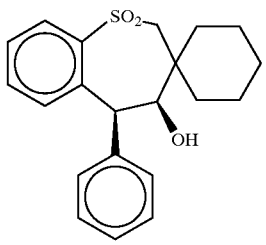
(60)

To a solution of 0.2 g (0.56 mmole) of 59 in 20 ml of $CH_2Cl_2$, was added 8 g of 50% NaOH and one drop of Aliquat-336 (methyltricaprylylammonium chloride) phase transfer catalyst. The reaction mixture was stirred for 10 h at room temperature. Twenty g of ice was added to the mixture and the mixture was extracted with $CH_2Cl_2$ (3×10 ml) washed with water, brine and dried over $MgSO_4$ and concentrated in vacuo to recover 0.15 g of crude product. This was recrystallized from Hexane/EtOAc to give 125 mg of white crystal, mp 209–210° C. Proton and carbon NMR and mass spectra were consistent with the product.

Example 32

(3a,4a,5a) 3-Butyl-3-ethyl-4-hydroxy-5-phenyl-2,3,4,5-tetrahydrobenzothiepine (61), and (3a,4b,5b) 3-Butyl-3-ethyl-4-hydroxy-5-phenyl-2,3,4,5-tetrahydrobenzothiepine (62)

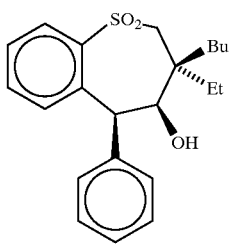
(61)

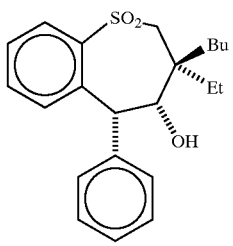
(62)

To a solution of 0.5 g (1.47 mmole) of compound 47 in 5 ml of anhydrous THF was added 0.17 g (1.47 mmole) of 95% potassium t-butoxide. The reaction mixture was stirred at room temperature for 18 h and quenched with 10 ml of 10% HCl. The organic was extracted into methylene chloride. The methylene chloride extract was dried over magnesium sulfate and concentrated in vacuo. The residue was purified by HPLC (2% EtOAc-hexane) to give 47 mg of 61 in the second fraction and 38 mg of 62 in the third fraction. Proton NMR and mass spectra were consistent with the assigned structures.

Example 33

(3a,4a,5a) 3-Butyl-3ethyl-4-hydroxy-7-amino-5-phenyl-2,3,4,5-tetrahydrobenzothiepine-1,1-dioxide (63) and (3a,4b,5b) 3-Butyl-3-ethyl-4-hydroxy-7-amino-5-phenyl-2,3,4,5-tetrahydrobenzothiepine-1,1-dioxide (64)

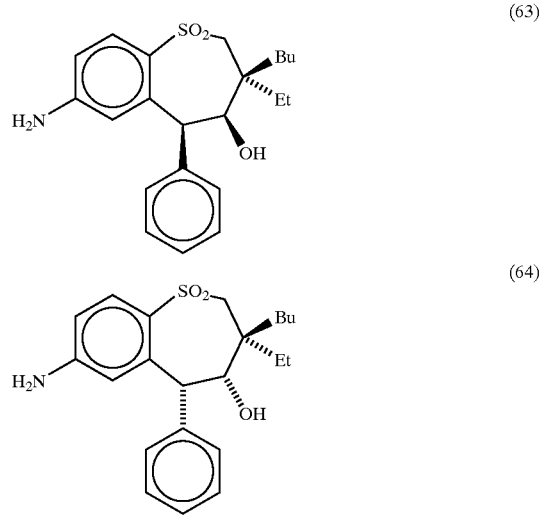

An autoclave was charged with 200 mg of 37 in 40 cc ethanol and 0.02 g 10% Pd/C. After purging with nitrogen the clave was charged with 100 psi hydrogen and heated to 55 C. The reaction was monitored by TLC and mass spec and allowed to proceed until all of 37 was consumed. After the reaction was complete the catalyst was filtered and the solvent was removed in vacuo and the only observable product was amine 63. This same procedure was used to produce 64 from 38.

Example 34

(3a,4a,5a) 3-Butyl-3-ethyl-4-hydroxy-7-methoxy-5-(3'-methoxyphenyl)-2,3,4,5-tetrahydrobenzothiepine-1,1-dioxide (65), and (3a,4b,5b) 3-Butyl-3-ethyl-4-hydroxy-7-methoxy-5-(3'-methoxyphenyl)-2,3,4,5-tetrahydrobenzothiepine-1,1-dioxide (66).

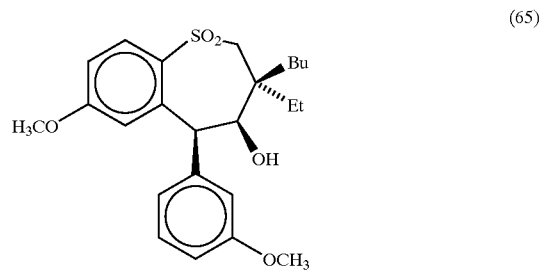
(65)

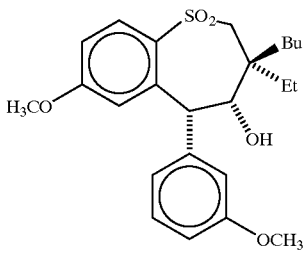
(66)

Alkylation of e-methoxyphenol with 3-methoxybenzyl chloride according to the procedure described in J. Chem. Soc, 2431 (1958) gave 4-methoxy-2-(3'-methoxybenzyl) phenol in 35% yield. This material was converted to compound 65, mp 138.5–141.5° C., and compound 66, mp 115.5–117.5° C., by the procedure similar to that in Example 18 method B.

Example 35

(3a,4a,5a) 3-Butyl-3-ethyl-4-hydroxy-7-methoxy-5-(3'-(trifluoromethyl)phenyl)-2,3,4,5-tetrahydrobenzothiepine-1,1-dioxide (67), and (3a,4b,5b) 3-Butyl-3-ethyl-4-hydroxy-7-methoxy-5-(3'-(trifluoromethyl)phenyl)-2,3,4,5-tetrahydrobenzothiepine-1,1-dioxide (68).

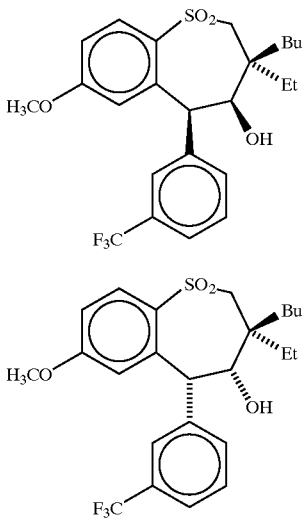
(67)

(68)

Alkylation of 4-methoxyphenol with 3-(trifluoromethyl) benzyl chloride according to the procedure described in J. Chem. Soc. 2431 (1958) gave 4-methoxy-2-(3'-(trifluoromethyl)benzyl)phenol. This material was converted to compound 67, mp 226.5–228° C., and compound 68, mp 188–190° C., byu the procedure similar to that in Example 18 method B.

Example 36

(3a,4a,5a) 3-Butyl-3-ethyl-5-(4'-fluorophenyl)-4-hydroxy-7-methoxy-2,3,4,5-tetrahydrobenzothiepine-1,1-dioxide (69), and (3a,4b,5b) 3-Butyl-3-ethyl-5-(4'-fluorophenyl)-4-hydroxy-7-methoxy-2,3,4,5-tetrahydrobenzothiepine-1,1-dioxide (70).

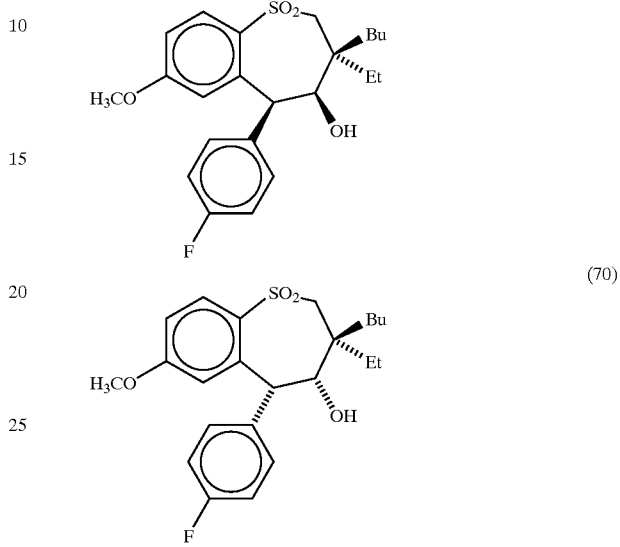
(69)

(70)

Alkylation of 4-methoxyphenol with 4-fluorobenzyl chloride according to the procedure described in J. Chem. Soc, 2431 (1958) gave 4-methoxy-2-(4'-fluorobenzyl)phenol. This material was converted to compound 69 and compound 70 by the procedure similar to that in Example 18 method B.

Example 37

(3a,4a,5a) 3-Butyl-3-ethyl-5-(3'-fluorophenyl)-4-hydroxy-7-methoxy-2,3,4,5-tetrahydrobenzothiepine-1,1-dioxide (71), and (3a,4b,5b) 3-Butyl-3-ethyl-5-(3'-fluorophenyl)-4-hydroxy-7-methoxy-2,3,4,5-tetrahydrobenzothiepine-1,1-dioxide (72).

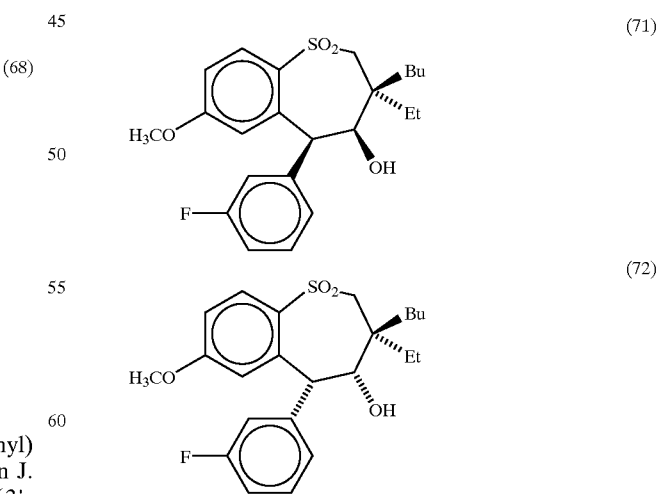
(71)

(72)

Alkylation of 4-methoxyphenol with 3-fluorobenzyl chloride according to the procedure described in J. Chem. Soc, 2431 (1958) gave 4-methoxy-2-(3'-fluorobenzyl)phenol.

This material was converted to compound 71 and compound 72 by the procedure similar to that in Example 18 method B.

Example 38

(3a,4a,5a) 3-Butyl-3-ethyl-5-(2'-fluorophenyl)-4-hydroxy-7-methoxy-2,3,4,5-tetrahydrobenzothiepine-1,1-dioxide (73), and (3a,4b,5b) 3-Butyl-3-ethyl-5-(2'-fluorophenyl)-4-hydroxy-7-methoxy-2,3,4,5-tetrahydrobenzothiepine-1,1-dioxide (74).

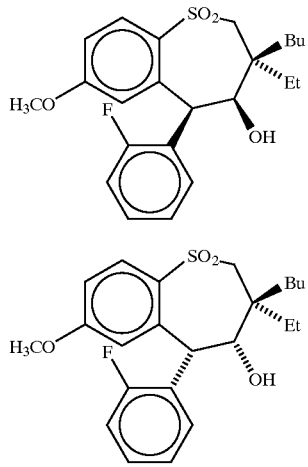

Alkylation of 4-methoxyphenol with 2-fluorobenzyl chloride according to the procedure described in J. Chem. Soc, 2431 (1958) gave 4-methoxy-2-(2'-fluorobenzyl)phenol. This material was converted to compound 73 and compound 74 by the procedure similar to that in Example 18 method B.

Example 39

(3a,4a,5a) 3-Butyl-7-bromo-3-ethyl-4-hydroxy-5-(3'-methoxyphenyl)-2,3,4,5-tetrahydrobenzothiepine-1,1-dioxide (75), and (3a,4b,5b) 3-Butyl-7-bromo-3-ethyl-4-hydroxy-5-(3'-methoxyphenyl)-2,3,4,5-tetrahydrobenzothiepine-1,1-dioxide (76).

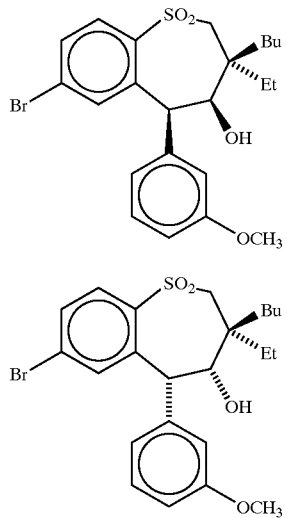

Alkylation of 4-bromophenol with 3-methoxybenzyl chloride according to the procedure described in J. Chem. Soc, 2431 (1958) gave 4-bromo-2-(3'-methoxybenzyl)phenol. This material was converted to compound 75, mp 97–101.5° C., and compound 76, mp 102–106° C., by the procedure similar to that in Example 18 method B.

Example 40

(3a,4a,5a) 3-Butyl-3-ethyl-7-fluoro-5-(4'-fluorophenyl)-4-hydroxy-2,3,4,5-tetrahydrobenzothiepine-1,1-dioxide (77), and (3a,4b,5b) 3-Butyl-3-ethyl-7-fluoro-5-(4'-fluorophenyl)-4-hydroxy-2,3,4,5-tetrahydrobenzothiepine-1,1-dioxide (78).

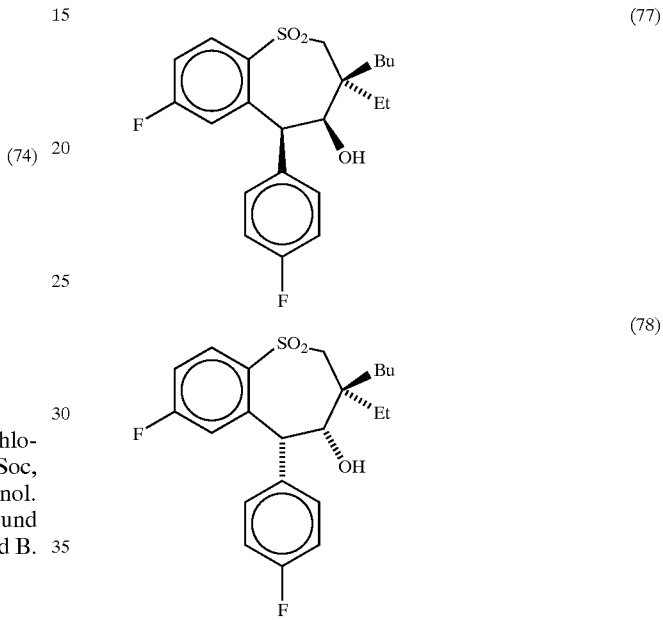

Alkylation of 4-fluorophenol with 4-fluorobenzyl chloride according to the procedure described in J. Chem. Soc, 2431 (1958) gave 4-fluoro-2-(4'-fluorobenzyl)phenol. This material was converted to compound 77, mp 228–230° C., and compound 78, mp 134.5–139° C., by the procedure similar to that in Example 18 method B.

Example 41

(3a,4a,5a) 3-Butyl-3-ethyl-7-fluoro-4-5-(3'-methoxyphenyl)-2,3,4,5-tetrahydrobenzothiepine-1,1-dioxide (79), and (3a,4b,5b) 3-Butyl-3-ethyl-7-fluoro-4 0hydroxy-5-(3'-methoxyphenyl)-2,3,4,5-tetrahydrobenzothiepine-1,1-dioxide (80).

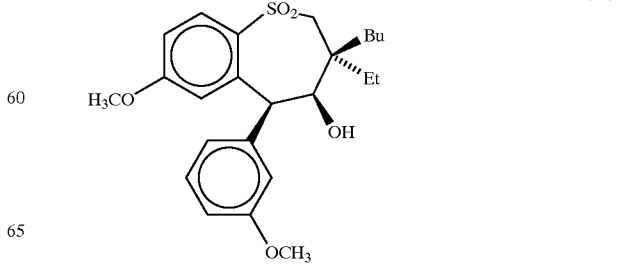

-continued

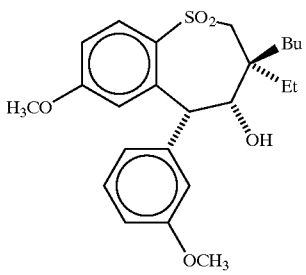
(80)

Alkylation of 4-fluorophenol with 3-methoxybenzyl chloride according to the procedure described in J. Chem. Soc, 2431 (1958) gave 4-fluoro-2-(3'-methoxybenzyl)phenol. This material was converted to compound 79, as a solid and compound 80, mp 153–155° C., by the procedure similar to that in Example 18 method B.

Example 42

(3a,4b,5b) 3-Butyl-3-ethyl-5-(4'-fluorophenyl)-4-hydroxy-7-methylthio-2,3,4,5-tetrahydrobenzothiepine-1,1-dioxide (81).

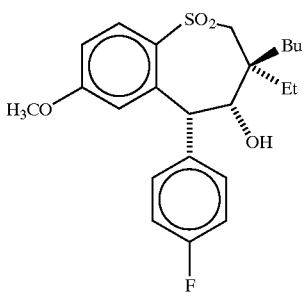
(81)

A mixture of 0.68 (1.66 mmol) of compound 77, 0.2 g (5 mmol) of sodium methanethiolate and 15 ml of anhydrous DMF was stirred at room temperature for 16 days. The reaction mixture was dilute with ether and washed with water and brine and dried over $M_gSO_4$. The ether solution was concentrated in vacuo. The residue was purified by HPLC (20% ethyl acetate in hexanes). The first fraction was impure (3a,4a,5a) 3-butyl-3-ethyl-4-hydroxy-7-methylthio-5-(4'-fluorophenyl)-2,3,4,5-tetrahydrobenzothiepine-1,1-dioxide. The second fraction was compound 81, mp 185–186.5° C.

Example 43

(3a,4b,5b) 3-Butyl-3-ethyl-5-(4'-fluorophenyl)-4-hydroxy-7-(1-pyrrolidinyl)-2,3,4,5-tetrahydrobenzothiepine-1,1-dioxide (82).

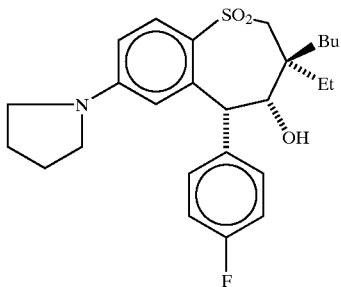
(82)

A mixture of 0.53 g (1.30 mmol) of compound 78 and 5 ml of pyrrolidine was held at reflux for 1 h. The reaction mixture was diluted with ether and washed with water and brine and dried over $M_gSO_4$. The ether solution was concentrated in vacuo. The residue was crystallized from ether-hexanes to give compound 82, mp 174.5–177° C.

Example 44

(3a,4b,5b) 3-Butyl-3-ethyl-5-(4'-fluorophenyl)-4-hydroxy-7-(1-morpholinyl)-2,3,4,5-tetrahydrobenzothiepine-1,1-dioxide (83).

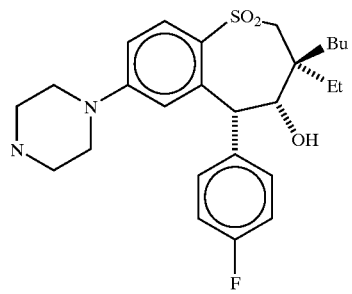
(83)

A mixture of 0.4 g (0.98 mmol) of compound 78 and 5.0 g (56 mmol) of morpholine was held at reflux for 2 h and concentrated in vacuo. The residue was diluted with ether (30 ml) and washed with water and brine and dried over $M_gSO_4$. The ether solution was concentrated in vacuo. The residue was recrystallized from ether-hexanes to give compound 83, mp 176.5–187.5° C.

Example 45

(3a,4a,5a) 3-Butyl-3-ethyl-5-(4'-fluorophenyl)-4-hydroxy-7-methyl-2,3,4,5-tetrahydrobenzothiepine-1,1-dioxide (84), and (3a,4b,5b) 3-Butyl-3-ethyl-5-(4'-fluorophenyl)-4-hydroxy-7-methyl-2,3,4,5-tetrahydrobenzothiepine-1,1-dioxide (85).

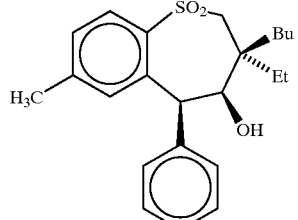
(84)

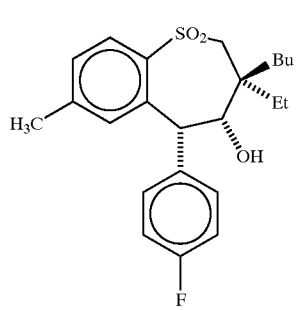
(85)

Alkylation of 4-methylphenol with 4-fluorobenzyl chloride according to the procedure described in J. Chem. Soc, 2431 (1958) gave 4-methyl-2-(4'-fluorobenzyl)phenol. This material was converted to compound 84 and compound 85 by the procedure similar to that in Example 18 method B.

Example 46

(3a,4b,5b) 3-Butyl-3-ethyl-4-hydroxy-5-(4'-hydroxyphenyl)-7-methoxy-2,3,4,5-tetrahydrobenzothiepine-1,1-dioxide (86), and (3a,4b,5b) 3-Butyl-3-ethyl-4,7-dihydroxy-5-(4'-hydroxphenyl)-2,3,4,5-tetrahydrobenzothiepine-1,1-dioxide (87).

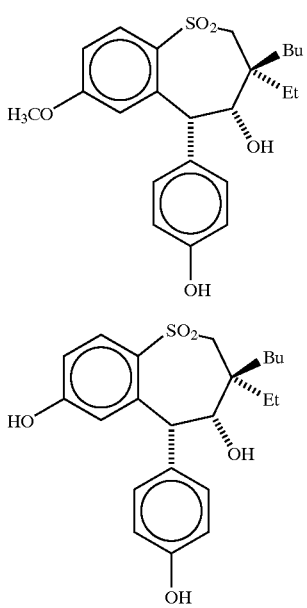

To a solution of 0.52 (1.2 mmol) of compound 66 in 20 ml of methylene chloride was added 1.7 g (6.78 mmol) of born tribromide. The reaction mixture was cooled to –78° C. and was stirred for 4 min. An additional 0.3 ml of boron tribromide was added to the reaction mixture and the reaction mixture was stirred at –78° C. for 1 h and quenched with 2 N HCl. The organic was extracted into ether. The ether layer was washed with brine, dried over $M_gSO_4$, and concentrated in vacuo. The residue (0.48 g) was purified by HPLC (30% ethyl acetate in hexanes). The first fraction was 0.11 g of compound 86 as a white solid, mp 171.5–173° C. The second fraction was crystallized from chloroform to give 0.04 g of compound 87 as a white solid, mp 264° C. (dec).

Example 47

(3a,4b,5b) 3-Butyl-3-ethyl-4,7-dihydroxy-5-(4'-fluorophenyl)-2,3,4,5-tetrahydrobenzothiepine-1,1-dioxide (88).

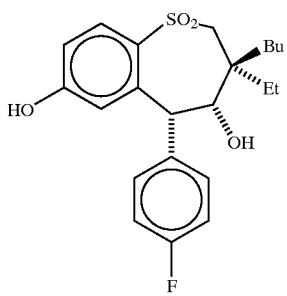

Reaction of compound 70 with excess boron tribromide at room temperature and worked up as in Example 46 gave compound 88 after an HPLC purification.

Example 48

(3a,4b,5b) 3-Butyl-3-ethyl-5-(4'-fluorophenyl)-4-hydroxy-7-(1-azetidinyl)-2,3,4,5-tetrahydrobenzothiepine-1,1-dioxide (89).

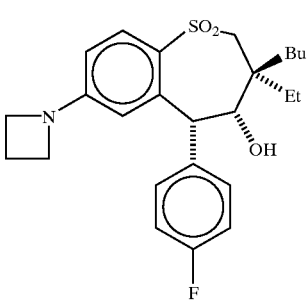

A mixture of 0.20 g (0.49 mmol) of compound 78, and 2.0 g (35 mmol) of aztidine was held at reflux for 3 h and concentrated in vacuo. The residue was diluted with ether (30 ml) and washed with water and brine and dried over MgSO4. The ether solution was concentrated on a steam bath. The separated crystals were filtered to give 0.136 g of 89 as prisms, mp 196.5–199.5° C.

Example 49

(3a,4a,5a) 3-Butyl-3-ethyl-5-(3'-methoxyphenyl)-4-hydroxy-7-methylthio-2,3,4,5-tetrahydrobenzothiepine-1,1-dioxide (90). (3a,4b,5b) 3-Butyl-3-ethyl-5-(3'-methoxyphenyl)-4-hydroxy-7-methylthio-2,3,4,5-tetrahydrobenzothiepine-1,1-dioxide (91).

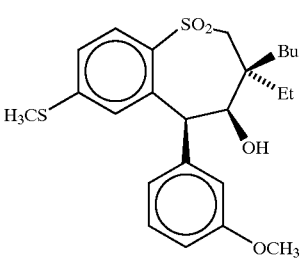

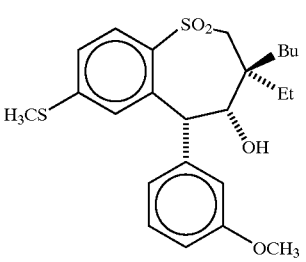

A mixture of 0.4 g (0.95 mmol) of compound 79, 0.08 g (1.14 mmol) of sodium methanethiolate and 15 ml of anhydrous DMF was stirred at 60° C. for 2 h. An additional 1.4 mmol of sodium methanethiolate was added to the reaction mixture and the mixture was stirred at 60° C. for an additional 2 h. The reaction mixture was triturated with 100 ml of water and extracted methylene chloride. The methylene chloride water mixture was filtered through Celite and the methylene chloride layer was dried over $M_gSO_4$ and concentrated in vacuo. The first fraction (0.1 g) was compound 90, mp 117–121° C. The second fraction (0.16 g) was compound 91, mp 68–76° C.

Example 50
Preparation of polyethyleneglycol functionalized benzothiepine A.

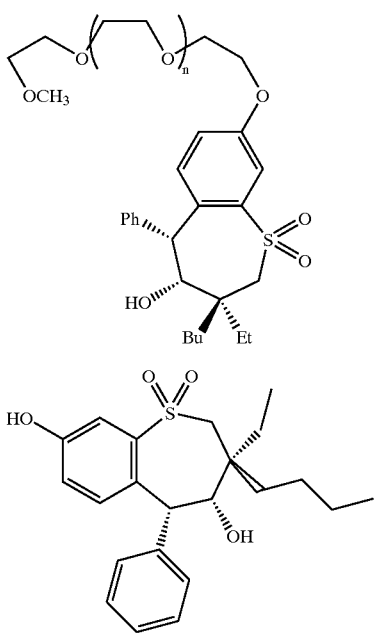

No. 141

No. 136

A 50 ml rb flash under a nitrogen atmosphere was charged with 0.54 g of M-Tres-5000 (Polyethyleneglycol Tresylate [methoxy-PEG-Tres,MW 5000] purchased from Shearwater Polymers Inc., 2130 Memorial Parkway, SW, Huntsville, Ala. 35801), 0.055 g Compound No. 136, 0.326 $C_8CO_3$ and 2 cc anhydrous acetonitrile. The reaction was stirred at 30 C for 5 days and then the solution was filtered to remove salts. Next, the acetonitrile was removed under vacuum and the product was dissolved in THF and then precipitated by addition of hexane. The polymer precipitate was isolate by filtration from the solvent mixture (THF/hexane). This precipitation procedure was continued until no Compound No. 136 was detected in the precipitated product (by TLC SiO2). Next, the polymer precipitate was dissolved in water and filtered and the water soluble polymer was dialyzed for 48 hours through a cellulose dialysis tube (spectrum® 7, 45 mm×0.5 ft, cutoff 1,000 MW). The polymer solution was then removed from the dialysis tube and lyophilized until dried. The NMR was consistent with the desired product A and gel permeation chromatography indicated the presence of a 4500 MW polymer and also verified that no free Compound No. 136 was present. This material was active in the IBAT in vitro cell assay.

Example 51
Preparation of Compound 140

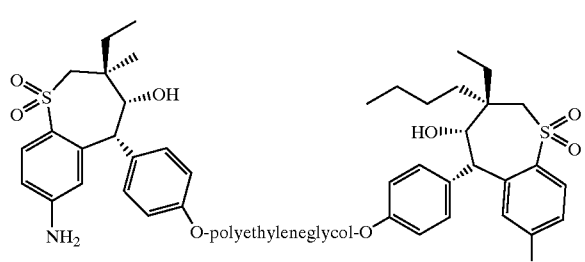

No. 140

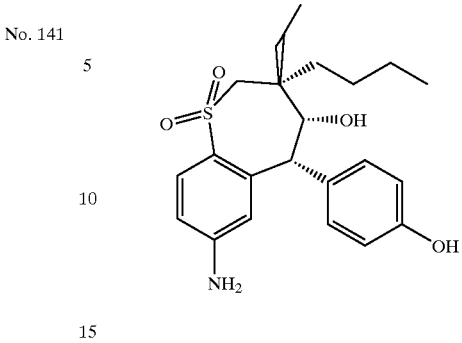

No. 111

A 2-necked 50 ml round bottom Flask was charged with 0.42 g of Tres-3400 (Polyethyleneglycol Tresylate [Tres-PEG-Tres,MW 3400] purchased from Shearwater Polymers Inc., 2130 Memorial Parkway, SW, Huntsville, Ala. 35801), 0.1 potassium carbonate, 0.100 g of Compound No. 111 and 5 ml anhydrous DMF. Stir for 6 days at 27° C. TLC indicated the disappearance of the starting Compound No. 111. The solution was transferred to a separatory funnel and diluted with 50 cc methylene chloride and then extracted with water. The organic layer was evaporated to dryness by means of a rotary evaporator. Dry wgt. 0.4875 g. Next, the polymer was dissolved in water and then dialyzed for 48 hours at 40° C. through a cellulose dialysis tube (spectrum® 7, 45 mm×0.5 ft, cutoff 1,000 MW). The polymer solution was then removed from the dialysis tube and lyophilized until dried 0.341 g). NMR was consistent with the desired product B.

Example 52

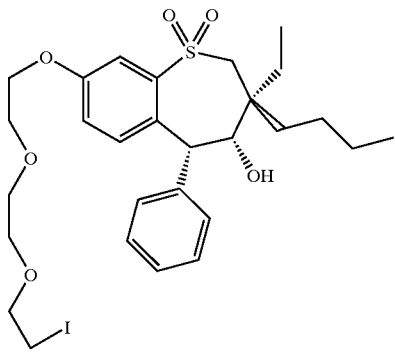

No. 134

A 10 cc vial was charged with 0.21 g of Compound No. 136 (0.5 mmoles), 0.17 g (1.3 mmoles) potassium carbonate, 0.6 g (1.5 mmoles) of 1,2-bis-(2-iodoethoxy)-ethane and 10 cc DMF. The reaction was stirred for 4 days at room temperature and then worked up by washing with ether/water. The ether layer was stripped to dryness and the desired product Compound No. 134 was isolated on a silica gel column using 80/20 hexane ethyl acetate.

Example 53

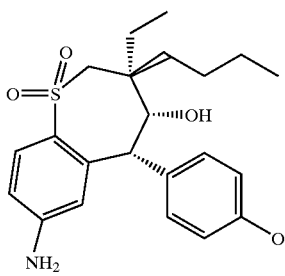

No. 112

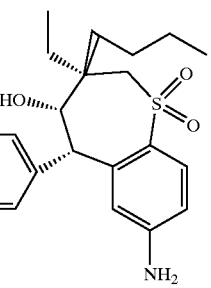

Example 54

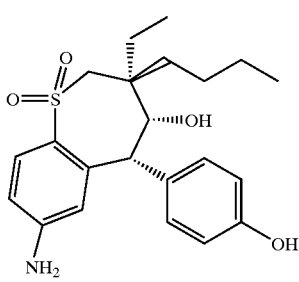

No. 113

-continued

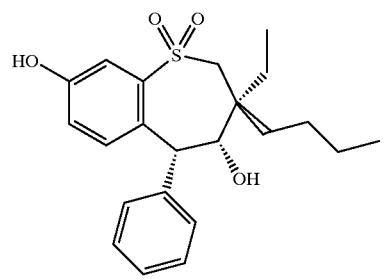

No. 136

A two necked 25 ml round bottom Flask was charged with 0.5 g (1.24 mmoles) of 69462, 13 mls of anhydrous DMF, 0.055 g of 60% NaH dispersion and 0.230 g (0.62 mmoles) of 1,2-Bis [2-iodoethoxylethane] at 10° C. under nitrogen. Next, the reaction was slowly heated to 40° C. After 14 hours all of the Compound No. 113 was consumed and the reaction was cooled to room temperature and extracted with ether/water. The ether layer was evaporated to dryness and then chromatographed on Silicage (80/20 ethyl acetate/hexane). Isolated Compound No. 112 (0.28 g) was characterized by NMR and mass spec.

In a 50 ml round bottom Flask, add 0.7 g (1.8 mmoles) of Compound No. 136, 0.621 g of potassium carbonate, 6 ml DMF, and 0.33 g of 1,2-Bis [2-iodoethoxylethane]. Stir at 40° C. under nitrogen for 12 hours. The workup and isolation was the same procedure for Compound No. 112.

Example 55

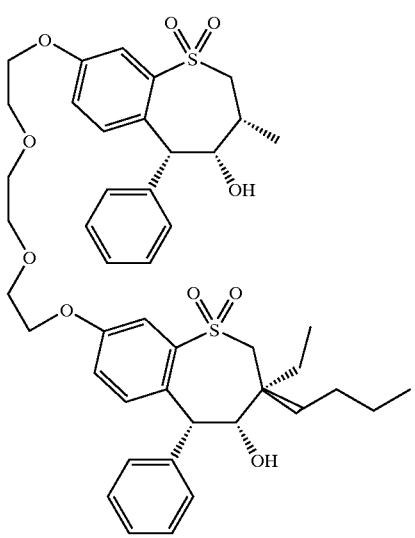

No. 135

Examples 56 and 57 (Compound Nos. 131 and 137)

The compositions of these compounds are shown in Table 3.

The same procedure as for Example 55 except appropriate benzothiepine was used.

Example 58 (Compound No. 139)

The composition of this compound is shown in Table 3. Same procedure as for Example 55 with appropriate benzothiepine 1,6 diiodohexane was used instead of 1,2-Bis [2-iodoethoxylethane].

Example 59 (Compound No. 101)

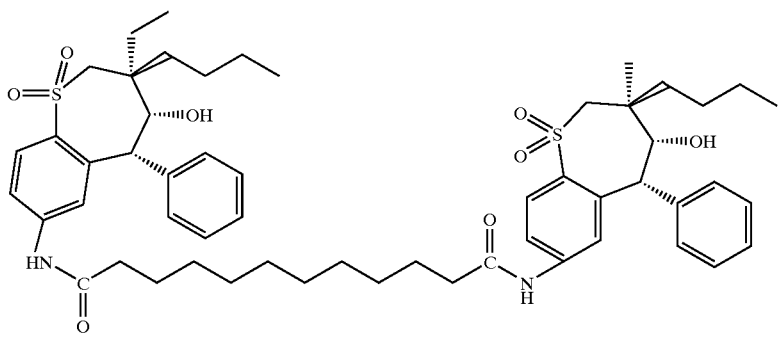

This compound is prepared by condensing the 7-NH$_2$ benzothiepine with the 1,12-dodecane dicarboxylic acid or acid halide.

Example 60 (Compound No. 104)

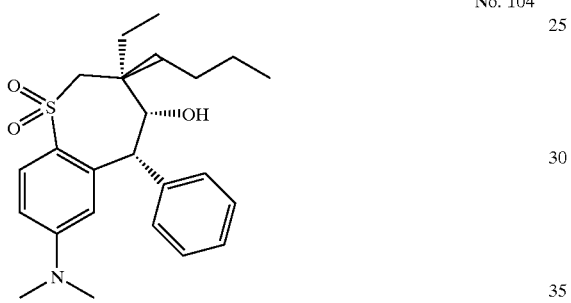

2-Chloro-4-nitrobenzophenone is reduced with triethylsilane and trifluoromethane sulfonic acid to 2-chloro-4-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIV (see Scheme 5). Reduction of the sulfone-aldehyde XXV formaldehyde and 100 psi hydrogen and 55 C for 12 hours catalyzed by palladium on carbon in the same reaction vessel yields the substituted dimethylamine derivative XXVIII. Cyclization of XXVII with potassium t-butoxide yields a mixture of substituted amino derivatives of this invention Compound No. 104.

Scheme 6

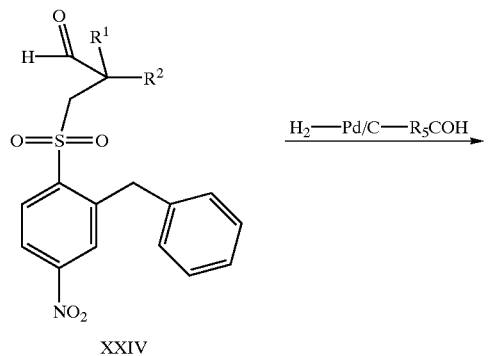

-continued

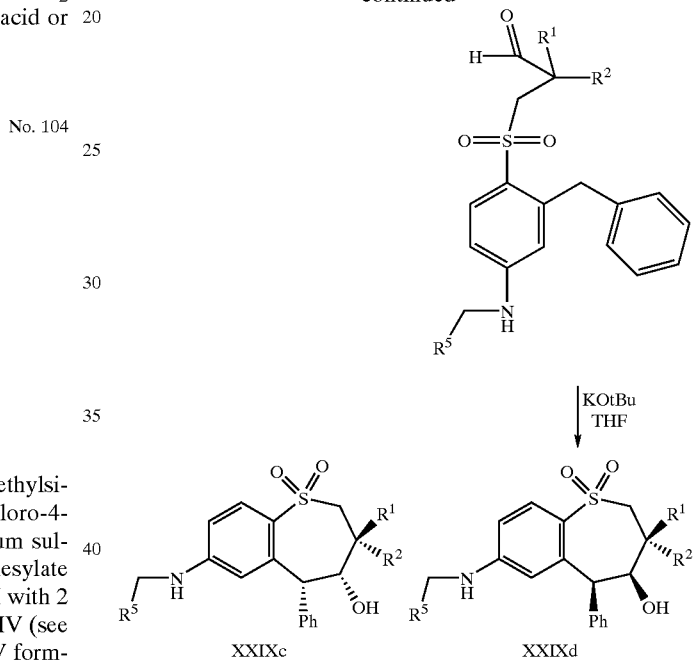

Example 61

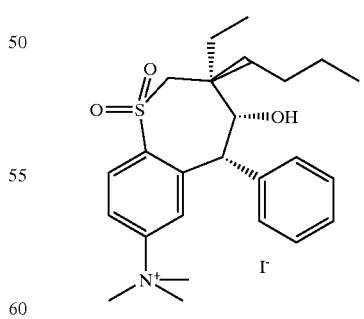

A 1 oz. Fisher-porter bottle was charged with 0.14 g (0.34 mmoles) of 70112, 0.97 gms (6.8 mmoles) of methyl iodide, and 7 ml of anhydrous acetonitrile. Heat to 50° C. for 4 days. The quat. Salt Compound No. 192 was isolated by concentrating to 1 cc acetonitrile and then precipitating with diethyl ether.

Example 62

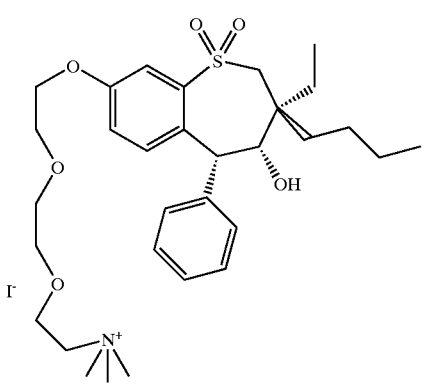

A 0.1 g (0.159 mmoles) sample of Compound No. 134 was dissolved in 15 ml of anhydrous acetonitrile in a Fischer-porter bottle and then trimethylamine was bubbled through the solution for 5 minutes at 0° C. and then capped and warmed to room temperature. The reaction was stirred overnight and the desired product was isolated by removing solvent by rotary evaporation.

Example 63 (Compound No. 295)

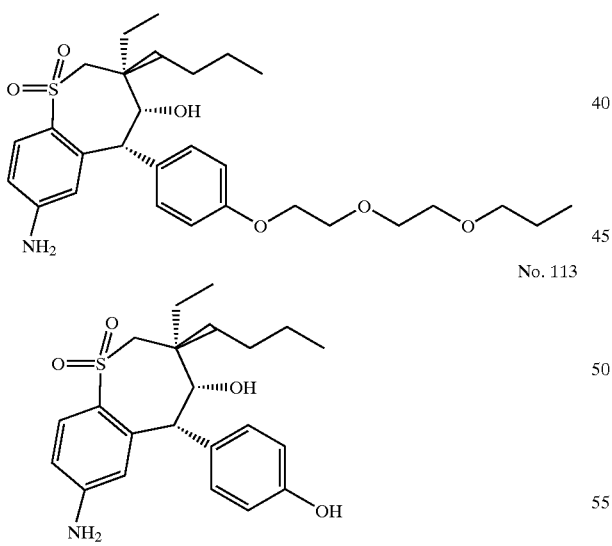

Sodium Hydride 60% (11 mg, 0.27 mmoles) in 1 cc of acetonitrile at 0° C. was reacted with 0.248 mmoles (0.10 g) of Compound No. 54 in 2.5 cc of acetonitrile at 0° C. Next, 0. (980 g 2.48 mmoles) of 1,2-Bis [2-iodoethoxylethane]. After warming to room temperature, stir for 14 hours. The product was isolated by column chromatography.

Example 64 (Compound No. 286)

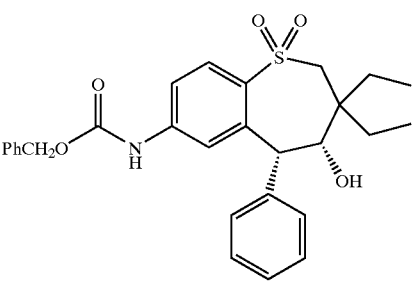

Following a procedure similar to the one described in Example 86, infra (see Compound No. 118), the title compound was prepared and purified as a colorless solid; mp 180–181° C.; $^1$H NMR (CHCl$_3$) δ 0.85 (t, J=6 Hz, 3H), 0.92 (t, J=6 Hz, 3H), 1.24–1.42 (m, 2H), 1.46–1.56 (m, 1H), 1.64–1.80 (m, 1H), 2.24–2.38 (m, 1H), 3.15 (AB, J$_{AB}$=15 Hz, Δv=42 Hz, 2H), 4.20 (d, J=8 Hz, 1H), 5.13 (s, 2H), 5.53 (s, 1H), 6.46 (s, 1H), 6.68 (s, 1H), 7.29–7.51 (m, 10H), 7.74 (d, J=8 Hz, 1H), 8.06 (d, J=8 Hz, 1H), FABMS m/z 494 (M+H), HRMS calcd for (M+H) 494.2001, found 494.1993. Anal. Calcd. for C$_{28}$H$_{31}$NO$_5$S: C, 68.13; H, 6.33; N, 2.84. Found: C, 68.19; H, 6.56; N, 2.74.

Example 65 (Compound No. 287)

Following a procedure similar to the one described in Example 89, infra (see Compound No. 121), the title compound was prepared and purified as a colorless solid: mp 245–246° C., $^1$H NMR (CDCl$_3$) δ 0.84 (t, J=6 Hz, 3H), 0.92 (t, J=6 Hz, 3H), 1.28, (d, J=8 Hz, 1H), 1.32–1.42 (m, 1H), 1.48–1.60 (m, 1H), 1.64–1.80 (m, 1H), 2.20–2.36 (m, 1H), 3.09 (AB, J$_{AB}$=15 Hz, Δv=42 Hz, 2H), 3.97 (bs, 2H), 4.15 (d, J=8 Hz, 1H), 5.49 (s, 1H), 5.95 (s, 1H), 6.54 (d, J=7 Hz, 1H), 7.29–7.53 (m, 5H), 7.88 (d, J=8 Hz, 1H); ESMS 366 (M+Li). Anal. Calcd. for C$_{20}$H$_{25}$NO$_3$S: C, 66.82; H, 7.01; N, 3.90. Found: C, 66.54; H, 7.20; N, 3.69.

Example 66 (Compound No. 288)

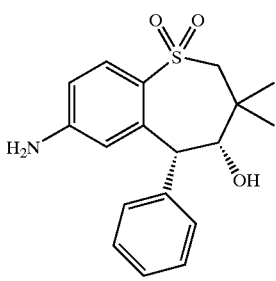

No. 288

Following a procedure similar to the one described in Example 89, infra (see Compound No. 121), the title compound was prepared and purified by silica gel chromatography to give the desired product as a colorless solid: mp 185–186° C.; $^1$H NMR (CDCl$_3$) δ1.12 (s, 3H), 1.49 (s, 3H), 3.00 (d, J=15 Hz, 1H), 3.28 (d, J=15 Hz, 1H), 4.00 (s, 1H), 5.30 (s, 1H), 5.51 (s, 1H), 5.97 (s, 1H), 6.56 (dd, J=2.1, 8.4 Hz, 1H), 7.31–7.52 (m, 5H), 7.89 (d, J=8.4 Hz, 1H). MS (FAB+) (M+H) m/z 332.

Example 67 (Compound No. 289)

No. 289

Following a procedure similar to the one described in Example 89 (see Compound No. 121), the title compound was prepared and purified by silica gel chromatography to give the desired product as a white solid: mp 205–206° C.; $^1$H NMR (CDCl$_3$) δ 0.80–0.95 (m, 6H), 1.10–1.70 (m, 7H), 2.15 (m, 1H), 3.02 (d, J=15.3 Hz, 2H), 3.15 (d, J=15.1 Hz, 2H), 3.96 (s, br, 2H), 4.14 (d, J=7.8 Hz, 1H), 5.51 (s, 1H), 5.94 (d, J=2.2, 1H), 6.54 (dd, J=8.5, 2.2 Hz, 1H), 7.28–7.50 (m, 6H), 7.87 (d, J=8.5 Hz, 1H). MS (FAB): m/z 388 (M+H).

Example 68 (Compound No. 290)

No. 290

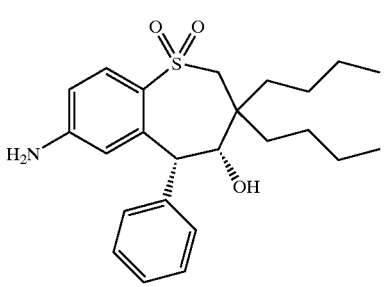

Following a procedure similar to the one described in Example 89, infra (see Compound No. 121), the title compound was prepared and purified as a colorless solid: mp=96–98° C., $^1$H NMR (CDCl$_3$) δ 0.92 (t, J=7 Hz, 6H), 1.03–1.70 (m, 11H), 2.21 (t, J=8 Hz, 1H), 3.09 (AB, J$_{AB}$=–18 Hz, Δv=38 Hz, 2H), 3.96 (bs, 2H), 4.14 (d, J=7 Hz, 1H), 5.51 (s, 1H), 5.94 (s, 1H), 6.56 (d, J=9 Hz, 1H), 7.41–7.53 (m, 6H), 7.87 (d, J=8 Hz, 1H); FABMS m/z 416 (M+H).

Example 69

No. 291

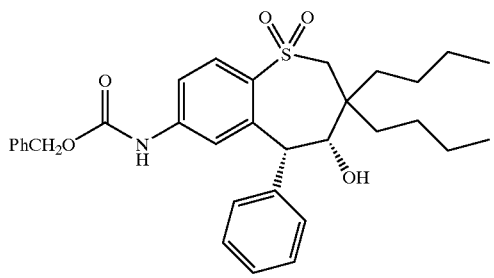

Following a procedure similar to the one described in Example 86, infra (see Compound No. 118), the title compound was prepared and purified as a colorless solid: $^1$H NMR (CDCl$_3$) δ 0.91 (t, J=7 Hz, 6H), 1.02–1.52 (m, 11H), 1.60–1.70 (m, 1H), 2.23 (t, J=8 Hz, 1H), 3.12 (AB, J$_{AB}$=18 Hz, Δv=36 Hz, 2H), 4.18 (d, J=7 Hz, 1H), 5.13 (s, 2H), 5.53 (s, 1H), 6.43 (s, 1H), 6.65 (s, 1H), 7.29–7.52 (m, 10H), 7.74 (d, J=9 Hz, 1H), 8.03 (d, J=8 Hz, 1H); ESMS m/z 556 (M+Li).

Example 70 (Compound No. 292)

No. 292

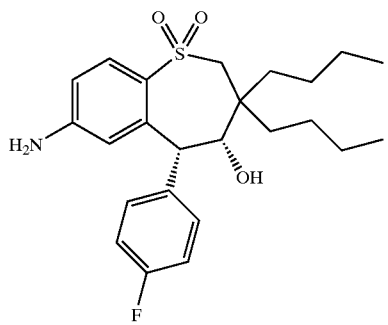

Following a procedure similar to the one described in Example 89, infra (see Compound No. 121), the title compound was prepared and purified as a colorless solid: mp=111–112.5° C., $^1$H NMR (CDCl$_3$) δ 0.90 (t, J=8 Hz, 6H), 1.03–1.50 (m, 10H), 1.55–1.70 (m, 2H), 2.18 (t, J=12 Hz, 2H), 3.07 (AB, J$_{AB}$=15 Hz, Δv=45 Hz, 2H), 4.09 (bs, 2H), 5.49 (s, 1H), 5.91 (s, 1H), 6.55 (d, J=9 Hz, 1H), 7.10 (t, J=7 Hz, 2H), 7.46 (t, J=6 Hz, 2H), 7.87 (d, J=9 Hz, 1H).

Example 71 (Compound No. 293)

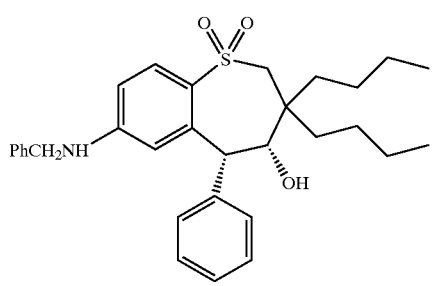

No. 293

During the preparation of Compound No. 290 from Compound No. 291 using BBr$_3$, the title compound was isolated: $^1$H NMR (CDCl$_3$) δ 0.85 (t, J=6 Hz, 6H), 0.98–1.60 (m, 10H), 1.50–1.66 (m, 2H), 2.16 (t, J=8 Hz, 1H), 3.04 (AB, J$_{AB}$=15 Hz, Δv=41 Hz, 2H), 4.08 (s, 1H), 4.12 (s, 1H), 5.44 (s, 1H), 5.84 (s, 1H), 6.42 (d, J=9 Hz, 1H), 7.12 (d, J=8 Hz, 2H), 7.16–7.26 (m, 10H), 7.83 (d, J=8 Hz, 1H); ESMS m/z 512 (M+Li).

Example 72 (Compound No. 294)

Following a procedure similar to the one described in Example 60 (Compound No. 104), the title compound was prepared and purified as a colorless solid: $^1$H NMR (CDCl$_3$) δ 0.90 (t, J=6 Hz, 6H), 1.05–1.54 (m, 9H), 1.60–1.70 (m, 1H), 2.24 (t, J=8 Hz, 1H), 2.80 (s, 6H), 3.05 (AB, J$_{AB}$=15 Hz, Δv=42 Hz, 2H), 4.05–4.18 (m, 2H), 5.53 (s, 1H), 5.93 (s, 1H), 6.94 (d, J=9 Hz, 1H), 7.27–7.42 (m, 4H), 7.45 (d, J=8 Hz, 2H), 7.87 (d, J=9 Hz, 1H); ESMS m/z 444 (M+H).

Structures of the compounds of Examples 33 to 72 are shown in Tables 3 and 3A.

Examples 73–79, 87, 88 and 91–102

Using in each instance a method generally described in those of Examples 1 to 72 appropriate to the substituents to be introduced, compounds were prepared having the structures set forth in Table 3. The starting materials illustrated in the reaction schemes shown above were varied in accordance with principles of organic synthesis well known to the art to introduce the indicated substituents in the 4- and 5-positions (R$^3$, R$^4$, R$^5$, R$^6$) and in the indicated position on the benzo ring (R$^x$).

Structures of the compounds produced in Examples 73–102 are set forth in Tables 3 and 3A.

Examples 80–84
Preparation of 115, 116, 111, 113
Preparation of 4-chloro-3-[4-methoxy-phenylmethyl]-nitrobenzene.

In a 500 ml 2-necked rb flash weigh out 68.3 gms phosphorus pentachloride (0.328 mole 1.1 eq). Add 50 mls chlorobenzene. Slowly add 60 gms 2-chloro-5-nitrobenzoic acid (0.298 mole). Stir at room temp overnight under N2 then heat 1 hr at 50 C.

Remove chlorobenzene by high vacuum. Wash residue with hexane. Dry wt=55.5 gms.

In the same rb flask, dissolve acid chloride (55.5 g 0.25 mole) from above with 100 mls anisole (about 3.4 eq). Chill solution with ice bath while purging with N2. Slowly add 40.3 g aluminum chloride (1.2 eq 0.3 mole). Stir under N$_2$ for 24 hrs.

After 24 hrs, the solution was poured into 300 mls 1N HCl soln. (cold). Stir this for 15 min. Extract several times with diethyl ether. Extract organic layer once with 2% aqueous NaOH then twice with water. Dry organic layer with MgSO4, dry on vac line. Solid is washed well with ether and then ethanol before drying. Wt=34.57 g (mixture of meta, ortho and para).

| Elemental | theory | found |
|---|---|---|
| C | 57.65 | 57.45 |
| H | 3.46 | 5.51 |
| N | 4.8 | 4.8 |
| Cl | 12.15 | 12.16 |

With the next step of the reduction of the ketone with trifluoromethane sulfonic acid and triethyl silane, crystallization with ethyl acetate/hexane affords pure 4-chloro-3-[4-methoxy-phenylmethyl]-nitrobenzene.

4-Chloro-3-[4-methoxy-phenylmethyl]-nitrobenzene was then reacted as specified in the synthesis of 117 and 118 from 2-chloro-4-nitrophenylmethane. From these procedures 115 and 116 can be synthesized. Compounds 111 and 113 can be synthesized from the procedure used to prepare compound 121.

Compound 114 can be prepared by reaction of 116 with ethyl mercaptan and aluminum trichloride.

Examples 85 and 86
Preparation of 117 and 118

2-Chloro-4-nitrobenzophenone is reduced with triethylsilane and trifluoromethane sulfonic acid to 2-chloro-4-nitrodiphenylmethane 32. Reaction of 32 with lithium sulfide followed by reacting the resulting sulfide with mesylate IV gives sulfide-aldehyde XXIII. Oxidation of XXIII with 2 equivalents of MCPBA yields sulfone-aldehyde XXIII. Oxidation of XXIII with 2 equivalents of MCPBA yields sulfone-aldehyde XXIV (see Scheme 5).

The sulfone-aldehyde (31.8 g) was dissolved in ethanol/toluene and placed in a parr reactor with 100 ml toluene and 100 ml of ethanol and 3.2 g of 10% Pd/C and heated to 55 C and 100 psi of hydrogen gas for 14 hours. The reaction was then filtered to remove the catalyst. The amine product (0.076 moles, 29.5 g) from this reaction was then reacted with benzyl chloroformate (27.4 g) in toluene in the presence of 35 g of potassium carbonate and stirred at room temperature overnight. After work up by extraction with water, the CBZ protected amine product was further purified by precipitation from toluene/hexane.

The CBZ protected amine product was then reacted with 3 equivalents of potassium t-butoxide in THF at 0 C to yield compounds 117 and 118 which were separated by silica gel column chromatography.

Examples 89 and 90
Preparation of 121 or 122

Compound 118 (0.013 moles, 6.79 g) is dissolved in 135 ml of dry chloroform and cooled to −78 C, next 1.85 ml of boron tribromide (4.9 g) was added and the reaction is allowed to warm to room temperature. Reaction is complete after 1.5 hours. The reaction is quenched by addition of 10% potassium carbonate at 0 C and extract with ether. Removal of ether yields compound 121. A similar procedure can be used to produce 122 from 117.

Examples 93–96

Compounds 126, 127, 128 and 129 as set forth in Table 3 were prepared substantially in the manner described above for compounds 115, 116, 111 and 113, respectively, except that fluorobenzene was used as a starting material in place of anisole.

TABLE 3

Specific compounds (#102–111, 113–130, 132–134, 136, 138, 142–144, 262–296)

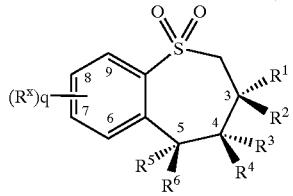

| Ex. | Cp# | R¹ | R² | R³ | R⁴ | R⁵ | R⁶ | (Rˣ)q |
|---|---|---|---|---|---|---|---|---|
| 61 | 102 | Et— | n-Bu— | HO— | H— | Ph— | H— | I⁻, 7-(CH₃)₃N⁺— |
| 73 | 103 | n-Bu— | Et— | HO— | H— | Ph— | H— | I⁻, 7-(CH₃)₃N⁺— |
| 60 | 104 | Et— | n-Bu— | HO— | H— | Ph— | H— | 7-(CH₃)₂N— |
| 74 | 105 | Et— | n-Bu— | HO— | H— | Ph— | H— | 7-CH₃SO₂NH— |
| 75 | 106 | Et— | n-Bu— | HO— | H— | Ph— | H— | 7-Br—CH₂—CONH— |
| 76 | 107 | n-Bu— | Et— | HO— | H— | p-n-C₁₀H₂₁—O—Ph— | H— | 7-NH₂— |
| 77 | 108 | Et— | n-Bu— | HO— | H— | Ph— | H— | 7-C₅H₁₁CONH— |
| 78 | 109 | Et— | n-Bu— | HO— | H— | p-n-C₁₀H₂₁—O—Ph— | H— | 7-NH₂— |
| 79 | 110 | Et— | n-Bu— | HO— | H— | Ph— | H— | 7-CH₃CONH— |
| 80 | 111 | n-Bu— | Et— | HO— | H— | p-HO—Ph— | H— | 7-NH₂— |
| 81 | 113 | Et— | n-Bu— | HO— | H— | p-HO—Ph— | H— | 7-NH₂— |
| 82 | 114 | Et— | n-Bu— | HO— | H— | p-CH₃O—Ph— | H— | 7-NH₂— |
| 83 | 115 | n-Bu— | Et— | HO— | H— | p-CH₃O—Ph— | H— | 7-NH—CEZ |
| 84 | 116 | Et— | n-Bu— | HO— | H— | p-CH₃O—Ph— | H— | 7-NH—CEZ |
| 85 | 117 | n-Bu— | Et— | HO— | H— | Ph— | H— | 7-NH—CEZ |
| 86 | 118 | Et— | n-Bu— | HO— | H— | Ph— | H— | 7-NH—CEZ |
| 87 | 119 | Et— | n-Bu— | HO— | H— | Ph— | H— | 7-NHCO₂-t-Bu |
| 88 | 120 | n-Bu— | Et— | HO— | H— | Ph— | H— | 7-NHCO₂-t-Bu |
| 89 | 121 | Et— | n-Bu— | HO— | H— | Ph— | H— | 7-NH₂— |
| 90 | 122 | n-Bu— | Et— | HO— | H— | Ph— | H— | 7-NH₂— |
| 91 | 123 | Et— | n-Bu— | HO— | H— | Ph— | H— | 7-n-C₆H₁₃—NH— |
| 92 | 124 | n-Bu— | Et— | HO— | H— | Ph— | H— | 7-n-C₆H₁₃—NH— |
| 62 | 125 | Et— | n-Bu— | HO— | H— | Ph— | H— | I⁻, 8-(CH₃)₃N⁺(CH₂CH₂O)₃— |
| 93 | 126 | n-Bu— | Et— | HO— | H— | p-F—Ph— | H— | 7-NH—CEZ |
| 94 | 127 | n-Bu— | Et— | HO— | H— | p-F—Ph— | H— | 7-NH₂— |
| 95 | 128 | Et— | n-Bu— | HO— | H— | p-F—Ph— | H— | 7-NH—CEZ |
| 96 | 129 | Et— | n-Bu— | HO— | H— | p-F—Ph— | H— | 7-NH₂— |
| 97 | 130 | Et— | n-Bu— | HO— | H— | Ph— | H— | I⁻, 8-(CH₃)₃N⁺C₆H₁₂O— |
| 98 | 132 | Et— | n-Bu— | HO— | H— | Ph— | H— | 8-phthal-imidyl-C₆H₁₂O— |
| 99 | 133 | Et— | n-Bu— | HO— | H— | Ph— | H— | 8-n-C₁₀H₂₁— |
| 52 | 134 | Et— | n-Bu— | HO— | H— | Ph— | H— | 8-I—(C₂H₄O)₃— |
| 100 | 136 | Et— | n-Bu— | HO— | H— | Ph— | H— | 8-HO— |
| 101 | 138 | n-Bu— | Et— | HO— | H— | Ph— | H— | 8-CH₃CO₂— |
| 49 | 90 | Et— | n-Bu— | H— | HO— | H— | m-CH₃O-Ph— | 7-CH₃S— |
| 49 | 91 | Et— | n-Bu— | HO— | H— | m-CH₃O—Ph— | H— | 7-CH₃S— |
| 48 | 89 | Et— | n-Bu— | HO— | H— | p-F-Ph— | H— | 7-(N)-azetidine |
| 34 | 66 | Et— | n-Bu— | HO— | H— | m-CH₃O—Ph— | H— | 7-CH₃O— |
| 34 | 65 | Et— | n-Bu— | H— | HO— | H— | m-CH₃O—Ph— | 7-CH₃O— |
| 35 | 68 | Et— | n-Bu— | HO— | H— | m-CF₃—Ph— | H— | 7-CH₃O— |
| 35 | 67 | Et— | n-Bu— | H— | HO— | H— | m-CF₃—Ph— | 7-CH₃O— |
| 46 | 87 | Et— | n-Bu— | HO— | H— | m-HO—Ph— | H— | 7-HO— |
| 46 | 86 | Et— | n-Bu— | HO— | H— | m-HO—Ph— | H— | 7-CH₃O— |
| 36 | 70 | Et— | n-Bu— | HO— | H— | p-F—Ph— | H— | 7-CH₃O— |
| 36 | 69 | Et— | n-Bu— | H— | HO— | H— | p-F—Ph— | 7-CH₃O— |
| 47 | 88 | Et— | n-Bu— | HO— | H— | p—F—Ph— | H— | 7-HO— |

TABLE 3-continued

Specific compounds (#102–111, 113–130, 132–134, 136, 138, 142–144, 262–296)

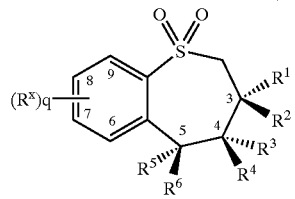

| Ex. | Cp# | $R^1$ | $R^2$ | $R^3$ | $R^4$ | $R^5$ | $R^6$ | $(R^x)q$ |
|---|---|---|---|---|---|---|---|---|
| 39 | 76 | Et— | n-Bu— | HO— | H— | m-CH$_3$O—Ph— | H— | 7-Br— |
| 39 | 75 | Et— | n-Bu— | H— | HO— | H— | m-CH$_3$O—Ph— | 7-Br— |
| 40 | 77 | Et— | n-Bu— | H— | HO— | H— | p-F—Ph— | 7-F— |
| 40 | 78 | Et— | n-Bu— | HO— | H— | p-F—Ph— | H— | 7-F— |
| 41 | 79 | Et— | n-Bu— | H— | HO— | H— | m-CH$_3$O—Ph— | 7-F— |
| 41 | 80 | Et— | n-Bu— | HO— | H— | m-CH$_3$O—Ph— | H— | 7-F— |
| 37 | 72 | Et— | n-Bu— | HO— | H— | m-F—Ph— | H— | 7-CH$_3$O— |
| 38 | 73 | Et— | n-Bu— | H— | HO— | H— | o-F—Ph— | 7-CH$_3$O— |
| 37 | 71 | Et— | n-Bu— | H— | HO— | H— | m-F-Ph— | 7-CH$_3$O— |
| 38 | 74 | Et— | n-Bu— | HO— | H— | o-F—Ph— | H— | 7-CH$_3$O— |
| 42 | 81 | Et— | n-Bu— | HO— | H— | p-F—Ph— | H— | 7-CH$_3$S— |
| 45 | 85 | Et— | n-Bu— | HO— | H— | p-F—Ph— | H— | 7-CH$_3$— |
| 45 | 84 | Et— | n-Bu— | H— | HO— | H— | p-F—Ph— | 7-CH$_3$— |
| 44 | 83 | Et— | n-Bu— | HO— | H— | p-F—Ph— | H— | 7-(N)—morpholine |
| 43 | 82 | Et— | n-Bu— | HO— | H— | p-F—Ph— | H— | 7-(N)—pyrrolidine |
| 64 | 286 | Et— | Et— | HO— | H— | Ph— | H— | 7-NH—CEZ |
| 65 | 287 | Et— | Et— | HO— | H— | Ph— | H— | 7-NH$_2$— |
| 66 | 288 | CH$_3$— | CH$_3$— | HO— | H— | Ph— | H— | 7-NH$_2$— |
| 67 | 289 | n-C$_3$H$_7$— | n-C$_3$H$_7$— | HO— | H— | Ph— | H— | 7-NH$_2$— |
| 68 | 290 | n-Bu— | n-Bu— | HO— | H— | Ph— | H— | 7-NH$_2$— |
| 69 | 291 | n-Bu— | n-Bu— | HO— | H— | Ph— | H— | 7-NH—CEZ |
| 70 | 292 | n-Bu— | n-Bu— | HO— | H— | p-F—Ph— | H— | 7-NH$_2$— |
| 71 | 293 | n-Bu— | n-Bu— | HO— | H— | Ph— | H— | 7-PhCH$_2$N— |
| 72 | 294 | n-Bu— | n-Bu— | HO— | H— | Ph— | H— | 7-(CH$_3$)$_2$N— |
| 63 | 295 | Et— | n-Bu— | HO— | H— | p-I—(C$_2$H$_4$O)$_3$—Ph— | H— | 7-NH$_2$— |
| 102 | 296 | Et— | n-Bu— | HO— | H— | I$^-$, p-(CH$_3$)$_3$N$^+$(C$_2$H$_4$O$_3$—Ph— | H— | 7-NH$_2$— |

TABLE 3A

Bridged Benzothiephenes (#101, 112, 131, 135, 137, 139–141)

CPD #101 (Ex. 59)

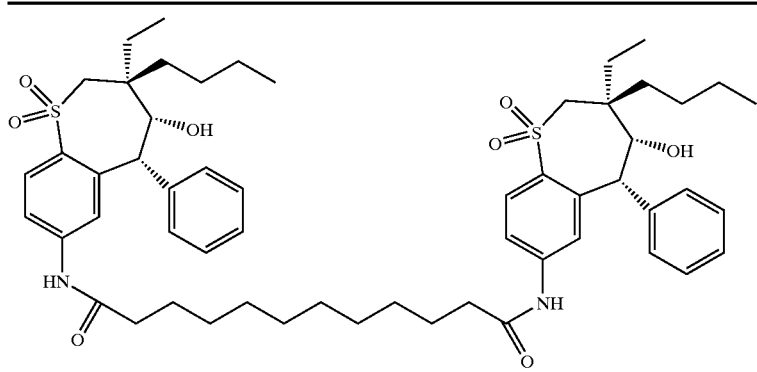

TABLE 3A-continued
Bridged Benzothiephenes (#101, 112, 131, 135, 137, 139–141)
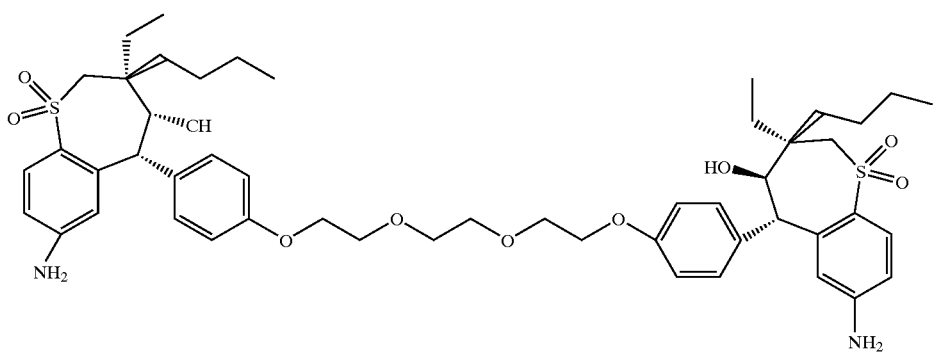
CPD #112 (Ex. 53)
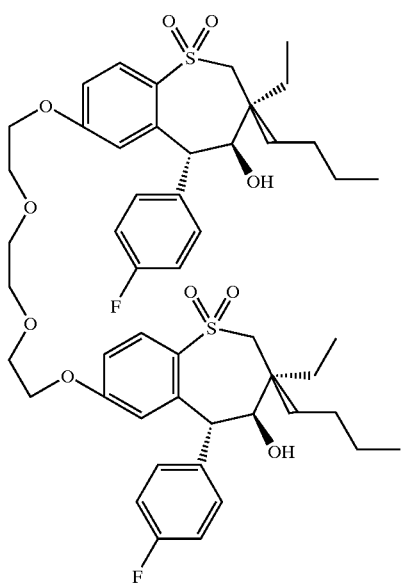
CPD #131 (Ex. 56)
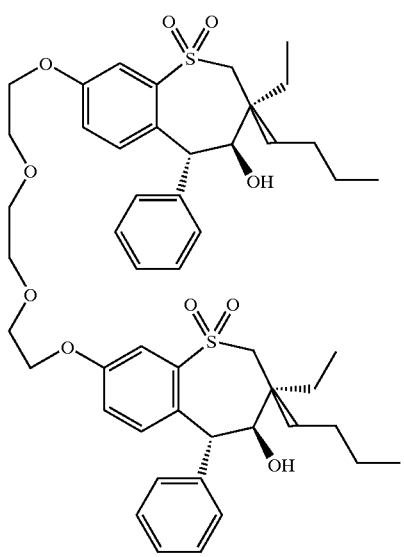
CPD #135 (Ex. 55)

TABLE 3A-continued

Bridged Benzothiephenes (#101, 112, 131, 135, 137, 139–141)

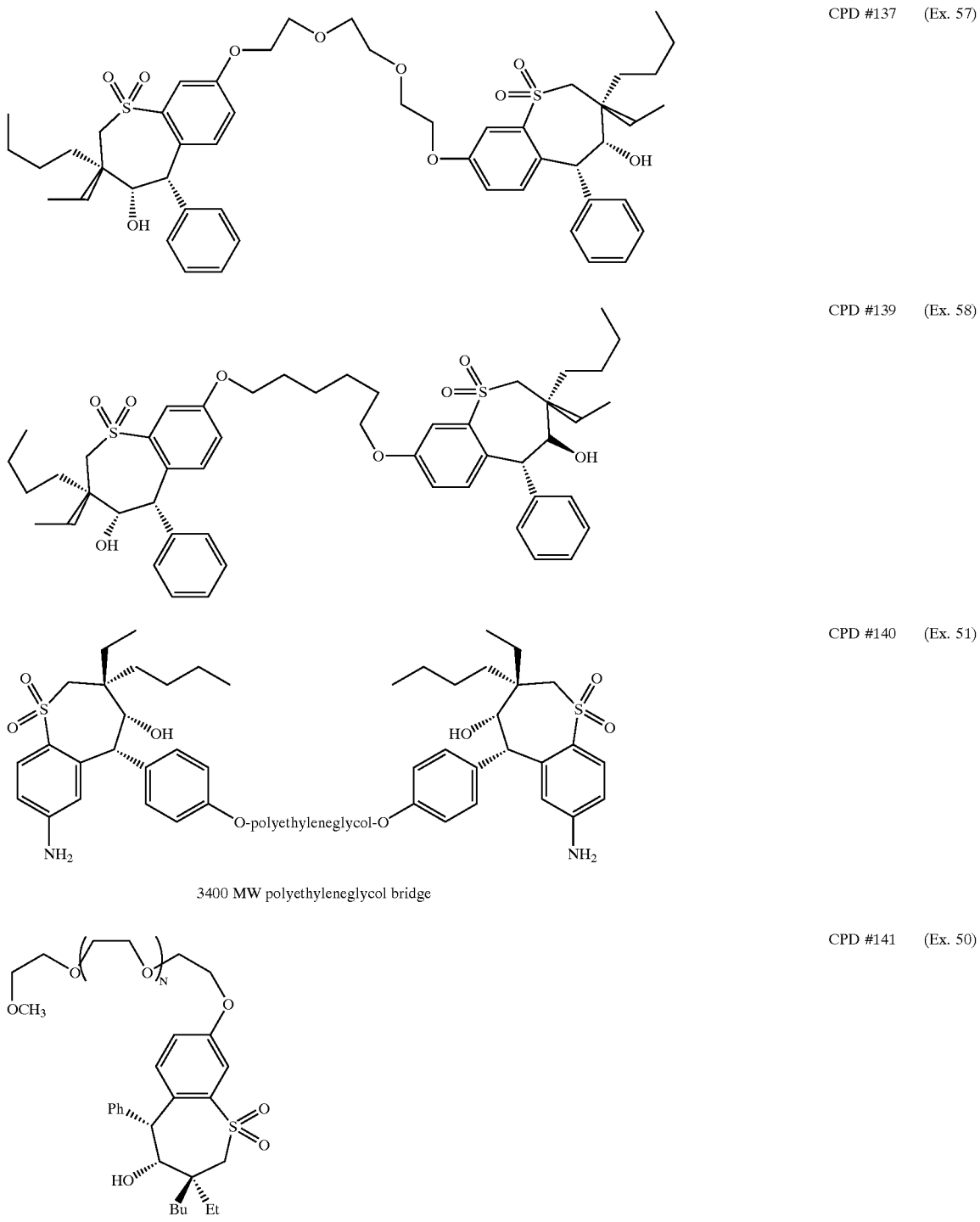

CPD #137 (Ex. 57)

CPD #139 (Ex. 58)

CPD #140 (Ex. 51)

3400 MW polyethyleneglycol bridge

CPD #141 (Ex. 50)

Examples 104–231

Using in each instance a method generally described in those of Examples 1 to 72 appropriate to the substituents to be introduced, including where necessary other common synthesis expedients well known to the art, compounds are prepared having the structures set forth in Table 4. The starting materials illustrated in the reaction schemes shown above are varied in accordance with principles of organic synthesis well known to the art in order to introduce the indicated substituents in the 4- and 5-positions ($R^3$, $R^4$, $R^5$, $R^6$) and in the indicated position on the benzo ring ($R^x$).

TABLE 4

Alternative compounds #1 (#302–312, 314–430)

| Cpd# | R⁵ | (Rˣ)q |
|---|---|---|
| 302 | p-F—Ph— | 7-(1-aziridine) |
| 303 | p-F—Ph— | 7-EtS— |
| 304 | p-F—Ph— | 7-CH₃S(O)— |
| 305 | p-F—Ph— | 7-CH₃S(O)₂— |
| 306 | p-F—Ph— | 7-PhS— |
| 307 | p-F—Ph— | 7-CH₃S—<br>9-CH₃S— |
| 308 | p-F—Ph— | 7-CH₃O—<br>9-CH₃O— |
| 309 | p-F—Ph— | 7-Et— |
| 310 | p-F—Ph— | 7-iPr— |
| 311 | p-F—Ph— | 7-t-Bu— |
| 312 | p-F—Ph— | 7-(1-pyrazole) |
| 314 | m-CH₃O—Ph | 7-(1-azetidine) |
| 315 | m-CH₃O—Ph— | 7-(1-aziridine) |
| 316 | m-CH₃O—Ph— | 7-EtS— |
| 317 | m-CH₃O—Ph— | 7-CH₃S(O)— |
| 318 | m-CH₃O—Ph— | 7-CH₃S(O)₂— |
| 319 | m-CH₃O—Ph— | 7-PhS— |
| 320 | m-CH₃O—Ph— | 7-CH₃S—<br>9-CH₃S— |
| 321 | m-CH₃O—Ph— | 7-CH₃O—<br>9-CH₃O— |
| 322 | m-CH₃O—Ph— | 7-Et— |
| 323 | m-CH₃O—Ph— | 7-iPr— |
| 324 | m-CH₃O—Ph— | 7-t-Bu— |
| 325 | p-F—Ph— | 6-CH₃O—<br>7-CH₃O—<br>8-CH₃O— |
| 326 | p-F—Ph— | 7-(1-azetidine)<br>9-CH₃— |
| 327 | p-F—Ph— | 7-EtS—<br>9-CH₃— |
| 328 | p-F—Ph— | 7-CH₃S(O)—<br>9-CH₃— |
| 329 | p-F—Ph— | 7-CH₃S(O)₂—<br>9-CH₃— |
| 330 | p-F—Ph— | 7-PhS—<br>9-CH₃— |
| 331 | p-F—Ph— | 7-CH₃S—<br>9-CH₃— |
| 332 | p-F—Ph— | 7-CH₃O—<br>9-CH₃— |
| 333 | p-F—Ph— | 7-CH₃—<br>9-CH₃— |
| 334 | p-F—Ph— | 7-CH₃O—<br>9-CH₃O— |
| 335 | p-F—Ph— | 7-(1-pyrrole) |
| 336 | p-F—Ph— | 7-(N)—N'-methylpiperazine |
| 337 | p-F—Ph— | Ph— |
| 338 | p-F—Ph— | 7-CH₃C(=CH₂)— |
| 339 | p-F—Ph— | 7-cyclpropyl |
| 340 | p-F—Ph— | 7-(CH₃)₂NH— |
| 341 | p-F—Ph— | 7-(N)-azetidine<br>9-CH₃S— |
| 342 | p-F—Ph— | 7-(N-pyrrolidine)<br>9-CH₃S— |
| 343 | p-F—Ph— | 7-(CH₃)₂N-<br>9-CH₃S— |
| 344 | m-CH₃O—Ph— | 7-(1-pyrazole) |
| 345 | m-CH₃O—Ph— | 7-(N)N'-methylpiperazine |
| 346 | m-CH₃O—Ph— | Ph— |
| 347 | m-CH₃O—Ph— | 7-CH₃C(=CH₂)— |
| 348 | m-CH₃O—Ph— | 7-cyclopropyl |
| 349 | m-CH₃O—Ph— | 7-(CH₃)₂NH— |
| 350 | m-CH₃O—Ph— | 7-(N)-azetidine<br>9-CH₃S— |
| 351 | m-CH₃O—Ph— | 7-(N-pyrrolidine)-<br>9-CH₃S— |
| 352 | m-CH₃O—Ph— | 7-(CH₃)₂N-<br>9-CH₃S— |
| 353 | m-CH₃O—Ph— | 6-CH₃O—<br>7-CH₃O—<br>8-CH₃O— |
| 354 | m-CH₃O—Ph— | 7-(1-azetidine)<br>9-CH₃— |
| 355 | m-CH₃O—Ph— | 7-EtS—<br>9-CH₃— |
| 356 | m-CH₃O—Ph— | 7-CH₃S(O)—<br>9-CH₃— |
| 357 | m-CH₃O—Ph— | 7-CH₃S(O)₂—<br>9-CH₃— |
| 358 | m-CH₃O—Ph— | 7-PhS—<br>9-CH₃— |
| 359 | m-CH₃O—Ph— | 7-CH₃S—<br>9-CH₃— |
| 360 | m-CH₃O—Ph— | 7-CH₃O—<br>9-CH₃— |
| 361 | m-CH₃O—Ph— | 7-CH₃—<br>9-CH₃— |
| 362 | m-CH₃O—Ph— | 7-CH₃O—<br>9-CH₃O— |
| 363 | thien-2-yl | 7-(1-aziridine) |
| 364 | thien-2-yl | 7-EtS— |
| 365 | thien-2-yl | 7-CH₃S(O)— |
| 366 | thien-2-yl | 7-CH₃S(O)₂— |
| 367 | thien-2-yl | 7-PhS— |
| 368 | thien-2-yl | 7-CH₃S—<br>9-CH₃S— |
| 369 | thien-2-yl | 7-CH₃O—<br>9-CH₃O— |
| 370 | thien-2-yl | 7-Et— |
| 371 | thien-2-yl | 7-iPr— |
| 372 | thien-2-yl | 7-t-Bu— |
| 373 | thien-2-yl | 7-(1-pyrrole)- |
| 374 | thien-2-yl | 7-CH₃O— |
| 375 | thien-2-yl | 7-CH₃S— |
| 376 | thien-2-yl | 7-(1-azetidine) |
| 377 | thien-2-yl | 7-Me— |
| 378 | 5-Cl-thien-2-yl | 7-(1-azetidine) |
| 379 | 5-Cl-thien-2-yl | 7-(1-aziridine) |
| 380 | 5-Cl-thien-2-yl | 7-EtS— |
| 381 | 5-Cl-thien-2-yl | 7-CH₃S(O)— |
| 382 | 5-Cl-thien-2-yl | 7-CH₃S(O)₂— |
| 383 | 5-Cl-thien-2-yl | 7-PhS— |
| 384 | 5-Cl-thien-2-yl | 7-CH₃S—<br>9-CH₃S— |
| 385 | 5-Cl-thien-2-yl | 7-CH₃O—<br>9-CH₃O— |
| 386 | 5-Cl-thien-2-yl | 7-Et— |
| 387 | 5-Cl-thien-2-yl | 7-iPr— |
| 388 | 5-Cl-thien-2-yl | 7-t-Bu— |
| 389 | 5-Cl-thien-2-yl | 7-CH₃O— |
| 390 | 5-Cl-thien-2-yl | 7-CH₃S— |
| 391 | 5-Cl-thien-2-yl | 7-Me |
| 392 | thien-2-yl | 7-(1-azetidine)<br>9-CH₃— |
| 393 | thien-2-yl | 7-EtS—<br>9-CH₃— |

TABLE 4-continued

Alternative compounds #1 (#302–312, 314–430)

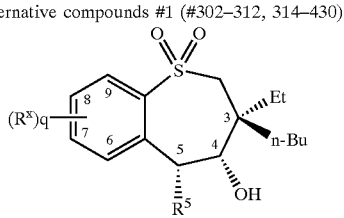

| Cpd# | R⁵ | (Rˣ)q |
|------|-----|-------|
| 394 | thien-2-yl | 7-CH₃S(O)—<br>9-CH₃— |
| 395 | thien-2-yl | 7-CH₃S(O)₂—<br>9-CH₃— |
| 396 | thien-2-yl | 7-PhS—<br>9-CH₃— |
| 397 | thien-2-yl | 7-CH₃S—<br>9-CH₃— |
| 398 | thien-2-yl | 7-CH₃O—<br>9-CH₃— |
| 399 | thien-2-yl | 7-CH₃—<br>9-CH₃— |
| 400 | thien-2-yl | 7-CH₃O—<br>9-CH₃O— |
| 401 | thien-2-yl | 7-(1-pyrazrole) |
| 402 | thien-2-yl | 7-(N)—N'-methylpiperazine |
| 403 | thien-2-yl | Ph— |
| 404 | thien-2-yl | 7-CH₃C(=CH₂)— |
| 405 | thien-2-yl | 7-cyclpropyl |
| 406 | thien-2-yl | 7-(CH₃)₂NH— |
| 407 | thien-2-yl | 7-(N)-azetidine<br>9-CH₃S— |
| 408 | thien-2-yl | 7-(N-pyrrolidine)<br>9-CH₃S— |
| 409 | thien-2-yl | 7-(CH₃)₂N-<br>9-CH₃S— |
| 411 | 5-Cl-thien-2-yl | 7-(1-pyrazole) |
| 412 | 5-Cl-thien-2-yl | 7-(N)N'-methylpiperazine |
| 413 | 5-Cl-thien-2-yl | Ph— |
| 414 | 5-Cl-thien-2-yl | 7-CH₃C(=CH₂)— |
| 415 | 5-Cl-thien-2-yl | 7-cyclopropyl |
| 416 | 5-Cl-thien-2-yl | 7-(CH₃)₂NH— |
| 417 | 5-Cl-thien-2-yl | 7-(N)-azetidine<br>9-CH₃S— |
| 418 | 5-Cl-thien-2-yl | 7-(N-pyrrolidine)<br>9-CH₃S— |
| 419 | 5-Cl-thien-2-yl | 7-(CH₃)₂N-<br>9-CH₃S— |
| 420 | 5-Cl-thien-2-yl | 7-(N)-azetidine<br>9-CH₃S— |
| 421 | 5-Cl-thien-2-yl | 7-EtS—<br>9-CH₃— |
| 422 | 5-Cl-thien-2-yl | 7-CH₃S(O)—<br>9-CH₃— |
| 423 | 5-Cl-thien-2-yl | 7-CH₃S(O)₂—<br>9-CH₃— |
| 424 | 5-Cl-thien-2-yl | 7-PhS—<br>9-CH₃— |
| 425 | 5-Cl-thien-2-yl | 7-CH₃S—<br>9-CH₃— |
| 426 | 5-Cl-thien-2-yl | 7-CH₃O—<br>9-CH₃— |
| 427 | 5-Cl-thien-2-yl | 7-CH₃—<br>9-CH₃— |
| 428 | 5-Cl-thien-2-yl | 7-CH₃O—<br>9-CH₃O— |
| 429 | thien-2-yl | 6-CH₃O—<br>7-CH₃O—<br>8-CH₃O— |
| 430 | 5-Cl-thien-2-yl | 6-CH₃O—<br>7-CH₃O—<br>8-CH₃O— |

Examples 232–1394

Using in each instance a method generally described in those of Examples 1 to 72 appropriate to the substituents to be introduced, including where necessary other common synthesis expedients well known to the art, compounds are prepared having the structures set forth in Table 1. The starting materials illustrated in the reaction schemes shown above are varied in accordance with principles of organic synthesis well known to the art in order to introduce the indicated substituents in the 4- and 5-positions (R³, R⁴, R⁵, R⁶) and in the indicated position on the benzo ring (Rˣ).

Example 1395

Dibutyl 4-fluorobenzene dialdehyde

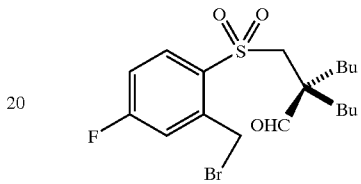

Step 1: Preparation of dibutyl 4-fluoro benzene dialdehyde

To a stirred solution of 17.5 g (123 mmol) of 2,5-difluorobenzaldehyde (Aldrich) in 615 mL of DMSO at ambient temperature was added 6.2 g (135 mmol) of lithium sulfide (Aldrich). The dark red solution was stirred at 75 C. for 1.5 hours, or until the starting material was completely consumed, and then 34 g (135 mmol) of dibutyl mesylate aldehyde was added at about 50 C. The reaction mixture was stirred at 75 C. for three hours or until the reaction was completed. The cooled solution was poured into water and extracted with ethyl acetate. The combined extracts were washed with water several times, dried (MgSO₄) and concentrated in vacuo. Silica gel chromatographic purification of the crude product gave 23.6 g (59%) of fluorobenzene dialdehyde as a yellow oil: ¹H NMR (CDCl₃) d 0.87 (t, J=7.05 Hz, 6H), 1.0–1.4 (m, 8H), 1.5–1.78 (m, 4H), 3.09 (s, 2H), 7.2–7.35 (m, 1H), 7.5–7.6 (m, 2H), 9.43 (s, 1H), 10.50 (d, J=2.62 Hz, 1H).

Step 2: Preparation of dibutyl 4-fluorobenzyl alcohol

To a solution of 22.6 g (69.8 mmol) of the dialdehyde obtained from Step 1 in 650 mL of THF at −60 C. was added 69.8 mL (69.8 mmol) of DIBAL (1M in THF) via a syringe. The reaction mixture was stirred at −40 C. for 20 hours. To the cooled solution at −40 C. was added sufficient amount of ethyl acetae to quench the excess of DIBAL, followed by 3 N HCl. The mixture was extracted with ethyl acetate, washed with water, dried (MgSO₄), and concentrated in vacuo. Silica gel chromatographic purification of the crude product gave 13.5 (58%) of recovered starting material, and 8.1 g (36%) of the desired fluorobenzyl alcohol as a colorless oil: ¹H NMR (CDCl₃) d 0.88 (t, J=7.05 Hz, 6H), 1.0–1.4 (m, 8H), 1.5–1.72 (m, 4H), 1.94 (br s, 1H), 3.03 (s, 2H), 4.79 (s, 2H), 6.96 (dt, J=8.46, 3.02 Hz, 1H), 7.20 (dd, J=9.47, 2.82 Hz, 1H), 7.42 (dd, J=8.67, 5.64, 1H), 9.40 (s, 1H).

Step 3: Preparation of dibutyl 4-fluorobenzyl bromide

To a solution of 8.1 g (25 mmol) of benzyl alcohol obtained from Step 2 in 100 mL of DMF at −40 C. was added 47 g (50 mmol) of bromotriphenyphosphonium bromide (Aldrich). The resulting solution was stirred cold for 30 min, then was allowed to warm to 0 C. To the mixture was added 10% solution of sodium sulfite and ethyl acetate. The extract was washed a few times with water, dried (MgSO₄), and concentrated in vacuo. The mixture was stirred in small amount of ethyl acetate/hexane mixture (1:4 ratio) and filtered through a pad of silica gel, eluting with same solvent mixture. The combined filtrate was concentrated in vacuo to give 9.5 g (98%) of the desired product as a colorless oil: $^1$H NMR (CDCl$_3$) d 0.88 (t, J=7.05 Hz, 6H), 1.0–1.4 (m, 8H), 1.55–1.78 (m, 4H), 3.11 (s, 2H), 4.67 (s, 2H), 7.02 (dt, J=8.46, 3.02 Hz, 1H), 7.15 (dd, J=9.47, 2.82 Hz, 1H), 7.46 (dd, J=8.67, 5.64 Hz, 1H), 9.45 (s, 1H).

Step 4: Preparation of sulfonyl 4-flurorbenzyl bromide

To a solution of 8.5 g (25 mmol) of sulfide obtained from Step 3 in 200 mL of CH$_2$Cl$_2$ at 0° C. was added 15.9 g (60 mmol) of mCPBA (64% peracid). The resulting solution was stirred cold for 10 min, then was allowed to stirred ambient temperature for 5 hours. To the mixture was added 10% solution of sodium sulfite and ethyl acetate. The extract was washed several times with saturated Na$_2$CO$_3$, dried (MgSO$_4$), and concentrated in vacuo to give 10.2 g (98%) of the desired product as a colorless oil: $^1$H NMR (CDCl$_3$) d 0.91 (t, J=7.05 Hz, 6H), 1.03–1.4 (m, 8H), 1.65–1.82 (m, 2H), 1.90–2.05 (m, 2H), 3.54 (s, 2H), 5.01 (s, 2H), 7.04–7.23 (m, 1H), 7.30 (dd, J=8.87, 2.42 Hz, 1H), 8.03 (dd, J=8.86, 5.64, 1H), 9.49 (s, 1H).

Example 1396

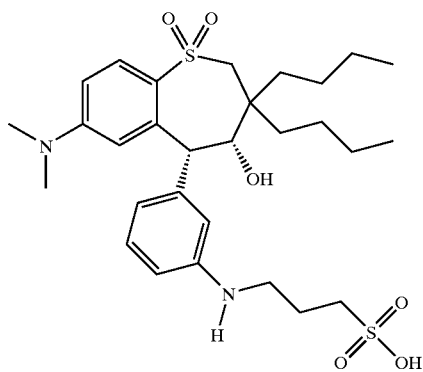

Generic Scheme X

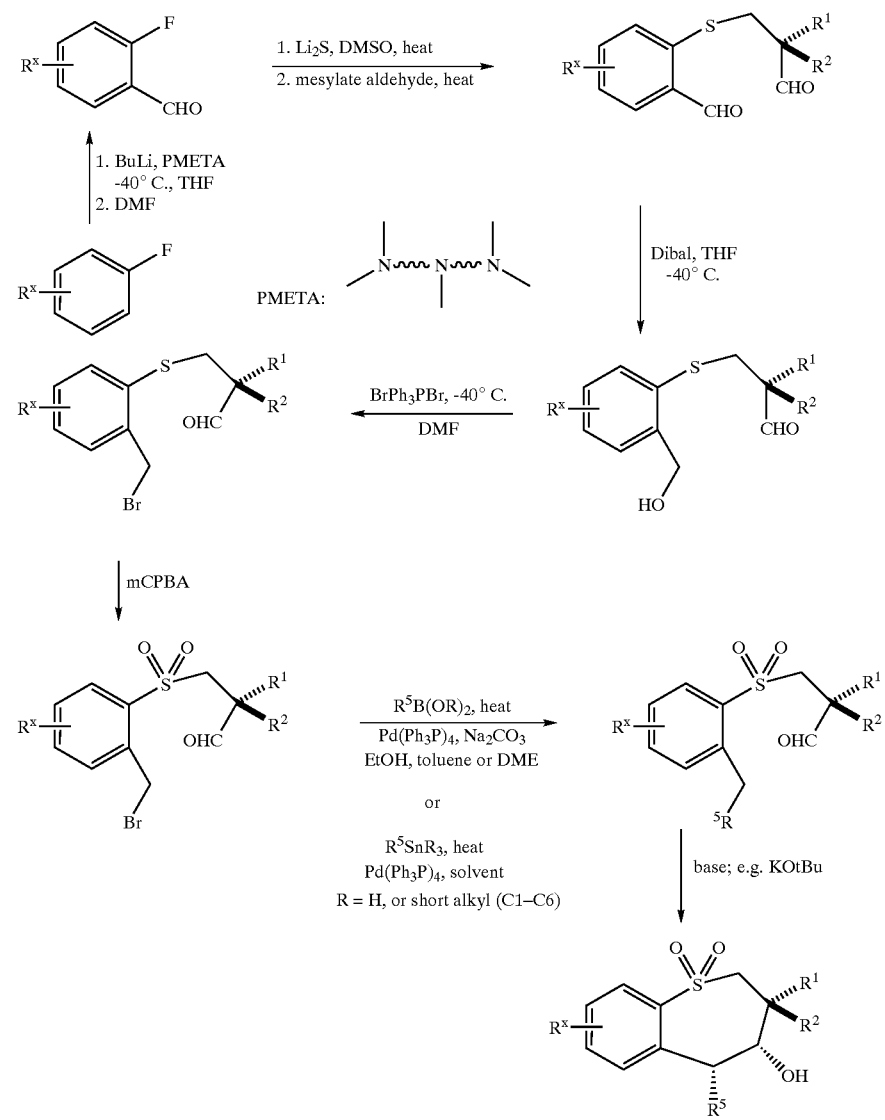

Generic Scheme X: The nucleophilic substitution of an appropriately substituted 2-fluorobenzaldehyde with lithium sulfide or other nucleophilic sulfide anion in polar solvent (such as DMF, DMA, DMSO, etc), followed by the addition of dialkyl mesylate aldehyde (X), provided a dialkyl benzene dialdehyde Y. DIBAL reduction of the dialdehyde at low temperature yielded benzyl alcohol monoaldehyde Z. Conversion of benzyl alcohol to benzyl bromide, followed oxidation of sulfide to sulfone yielded the key intermediate W.

Preparation of N-propylsulfonic acid

To a solution of 51 mg (111 μm) Compound X in ethanol (400 μl) was added 1,3 propane sultone (19.5 μl, 222 μm). The reaction was stirred in a sealed vial at 55° C. for 25 hr. Sample was concentrated under a nitrogen stream and purified by reversed phase chromatography using acetonitrile/water as eluent (30–45%) and afforded the desired material as an off-white solid (28.4 mg, 44%): $^1$H NMR (CDCL$_3$) d 0.82–0.96 (m, 6H), 1.11–1.52 (m of m, 10H), 1.58–1.72 (m, 1H), 2.08–2.21 (m, 1H), 2.36–2.50 (m, 2H), 2.93 (s, 6H), 3.02–3.22 (m of m, 5H), 3.58–3.76 (m, 2H), 4.15 (s, 1H), 5.51 (s, 1H), 6.45–6.58 (m, 1H), 6.92–7.02 (m, 1H), 7.35–7.41 (m, 1H), 7.41–7.51 (m, 2H), 8.08 (d, J=8.1 Hz, 1H), 8.12–8.25 (m, 1H); MS ES- M-H m/z 579.

Example 1397

The 7-fluoro, 9-fluoro and 7,9-difluoro analogs of benzothiepine compounds of this invention can be reacted with sulfur and nitrogen nucleophiles to give to corresponding sulfur and nitrogen substituted analogs. The following example demonstrates the synthesis of these analogs.

3,3-Dibutyl-5a-(4'-fluorophenyl)-4a-hydroxy-7-methylthio-2,3,4,5-tetrahydrobenzothiepine-1,1-dioxide.

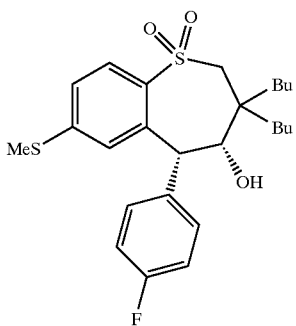

A mixture of 0.4 g of 3,3-dibutyl-7-fluoro-5a-(4'-fluorophenyl)-4a-hydroxy-2,3,4,5-tetrahydrobenzothiepine-1,1-dioxide, prepared by previously described method, 0.12 g of sodium methanethiolate and 20 ml of DMF was stirred at 50 C. for 3 days. An additional 0.1 g of sodium methanethiolate was added to the reaction mixture and the mixture was stirred for additional 20 h at 50 C. then was concentrated in vacuo. The residue was triturated with water and extracte wiith ether. The ether extract was dried over MgSO$_4$ and concentrated in vacuo to 0.44 g of an oil. Purification by HPLC (10% EtOAc in hexane) gave 0.26 g of needles, mp 164–165.5% C.

3,3-Dibutyl-9-dimethylamino-7-fluoro-5a-(4'-fluorophenyl)-4a-hydroxy-2,3,4,5-tetrahydrobenzothiepine-1,1-dioxide and 7,9-Bis(dimethylamino)-3,3-dibutyl-5a-(4'-fluorophenyl)-4a-hydroxy-2,3,4,5-tetrahydrobenzothiepine-1,1-dioxide.

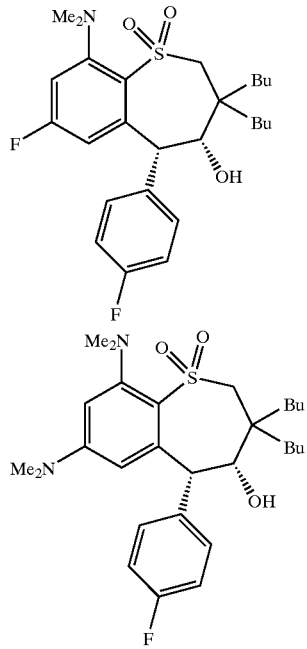

A solution of 0.105 g of 3,3-dibutyl-7,9-difluoro-5a-(4'-fluorophenyl)-4a-hydroxy-2,3,4,5-tetrahydrobenzothiepine-1,1-dioxide, prepared by the method described previously, in 20 ml of 2 N dimethylamine in THF was heated at 160 C. in a sealed Parr reactor overnight. The reaction mixture was cooled and concentrated in vacuo. The residue was triturated with 25 ml of water and extracted with ether. The ether extract was dried over MgSO$_4$ and concentrated in vacuo. The resdue was purified by HPLC (10% EtOAc in hexane) to give 35 mg of an earlier fraction which was identified as 3,3-dibutyl-9-dimethylamino-7-fluoro-5a-(4'-fluorophenyl)-4a-hydroxy-2,3,4,5-tetrahydrobenzothiepine-1,1-dioxide, MS (CI) m/e 480 (M$^{30}$+1), and 29 mg of a later fraction which was identified as 7,9-bis(dimethylamino)-3,3-dibutyl-5a-(4'-fluorophenyl)-4a-hydroxy-2,3,4,5-tetrahydrobenzothiepine-1,1-dioxide, MS (CI) m/e 505 (M$^{30}$+1).

The compounds of this invention can also be synthesized using cyclic sulfate (A, below) as the reagent as shown in the following scheme. The following example describes a procedure for using the cyclic sulfate as the reagent.

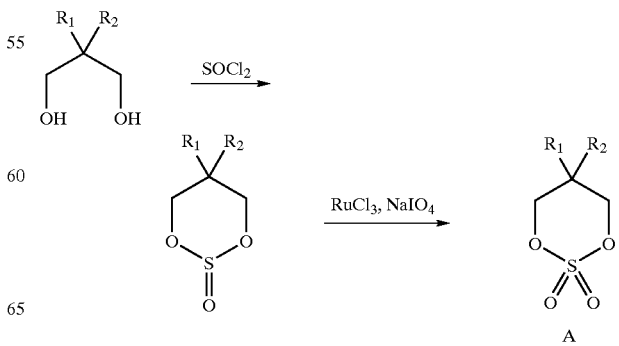

-continued

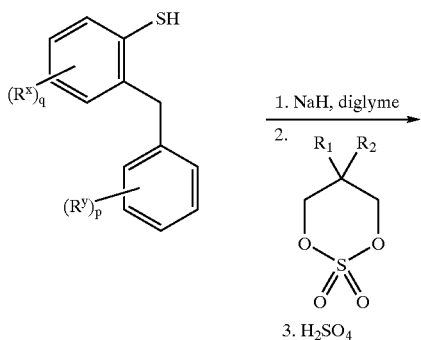

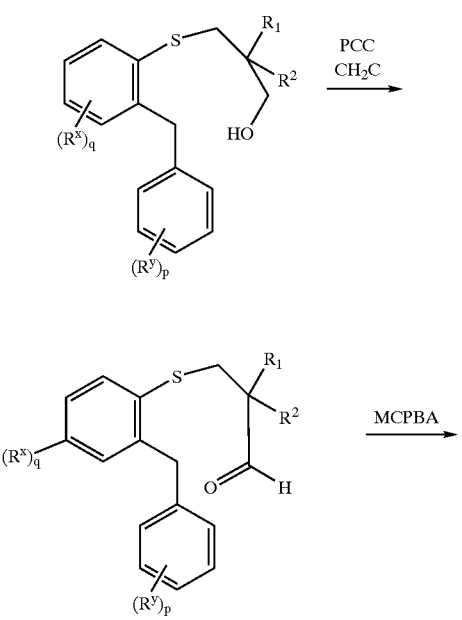

Dibutyl cyclic sulfite:

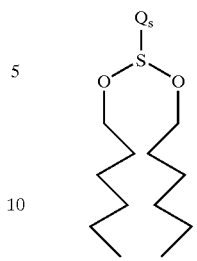

A solution of 2,2-dibutyl-1,3-propandiol (103 g, 0.548 mol) and triethylamine (221 g, 2.19 mol) in anhydrous methylene chloride (500 ml) and was stirred at 0 degrees C. under nitrogen. To the mixture, thionyl chloride (97.8 g, 0.82 mol) was added dropwise and within 5 min the solution turned yellow and then turned black when the addition was completed within half an hour. The reaction mixture was stirred for 3 hrs. GC showed that there was no starting material left. The mixture was washed with ice water twice then with brine twice. The organic phase was dried over magnesium sulfate and concentrated under vacuum to give the cyclic sulfite 128 g (100%) as a black oil. Mass spectrum (MS) was consistent with the product.

To a solution of the above compound (127.5 g, 0.54 mol) in 600 ml acetonitrile and 500 ml of water cooled in an ice bath under nitrogen was added ruthenium(III) chloride (1 g) and sodium periodate (233 g, 1.08 mol). The reaction was stirred overnight and the color of the solution turned black. GC showed that there was no starting material left. The mixture was extracted with 300 ml of ether and the ether extract was washed three times with brine. The organic phase was dried over magnesium sulfate and passed through celite. The filtrate was concentrated under vacuum and gave the cyclic sulfate 133 g (97.8%) as an oil. Proton, carbon NMR and MS were consistent with the product.

2-[(2-(4'-Fluorobenzyl)-4-methylphenylthio)methyl]-2-butylhexanol:

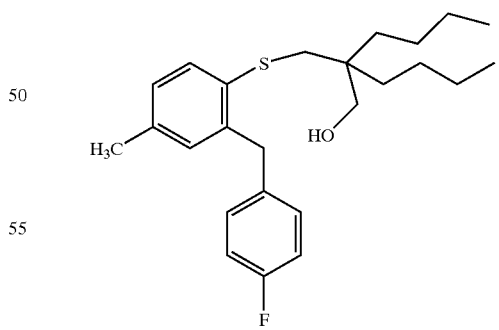

Sodium hydride (60% oil dispersion), 0.27 g (6.68 mmole), was washed with hexane and the hexane wash was decanted. To the washed sodium hydride was added 20 ml of 2-methoxyethyl ether (diglyme) and the mixture was cooled in an ice bath. A solution of 1.55 g (6.68 mmole) of 2-(4'-fluorobenzyl)-4-methylbenzenethiol in 10 ml of

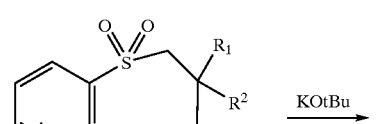

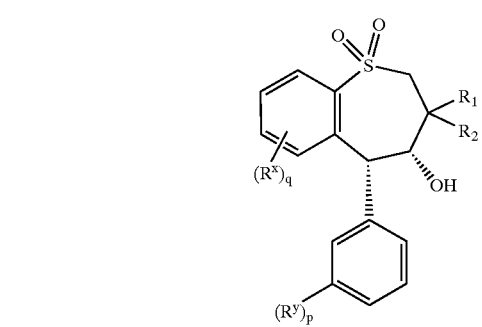

2-methoxyethyl ether was added dropwise to the reaction mixture in 15 min. A mixture of 2.17 g (8.68 mmole) of the dibutyl cyclic sulfate in 10 ml of 2-methoxyethyl ether was added once and stirred for 30 min at 0 C. then at room temperature for 1 hr under nitrogen. GC showed that there was no thiol left. The solvent was evaporated and triturated wth water then was extracted with ether twice. The water layer was separated, treated with 20 ml of 10% NaOH then was boiled for 30 min and cooled, acidified with 6 N HCl and boiled for 10 min. The reaction mixture was cooled and extracted with ether. The organic layer was washed successively with water and brine, dried over magnesium sulfate and concentrated under vacuum to give 2.47 g (92.5%) of an oil. Proton NMR, $^{13}$C NMR and MS were consistent with the product.

2-[(2-(4'-Fluorobenzyl)-4-methylphenylthio)methyl]-2-butylhexanal:

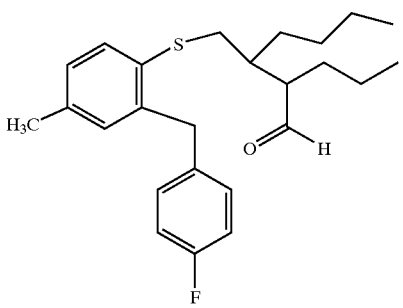

To a solution of the above product (2 g, 4.9 mmol) in 40 ml methylene chloride cooled in an ice bath under nitrogen was added pyridinium chlorochromate (2.18 g, 9.9 mmol) at once. The reaction was stirred with 3 hrs and filtered through a bed of silica gel. The filtrate was concentrated under vacuum to give 1.39 g (70%) of an oil. Proton, carbon NMR and MS were consistent with the product.

2-[(2-(4'-Fluorobenzyl)-4-methylphenylsulfonyl)methyl]-2-butylhexanal

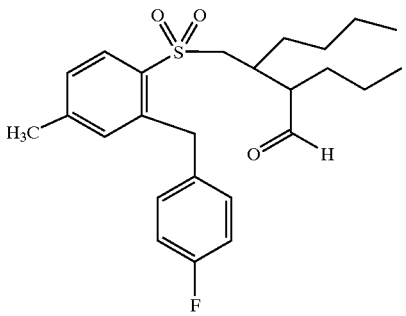

To a solution of the above product (0.44 g, 1.1 mmole) in 20 ml methylene chloride solution cooled in an ice bath under nitrogen was added 70% m-chloroperbenzoic acid (0.54 g, 2.2 mmol) at once. The reaction mixture was stirred for 18 hrs and filtered.

The filtrate was washed successively with 10% NaOH (3×), water and brine, dried over magnesium sulfate and concentrated under vacum to give 0.42 g (90%) of an oil. Proton, carbon NMR and MS were consistent with the product.

3,3-Dibutyl-7-methyl-5a-(4'-fluorophenyl)-4a-hydroxy-2,3,4,5-tetrahydrobenzothiepine-1,1-dioxide:

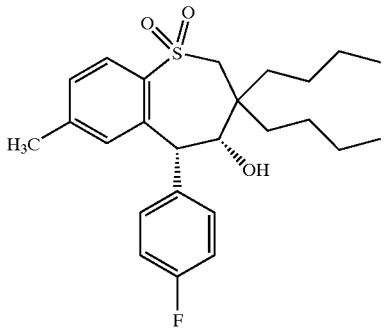

A mixture of 0.37 g (0.85 mmol) of the above product in 30 ml of anhydrous THF was stirred at 0% C. Then potassium t-butoxide (102 mg, 0.85 mmol) was added. After 3 hrs, TLC showed that there was a product and some starting material left. The crude reaction mixture was acidified with 10% HCl and extracted with ether. The ether extract was washed successively with water and brine, dried with MgSO$_4$ and concentrated under vacuum. The residue was purified by HPLC (10% EtOAc-Hexane). The first fraction was 0.1 g of starting material as an oil and the second fraction was a white solid, 0.27 g (75%). Proton NMR and carbon NMR were consistent with the desired product. Mass spectrum (CI) also confirmed the product, m/e 433 (M$^+$1).

Example 1398

Step 1

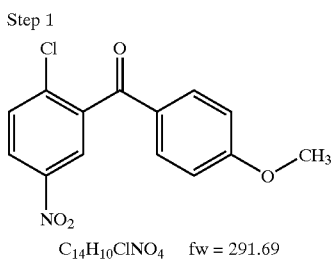

C$_{14}$H$_{10}$ClNO$_4$    fw = 291.69

In an inert atmosphere, weigh out 68.3 gms phosphorus pentachloride (0.328 mole Aldrich 15,777-5) into a 2-necked 500 ml around bottom flask. Fit flask with a N$_2$ inlet adapter and suba seal. Remove from inert atmosphere and begin N$_2$ purge. Add 50 mls anhydrous chlorobenzene (Aldrich 28,451-3) to the PCl$_5$ via syringe and begin stirring with magnetic stir bar.

Weigh out 60 gms 2-chloro-5-nitrobenzoic acid (0.298 mole Aldrich 12,511-3). Slowly add to the chlorobenzene solution while under N$_2$ purge. Stir at room temperature overnight. After stirring at room temperature for ~20 hrs, place in oil bath and heat at 50 C. for 1 hr. Remove chlorobenzene by high vacuum. Wash residue with anhydrous hexane. Dry acid chloride wt=61.95 gms. Store in inert and dry atmosphere.

In inert atmosphere, dissolve acid chloride with 105 mls anhydrous anisole (0.97 mole Aldrich 29,629-5). Place solution in a 2-necked 500 ml round bottom flask.

Weigh out 45.1 gms aluminum chloride (0.34 moles Aldrich 29,471-3) and place in a solid addition funnel. Fit reaction flask with addition funnel and a N$_2$ inlet adapter. Remove from inert atmosphere. Chill reaction solution with ice bath and begin N$_2$ purge. Slowly add AlCl$_3$ to chilled solution. After addition is complete, allow to warm to room temperature. Stir overnight.

Quench reaction by pouring into a solution of 300 mls 1 N HCl and ice. Stir 15 min. Extract twice with ether. Combine organic layers and extract twice with 2% NaOH, then twice with deionized H₂O. Dry with MgSO₄, filter and rotovap to dryness. Remove anisole by high vacuum. Crystalize product from 90% ethanol 10% ethyl acetate. Dry on vacuum line. Wt=35.2 gms. Yield 41%. Obtain NMR and mass spec (m/z=292).

Step 2

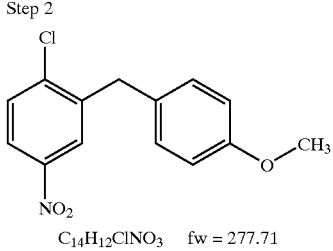

$C_{14}H_{12}ClNO_3$   fw = 277.71

Dissolve 38.10 gms (0.131 moles) of the benzophenone from step 1 in 250 mls anhydrous methylene chloride. Place in a 3 liter flask fitted with N₂ inlet, addition funnel and stopper. Stir with magnetic stir bar. Chill solution with ice bath.

Prepare a solution of 39.32 gms trifluoromethane sulfonic acid (0.262 mole Aldrich 15,853-4) and 170 mls anhydrous methylene chloride. Place in addition funnel and add dropwise to chilled solution under N₂. Stir 5 minutes after addition is complete.

Prepare a solution of 22.85 gms triethyl silane (0.197 mole Aldrich 23,019-7) and 170 mls anhydrous methylene chloride. Place in addition funnel and add dropwise to chilled solution under N₂. Stir 5 minutes after addition is complete.

Prepare a second solution of 39.32 gms trifluoromethane sulfonic acid and 170 mls anhydrous methylene chloride. Place in addition funnel and add dropwise to chilled solution under N₂. Stir 5 minutes after addition is complete.

Prepare a second solution of 22.85 gms triethyl silane and 170 mls anhydrous methylene chloride. Place in addition funnel and add dropwise to chilled solution under N₂. After all additions are made allow to slowly warm to room temperature overnight. Stir under N₂ overnight.

Prepare 1300 mls saturated NaHCO₃ in a 4 liter beaker. Chill with ice bath. While stirring vigorously, slowly add reaction mixture. Stir at chilled temperature for 30 min. Pour into a separatory funnel and allow separation. Remove organic layer and extract aqueous layer 2 times with methylene chloride. Dry organic layers with MgSO₄. Crystallize from ethanol. Dry on vacuum line. Dry wt=28.8 gms. Confirm by NMR and mass spec (m/z=278).

Step 3

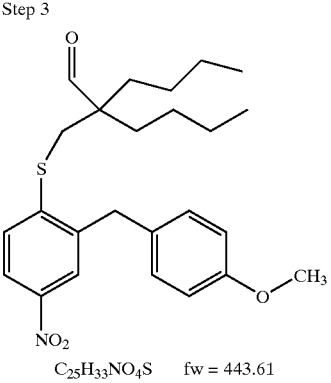

$C_{25}H_{33}NO_4S$   fw = 443.61

Dissolve 10.12 gms (0.036 moles) of product 2 with 200 mls anhydrous DMSO. Place in a 500 ml round bottom flask with magnetic stir bar. Fit flask with water condenser, N₂ inlet, and stopper. Add 1.84 gms Li₂S (0.040 moles Aldrich 21,324-1). Place flask in oil bath and heat at 75° C. under N₂ overnight then cool to room temperature.

Weigh out 10.59 gms dibutyl mesylate (0.040 moles). Dissolve with anhydrous DMSO and add to reaction solution. Purge well with N₂, heat overnight at 80° C.

Cool to room temperature. Prepare 500 mls of 5% acetic acid in a 2 liter beaker. While stirring, slowly add reaction mixture. Stir 30 min. Extract with ether 3 times. Combine organic layers and extract with water and sat'd NaCl. Dry organic layer with MgSO₄, filter and rotovap to dryness. Dry oil on vacuum line. Obtain pure product by column chromatography using 95% hexane and 5% ethyl acetate as the mobile phase. Dry wt=7.8 gms. Obtain NMR and mass spec (m/z=444).

Step 4

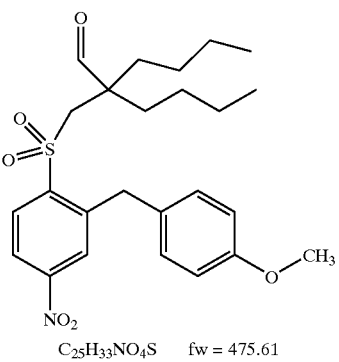

$C_{25}H_{33}NO_4S$   fw = 475.61

Dissolve 9.33 gms (0.021 moles) of product 3 with 120 mls anhydrous methylene chloride. Place in a 250 ml round bottom flask with magnetic stir bar. Fit flask with N₂ inlet and stopper. Chill solution with ice bath under N₂ purge. Slowly add 11.54 gms 3-chloroperbenzoic acid (0.0435 moles, Fluka 25800, ~65%). After addition is complete warm to room temperature and monitor reaction by TLC. Reaction goes quickly to the sulphoxide intermediate but takes 8 hrs to convert to the sulphone. Chill solution over night in freezer. Filter solid from reaction, extract filtrate with 10% K₂CO₃. Extract aqueous layer twice with methylene chloride. Combine organic layers and dry with MgSO₄. Filter and rotovap to dryness. Obtain pure product by crystallizing from ethanol or isolating by column chromatography. Obtain NMR and mass spec (m/z=476).

Step 5

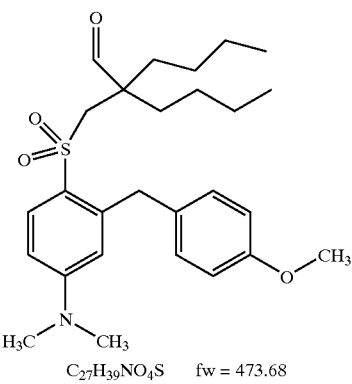

C₂₇H₃₉NO₄S   fw = 473.68

Reaction is done in a 300 ml stainless steel Parr stirred mini reactor. Place 9.68 gms (0.0204 moles) of product 4 in reactor base. Add 160 mls ethanol. For safety reasons next two compounds are added in a N₂ atmosphere glove bag. In glove bag, add 15.3 mls formaldehyde (0.204 moles, Aldrich 25,254-9, about 37 wt % in water) and 1.45 gms 10% Pd/Carbon (Aldrich 20,569-9). Seal reactor before removing from glove bag. Purge reactor three times with H₂. Heat to 55° C. under H₂. Run reaction at 200 psig H₂, 55° C., and a stir rate of 250 rpm. Run overnight under these conditions.

Cool reactor and vent H₂. Purge with N₂. Check progress of run by TLC. Reaction is a mixture of desired product and intermediate. Filter reaction mixture over a bed of celite washing well with ether. Rotovap and redissolve with ether. Extract with water. Dry organic layer with MgSO₄, filter and rotovap to dryness. Dry on vacuum line.

Charge reactor again with same amounts, seal reactor and run overnight under same conditions. After second run all of the material has been converted to the desired product. Cool and vent H₂ pressure. Purge with N₂. Filter over a bed of celite, washing well with ether. Rotovap to dryness. Dissolve with ether and extract with water. Dry organic layer with MgSO₄, filter and rotovap to dryness. Dry on vacuum line. Obtain NMR and mass spec (m/z=474).

Step 6

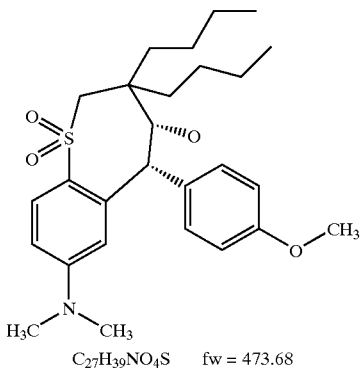

C₂₇H₃₉NO₄S   fw = 473.68

Dissolve 8.97 gms (0.0189 mole) of product 5 with 135 mls anhydrous THF. Place in a 250 ml round bottom flask with magnetic stir bar. Fit flask with N₂ inlet and stopper. Chill solution with ice/salt bath under N₂ purge. Slowly add 2.55 gms potassium t-butoxide (0.227 mole Aldrich 15,667-1). After addition is complete, continue to stir at −10° C. monitoring by TLC. Once reaction is complete, quench by adding 135 mls 10% HCl stirring 10 min. Extract three times with ether. Dry organic layer with MgSO₄, filter and rotovap to dryness. Crystallize from ether. Obtain NMR and mass spec (m/z=474).

Step 7

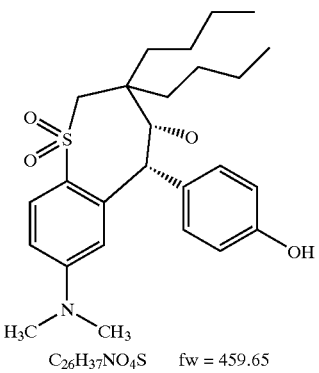

C₂₆H₃₇NO₄S   fw = 459.65

Dissolve 4.67 gms (0.01 moles) of product 6 with 100 mls anhydrous chloroform. Place in a 250 ml round bottom flask with magnetic stir bar. Fit flask with N₂ inlet adapter and suba seal. Chill solution with dry ice/acetone bath under a N₂ purge. Slowly add, via syringe, 2.84 mls boron tribromide (0.03 moles Aldrich 20,220-7). Stir at cold temperature for 15 min after addition then allow to warm to room temperature. Monitor reaction progress by TLC. Reaction is usually complete in 3 hrs.

Chill solution with ice bath. Quench with 100 mls 10% K₂CO₃ while stirring rapidly. Stir 10 min. then transfer to sep funnel and allow separation. Remove aqueous layer. Extract organic layer once with 10% HCl, once H₂O, and once with saturated NaCl solution. Dry organic layer with MgSO₄, filter and rotovap to dryness. Crystallize product from ether. Obtain NMR and mass spec (m/z=460).

Step 8

C₃₂H₄₈NO₄SI   fw = 701.71

Weigh 0.38 gms NaH (9.57 mmoles Aldrich 19,923-0 60% disp. in mineral oil) in a 250 ml round bottom flask with magnetic stir bar. Fit flask with N₂ inlet and stopper. Chill NaH with ice bath and begin N₂ purge.

Dissolve 4.0 gms (8.7 mmoles) of product 7 with 60 mls anhydrous DMF. Add to the cold NaH. Stir at cold temperature for 30 min. Add 1.33 gms K₂CO₃ (9.57 mmoles Fisher P-208).

Dissolve 16.1 gms 1,2-bis-(2-iodoethoxy) ethane (43.5 mmoles Aldrich 33,343-3) with 60 mls anhydrous DMF. Add to cold reaction mixture. Warm to room temperature then heat to 40° C. overnight under N₂.

Cleanup by diluting with ether and extracting sequentially with 5% NaOH, H₂O, and saturated NaCl. Dry organic layer with MgSO$_4$, filter and dry. Obtain pure product by column chromatography using 75% hexane 25% ethyl acetate as the mobile phase. Obtain NMR and mass spec (m/z=702).

Step 9

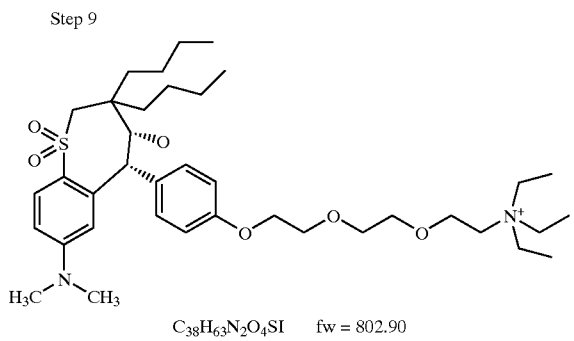

C$_{38}$H$_{63}$N$_2$O$_4$SI    fw = 802.90

Dissolve 1.0 gms (1.43 mmoles) of product 8 with 10 mls anhydrous acetonitrile. Place in a 3 ounce Fischer-Porter pressure reaction vessel with magnetic stir bar. Add 2.9 gms triethyl amine (28.6 mmoles Aldrich 23,962-3) dissolved in 10 mls anhydrous acetonitrile. Purge well with N$_2$ then close system. Heat at 45° C. Monitor reaction by TLC. Reaction is usually complete in 48 hrs.

Perform cleanup by removing acetonitrile under vacuum. Redissolve with anhydrous chloroform and precipitate quaternary ammonium salt with ether. Repeat several times. Dry to obtain crystalline product. Obtain NMR and mass spec (m/z=675).

Example 1399

Step 1. Preparation of 1

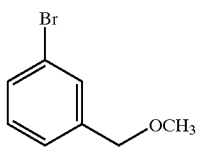

To a solution of 144 g of KOH (2560 mmol) in 1.1 L of DMSO was added 120 g of 2-bromobenzyl alcohol (641 mmol) slowly via addition funnel. Then was added 182 g of methyliodide (80 mL, 1282 mmol) via addition funnel. Stirred at ambient temperature for fifteen minutes. Poured reaction contents into 1.0 L of water and extracted three times with ethyl acetate. The organic layer was dried over MgSO$_4$ and concentrated in vacuo. Purified by silica-gel chromatography through a 200 mL plug using hexanes (100%) as elutant yielded 103.2 g (80%) of 1 as a clear colorless liquid. $^1$H NMR (CDCl$_3$) d 3.39 (s, 3H), 4.42 (s, 2H), 7.18–7.27 (m, 2H), 7.12 (d, J=7.45, 1H), 7.50 (s, 1H).

Step 2. Preparation of 2

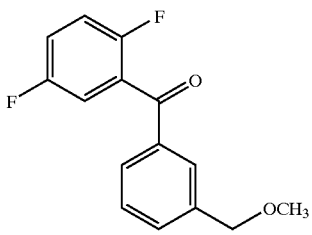

To a cooled (−78° C.) solution of 95 g (472 mmol) of 1 in 1.5 L THF was added 240 mL of 2.5 M n-butyl lithium (576 mmol). The mixture was stirred for one hour, and then to it was added 180 g of zinc iodide (566 mmol) dissolved in 500 ml THF. The mixture was stirred thirty minutes, allowed to warm to 5 C., cooled to −10° C. and to it was added 6 g of Pd(PPh$_3$)$_4$ (5.2 mmol) and 125 g 2,5-difluorobenzoyl chloride (708 mmol). The mixture was stirred at ambient temperature for 18 hours and then cooled to 10° C., quenched with water, partitioned between ethyl acetate and water, and washed organic layer with 1 N HCL and with 1 N NaOH. The organic layer was dried over MgSO$_4$ and concentrated in vacuo. Purification by silica gel chromatography (Waters Prep-500) using 5% ethyl acetate/hexanes as elutant gave 53.6 g (43%) of 2 as an orange oil. $^1$H NMR (CDCl$_3$) d 3.40 (s, 3H), 4.51 (s, 2H), 7.12–7.26 (m, 3H), 7.47 (t, J=7.50, 1H), 7.57 (d, J=7.45, 1H), 1H), 7.73 (d, J=7.45, 1H), 7.80 (s, 1H).

Step 3. Preparation of 3

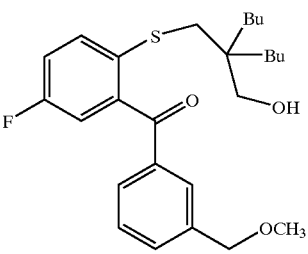

A solution of 53 g (202.3 mmol) of 2 and 11.2 g Li2S (242.8 mmol) in 250 mL DMF was heated to 100° C. for 18 hours. The reaction was cooled (0° C.) and 60.7 g of X' (the cyclic sulfate compound of example 1397) (242.8 mmol) in 50 mL DMF was added. Stirred at ambient temperature for 18 hours then condensed in vacuo. Add 1 L water to organic residue and extracted twice with diethyl ether. Aqueous layer acidified (pH 1) and refluxed 2 days. Cooled to ambient temperature and extracted with methylene chloride, dried organic layer over MgSO$_4$ and condensed in vacuo. Purification by silica gel chromatography (Waters Prep-500) using 10% ethyl acetate/hexanes as elutant gave 42.9 g (48%) of 3 as a yellow oil. $^1$H NMR (CDCl$_3$) d 0.86 (t, J=7.25 Hz, 6H), 1.10–1.26 (m, 12H), 2.83 (s, 2H), 3.32 (s, 2H), 3.40 (s, 3H), 4.48 (s, 3H), 7.02 (dd, J=8.26 Hz and 2.82 Hz, 1H), 7.16 (dt, J=8.19 Hz and 2.82 Hz, 1H), 7.45 (t, J=7.65 Hz, 1H), 7.56–7.61 (m, 2H), 7.69 (d, J=7.85 Hz, 1H), 7.74 (s, 1H).

Step 4. Preparation of 4

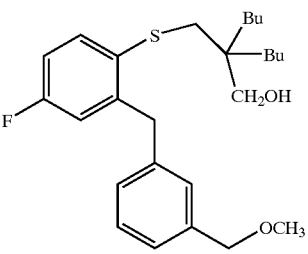

To a cooled (−40° C.) solution of 42.9 g (96.2 mmol) of 3 in 200 mL of methylene chloride was added 21.6 g trifluoromethane sulfonic acid (12.8 mL, 144 mmol) followed by the addition of 22.4 g triethyl silane (30.7 mL, 192.4 mmol). Stirred at −20° C. for two hours, quenched with water and warmed to ambient temperature. Partitioned between methylene chloride and water, dried the organic layer over MgSO$_4$ and condensed in vacuo. Purification by silica gel chromatography (Waters Prep-500) using 10% ethyl acetate/hexanes as elutant gave 24.2 g (60%) of 4 as a oil. $^1$H NMR (CDCl$_3$) d 0.89 (t, J=7.05 Hz, 6H), 1.17–1.40 (m, 12H), 1.46 (t, J=5.84 Hz, 1H), 2.81 (s, 2H), 3.38 (s, 3H), 3.43 (d, J=5.23 Hz, 2H), 4.16 (s, 2H), 4.42 (s, 2H), 6.80 (d, J=9.67 Hz, 1H), 6.90 (t, J=8.46 Hz, 1H), 7.09 (d, J=7.45 Hz, 1H), 7.15–7.21 (m, 2H), 7.25–7.32 (m, 2H), 7.42 (m, 1H).

Step 5. Preparation of 5

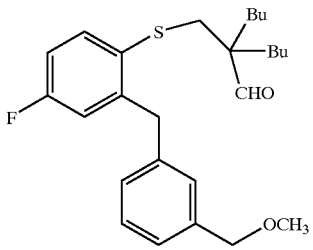

To a cooled (15–18° C.) solution of 24.2 g (55.8 mmol) of 4 in 100 mL DMSO was added 31.2 g sulfur trioxide pyridine complex (195 mmol). Stirred at ambient temperature for thirty minutes. Poured into cold water and extracted three times with ethyl acetate. Washed organics with 5% HCl (300 mL) and then with brine (300 mL), dired organics over MgSO$_4$ and condensed in vacuo to give 23.1 g (96%) of 5 as a light brown oil. $^1$H NMR (CDCl$_3$) d 0.87 (t, J=7.05 Hz, 6H), 1.01–1.32 (m, 8H), 1.53–1.65 (m, 4H), 2.98 (s, 2H), 3.38 (s, 3H), 4.15 (s, 2H), 4.43 (s, 2H), 6.81 (dd, J=9.66 Hz and 2.82 Hz, 1H), 6.91 (t, J=8.62 Hz, 1H), 7.07 (d, J=7.46 Hz, 1H), 7.14 (s, 1H), 7.19 (d, J=7.65 Hz, 1H), 7.26–7.32 (m, 1H), 7.42 (dd, J=8.66 Hz and 5.64 Hz, 1H), 9.40 (s, 1H).

Step 6. Preparation of 6

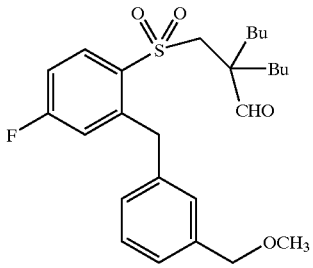

To a cooled (0° C.) solution of 23.1 g (53.6 mmol) of 5 in 200 mL methylene chloride was added 28.6 g meta cholorperoxy-benzoic acid (112.6 mmol). Stirred at ambient temperature for 24 hours. Quenched with 100 mL 10% Na$_2$SO$_3$, partitioned between water and methylene chloride. Dried organic layer over MgSO$_4$ and condensed in vacuo to give 24.5 g (98%) of 6 as a light yellow oil. $^1$H NMR (CDCl$_3$) d 0.86–1.29 (m, 14H), 1.58–1.63 (m, 2H), 1.82–1.91 (m, 2H), 3.13 (s, 2H), 3.39 (s, 3H), 4.44 (s, 2H), 4.50 (s, 2H), 6.93 (d, J=9.07 Hz, 1H), 7.10–7.33 (m, 5H), 8.05 (s, 1H), 9.38 (s, 1H).

Step 7. Preparation of 7

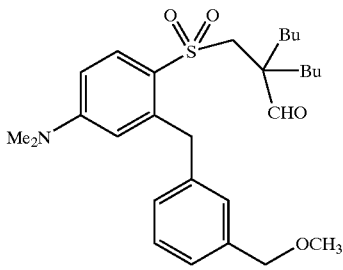

To a solution of 24.5 g (52.9 mmol) of 6 in 20 mL of THF contained in a stainless steel reaction vessel was added 100 mL of a 2.0 M solution of dimethyl amine and 20 mL of neat dimethyl amine. The vessel was sealed and heated to 110° C. for 16 hours. The reaction vessel was cooled to ambient temperature and the contents concentrated in vacuo. Purification by silica gel chromatography (Waters Prep-500) using 15% ethyl acetate/hexanes gave 21.8 g (84%) of 7 as a clear colorless oil. $^1$H NMR (CDCl$_3$) d 0.85 (t, J=7.25 Hz, 6H), 0.93–1.29 (m, 8H), 1.49–1.59 (m, 2H), 1.70–1.80 (m, 2H), 2.98 (s, 8H), 3.37 (s, 3H), 4.41 (s, 2H), 4.44 (s, 2H), 6.42 (s, 1H), 6.58 (dd, J=9.0 Hz and 2.61 Hz, 1H), 7.13 (d, J=7.45 Hz, 1H), 7.21 (s, 1H), 7.28 (t, J=7.85 Hz, 1H), 7.82 (d, J=9.06 Hz, 1H), 9.36 (s, 1H).

Step 8. Preparation of 8

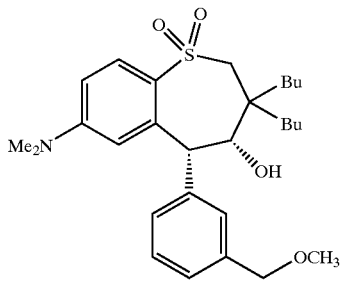

A solution of 21.8 g (44.8 mmol) of 7 in 600 mL of THF was cooled to 0° C. 58.2 mL of a 1 M solution of potassium t-butoxide was added slowly, maintaining the temperature at <5° C. Stirred for 30 minutes, then quenched with 50 mL of saturated ammonium chloride. The organic layer was partitioned between ethyl acetate and water, dried over MgSO$_4$ and concentrated in vacuo. Purification by recrystalization from ~10% ethyl acetate/hexanes gave 15.1 g of 8 as a white solid. The mother liquor was purified by silica gel chromatography (Waters Prep-500) using 30% ethyl acetate/hexanes as the elutant to give 3.0 g of 8 as a white solid. MS (FABLi$^-$) m/e 494.6. HRMS (EI$^-$) calculated for M+H 487.2756. Found 487.2746.

Step 9. Preparation of 9

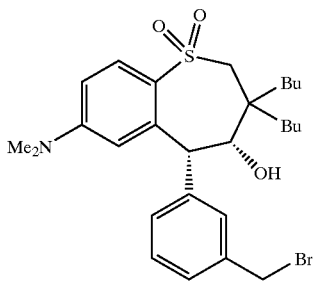

A solution of 2.0 g (4.1 mmol) of 8 in 20 mL of methylene chloride was cooled to −60° C. 4.1 mL of a 1M solution of boron tribromide was added. Stirred at ambient temperature for thirty minutes. Cooled reaction to −10° C. and quenched with 50 mL of water. The organic layer was partitioned between methylene chloride and water, dried over MgSO$_4$ and concentrated in vacuo. Purification by recrystalization from 50% ethyl acetate/methylene chloride gave 1.95 g (89%) of 9 as a white solid. MS (FABH$^+$) m/e 537. HRMS (FAB) calculated for M 536.1834. Found 536.1822.

Step 10. Preparation of 10

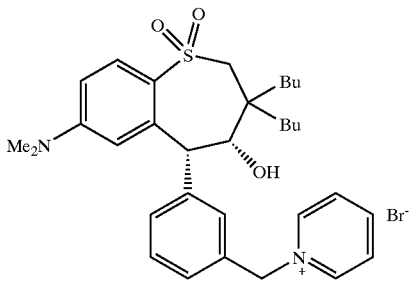

A solution of 1.09 g (2.0 mmol) of 9 and 4.9 g (62 mmol) of pyridine in 30 mL of acetonitrile was stirred at ambient temperature for 18 hours. The reaction was concentrated in vacuo. Purification by recrystallization from methanol/diethyl ether gave 1.19 g (96%) of 10 as an off white solid. MS (FAB$^+$) m/e 535.5.

Example 1398

Step 1. Preparation of 2

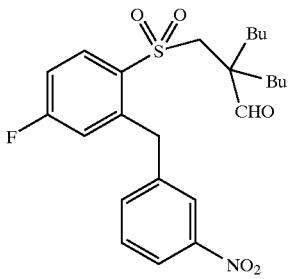

To a solution of 6.0 g of dibutyl 4-fluorobenzene dialdehyde of Example 1395 (14.3 mmol) in 72 mL of toluene and 54 mL of ethanol was added 4.7 g 3-nitrobenzeneboronic acid (28.6 mmol), 0.8 g of tetrakis (triphenylphosphine) palladium(0) (0.7 mmol) and 45 mL of a 2 M solution of sodium carbonate in water. This heterogeneous mixture was refluxed for three hours, then cooled to ambient temperature and partitioned between ethyl acetate and water. The organic layer was dried over MgSO$_4$ and concentrated in vacuo. Purification by silica gel chromatography (Waters Prep-2000) using ethyl acetate/hexanes (25/75) gave 4.8 g (73%) of the title compound as a yellow solid. $^1$H NMR (CDCl$_3$) d 0.88 (t, J=7.45 Hz, 6H), 0.99–1.38 (m, 8H), 1.6214 1.75 (m, 2H), 1.85–2.00 (m, 2H), 3.20 (s, 2H), 4.59 (s, 2H), 6.93 (dd, J=10.5 and 2.4 Hz, 1H), 7.15 (dt, J=8.4 and 2.85 Hz, 1H), 7.46–7.59 (m, 2H), 8.05–8.16 (m, 3H), 9.40 (s, 1H).

Step 3. Preparation of 3

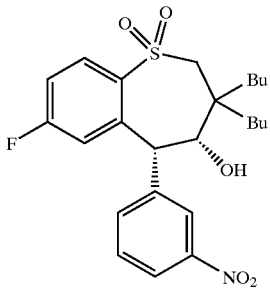

A solution of 4.8 g (10.4 mmol) of 2 in 500 mL THF was cooled to 0° C. in an ice bath. 20 mL of a 1 M solution of potassium t-butoxide was added slowly, maintaining the temperature at <5° C. Stirring was continued for 30 minutes, then the reaction was quenched with 100 mL of saturated ammonium chloride. The mixture was partitioned between ethyl acetate and water; the organic layer was washed with brine, then dried (MgSO$_4$) and concentrated in vacuo. Purification by silica gel chromatography through a 100 ml plug using CH$_2$Cl$_2$ as eluent yield 4.3 g (90%) of 3 as a pale yellow foam. $^1$H NMR (CDCl$_3$) d 0.93 (t, J=7.25 Hz, 6H), 1.00–1.55 (m, 8H), 1.59–1.74 (m, 3H), 2.15–2.95 (m, 1H), 3.16 (q$_{AB}$, J$_{AB}$=15.0 Hz, ΔV=33.2 Hz, 2H), 4.17 (d, J=6.0 Hz, 1H), 5.67 (s, 1H), 6.34 (dd, J=9.6 and 3.0 Hz, 1H), 7.08 (dt, J=8.5 and 2.9 Hz, 1H), 7.64 (t, J=8.1 Hz, 1H), 7.81 (d, J=8.7 Hz, 1H), 8.13 (dd, J=9.9 and 3.6 Hz, 1H), 8.23–8.30 (m, 1H), 8.44 (s, 1H). MS(FABH$^+$) m/e (relative intensity) 464.5 (100), 446.6 (65). HRMS calculated for M+H 464.1907. Found 464.1905.

Step 4. Preparation of 4

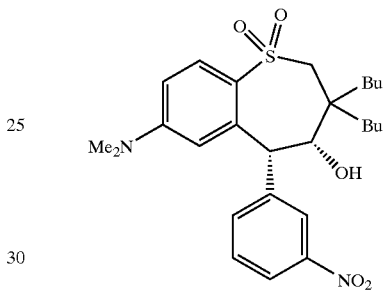

To a cooled (0° C.) solution of 4.3 g (9.3 mmol) of 3 in 30 ml THF contained in a stainless steel reaction vessel was added 8.2 g dimethyl amine (182 mmol). The vessel was sealed and heated to 110° C. for 16 hours. The reaction vessel was cooled to ambient temperature and the contents concentrated in vacuo. Purification by silica gel chromatography (Waters Prep-2000) using an ethyl acetate/hexanes gradient (10–40% ethyl acetate) gave 4.0 g (88%) of 4 as a yellow solid. $^1$H NMR (CDCl$_3$) d 0.80–0.95 (m, 6H), 0.96–1.53 (m, 8H), 1.60–1.69 (m, 3H), 2.11–2.28 (m, 1H), 2.79 (s, 6H), 3.09 (q$_{AB}$, J$_{AB}$=15.0 Hz, DV=45.6 Hz, 2H), 4.90 (d, J=9.0 Hz, 1H), 5.65 (s, 1H), 5.75 (d, J=2.1 Hz, 1H), 6.52 (dd, J=9.6 and 2.7 Hz, 1H), 7.59 (t, J=8.4 Hz, 1H), 7.85 (d, J=7.80 Hz, 1H), 7.89 (d, J=9.0 Hz, 1H), 8.20 (dd, J=8.4 and 1.2 Hz, 1H), 8.43 (s, 1H). MS(FABH$^+$) m/e (relative intensity) 489.6 (100), 471.5 (25). HRMS calculated for M+H 489.2423. Found 489.2456.

Step 5. Preparation of 5

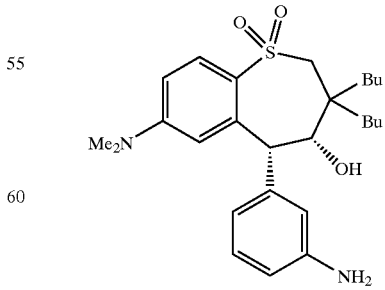

To a suspension of 1.0 g (2.1 mmol) of 4 in 100 ml ethanol in a stainless steel Parr reactor was added 1 g 10% palladium on carbon. The reaction vessel was sealed, purged twice with H₂, then charged with H₂ (100 psi) and heated to 45° C. for six hours. The reaction vessel was cooled to ambient temperature and the contents filtered to remove the catalyst. The filtrate was concentrated in vacuo to give 0.9 g (96%) of 5. ¹H NMR (CDCl₃) d 0.80–0.98 (m, 6H), 1.00–1.52 (m, 10H), 1.52–1.69 (m, 1H), 2.15–2.29 (m, 1H), 2.83 (s, 6H), 3.07 ($q_{AB}$, $J_{AB}$=15.1 Hz, DV=44.2 Hz, 2H), 3.70 (s, 2H), 4.14 (s, 1H), 5.43 (s, 1H), 6.09 (d, J=2.4 Hz, 1H), 6.52 (dd, J=12.2 and 2.6 Hz, 1H), 6.65 (dd, J=7.8 and 1.8 Hz, 1H), 6.83 (s, 1H), 6.93 (d, J=7.50 Hz, 1H), 7.19 (t, J=7.6 Hz, 1H), 7.89 (d, J=8.9 Hz, 1H). MS(FABH⁺) m/e (relative intensity) 459.7 (100). HRMS calculated for M+H 459.2681. Found 459.2670.

Step 6. Preparation of 6

To a solution of 914 mg (2.0 mmol) of 5 in 50 ml THF was added 800 mg (4.0 mmol) 5-bromovaleroyl chloride. Next was added 4 g (39.6 mmol) TEA. The reaction was stirred 10 minutes, then partitioned between ethyl acetate and brine. The organic layer was dried (MgSO₄) and concentrated in vacuo. Purification by silica gel chromatograhy through a 70 ml MPLC column using a gradient of ethyl acetate (20–50%) in hexane as eluent yielded 0.9 g (73%) of 6 as a pale yellow oil. ¹H NMR (CDCl₃) d 0.84–0.95 (m, 6H), 1.02–1.53 (m, 10H), 1.53–1.68 (m, 1H), 1.80–2.00 (m, 4H), 2.12–2.26 (m, 4H), 2.38 (t, J=6.9 Hz, 2H), 2.80 (s, 6H), 3.07 ($q_{AB}$, $J_{AB}$=15.6 Hz, DV=40.4 Hz, 2H), 3.43 (t, J=6.9 Hz, 2H), 4.10 (s, 1H), 5.51 (s, 1H), 5.95 (d, J=2.4 Hz, 1H), 6.51 (dd, J=9.3 and 2.7 Hz, 1H), 7.28 (s, 1H), 7.32–7.41 (m, 2H), 7.78 (d, J=8.1 Hz, 1H), 7.90 (d, J=9.0 Hz, 1H).

Step 7. Preparation of 7

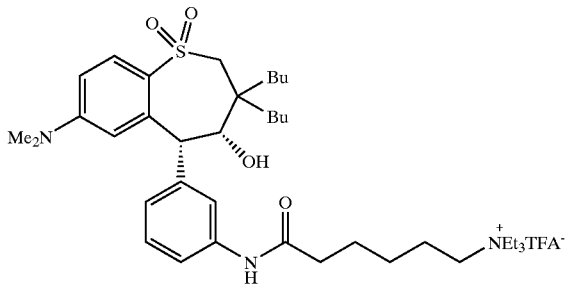

To a solution of 0.9 g (1.45 mmol) of 6 in 25 ml acetonitrile add 18 g (178 mmol) TEA. Heat at 55° C. for 16 hours. The reaction mixture was cooled to ambient temperature and concentrated in vacuo. Purification by reverse-phase silica gel chromatography (Waters Delta Prep 3000) using an acetonitrile/water gradient containing 0.05% TFA (20–65% acetonitrile) gave 0.8 g (73%) of 7 as a white foam. ¹H NMR (CDCl₃) d 0.80–0.96 (m, 6H), 0.99–1.54 (m, 19H), 1.59–1.84 (m, 3H), 2.09–2.24 (m, 1H), 2.45–2.58 (m, 2H), 2.81 (s, 6H), 3.09 ($q_{AB}$, $J_{AB}$=15.6 Hz, DV=18.5 Hz, 2H), 3.13–3.31 (m, 8H), 4.16 (s, 1H), 5.44 (s, 1H), 6.08 (d, J=1.8 Hz, 1H), 6.57 (dd, J=9.3 and 2.7 Hz, 1H), 7.24 (t, J=7.5 Hz, 1H), 7.34 (t, J=8.4 Hz, 1H), 7.56 (d, J=8.4 Hz, 1H), 7.74 (s, 1H), 7.88 (d, J=9.0 Hz, 1H), 9.22 (s, 1H). HRMS calcd 642.4304; observed 642.4343.

Example 1400

Step 1

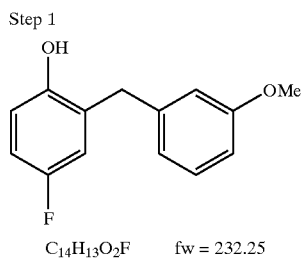

$C_{14}H_{13}O_2F$    fw = 232.25

A 12-liter, 4-neck round-bottom flask was equipped with reflux condenser, N₂ gas adaptor, mechanical stirrer, and an addition funnel. The system was purged with N₂. A slurry of sodium hydride (126.0 g/4.988 mmol) in toluene (2.5 L) was added, and the mixture was cooled to 6 C. A solution of 4-fluorophenol (560.5 g/5.000 mol) in toluene (2.5 L) was added via addition funnel over a period of 2.5 h. The reaction mixture was heated to reflux (100 C.) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into H₂O (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aq. KOH solutions were combined and acidified with concentrated HCl. The acidic solution was extracted three times with ethyl ether, dried (MgSO₄), filtered and concentrated in vacuo. The crude product was purified by Kugelrohr distillation to give a clear, colorless oil (449.0 g/39% yield). b.p.: 120–130 C./50 mtorrHg. ¹H NMR and MS [(M+H)⁺=233] confirmed desired structure.

Step 2

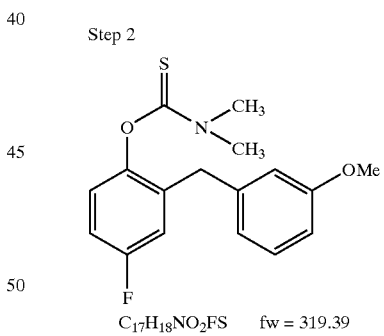

$C_{17}H_{18}NO_2FS$    fw = 319.39

A 12-liter, 3-neck round-bottom flask was fitted with mechanical stirrer and N₂ gas adaptor. The system was purged with N₂. 4-Fluoro-2-(3-methoxybenyzyl)-phenol (455.5 g/1.961 mmol) and dimethylformamide were added. The solution was cooled to 6 C. and sodium hydride (55.5 g/2.197 mmol) was added slowly. After warming to room temperature, dimethylthiocarbamoyl chloride (242.4 g/1.961 mmol) was added. After 15 h, the reaction mixture was poured into H₂O (4.0 L), and extracted two times with ethyl ether. The combined organic layers were washed with H₂O and saturated aqueous NaCl, dried (MgSO₄), filtered, and concentrated in vacuo to give the product (605.3 g, 97% yield). ¹H NMR and MS [(M+H)⁺=320] confirm desired structure.

Step 3

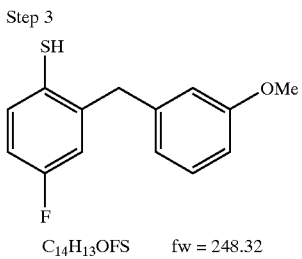

C$_{14}$H$_{13}$OFS    fw = 248.32

A 12-liter, round-bottom flask was equipped with N$_2$ gas adaptor, mechanical stirrer, and reflux condenser. The system was purged with N$_2$. 4-Fluoro-2-(3-methoxybenzyl)-phenyldimethylthiocarbamate (605.3 g/1.895 mmol) and phenyl ether (2.0 kg) were added, and the solution was heated to reflux for 2 h. The mixture was stirred for 64 h. at room temperature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temperature, the mixture was concentrated by rotavap, dissolved in ethyl ether (1.0 L), and extracted with H$_2$O. The aqueous extracts were combined, acidified with concentrated HCl, and extracted with ethyl ether. The ether extracts were dried (MgSO$_4$), filtered, and concentrated in vacuo to give an amber oil (463.0 g, 98% yield). $^1$H NMR confirmed desired structure.

Step 4

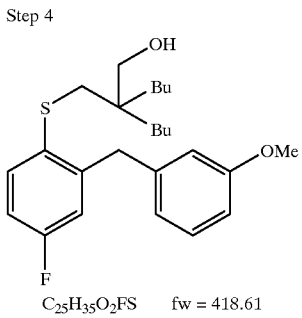

C$_{25}$H$_{35}$O$_2$FS    fw = 418.61

A 5-liter, 3-neck, round-bottom flask was equipped with N$_2$ gas adaptor and mechanical stirrer. The system was purged with N$_2$. 4-Fluoro-2-(3-methoxybenzyl)thiophenol (100.0 g/403.2 mmol) and 2-methoxyethyl ether (1.0 L) were added and the solution was cooled to 0 C. Sodium hydride (9.68 g/383.2 mmol) was added slowly, and the mixture was allowed to warm to room temperature, 2,2-Dibutylpropylene sulfate (110.89 g/443.6 mmol) was added, and the mixture was stirred for 64 h. The reaction mixture was concentrated by rotavap and dissolved in H$_2$O. The aqueous solution was washed with ethyl ether, and concentrated H$_2$SO$_4$ was added. The aqueous solution was heated to reflux for 30 min, cooled to room temperature, and extracted with ethyl ether. The ether solution was dried (MgSO$_4$), filtered, and conc'd in vacuo to give an amber oil (143.94 g/85% yield). $^1$H NMR and MS [(M+H)$^+$=419] confirm the desired structure.

Step 5

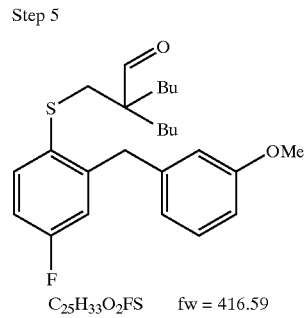

C$_{25}$H$_{33}$O$_2$FS    fw = 416.59

A 2-liter, 4-neck, round-bottom flask was equipped with N$_2$ gas adaptor, and mechanical stirrer. The system was purged with N$_2$. The corresponding alcohol (143.94 g/343.8 mmol) and CH$_2$Cl$_2$ (1.0 L) were added and cooled to 0 C. Pyridinium chlorochromate (140.53 g/651.6 mmol) was added. After 6 h., CH$_2$Cl$_2$ was added. After 20 min, the mixture was filtered through silica gel, washing with CH$_2$Cl$_2$. The filtrate was concentrated in vacuo to give a dark yellow-red oil (110.6 g, 77% yield). $^1$H NMR and MS [(M+H)$^+$=417] confirm the desired structure.

Step 6

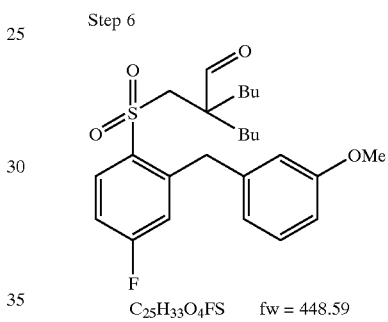

C$_{25}$H$_{33}$O$_4$FS    fw = 448.59

A 2-liter, 4-neck, round-bottom flask was equipped with N$_2$ gas adaptor, and mechanical stirrer. The system was purged with N$_2$. The corresponding sulfide (110.6 g/265.5 mmol) and CH$_2$Cl$_2$ (1.0 L) were added. The solution was cooled to 0 C., and 3-chloroperbenzoic acid (158.21 g/531.7 mmol) was added portionwise. After 30 min, the reaction mixture was allowed to warm to room temperature. After 3.5 h, the reaction mixture was cooled to 0 C. and filtered through a fine fritted funnel. The filtrate was washed with 10% aqueous K$_2$CO$_3$. An emulsion formed which was extracted with ethyl ether. The organic layers were combined, dried (MgSO$_4$), filtered, and concentrated in vacuo to give the product (93.2 g, 78% yield). $^1$H NMR confirmed the desired structure.

Step 7

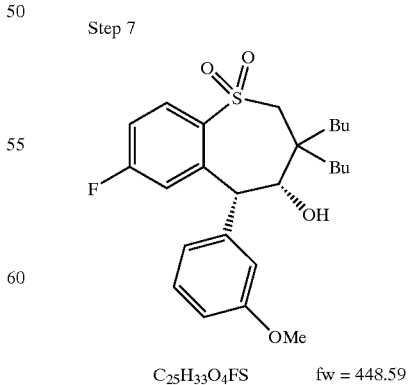

C$_{25}$H$_{33}$O$_4$FS    fw = 448.59

A 2-liter, 4-neck, round-bottom flask was equipped with N$_2$ gas adaptor, mechanical stirrer, and a powder addition funnel. The system was purged with N$_2$. The corresponding aldehyde (93.2 g/208 mmol) and THF (1.0 L) were added, and the mixture was cooled to 0 C. Potassium tert-butoxide (23.35 g/208.1 mmol) was added via addition funnel. After 1 h, 10% aq/HCl (1.0 L) was added. After 1 h, the mixture was extracted three times with ethyl ether, dried (MgSO$_4$), filtered, and concentrated in vacuo. The crude product was purified by recryst. from 80/20 hexane/ethyl acetate to give a white solid (32.18 g). The mother liquor was concentrated in vacuo and recrystelized from 95/5 toluene/ethyl acetate to give a white solid 33.60 g/combined yield: 71%). $^1$H NMR confirmed the desired product.

Step 8

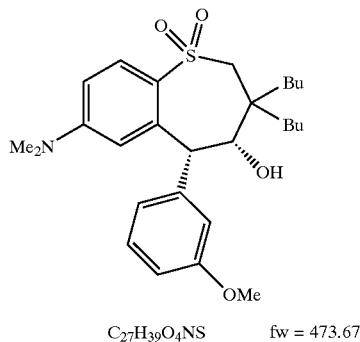

C$_{27}$H$_{39}$O$_4$NS    fw = 473.67

A Fisher porter bottle was fitted with N$_2$ line and magnetic stirrer. The system was purged with N$_2$. The corresponding fluoro-compound (28.1 g/62.6 mmol) was added, and the vessel was sealed and cooled to −78 C. Dimethylamine (17.1 g/379 mmol) was condensed via a CO$_2$/acetate bath and added to the reaction vessel. The mixture was allowed to warm to room temperature and was heated to 60 C. After 20 h, the reaction mixture was allowed to cool and was dissolved in ethyl ether. The ether solution was washed with H$_2$O, saturated aqueous NaCl, dried (MgSO$_4$), filtered, and concentrated in vacuo to give a white solid (28.5 g/96% yield). $^1$H NMR confirmed the desired structure.

Step 9

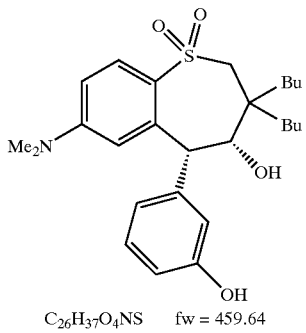

C$_{26}$H$_{37}$O$_4$NS    fw = 459.64

A 250-mL, 3-neck, round-bottom flask was equipped with N$_2$ gas adaptor and magnetic stirrer. The system was purged with N$_2$. The corresponding methoxy-compound (6.62 g/14.0 mmol) and CHCl$_3$ (150 mL) were added. The reaction mixture was cooled to −78 C., and boron tribromide (10.50 g/41.9 mmol) was added. The mixture was allowed to warm to room temperature. After 4 h, the reaction mixture was cooled to 0 C. and was quenched with 10% K$_2$CO$_3$ (100 mL). After 10 min, the layers were separated, and the aqueous layer was extracted two times with ethyl ether. The CHCl$_3$ and ether extracts were combined, washed with saturated aqueous NaCl, dried (MgSO$_4$), filtered, and con- centrated in vacuo to give the product (6.27 g/98% yield). $^1$H NMR confirmed the desired structure.

Step 10

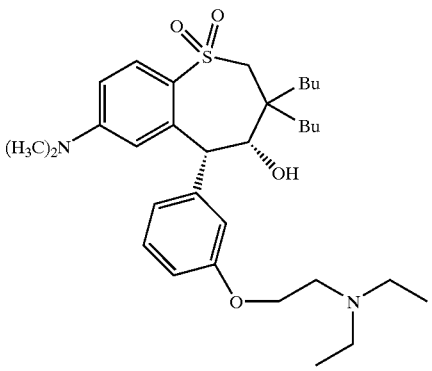

In a 250 ml single neck round bottom Flask with stir bar place 2-diethylamineoethyl chloride hydrochloride (fw 172.10 g/mole) Aldrich D8, 720-1 (2.4 mmol, 4.12 g), 34 ml dry ether and 34 ml of 1N KOH (aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, 2.6 mmol) and 34 ml of DMF. Cool to ice temperature. Next add phenol product (previous step) 1.1 g (2.4 mmilo- moles in 5 ml DMF and the ether solution prepared above. Heat to 40 C. for 3 days. The product which contained no starting material by TLC was diluted with ether and extracted with 1 portion of 5% NaOH, followed by water and then brine. The ether layer was dried over magnesium sulfate and isolated by removing ether by rotary evaporation (1.3 gms). The product may be further purified by chroma- tography (SiO2 99% ethyl acetate/1% NH4OH at 5 ml/min.) Isolated yield: 0.78 g (mass spec., and H1 NMR)

Step 11

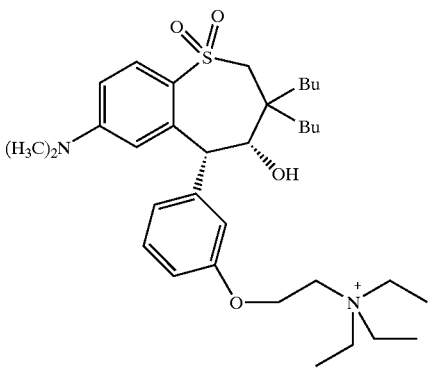

The product from step 10 (0.57 gms, 1.02 millimole fw 558.83 g/mole) and 1.6 gms iodoethane (10.02 mmol) was placed in 5 ml acetonitrile in a fischer-porter bottle and heated to 45 C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M−I=587.9, H NMR).

Example 1401

Step 1

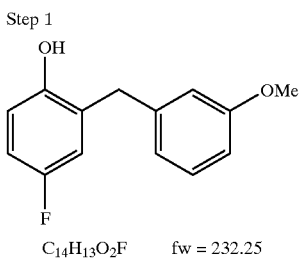

C$_{14}$H$_{13}$O$_2$F   fw = 232.25

A 12-liter, 4-neck round-bottom flask was equipped with reflux condenser, N$_2$ gas adaptor, mechanical stirrer, and an addition funnel. The system was purged with N$_2$. A slurry of sodium hydride (126.0 g/4.988 mol) in toluene (2.5 L) was added, and the mixture was cooled to 6 C. A solution of 4-fluorophenol (560.5 g/5.000 mol) in toluene (2.5 L) was added via addition funnel over a period of 2.5 h. The reaction mixture was heated to reflux (100 C.) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into H$_2$O (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aqueous KOH solutions were combined and acidified with concentrated HCl. The acidic solution was extracted three times with ethyl ether, dried over MgSO$_4$, filtered and concentrated in vacuo. The crude product was purified by Kugelrohr distillation to give a clear, colorless oil (449.0 g/39% yield). b.p.: 120–130 C./50 mtorrHg. $^1$H NMR and MS [(M+H)$^+$=233] confirmed desired structure.

Step 2

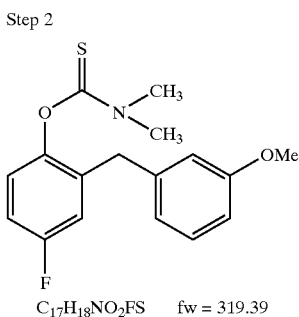

C$_{17}$H$_{18}$NO$_2$FS   fw = 319.39

A 12-liter, 3-neck round-bottom flask was fitted with mechanical stirrer and N$_2$ gas adaptor. The system was purged with N$_2$. 4-Fluoro-2-(3-methoxybenzyl)phenol (455.5 g/1.961 mol) and dimethylformamide were added. The solution was cooled to 6 C., and sodium hydride (55.5 g/2.197 mol) was added slowly. After warming to room temperature, dimethylthiocarbamoyl chloride (242.2 g/1.961 mol) was added. After 15 h, the reaction mixture was poured into H$_2$O (4.0 L), and extracted two times with ethyl ether. The combined organic layers were washed with H$_2$O and saturated aqueous NaCl, dried over MgSO$_4$, filtered, and concentrated in vacuo to give the product (605.3 g, 97% yield). $^1$H NMR and MS [(M+H)$^+$=320] confirm desired structure.

Step 3

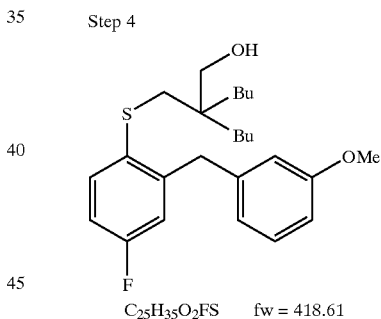

C$_{14}$H$_{13}$OFS   fw = 248.32

A 12-liter, round-bottom flask was equipped with N$_2$ gas adaptor, mechanical stirrer, and reflux condenser. The system was purged with N$_2$. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temperature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temperature, the mixture was concentrated by rotavap, dissolved in ethyl ether (1.0 L), and extracted with H$_2$O. The aqueous extracts were combined, acidified with conc. HCl, and extracted with ethyl ether. The ether extracts were dried (MgSO$_4$), filtered, and concentrated in vacuo to give an amber oil (463.0 g, 98% yield). $^1$H NMR confirmed desired structure.

Step 4

C$_{25}$H$_{35}$O$_2$FS   fw = 418.61

A 5-liter, 3-neck, round-bottom flask was equipped with N$_2$ gas adaptor and mechanical stirrer. The system was purged with N$_2$. 4-Fluoro-2-(3-methoxybenzyl)thiophenol (100.0 g/403.2 mmol) and 2-methoxyethyl ether (1.0 L) were added and the solution was cooled to 0 C. Sodium hydride (9.68 g/383.2 mmol) was added slowly, and the mixture was allowed to warm to room temperature 2,2-Dibutylpropylene sulfate (110.89 g/443.6 mmol) was added, and the mixture was stirred for 64 h. The reaction mixture was concentrated by rotavap and dissolved in H$_2$O. The aqueous solution was washed with ethyl ether, and conc. H$_2$SO$_4$ was added. The aqueous solution was heated to reflux for 30 min, cooled to room temperature, and extracted with ethyl ether. The ether solution was dried (MgSO$_4$), filtered, and concentrated in vacuo to give an amber oil (143.94 g/85% yield). $^1$H NMR and MS [(M+H)$^+$=419] confirm the desired structure.

Step 5

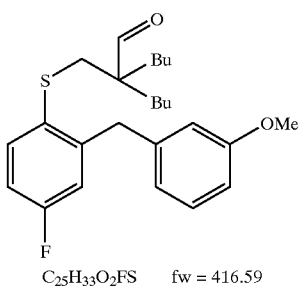

C₂₅H₃₃O₂FS    fw = 416.59

A 2-liter, 4-neck, round-bottom flask was equipped with N₂ gas adaptor, and mechanical stirrer. The system was purged with N₂. The corresponding alcohol (143.94 g/343.8 mmol) and CH₂Cl₂ (1.0 L) were added and cooled to 0 C. Pyridinium chlorochromate (140.53 g/651.6 mmol) was added. After 6 h., CH₂Cl₂ was added. After 20 min, the mixture was filtered through silica gel, washing with CH₂Cl₂. The filtrate was concentrated in vacuo to give a dark yellow-red oil (110.6 g, 77% yield). ¹H NMR and MS [(M+H)⁺=417] confirm the desired structure.

Step 6

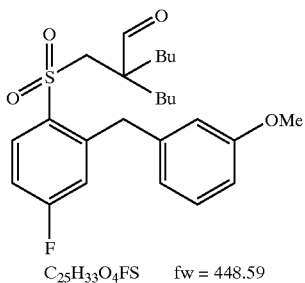

C₂₅H₃₃O₄FS    fw = 448.59

A 2-liter, 4-neck, round-bottom flask was equipped with N₂ gas adaptor and mechanical stirrer. The system was purged with N₂. The corresponding sulfide (110.6 g/265.5 mmol) and CH₂Cl₂ (1.0 L) were added. The solution was cooled to 0 C., and 3-chloroperbenzoic acid (158.21 g/531.7 mmol) was added portionwise. After 30 min, the reaction mixture was allowed to warm to room temperature. After 3.5 h, the reaction mixture was cooled to 0 C. and filtered through a fine fritted funnel. The filtrate was washed with 10% aqueous K₂CO₃. An emulsion formed which was extracted with ethyl ether. The organic layers were combined, dried (MgSO₄), filtered, and concentrated in vacuo to give the product (93.2 g, 78% yield). ¹H NMR confirmed the desired structure.

Step 7

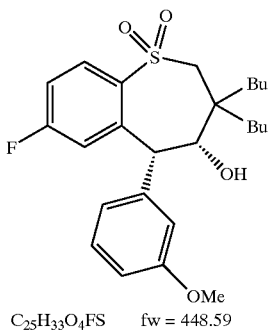

C₂₅H₃₃O₄FS    fw = 448.59

A 2-liter, 4-neck, round-bottom flask was equipped with N₂ gas adaptor, mechanical stirrer, and a powder addition funnel. The system was purged with N₂. The corresponding aldehyde (93.2 g/208 mmol) and THF (1.0 L) were added, and the mixture was cooled to 0 C. Potassium tert-butoxide (23.35 g/208.1 mmol) was added via addition funnel. After 1 h, 10% aq/HCl (1.0 L) was added. After 1 h, the mixture was extracted three times with ethyl ether, dried (MgSO₄), filtered, and concentrated in vacuo. The crude product was purified by recrystallized from 80/20 hexane/ethyl acetate to give a white solid (32.18 g). The mother liquor was concentrated in vacuo and recrystallized from 95/5 toluene/ethyl acetate to give a white solid (33.60 g, combined yield: 71%). ¹H NMR confirmed the desired product.

Step 8

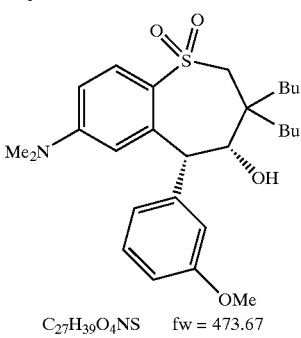

C₂₇H₃₉O₄NS    fw = 473.67

A Fisher porter bottle was fitted with N₂ line and magnetic stirrer. The system was purged with N₂. The corresponding fluoro-compound (28.1 g/62.6 mmol) was added, and the vessel was sealed and cooled to −78 C. Dimethylamine (17.1 g/379 mmol) was condensed via a CO₂/acetone bath and added to the reaction vessel. The mixture was allowed to warm to room temperature and was heated to 60 C. After 20 h, the reaction mixture was allowed to cool and was dissolved in ethyl ether. The ether solution was washed with H₂O, saturated aqueous NaCl, dried over MgSO₄, filtered, and concentrated in vacuo to give a white solid (28.5 g/96% yield). ¹H NMR confirmed the desired structure.

Step 9

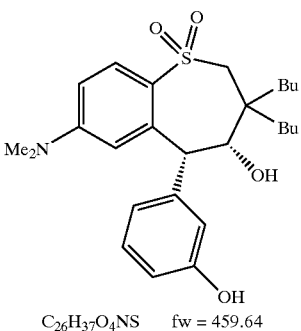

C₂₆H₃₇O₄NS    fw = 459.64

A 250-mL, 3-neck, round-bottom flask was equipped with N₂ gas adaptor and magnetic stirrer. The system was purged with N₂. The corresponding methoxy-compound (6.62 g/14.0 mmol) and CHCl₃ (150 mL) were added. The reaction mixture was cooled to −78 C., and boron tribromide (10.50 g/41.9 mmol) was added. The mixture was allowed to warm to room temperature. After 4 h, the reaction mixture was cooled to 0 C. and was quenched with 10% K₂CO₃ (100 mL). After 10 min, the layers were separated, and the aqueous layer was extracted two times with ethyl ether. The CHCl₃ and ether extracts were combined, washed with saturated aqueous NaCl, dried over MgSO₄, filtered, and concentrated in vacuo to give the product (6.27 g/98% yield). ¹H NMR confirmed the desired structure.

Step 10

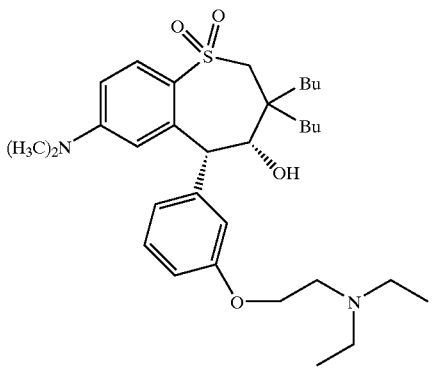

In a 250 ml single neck round bottom flask with stir bar place 2- diethylamineoethyl chloride hydrochloride (fw 172.10 g/mole). Aldrich D8, 720-1 (2.4 millimoles, 4.12 g), 34 ml dry ether and 34 ml of 1N KOH (aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, (2.6 mmol) and 34 ml of DMF. Cool to ice temperature. Next add phenol product (previous step) 1.1 g (2.4 mmol in 5 ml DMF and the ether solution prepared above. Heat to 40° C. for 3 days. The product which contained no starting material by TLC was diluted with ether and extracted with 1 portion of 5% NaOH, followed by water and then brine. The ether layer was dried over Magnesium sulfate and isolated by removing ether by rotary evaporation (1.3 gms). The product may be further purified by chromatography (silica 99% ethyl acetate/1% NH4OH at 5 ml/min.). Isolated yield: 0.78 g (mass spec, and H1 NMR)

Step 11

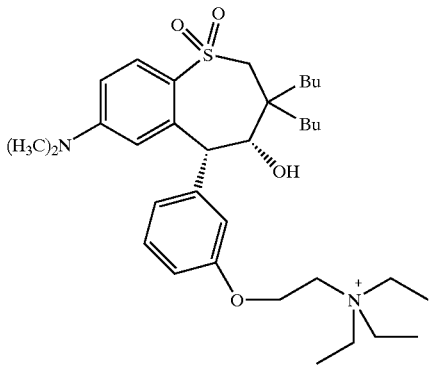

The product from step 10 (0.57 gms, 1.02 millimole fw 558.83 g/mole) and iodoethane (1.6 gms (10.02 mmol) was place in 5 ml acetonitrile in a Fischer-Porter bottle and heated to 45 C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M-I=587.9, ¹H NMR).

BIOLOGICAL ASSAYS

The utility of the compounds of the present invention is shown by the following assays. These assays are performed in vitro and in animal models essentially using a procedure recognized to show the utility of the present invention.

In Vitro Assay of compounds that inhibit IBAT-mediate uptake of [¹⁴C]-taurocholate (TC) in H14 Cells Baby hamster kidney cells (BHK) transfected with the cDNA of human IBAT (H14 cells) are seeded at 60,000 cells/well in 96 well Top-Count tissue culture plates for assays run within in 24 hours of seeding, 30,000 cells/well for assays run within 48 hours, and 10,000 cells/well for assays run within 72 hours.

On the day of assay, the cell monolayer is gently washed once with 100 ml assay buffer (Dulbecco's Modified Eagle's medium with 4.5 g/L glucose+0.2% (w/v) fatty acid free bovine serum albumin- (FAF)BSA). To each well 50 ml of a two-fold concentrate of test compound in assay buffer is added along with 50 ml of 6 mM [¹⁴C]-taurocholate in assay buffer (final concentration of 3 mM [¹⁴C]-taurocholate). The cell culture plates are incubated 2 hours at 37° C. prior to gently washing each well twice with 100 ml 4° C. Dulbecco's phosphate-buffered saline (PBS) containing 0.2% (w/v) (FAF)BSA. The wells are then gently washed once with 100 ml 4° C. PBS without (FAF)BSA. To each 200 ml of liquid scintillation counting fluid is added, the plates are heat sealed and shaken for 30 minutes at room temperature prior to measuring the amount of radioactivity in each well on a Packard Top-Count instrument.

In Vitro Assay of compounds that inhibit uptake of [¹⁴C]-Alanine

The alanine uptake assay is performed in an identical fashion to the taurocholate assay, with the exception that labeled alanine is substituted for the labeled taurocholate.

In Vivo Assay of compounds that inhibit Rat Ileal uptake of [¹⁴C]-Taurocholate into Bile (See "Metabolism of 3a, 7b-dihydroxy-7a-methyl-5b-cholanoic acid and 3a, 7b-dihydroxy-7a-methyl-5b-cholanoic acid in hamsters" in Biochimica et Biophysica Acta 833 (1985) 196–202 by Une et al.)

Male wistar rats (200–300 g) are anesthetized with inactin @100 mg/kg. Bile ducts are cannulated with a 10" length in PE10 tubing. The small intestine is exposed and laid out on a gauze pad. A canulae (⅛" luer lock, tapered female adapter) is inserted at 12 cm from the junction of the small intestine and the cecum. A slit is cut at 4 cm from this same junction (utilizing a 8 cm length of ileum). 20 ml of warm Dulbecco's phosphate buffered saline, pH 6.5 (PBS) is used to flush out the intestine segment. The distal opening is cannulated with a 20 cm length of silicone tubing (0.02" I.D.x0.037" O.D.). The proximal cannulae is hooked up to a peristaltic pump and the intestine is washed for 20 min with warm PBS at 0.25 ml/min. Temperature of the gut segment is monitored continuously. At the start of the experiment, 2.0 ml of controls ample ([¹⁴C]-taurocholate @ 0.05 mi/ml with 5 mM cold taurocholate) is loaded into the gut segment with a 3 ml syringe and bile sample collection is begun. Control sample is infused at a rate of 0.25 ml/min for 21 min. Bile samples fractions are collected every 3 minute for the first 27 minutes of the procedure. After the 21 min of sample infusion, the ileal loop is washed out with 20 ml of warm PBS (using a 30 ml syringe), and then the loop is washed out for 21 min with warm PBS at 0.25 ml/min. A second perfusion is initiated as described above but this with test compound being administered as well (21 min administration followed by 21 min of wash out) and bile sampled every 3 min for the first 27 min. If necessary, a third perfusion is performed as above that typically contains the control sample.

Measurement of Hepatic Cholesterol Concentration (HEPATIC CHOL)

Liver tissue was weighed and homogenized in chloroform:methanol (2:1). After homogenization and centrifugation the supernatant was separated and dried under nitrogen. The residue was dissolved in isopropanol and the cholesterol content was measured enzymatically, using a combination of cholesterol oxidase and peroxidase, as described by Allain, C. A., et al. (1974) *Clin. Chem.* 20, 470.

Measurement of Hepatic HMG CoA-Reductase Activity (HMG COA)

Hepatic microsomes were prepared by homogenizing liver samples in a phosphate/sucrose buffer, followed by centrifugal separation. The final pelleted material was resuspended in buffer and an aliquot was assayed for HMG CoA reductase activity by incubating for 60 minutes at 37° C. in the presence of $^{14}$C-HMG-CoA (Dupont-NEN). The reaction was stopped by adding 6N HCl followed by centrifugation. An aliquot of the supernatant was separated, by thin-layer chromatography, and the spot corresponding to the enzyme product was scraped off the plate, extracted and radioactivity was determined by scintillation counting. (Reference: Akerlund, J. and Bjorkhem, I. (1990) *J. Lipid Res.* 31, 2159).

Determination of Serum Cholesterol (SER.CHOL, HDL-CHOL, TGI and VLDL+LDL)

Total serum cholesterol (SER.CHOL) was measured enzymatically using a commercial kit from Wako Fine Chemicals (Richmond, Va.); Cholesterol C11, Catalog No. 276-64909. HDL cholesterol (HDL-CHOL) was assayed using this same kit after precipitation of VLDL and LDL with Sigma Chemical Co. HDL Cholesterol reagent, Catalog No. 352-3 (dextran sulfate method). Total serum triglycerides (blanked) (TGI) were assayed enzymatically with Sigma Chemical Co. GPO-Trinder, Catalog No. 337-B. VLDL and LDL (VLDL+LDL) cholesterol concentrations were calculated as the difference between total and HDL cholesterol.

Measurement of Hepatic Cholesterol 7-a-Hydroxylase Activity (7a-OHase)

Hepatic microsomes were prepared by homogenizing liver samples in a phosphate/sucrose buffer, followed by centrifugal separation. The final pelleted material was resuspended in buffer and an aliquot was assayed for cholesterol 7-a-hydroxylase activity by incubating for 5 minutes at 37° C. in the presence of NADPH. Following extraction into petroleum ether, the organic solvent was evaporated and the residue was dissolved in acetonitrile/methanol. The enzymatic product was separated by injecting an aliquot of the extract onto a $C_{18}$ reversed phase HPLC column and quantitating the eluted material using UV detection at 240 nm. (Reference: Horton, J. D., et al. (1994) *J. Clin. Invest.* 93, 2084).

Measurement of Fecal Bile Acid Concentration (FBA)

Total fecal output from individually housed hamsters was collected for 24 or 48 hours, dried under a stream of nitrogen, pulverized and weighed. Approximately 0.1 gram was weighed out and extracted into an organic solvent (butanol/water). Following separation and drying, the residue was dissolved in methanol and the amount of bile acid present was measured enzymatically using the 3a-hydroxysteroid steroid dehydrogenase reaction with bile acids to reduce NAD. (Reference: Mashige, F., et al. (1981) *Clin. Chem.* 27, 1352).

[$^3$H]Taurocholate Uptake in Rabbit Brush Border Membrane Vesicles (BBMV)

Rabbit Ileal brush border membranes were prepared from frozen ileal mucosa by the calcium precipitation method describe by Malathi et al. (Reference: (1979) *Biochimica Biophysica Acta*, 554, 259). The method for measuring taurocholate was essentially as described by Kramer et al. (Reference: (1992) *Biochimica Biophysica Acta*, 1111, 93) except the assay volume was 200 $\mu$l instead of 100 $\mu$l. Briefly, at room temperature a 190 $\mu$l solution containing 2 $\mu$M [$^3$H]-taurocholate (0.75 $\mu$Ci), 20 mM tris, 100 mM NaCl, 100 mM mannitol pH 7.4 was incubated for 5 sec with 10 $\mu$l of brush border membrane vesicles (60–120 $\mu$g protein). The incubation was initiated by the addition of the BBMV while vortexing and the reaction was stopped by the addition of 5 ml of ice cold buffer (20 mM Hepes-tris, 150 mM Kcl) followed immediately by filtration through a nylon filter (0.2 $\mu$m pore) and an additional 5 ml wash with stop buffer.

Acyl-CoA;cholesterol Acyl Transferase (ACAT)

Hamster liver and rat intestinal microsomes were prepared from tissue as described previously (Reference: (1980) *J. Biol. Chem.* 255, 9098) and used as a source of ACAT enzyme. The assay consisted of a 2.0 ml incubation containing 24 $\mu$M Oleoyl-CoA (0.05 $\mu$Ci) in a 50 mM sodium phosphate, 2 mM DTT ph 7.4 buffer containing 0.25% BSA and 200 $\mu$g of microsomal protein. The assay was initiated by the addition of oleoyl-CoA. The reaction went for 5 min at 37° C. and was terminated by the addition of 8.0 ml of chloroform/methanol (2:1). To the extraction was added 125 $\mu$g of cholesterol oleate in chloroform methanol to act as a carrier and the organic and aqueous phases of the extraction were separated by centrifugation after thorough vortexing. The chloroform phase was taken to dryness and then spotted on a silica gel 60 TLC plate and developed in hexane/ethyl ether (9:1). The amount of cholesterol ester formed was determined by measuring the amount of radioactivity incorporated into the cholesterol oleate spot on the TLC plate with a Packard instaimager.

Data from each of the noted compounds in the assays described above is as set forth in TABLES 5, 6, 7, and 8 as follows:

TABLE 5

| COMPOUND | IC50 μM* | In vitro % Inhibition of TC Uptake @ 100 μM # | % Inhibition of Alanine Uptake @ 100 μM # | % of Control Transport of TC in Rat Ileum @ 0.1 mM |
|---|---|---|---|---|
| Benzothiazepine = | 2 | | 0 | 45.4 +/- 0.7 |
| 12 | | 25 | | |
| 3 | | 0 | | |
| 4a | | 3 | | |
| 5a | | 34 | | |
| 5b | 40 | | 0 | 72.9 ± 5.4 @ 0.5 mM |
| 4b | | 9 | | |
| 18 | | 6 | | |
| 14b | | 18 | | |
| 14a | | 13 | | |
| 13 | | 23 | | |
| 15 | 60 | | | |
| 19a | | 0 | | |
| 19b | | 15 | | |
| 8a | | 41 | | |
| Mixture of 8a and 8b | | 69 | | |
| Mixture of 9a and 9b | 6 | | | |
| 6a | 5 | | | |
| 6b | | 85 | | |
| 9a | 5 | | 0% @ 25 mM | 53.7 +/- 3.3 |
| Mixture of 6a and 20 | 13 | | | |
| Mixture of 6d and 10a | 0.8 | | 14% @ 25 | |
| 21a | | 37 | | |
| 21c | | 52 | | |
| 21b | | 45 | | |
| 6c | 2 | | 58.5 | 68.8 +/- 5.7 at 0.4 mM |
| 6d | 0.6 | | 77.7 | 16.1 +/- 1.1 @ 0.5 mM |
| | | | | 30.2 +/- 0.9 @ 0.15 mM |
| 17 | | 10 | | |
| 7 | 50 | | 49.3 | |
| 10a | 7 | | 77.6 | 62.4 =/- 2.5 @ 0.2 mM |
| 10b | 15 | | 68.6 | |
| 25 | 0.1 | | 4% @ 10 mM | 26.0 +/- 3.3 |
| 26 | 2 | | 31% @ 25 mM | 87.9 +/- 1.5 |
| 27 | 5 | | 7% @ 20 mM | |
| 28 | 8 | | 31% @ 20 mM | |
| 29 | | 88 @ 50 mM | | |
| 30 | | 96 @ 50 mM | | |
| 31 | | 41 @ 50 mM | | |
| 37 | 3 | | 0% @ 5 mM | |
| 38 | 0.3 | | 11% @ 5 mM | 20.6 +/- 5.7 |
| 40 | | 49 @ 50 mM | | |
| 41 | 2 | | 0% @ 20 mM | |
| 42 | 1.5 | | | |
| 43 | 1.5 | | 16% @ 25 mM | |
| 48 | 2 | | 22% @ 20 mM | |
| 49 | 0.15 | | 21% @ 200 mM | 21.2 +/- 2.7 |
| 57 | | 51 @ 50 mM | | |
| 58 | | 20 @ 50 mM | | |
| 59 | 70 | | | |
| 60 | 9 | | 59 | |
| 61 | 30 | | 175 | |
| 62 | 10 | | | |
| 63 | | 90 @ 6 mM | | |
| 64 | 1 | | 100 @ 6 mM | |

*In vitro Taurocholate Cell Uptake
Unless otherwise noted
= Comparative Example is Example No. 1 in WO 93/16055

TABLE 6

| Compound | TC-uptake (H14 cells) IC(50) | TC-uptake Ileal Loop EC(50) | TC-uptake (BBMV) IC(50) | ACAT (liver) IC(50) | ACAT intestine IC(50) |
|---|---|---|---|---|---|
| COMP. EXAMPLE | 1 mM | 74 mM | 3 mM | 20 mM | 20 mM |
| 6d | 0.6 mM | 31 mM | 1.5 mM | 25 mM | 20 mM |
| 38 | 0.3 mM | 12 mM | 2 mM | 15 mM | N.D. |
| 49 | 0.1 mM | 12 mM | N.D. | 6 mM | N.D. |
| 25 | 0.1 mM | 20 mM | 0.8 mM | 8 mM | 8 mM |

Comparative Example is Example No. 1 in WO 93/16055

TABLE 7

| PARAMETER | CONTROL | 4% CHOLES-TYRAMINE | 0.2% CPD. NO. 25 |
|---|---|---|---|
| WEIGHT (G) | | | |
| day 1 | 117 (2) | 114 (6) | 117 (5) |
| day 14 | 127 (3) | 127 (3) | 132 (4) |
| LIVER WEIGHT (G) | 5.4 (0.3) | 4.9 (0.4) | 5.8 (0.2) |
| SER. CHOL (mg %) | 143 (7) | 119 (4)*A,B | 126 (2)*A,B |
| HDL-CHOL (mg %) | 89 (4) | 76 (3)*A,B | 76 (1)*A,B. |
| VLDL + LDL | 54 (7) | 42 (3)*A | 50 (3) |
| TGI (mg %) | 203 (32) | 190 (15) | 175 (11) |
| HEPATIC CHOL (mg/g) | 2.5 (0.3) | 1.9 (0.1)*A,B | 1.9 (0.1)*A,B |
| HMG COA (pm/mg/min.) | 15.8 (7.6) | 448.8 (21.6)*A,B | 312.9 (37.5)*A,B |
| 7a-OHase (pm/mg/min.) | 235.3 (25.1) | 357.2 (28.3)*A,B | 291.0 (6.0)*A |
| 24 HR. FECAL Wt (G) | 273 (0.1) | 2.7 (0.1)*AB | 2.4 (0.04) |
| FBA (mM/ 24 H/100 g) | 6.2 (0.8) | 12.3 (1.5)*A,B | 11.9 (0.5)*A,B |

(mean ± SEM, *p < 0.05, A-Student's t, B-Dunnett's)

TABLE 8

EFFICACY OF COMPOUND NO. 25 IN RAT ALZET MINIPUMP MODEL

| PARAMETER | CONTROL | 20 MPL/DAY CPD. NO. 25 |
|---|---|---|
| WEIGHT (G) | | |
| day 1 | 307 (4) | 307 (3) |
| day 8 | 330 (4) | 310 (4)*A,B |
| LIVER WEIGHT (G) | 15.5 (0.6) | 14.6 (0.4) |
| SER. CHOL (mg %) | 85 (3) | 84 (3) |
| HEPATIC CHOL (mg/g) | 21 (0.03) | 2.0 (0.03) |
| HMG COA pm/mg/min | 75.1 (6.4) | 318.0 (40.7)*A,B |
| 7a-OHase (pm/mg/min) | 281.9 (13.9) | 535.2 (35.7)*A,B |
| 24 HR. FECAL WT (G) | 5.8 (0.1) | 5.7 (0.4) |
| FBA (mM/24 H/100 g) | 17.9 (0.9) | 39.1 (4.5)*A,B |

(Mean ± SEM, *p < 0.05, A-Student's t, B-Dunnett's)

Additional taurocholate uptake tests were conducted in the following compounds listed in Table 9.

TABLE 9

Biological Assay Data for Some Compounds of the Present Invention

| Compound Number | Human TC IC$_{50}$ ($\mu$M) | Alanine Uptake Percent Inhibition @ $\mu$M |
|---|---|---|
| 101 | | 0 @ 1.0 |
| 102 | 0.083 | |
| 103 | | 13 @ 0.25 |
| 104 | 0.0056 | |
| 105 | 0.6 | |
| 106 | 0.8 | |
| 107 | | 14.0 @ 0.063 |
| 108 | 0.3 | |
| 109 | | 2.0 @ 0.063 |
| 110 | 0.09 | |
| 111 | 2.5 | |
| 112 | 3.0 | |
| 113 | 0.1 | |
| 114 | 0.19 | |
| 115 | 8 | |
| 116 | 0.3 | |
| 117 | | 12.0 @ 0.625 |
| 118 | 0.4 | |
| 119 | 1.3 | |
| 120 | | 34.0 @ 5.0 |
| 121 | 0.068 | |
| 122 | 1.07 | |
| 123 | 1.67 | |
| 124 | | 14.0 @ 6.25 |
| 125 | 18.0 | |
| 126 | | 18 @ 1.25 |
| 127 | 0.55 | |
| 128 | 0.7 | |
| 129 | 0.035 | |
| 131 | 1.25 | |
| 132 | | 5.4 @ 0.063 |
| 133 | 16.0 | |
| 134 | 0.3 | |
| 135 | 22.0 | |
| 136 | 0.09 | |
| 137 | 2.4 | |
| 138 | 3.0 | |
| 139 | >25.0 | |
| 142 | 0.5 | |
| 143 | 0.03 | |
| 144 | 0.053 | |
| 262 | 0.07 | |
| 263 | 0.7 | |
| 264 | 0.2 | |
| 265 | 2.0 | |
| 266 | 0.5 | |
| 267 | 0.073 | |
| 268 | 0.029 | |
| 269 | 0.08 | |
| 270 | 0.12 | |
| 271 | 0.07 | |
| 272 | 0.7 | |
| 273 | 1.9 | |
| 274 | 0.18 | |
| 275 | | 5.0 @ 0.25 |
| 276 | 0.23 | |
| 277 | 0.04 | |
| 278 | 3.0 | |
| 279 | 0.4 | |
| 280 | 0.18 | |
| 281 | 0.019 | |
| 282 | 0.021 | |
| 283 | 0.35 | |
| 284 | 0.08 | |
| 286 | 19.0 | |
| 287 | 4.0 | |
| 288 | | 10.0 @ 6.25 |
| 289 | 0.23 | |
| 290 | 0.054 | |
| 291 | 0.6 | |
| 292 | 0.046 | |
| 293 | 1.9 | |
| 294 | 0.013 | |
| 295 | 1.3 | |
| 296 | 1.6 | |
| 1005 | 0.0004 | |
| 1006 | 0.001 | |
| 1007 | 0.001 | |
| 1008 | 0.001 | |
| 1009 | 0.001 | |
| 1010 | 0.001 | |
| 1011 | 0.001 | |
| 1012 | 0.0015 | |
| 1013 | 0.002 | |
| 1014 | 0.002 | |
| 1015 | 0.002 | |
| 1016 | 0.002 | |
| 1017 | 0.002 | |
| 1018 | 0.002 | |
| 1019 | 0.002 | |
| 1020 | 0.002 | |
| 1021 | 0.002 | |
| 1022 | 0.002 | |
| 1023 | 0.002 | |
| 1024 | 0.002 | |
| 1025 | 0.002 | |
| 1026 | 0.002 | |
| 1027 | 0.002 | |
| 1028 | 0.002 | |
| 1029 | 0.002 | |
| 1030 | 0.002 | |
| 1031 | 0.002 | |
| 1032 | 0.002 | |
| 1033 | 0.002 | |
| 1034 | 0.002 | |
| 1035 | 0.002 | |
| 1036 | 0.002 | |
| 1037 | 0.0022 | |
| 1038 | 0.0025 | |
| 1039 | 0.0026 | |
| 1040 | 0.003 | |
| 1041 | 0.003 | |
| 1042 | 0.003 | |
| 1043 | 0.003 | |
| 1044 | 0.003 | |
| 1045 | 0.003 | |
| 1046 | 0.003 | |
| 1047 | 0.003 | |
| 1048 | 0.003 | |
| 1049 | 0.003 | |
| 1050 | 0.003 | |
| 1051 | 0.003 | |
| 1052 | 0.003 | |
| 1053 | 0.003 | |
| 1054 | 0.003 | |
| 1055 | 0.003 | |
| 1056 | 0.003 | |
| 1057 | 0.003 | |
| 1058 | 0.003 | |
| 1059 | 0.003 | |
| 1060 | 0.0036 | |
| 1061 | 0.004 | |
| 1062 | 0.004 | |
| 1063 | 0.004 | |
| 1064 | 0.004 | |
| 1065 | 0.004 | |
| 1066 | 0.004 | |
| 1067 | 0.004 | |
| 1068 | 0.004 | |
| 1069 | 0.004 | |
| 1070 | 0.004 | |

TABLE 9-continued

Biological Assay Data for Some Compounds of the Present Invention

| Compound Number | Human TC IC$_{50}$ ($\mu$M) | Alanine Uptake Percent Inhibition @ $\mu$M |
|---|---|---|
| 1071 | 0.004 | |
| 1072 | 0.004 | |
| 1073 | 0.004 | |
| 1074 | 0.004 | |
| 1075 | 0.0043 | |
| 1076 | 0.0045 | |
| 1077 | 0.0045 | |
| 1078 | 0.0045 | |
| 1079 | 0.005 | |
| 1080 | 0.005 | |
| 1081 | 0.005 | |
| 1082 | 0.005 | |
| 1083 | 0.005 | |
| 1084 | 0.005 | |
| 1085 | 0.005 | |
| 1086 | 0.005 | |
| 1087 | 0.005 | |
| 1088 | 0.0055 | |
| 1089 | 0.0057 | |
| 1090 | 0.006 | |
| 1091 | 0.006 | |
| 1092 | 0.006 | |
| 1093 | 0.006 | |
| 1094 | 0.006 | |
| 1095 | 0.006 | |
| 1096 | 0.006 | |
| 1097 | 0.006 | |
| 1098 | 0.006 | |
| 1099 | 0.0063 | |
| 1100 | 0.0068 | |
| 1101 | 0.007 | |
| 1102 | 0.007 | |
| 1103 | 0.007 | |
| 1104 | 0.007 | |
| 1105 | 0.007 | |
| 1106 | 0.0073 | |
| 1107 | 0.0075 | |
| 1108 | 0.0075 | |
| 1109 | 0.008 | |
| 1110 | 0.008 | |
| 1111 | 0.008 | |
| 1112 | 0.008 | |
| 1113 | 0.009 | |
| 1114 | 0.009 | |
| 1115 | 0.0098 | |
| 1116 | 0.0093 | |
| 1117 | 0.01 | |
| 1118 | 0.01 | |
| 1119 | 0.01 | |
| 1120 | 0.01 | |
| 1121 | 0.01 | |
| 1122 | 0.011 | |
| 1123 | 0.011 | |
| 1124 | 0.011 | |
| 1125 | 0.012 | |
| 1126 | 0.013 | |
| 1127 | 0.013 | |
| 1128 | 0.017 | |
| 1129 | 0.018 | |
| 1130 | 0.018 | |
| 1131 | 0.02 | |
| 1132 | 0.02 | |
| 1133 | 0.02 | |
| 1134 | 0.02 | |
| 1135 | 0.021 | |
| 1136 | 0.021 | |
| 1137 | 0.021 | |
| 1138 | 0.022 | |
| 1139 | 0.022 | |
| 1140 | 0.023 | |
| 1141 | 0.023 | |
| 1142 | 0.024 | |
| 1143 | 0.027 | |
| 1144 | 0.028 | |
| 1145 | 0.029 | |
| 1146 | 0.029 | |
| 1147 | 0.029 | |
| 1148 | 0.03 | |
| 1149 | 0.03 | |
| 1150 | 0.03 | |
| 1151 | 0.031 | |
| 1152 | 0.036 | |
| 1153 | 0.037 | |
| 1154 | 0.037 | |
| 1155 | 0.039 | |
| 1156 | 0.039 | |
| 1157 | 0.04 | |
| 1158 | 0.06 | |
| 1159 | 0.06 | |
| 1160 | 0.062 | |
| 1161 | 0.063 | |
| 1162 | 0.063 | |
| 1163 | 0.09 | |
| 1164 | 0.093 | |
| 1165 | 0.11 | |
| 1166 | 0.11 | |
| 1167 | 0.12 | |
| 1168 | 0.12 | |
| 1169 | 0.12 | |
| 1170 | 0.13 | |
| 1171 | 0.14 | |
| 1172 | 0.14 | |
| 1173 | 0.15 | |
| 1174 | 0.15 | |
| 1175 | 0.17 | |
| 1176 | 0.18 | |
| 1177 | 0.18 | |
| 1178 | 0.19 | |
| 1179 | 0.19 | |
| 1180 | 0.2 | |
| 1181 | 0.22 | |
| 1182 | 0.25 | |
| 1183 | 0.28 | |
| 1184 | 0.28 | |
| 1185 | 0.28 | |
| 1186 | 0.3 | |
| 1187 | 0.32 | |
| 1188 | 0.35 | |
| 1189 | 0.35 | |
| 1190 | 0.55 | |
| 1191 | 0.65 | |
| 1192 | 1.0 | |
| 1193 | 1.0 | |
| 1194 | 1.6 | |
| 1195 | 1.7 | |
| 1196 | 2.0 | |
| 1197 | 2.2 | |
| 1198 | 2.5 | |
| 1199 | 4.0 | |
| 1200 | 6.1 | |
| 1201 | 8.3 | |
| 1202 | 40.0 | |
| 1203 | | 0 @ 0.063 |
| 1204 | 0.05 | |
| 1205 | 0.034 | |
| 1206 | 0.035 | |
| 1207 | 0.068 | |
| 1208 | 0.042 | |
| 1209 | | 0 @ 0.063 |
| 1210 | 0.14 | |
| 1211 | 0.28 | |
| 1212 | 0.39 | |
| 1213 | 1.7 | |
| 1214 | 0.75 | |

TABLE 9-continued

Biological Assay Data for Some Compounds of the Present Invention

| Compound Number | Human TC IC$_{50}$ ($\mu$M) | Alanine Uptake Percent Inhibition @ $\mu$M |
|---|---|---|
| 1215 | 0.19 | |
| 1216 | 0.39 | |
| 1217 | 0.32 | |
| 1218 | 0.19 | |
| 1219 | 0.34 | |
| 1220 | 0.2 | |
| 1221 | 0.041 | |
| 1222 | 0.065 | |
| 1223 | 0.28 | |
| 1224 | 0.33 | |
| 1225 | 0.12 | |
| 1226 | 0.046 | |
| 1227 | 0.25 | |
| 1228 | 0.038 | |
| 1229 | 0.049 | |
| 1230 | 0.062 | |
| 1231 | 0.075 | |
| 1232 | 1.2 | |
| 1233 | 0.15 | |
| 1234 | 0.067 | |
| 1235 | 0.045 | |
| 1236 | 0.05 | |
| 1237 | 0.07 | |
| 1238 | 0.8 | |
| 1239 | 0.035 | |
| 1240 | 0.016 | |
| 1241 | 0.047 | |
| 1242 | 0.029 | |
| 1243 | 0.63 | |
| 1244 | 0.062 | |
| 1245 | 0.32 | |
| 1246 | 0.018 | |
| 1247 | 0.017 | |
| 1248 | 0.33 | |
| 1249 | 10.2 | |
| 1250 | 0.013 | |
| 1251 | 0.62 | |
| 1252 | 29. | |
| 1253 | 0.3 | |
| 1254 | 0.85 | |
| 1255 | 0.69 | |
| 1256 | 0.011 | |
| 1257 | 0.1 | |
| 1258 | 0.12 | |
| 1259 | 16.5 | |
| 1260 | 0.012 | |
| 1261 | 0.019 | |
| 1262 | 0.03 | |
| 1263 | 0.079 | |
| 1264 | 0.21 | |
| 1265 | 0.24 | |
| 1266 | 0.2 | |
| 1267 | 0.29 | |
| 1268 | 0.035 | |
| 1269 | 0.024 | |
| 1270 | 0.024 | |
| 1271 | 0.011 | |
| 1272 | 0.047 | |
| 1273 | 0.029 | |
| 1274 | 0.028 | |
| 1275 | 0.024 | |
| 1276 | 0.029 | |
| 1277 | 0.018 | |
| 1278 | 0.017 | |
| 1279 | 0.028 | |
| 1280 | 0.76 | |
| 1281 | 0.055 | |
| 1282 | 0.17 | |
| 1283 | 0.17 | |
| 1284 | 0.011 | |
| 1285 | 0.027 | |
| 1286 | 0.068 | |
| 1287 | 0.071 | |
| 1288 | 0.013 | |
| 1289 | 0.026 | |
| 1290 | 0.017 | |
| 1291 | 0.013 | |
| 1292 | 0.025 | |
| 1293 | 0.019 | |
| 1294 | 0.011 | |
| 1295 | 0.014 | |
| 1296 | 0.063 | |
| 1297 | 0.029 | |
| 1298 | 0.018 | |
| 1299 | 0.012 | |
| 1300 | 1.0 | |
| 1301 | 0.15 | |
| 1302 | 1.4 | |
| 1303 | 0.26 | |
| 1304 | 0.25 | |
| 1305 | 0.25 | |
| 1306 | 1.2 | |
| 1307 | 3.1 | |
| 1308 | 0.04 | |
| 1309 | 0.24 | |
| 1310 | 1.16 | |
| 1311 | 3.27 | |
| 1312 | 5.0 | |
| 1313 | 6.1 | |
| 1314 | 0.26 | |
| 1315 | 1.67 | |
| 1316 | 3.9 | |
| 1317 | 21.0 | |
| 1319 | | 11.0 @ 0.25 |
| 1321 | | 11.1 @ 5.0 |
| 1322 | | 3.0 @ 0.0063 |
| 1323 | | 4.0 @ 0.0063 |
| 1324 | | 43.0 @ 0.0008 |
| 1325 | | 1.0 @ 0.0063 |
| 1326 | | 36.0 @ 0.0008 |
| 1327 | | 3.0 @ 0.0063 |
| 1328 | | 68.0 @ 0.0063 |
| 1329 | | 2.0 @ 0.0063 |
| 1330 | | 9.0 @ 0.0063 |
| 1331 | | 57.0 @ 0.0008 |
| 1332 | | 43.0 @ 0.0008 |
| 1333 | | 0 @ 0.0063 |
| 1334 | | 50.0 @ 0.0008 |
| 1335 | | 38.0 @ 0.0008 |
| 1336 | | 45.0 @ 0.0008 |
| 1337 | | 0 @ 0.0063 |
| 1338 | | 1.0 @ 0.25 |
| 1339 | | 0 @ 0.063 |
| 1340 | | 9.0 @ 0.063 |
| 1341 | | 1.0 @ 0.063 |
| 1342 | | 1.0 @ 0.063 |
| 1345 | | 13.0 @ 0.25 |
| 1347 | 0.0036 | |
| 1351 | 0.44 | |
| 1352 | 0.10 | |
| 1353 | 0.0015 | |
| 1354 | 0.006 | |
| 1355 | 0.0015 | |
| 1356 | 0.22 | |
| 1357 | 0.023 | |
| 1358 | 0.008 | |

TABLE 9-continued

Biological Assay Data for Some Compounds of the Present Invention

| Compound Number | Human TC IC$_{50}$ ($\mu$M) | Alanine Uptake Percent Inhibition @ $\mu$M |
|---|---|---|
| 1359 | 0.014 | |
| 1360 | 0.003 | |
| 1361 | 0.004 | |
| 1362 | 0.019 | |
| 1363 | 0.008 | |
| 1364 | 0.006 | |
| 1365 | 0.008 | |
| 1366 | 0.015 | |
| 1367 | 0.002 | |
| 1368 | 0.005 | |
| 1369 | 0.003 | |
| 1370 | 0.002 | |
| 1371 | 0.004 | |
| 1372 | 0.004 | |
| 1373 | 0.008 | |
| 1374 | 0.007 | |
| 1375 | 0.002 | |
| 1449 | 0.032 | |
| 1450 | 0.039 | |
| 1451 | 0.014 | |

The examples herein can be repeated with similar success by substituting the generically or specifically described reactants and/or operating conditions of this invention for those used in the preceding examples.

Novel compositions of the invention are further illustrated in attached Exhibits A and B.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

TABLE C2

Alternative compounds #2 (Families F101–F123)

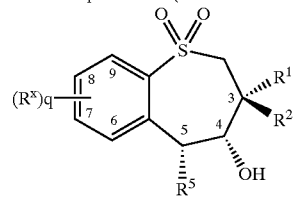

| Family Cpd# | R$^1$=R$^2$ | R$^5$ | (R$^x$)q |
|---|---|---|---|
| F101 | CHOSEN FROM TABLE D* | Ph— | CHOSEN FROM TABLE D |
| F102 | CHOSEN FROM TABLE D | p-F—Ph— | CHOSEN FROM TABLE D |
| F103 | CHOSEN FROM TABLE D | m-F—Ph— | CHOSEN FROM TABLE D |
| F104 | CHOSEN FROM TABLE D | p-CH$_3$O—Ph— | CHOSEN FROM TABLE D |
| F105 | CHOSEN FROM TABLE D | m-CH$_3$O—Ph— | CHOSEN FROM TABLE D |
| F106 | CHOSEN FROM TABLE D | p-(CH$_3$)$_2$N—Ph— | CHOSEN FROM TABLE D |
| F107 | CHOSEN FROM TABLE D | m-(CH$_3$)$_2$N—Ph | CHOSEN FROM TABLE D |
| F108 | CHOSEN FROM TABLE D | I$^-$, p-(CH$_3$)$_3$—N$^+$—Ph— | CHOSEN FROM TABLE D |
| F109 | CHOSEN FROM TABLE D | I$^-$, m-(CH$_3$)$_3$—N$^+$—Ph— | CHOSEN FROM TABLE D |
| F110 | CHOSEN FROM TABLE D | I$^-$, p-(CH$_3$)$_3$—N$^+$—CH$_2$CH$_2$—(OCH$_2$CH$_2$)$_2$—O—Ph— | CHOSEN FROM TABLE D |
| F111 | CHOSEN FROM TABLE D | I$^-$, m-(CH$_3$)$_3$—N$^+$—CH$_2$CH$_2$—(OCH$_2$CH$_2$)$_2$—O—Ph— | CHOSEN FROM TABLE D |
| F112 | CHOSEN FROM TABLE D | I$^-$, p-(N,N-dimethylpiperazine)-(N')—CH$_2$—(OCH$_2$CH$_2$)$_2$—O—Ph— | CHOSEN FROM TABLE D |
| F113 | CHOSEN FROM TABLE D | I$^-$, m-(N,N-dimethylpiperazine)-(N')—CH$_2$—(OCH$_2$CH$_2$)$_2$—O—Ph— | CHOSEN FROM TABLE D |
| F114 | CHOSEN FROM TABLE D | m-F—Ph— p-CH$_3$O— | CHOSEN FROM TABLE D |
| F115 | CHOSEN FROM TABLE D | 3,4,dioxy-methylene-Ph— | CHOSEN FROM TABLE D |
| F116 | CHOSEN FROM TABLE D | m-F—Ph— p-F—Ph— | CHOSEN FROM TABLE D |

TABLE C2-continued

Alternative compounds #2 (Families F101–F123)

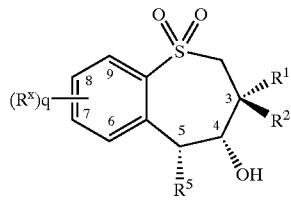

| Family Cpd# | R¹=R² | R⁵ | (Rˣ)q |
|---|---|---|---|
| F117 | CHOSEN FROM TABLE D | m-CH₃O— p-F—Ph— | CHOSEN FROM TABLE D |
| F118 | CHOSEN FROM TABLE D | 4-pyridine | CHOSEN FROM TABLE D |
| F119 | CHOSEN FROM TABLE D | N-methyl-4-pyridinium | CHOSEN FROM TABLE D |
| F120 | CHOSEN FROM TABLE D | 3-pyridine | CHOSEN FROM TABLE D |
| F121 | CHOSEN FROM TABLE D | N-methyl-3-pyridinium | CHOSEN FROM TABLE D |
| F122 | CHOSEN FROM TABLE D | 2-pyridine | CHOSEN FROM TABLE D |
| F123 | CHOSEN FROM TABLE D | p-CH₃O₂C—Ph— | CHOSEN FROM TABLE D |

Similar families can be generated where $R^1 < > R^2$, such as $R^1$=Et and $R^2$=n-Bu, but (Rˣ)q is chosen from table C1.

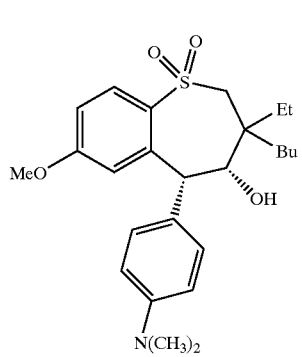

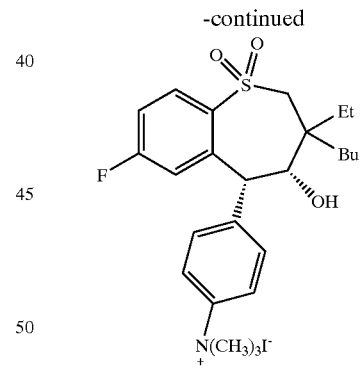

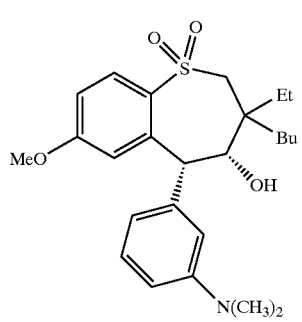

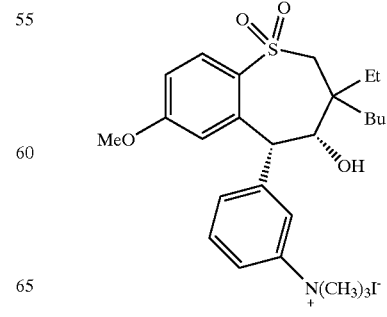

-continued
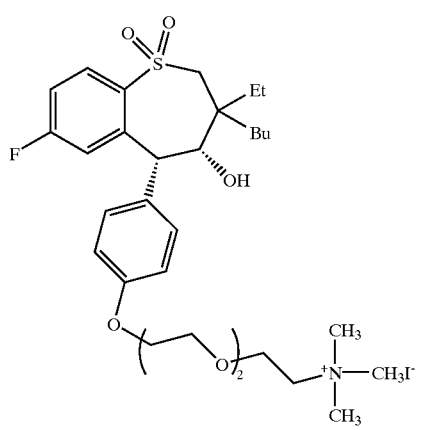
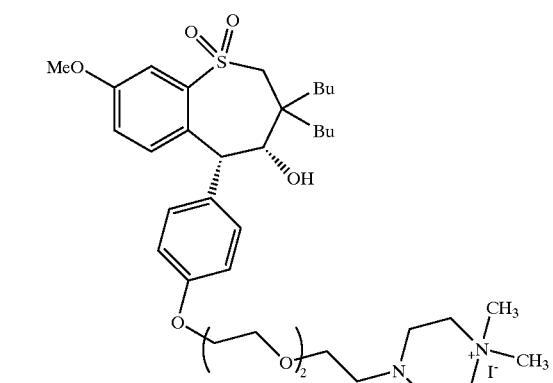
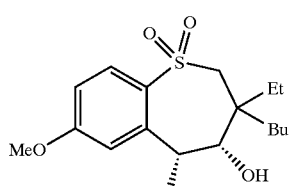
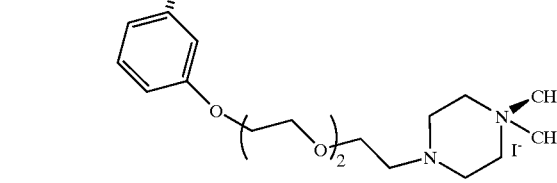
-continued
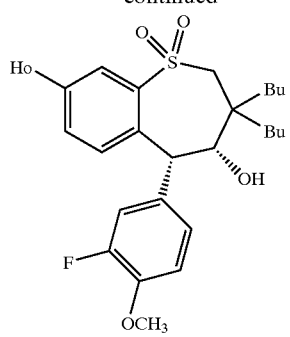
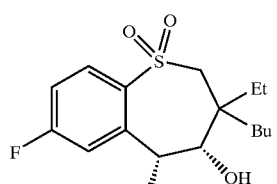
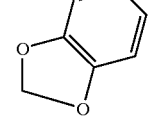
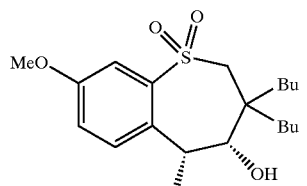
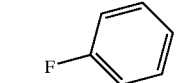
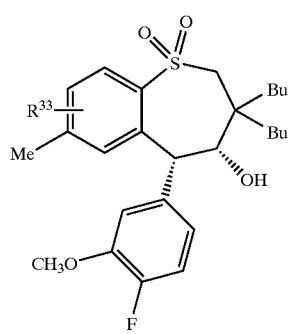
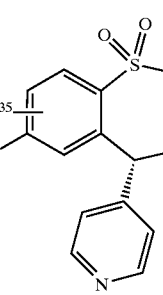

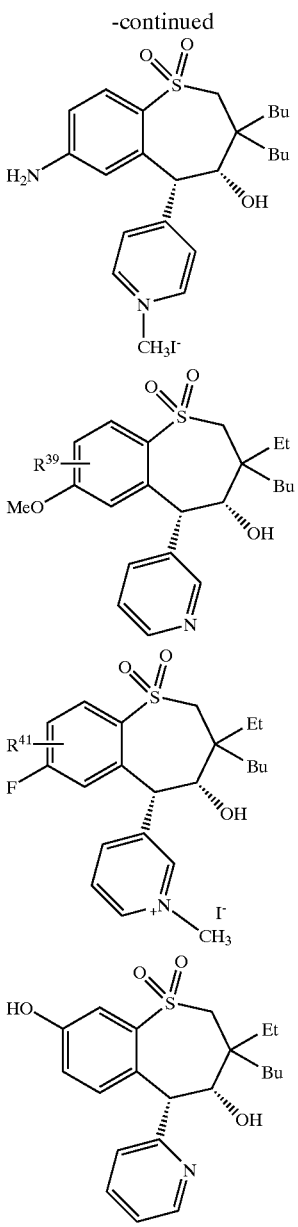

What is claimed is:

1. A composition comprising an ileal bile acid transport inhibitor and an HMG Co-A reductase inhibitor, wherein said ileal bile acid transport inhibitor has a core structure of formula (XYZ):

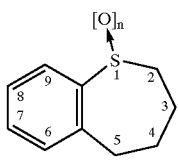

(XYZ)

wherein:

n is an integer from 0 to 2.

2. The composition of claim 1, wherein said HMG Co-A reductase inhibitor is selected from the group consisting of pitavastatin, rosuvastatin, mevastatin and cerivastatin.

3. The composition of claim 2, wherein said HMG Co-A reductase inhibitor comprises pitavastatin.

4. The composition of claim 2, wherein said HMG Co-A reductase inhibitor comprises rosuvastatin.

5. The composition of claim 2, wherein said HMG Co-A reductase inhibitor comprises mevastatin.

6. The composition of claim 2, wherein said HMG Co-A reductase inhibitor comprises cerivastatin.

7. A pharmaceutical composition, comprising:
a first amount of an ileal bile acid transport inhibitor,
a second amount of an HMG Co-A reductase inhibitor, and
a pharmaceutically acceptable carrier,
wherein said first and second amounts of said inhibitors together comprise an anti-hyperlipidermic condition effective amount of said inhibitors, and
wherein the ileal bile acid transport inhibitor has a core structure of formula (XYZ):

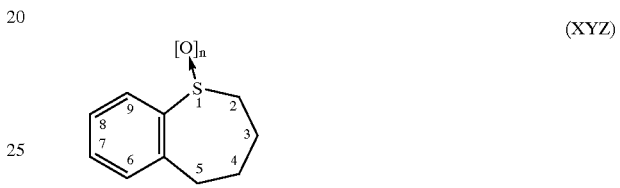

wherein:

n is an integer from 0 to 2.

8. The composition of claim 7, wherein said HMG Co-A reductase inhibitor is selected from the group consisting of pitavastatin, rosuvastatin, mevastatin and cerivastatin.

9. The composition of claim 8, wherein said HMG Co-A reductase inhibitor comprises pitavastatin.

10. The composition of claim 8, wherein said HMG Co-A reductase inhibitor comprises rosuvastatin.

11. The composition of claim 8, wherein said HMG Co-A reductase inhibitor comprises mevastatin.

12. The composition of claim 8, wherein said HMG Co-A reductase inhibitor comprises cerivastatin.

13. A combination therapy method for the treatment of a hyperlipidemic condition in a mammal in need thereof, comprising:
administering to said mammal a first amount of an ileal bile acid transport inhibitor, and
administering to said and second amounts of said inhibitors together comprise an anti-hyperlipidermic condition effective amount of said inhibitors, and
wherein the ileal bile acid transport inhibitor has a core structure of formula (XYZ):

wherein:

n is an integer from 0 to 2.

14. The composition of claim 13 wherein said HMG Co-A reductase inhibitor is selected from the group consisting of pitavastatin, rosuvastatin, mevastatin and cerivastatin.

15. The combination therapy method of claim 14, wherein said HMG Co-A reductase inhibitor comprises pitavastatin.

16. The combination therapy method of claim 14, wherein said HMG Co-A reductase inhibitor comprises rosuvastatin.

17. The combination therapy method of claim 14, wherein said HMG Co-A reductase inhibitor comprises mevastatin.

18. The combination therapy method of claim 14, wherein said HMG Co-A reductase inhibitor comprises cerivastatin.

* * * * *

UNITED STATES PATENT AND TRADEMARK OFFICE
CERTIFICATE OF CORRECTION

PATENT NO. : 6,642,268 B2  Page 1 of 1
DATED : November 4, 2003
INVENTOR(S) : Bradley T. Keller et al.

It is certified that error appears in the above-identified patent and that said Letters Patent is hereby corrected as shown below:

Title page,
Item [54], Title, please replace "BENSOTHIPINES" with -- BENZOTHIEPINES --.
Item [60], Related U.S. Application Data, please replace "Sep. 12, 1994" with -- Sep. 13, 1994 --.
Item [56], References Cited, OTHER PUBLICATIONS,
"J. Davignon et al.," referenc, please replace "Type Iii" with -- Type III --.
"R. Morin, Regulation of Lipid", reference, please replace "R. Morin" with -- R. Morton --.
"R. Patra et al.," reference, please replace "the Slide Chain" with -- the Side Chain --.
"Cayen, M. N.," reference, please replace "Dispositi9n" with -- Disposition --.

Column 348,
Lines 47-49, please replace with
-- administering to said mammal a second amount of HMG Co-A reductase inhibitor,
wherein said first and second amounts of said inhibitors together comprise an anti-hyperlipidemic condition effective amount of said inhibitors, and --

Signed and Sealed this

Eleventh Day of May, 2004

JON W. DUDAS
*Acting Director of the United States Patent and Trademark Office*